US011713320B2

(12) United States Patent
Kc et al.

(10) Patent No.: US 11,713,320 B2
(45) Date of Patent: Aug. 1, 2023

(54) 5-HETEROARYL SUBSTITUTED INDAZOLE-3-CARBOXAMIDES AND PREPARATION AND USE THEREOF

(71) Applicant: BioSplice Therapeutics, Inc., San Diego, CA (US)

(72) Inventors: Sunil Kumar Kc, San Diego, CA (US); Chi Ching Mak, San Diego, CA (US); Gopi Kumar Mittapalli, San Diego, CA (US); Brian Joseph Hofilena, San Diego, CA (US); Brian Walter Eastman, San Diego, CA (US); Jianguo Cao, San Diego, CA (US); Chandramouli Chiruta, San Diego, CA (US); Venkataiah Bollu, San Diego, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 48 days.

(21) Appl. No.: 17/138,098

(22) Filed: Dec. 30, 2020

(65) Prior Publication Data

US 2022/0402921 A1 Dec. 22, 2022

Related U.S. Application Data

(63) Continuation of application No. 16/283,366, filed on Feb. 22, 2019, now Pat. No. 10,934,297.

(60) Provisional application No. 62/634,656, filed on Feb. 23, 2018.

(51) Int. Cl.

| | |
|---|---|
| ***C07D 487/04*** | (2006.01) |
| ***C07D 403/04*** | (2006.01) |
| ***C07D 403/14*** | (2006.01) |
| ***C07D 401/14*** | (2006.01) |
| ***C07D 405/14*** | (2006.01) |
| ***C07D 417/14*** | (2006.01) |
| ***C07D 413/14*** | (2006.01) |
| ***A61P 19/04*** | (2006.01) |
| ***A61P 11/00*** | (2006.01) |
| ***A61P 17/06*** | (2006.01) |
| ***A61P 35/00*** | (2006.01) |

(52) U.S. Cl.

CPC ............ *C07D 487/04* (2013.01); *A61P 19/04* (2018.01); *C07D 401/14* (2013.01); *C07D 403/04* (2013.01); *C07D 403/14* (2013.01); *C07D 405/14* (2013.01); *C07D 413/14* (2013.01); *C07D 417/14* (2013.01); *A61P 11/00* (2018.01); *A61P 17/06* (2018.01); *A61P 35/00* (2018.01)

(58) Field of Classification Search

CPC ............................ C07D 403/14; C07D 405/14

See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 6,120,484 | A | 9/2000 | Silverstein |
| 6,377,849 | B1 | 4/2002 | Lenarz et al. |
| 6,440,102 | B1 | 8/2002 | Arenberg et al. |
| 6,648,873 | B2 | 11/2003 | Arenberg et al. |
| 6,911,211 | B2 | 6/2005 | Eini et al. |
| 7,482,342 | B2 | 1/2009 | D'Orchymont et al. |
| 7,842,711 | B2 | 11/2010 | D'Orchymont |
| 8,697,887 | B2 | 4/2014 | Hood et al. |
| 9,221,793 | B2 | 12/2015 | Hood et al. |
| 9,802,916 | B2 | 10/2017 | Hood et al. |
| 10,464,924 | B2 | 11/2019 | Hood et al. |
| 10,934,297 | B2 | 3/2021 | Kc et al. |
| 2006/0004000 | A1 | 1/2006 | D'Orchymont et al. |
| 2013/0079329 | A1 | 3/2013 | Hood et al. |
| 2014/0045815 | A1 | 2/2014 | Hood et al. |
| 2015/0266825 | A1 | 9/2015 | Hood et al. |
| 2016/0304488 | A1 | 10/2016 | Hood et al. |
| 2018/0237416 | A1 | 8/2018 | Hood et al. |
| 2019/0263821 | A1 | 8/2019 | Kc et al. |
| 2020/0239436 | A1 | 7/2020 | Hood et al. |

FOREIGN PATENT DOCUMENTS

| | | |
|---|---|---|
| CN | 101001856 | 7/2007 |
| CN | 103889976 | 6/2014 |
| CN | 103929963 | 7/2014 |
| CN | 104093712 | 10/2014 |
| CN | 106535890 | 3/2017 |
| JP | 2006-504711 | 2/2006 |
| JP | 2014-526510 | 10/2014 |
| JP | 2017-508763 | 3/2017 |

(Continued)

OTHER PUBLICATIONS

U.S. Appl. No. 11/337,815, filed Jan. 24, 2006, Lobl et al.
U.S. Appl. No. 13/614,296, filed Sep. 13, 2012, Hood & Kumar.
U.S. Appl. No. 14/019,229, filed Sep. 5, 2013, Hood & Kumar.
U.S. Appl. No. 14/664,517, filed Mar. 20, 2015, Hood et al.
Adaimy et al, "Mutation in WNT10A Is Associated with an Autosomal Recessive Ectodermal Dysplasia: The Odonto-onycho-dermal Dysplasia," Am. J. Hum. Genet, 2007, 81(4):821-828.
Andres, "Molecular genetics and animal models in autistic disorder," Brain Research Bulletin, 2002, 57(1):109-119.

(Continued)

*Primary Examiner* — Kamal A Saeed
(74) *Attorney, Agent, or Firm* — Fish & Richardson P.C.

(57) ABSTRACT

Indazole compounds for treating various diseases and pathologies are disclosed. More particularly, the present disclosure concerns the use of an indazole compound or analogs thereof, in the treatment of disorders characterized by the activation of Wnt pathway signaling (e.g., tendinopathy, dermatitis, psoriasis, morphea, ichthyosis, Raynaud's syndrome, Darier's disease, scleroderma, cancer, abnormal cellular proliferation, angiogenesis, Alzheimer's disease, lung disease, and osteoarthritis), the modulation of cellular events mediated by Wnt pathway signaling, as well as neurological conditions/disorders/diseases linked to overexpression of DYRK1A.

24 Claims, No Drawings

(56) References Cited

FOREIGN PATENT DOCUMENTS

| WO | WO 1987/005297 | 9/1987 |
|---|---|---|
| WO | WO 2001/053268 | 7/2001 |
| WO | WO 2004/014864 | 2/2004 |
| WO | WO 2004/029050 | 4/2004 |
| WO | WO 2004/031158 | 4/2004 |
| WO | WO 2005/009997 | 2/2005 |
| WO | WO 2005/092890 | 10/2005 |
| WO | WO 2011/050245 | 4/2011 |
| WO | WO 2013/040215 | 3/2013 |
| WO | WO 2013/124158 | 8/2013 |
| WO | WO 2013/151708 | 10/2013 |
| WO | WO 2015/143380 | 9/2015 |
| WO | WO 2016/040182 | 3/2016 |
| WO | WO 2017/079765 | 5/2017 |
| WO | WO 2017/210407 | 12/2017 |
| WO | WO 2018/075858 | 4/2018 |

OTHER PUBLICATIONS

Biason-Lauber et al, "A WNT4 Mutation Associated with Müllerian-Duct Regression and Virilization in a 46,XX Woman," Engl. J. Med., 2004, 351(8):792-798.
Blaydon et al, "The gene encoding R-spondin 4 (RSPO4), a secreted protein implicated in Wnt signaling, is mutated in inherited anonychia," Nat. Genet., 2006, 38(11):1245-1247.
Boyden et al, "High Bone Density Due to A Mutation In LDL-Recepter-Related Protein 5," N. Engl. J. Med., 2002, 346(20):1513-1521.
Chou & Talalay, "Quantitative analysis of dose-effect relationships: the combined effects of multiple drugs or enzyme inhibitors," Advances in Enzyme Regulation, 1984, 22:27-55.
Christodoulides et al, "WNT10B mutations in human obesity," Diabetologia, 2006, 49(4):678-84.
Datta et al, "Novel therapeutic approaches for pulmonary fibrosis," British Journal of Pharmacology, 2011, 163(1):141-172.
De Ferrari & Moon, "The ups and downs of Wnt signaling in prevalent neurological disorders," Oncogene, 2006, 25(57):7545-7553.
De Ferrari et al, "Common genetic variation within the Low-Density Lipoprotein Receptor-Related Protein 6 and late-onset Alzheimer's disease," Proc. Natl. Acad. Sci. USA, 2007, 104(22), 9434-9.
Florez et al, "TCF7L2 Polymorphisms and Progression to Diabetes in the Diabetes Prevention Program," N. Engl. J. Med., 2006, 355(3):241-50.
Freese et al, "Wnt signaling in development and disease," Neurobiology of Disease, 2010, 38(2):148-153.
Fukuzawa et al, "Beckwith-Wiedemann Syndromeassociated Hepatoblastoma: Wnt Signal Activation Occurs Later in Tumorigenesis in Patients with 11p15.5 Uniparental Disomy," Pediatric and Developmental Pathology, 2003, 6(4):299-306.
Giancarlo et al, "Wnt signaling function in Alzheimer's disease," Brain Research Reviews, 2000, 33(1):1-12.
Inestrosa & Toledo, "The role of Wnt signaling in neuronal dysfunction in Alzheimer's Disease," Molecular Neurodegeneration, 2008, 3:9, 13 pages.
Jenkins et al, "Germline mutations in WTX cause a sclerosing skeletal dysplasia but do not predispose to tumorigenesis," Nat. Genet., 2009, 41(1), 95-100.
Kanazawa et al, "Association of the Gene Encoding Wingless-Type Mammary Tumor Virus Integration-Site Family Member 5B (WNT5B) with Type 2 Diabetes," Am. J. Hum. Genet., 2004, 75(5):832-43.
Kibar et al, "Mutations in VANGL1 Associated with Neural-Tube Defects," N. Engl. J. Med., 2007, 356(14):1432-1437.

King et al, "BUILD-3: A Randomized, Controlled Trial of Bosentan in Idiopathic Pulmonary Fibrosis," The American Journal of Respiratory and Critical Care Medicine, 2011, 184(1):92-99.
Kondo et al, "Frizzled 4 gene (FZD4) mutations in patients with familial exudative vitreoretinopathy with variable expressivity," Nat. Genet., 2002, 32(2):326-30.
Kuwajima et al, "Necdin Promotes GABAergic Neuron Differentiation in Cooperation with Dlx Homeodomain Proteins," Journal of Neuroscience 2006, 26(20):5383-5392.
Lammi et al, "Mutations in AXIN2 Cause Familial Tooth Agenesis and Predispose to Colorectal Cancer," Am. J. Hum. Genet., 2004, 74(5):1043-1050.
Leyns et al, "Frzb-1 Is a Secreted Antagonist of Wnt Signaling Expressed in the Spemann Organizer Cell," 1997, 88(6):747-756.
Liu et.al., "Fibrotic Lung Fibroblasts Show Blunted Inhibition by cAMP Due to Deficient cAMP Response Element-Binding Protein Phosphorylation", Journal of Pharmacology and Experimental Therapeutics, 2005, 315(2):678-687.
Luo et al, "Fragile X Mental Retardation Protein Regulates Proliferation and Differentiation of Adult Neural Stem/Progenitor Cells," PLoS Genetics, 2010, 6(4):e1000898, 16 pages.
Mandel et al, "SERKAL Syndrome: An Autosomal-Recessive Disorder Caused by a Loss-of-Function Mutation in WNT4," Am. J. Hum. Genet., 2008, 82(1):39-47.
Mani et al, "LRP6 Mutation in a Family with Early Coronary Disease and Metabolic Risk Factors," Science, 2007, 315(5816):1278-1282.
Niemann et al, "Homozygous WNT3 Mutation Causes Tetra-Amelia in a Large Consanguineous Family," Am. J. Hum. Genet., 2004, 74(3):558-563.
Nishisho et al, "Mutations ofChromosome 5q21 Genes in FAP and Colorectal Cancer Patients," Science, 1991, 253(5020):665-669.
Oates et al, "Increased DNA Methylation at the AXIN1 Gene in a Monozygotic Twin from a Pair Discordant for a Caudal Duplication Anomaly," Am. J. Hum. Genet., 2006, 79(1):155-62.
Okerlund & Cheyette, "Synaptic Wnt signaling—a contributor to major psychiatric disorders?," Journal of Neurodevelopmental Disorders, 2011, 3(2):162-174.
PCT International Preliminary Report on Patentability in International Appln. No. PCT/US2019/019129, dated Sep. 3, 2020, 9 Pages.
PCT International Search Report and Written Opinion in International Appln. No. PCT/US2019/019129, dated Apr. 25, 2019, 16 pages.
Qin et al, "Complexity of the Genotype-Phenotype Correlation in Familial Exudative Vitreoretinopathy With Mutations in the LRP5 and/or FZD4 Genes," Hum. Mutat., 2005, 26(2):104-12.
Rivera et al, "An X Chromosome Gene, WTX, Is Commonly Inactivated in Wilms Tumor," Science, 2007, 315(5812):642-6455.
Seah et al, "Neuronal Death Resulting from Targeted Disruption of the Snf2 Protein ATRX Is Mediated by p53," The Journal of Neuroscience (2008), 28(47):12570-12580.
Ugur & Tolun, "Homozygous WNT10b mutation and complex inheritance in Split-Hand/Foot Malformation," Hum. Mol. Genet., 2008, 17(17):2644-2653.
Wang et al, "Mutations in X-linked PORCN, a putative regulator of Wnt signaling, cause focal dermal hypoplasia," Nat. Genet., 2007, 39(7):836-838.
Watts et.al., "RhoA signaling modulates cyclin D1 expression in human lung fibroblasts; implications for idiopathic pulmonary fibrosis", Respiratory Research, 2006, 7(1):88, 14 pages.
Webb et.al., "Retinoic acid receptor signaling preserves tendon stem cell characteristics and prevents spontaneous differentiation in vitro," Stem Cell Research & Therapy, 2016, 7:45, 11 pages.
Woods et al, "Mutations in WNT7A Cause a Range of Limb Malformations, Including Fuhrmann Syndrome and A1-Awadi/Raas-Rothschild/ Schinzel Phocomelia Syndrome," Am. J. Hum. Genet., 2006, 79(2):402-408.

5-HETEROARYL SUBSTITUTED INDAZOLE-3-CARBOXAMIDES AND PREPARATION AND USE THEREOF

RELATED APPLICATIONS

This application is a continuation of the U.S. application Ser. No. 16/283,366, filed Feb. 22, 2019, which claims the benefit of U.S. Provisional Application No. 62/634,656, filed Feb. 23, 2018, which is incorporated herein by reference in its entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., tendinopathy, dermatitis, psoriasis, morphea, ichthyosis, Raynaud's syndrome, Darier's disease, scleroderma, cancer, abnormal cellular proliferation, angiogenesis, Alzheimer's disease, lung disease, fibrotic disorders, cartilage (chondral) defects, and osteoarthritis; and/or for promoting wound healing), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states, as well as neurological conditions/disorders/diseases linked to overexpression of DYRK1A.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

Pathological activation of the Wnt pathway is also believed to be the initial event leading to colorectal cancer in over 85% of all sporadic cases in the Western world. Activation of the Wnt pathway has also been extensively reported for hepatocellular carcinoma, breast cancer, ovarian cancer, pancreatic cancer, melanomas, mesotheliomas, lymphomas and leukemias. In addition to cancer, inhibitors of the Wnt pathway can be used for stem cell research or for the treatment of any diseases characterized by aberrant Wnt activation such as diabetic retinopathy, pulmonary fibrosis, rheumatoid arthritis, scleroderma as well as mycotic and viral infections and bone and cartilage diseases. As such, it is a therapeutic target that is of great interest to the field.

In addition to cancer, there are many cases of genetic diseases due to mutations in Wnt signaling components. Examples of some of the many diseases are Alzheimer's disease [*Proc. Natl. Acad. Sci. USA* (2007), 104(22), 9434-9], osteoarthritis, polyposis coli [*Science* (1991), 253(5020), 665-669], bone density and vascular defects in the eye (osteoporosis-pseudoglioma syndrome, OPPG) [*N. Engl. J. Med.* (2002), 346(20), 1513-21], familial exudative vitreoretinopathy [*Hum. Mutat.* (2005), 26(2), 104-12], retinal angiogenesis [*Nat. Genet.* (2002), 32(2), 326-30], early coronary disease [*Science* (2007), 315(5816), 1278-82], tetra-amelia syndrome [*Am. J. Hum. Genet.* (2004), 74(3), 558-63], Müllerian-duct regression and virilization [*Engl. J. Med.* (2004), 351(8), 792-8], SERKAL syndrome [*Am. J. Hum. Genet.* (2008), 82(1), 39-47], diabetes mellitus type 2 [*Am. J. Hum. Genet.* (2004), 75(5), 832-43; *N Engl. J. Med.* (2006), 355(3), 241-50], Fuhrmann syndrome [*Am. J. Hum. Genet.* (2006), 79(2), 402-8], Al-Awadi/Raas-Rothschild/Schinzel phocomelia syndrome [*Am. J. Hum. Genet.* (2006), 79(2), 402-8], odonto-onycho-dermal dysplasia [*Am. J. Hum. Genet.* (2007), 81(4), 821-8], obesity [*Diabetologia* (2006), 49(4), 678-84], split-hand/foot malformation [*Hum. Mol. Genet.* (2008), 17(17), 2644-53], caudal duplication syndrome [*Am. J. Hum. Genet.* (2006), 79(1), 155-62], tooth agenesis [*Am. J. Hum. Genet.* (2004), 74(5), 1043-50], Wilms tumor [*Science* (2007), 315(5812), 642-5], skeletal dysplasia [*Nat. Genet.* (2009), 41(1), 95-100], focal dermal hypoplasia [*Nat. Genet.* (2007), 39(7), 836-8], autosomal recessive anonychia [*Nat. Genet.* (2006), 38(11), 1245-7], neural tube defects [*N. Engl. J. Med.* (2007), 356(14), 1432-7], alpha-thalassemia (ATRX) syndrome [*The Journal of Neuroscience* (2008), 28(47), 12570-12580], fragile X syndrome [*PLoS Genetics* (2010), 6(4), e1000898], ICF syndrome, Angelman syndrome [*Brain Research Bulletin* (2002), 57(1), 109-119], Prader-Willi syndrome [*Journal of Neuroscience* (2006), 26(20), 5383-5392], Beckwith-Wiedemann Syndrome [*Pediatric and Developmental Pathology* (2003), 6(4), 299-306] and Rett syndrome.

Regulation of cell signaling by the Wnt signaling pathway is critical for the formation of neuronal circuits. Wnt pathway modulates in neural tissue, among other things, axon pathfinding, dendritic development, and synaptic assembly. Through different receptors, Wnt pathway activates and/or regulates diverse signaling pathways and other processes that lead to local changes on the cytoskeleton or global cellular changes involving nuclear function. Recently, a link between neuronal activity, essential for the formation and refinement of neuronal connections, and Wnt signaling has been uncovered. Indeed, neuronal activity regulates the release of various Wnt proteins and the localization of their receptors. Wnt pathway mediates synaptic structural changes induced by neuronal activity or experience. Evidence suggests that dysfunction in Wnt signaling contributes to neurological disorders [*Brain Research Reviews* (2000), 33(1), 1-12; *Oncogene* (2006) 25(57), 7545-7553; *Molecular Neurodegeneration* (2008), 3, 9; Neurobiology of Disease (2010), 38(2), 148-153; *Journal of Neurodevelopmental Disorders* (2011), 3(2), 162-174 and *Cold Spring Harbor Perspectives in Biology* February (2012), 4(2)].

Tendinopathies are chronic disorders or injuries of the tendons, that typically result from gradual wear and tear to the tendon, e.g., from overuse or aging, and leading to is tendon degeneration, weakness, tearing, and pain. Individuals who tend to make multiple, repeated motions in their jobs, sports, or regular daily activities tend to be more likely to develop tendinopathies. Tendinopathy usually causes pain, stiffness, and loss of strength in the affected area.

Skin disorders are common afflictions for many people. Some of the most common are dermatitis (also known as eczema) and psoriasis. Both dermatitis and psoriasis can cause serious physical and/or psychological suffering to the subject regardless of the location on the body that these conditions occur.

Dual specificity tyrosine-phosphorylation-regulated kinase 1A is an enzyme that in humans is encoded by the DYRK1A gene. DYRK1A is a member of the dual-specificity tyrosine phosphorylation-regulated kinase (DYRK) family. DYRK1A contains a nuclear targeting signal sequence, a protein kinase domain, a leucine zipper motif, and a highly conservative 13-consecutive-histidine repeat. It catalyzes its autophosphorylation on serine/threonine and tyrosine residues. It may play a significant role in a signaling pathway regulating cell proliferation and may be involved in brain development. DYRK1A is localized in the Down syndrome critical region of chromosome 21, and is considered to be a candidate gene for learning defects associated with Down syndrome. DYRK1A is also expressed in adult brain neurons, indicating that DYRK1A may play a role in the mature central nervous system. Thus, several lines of evidence point to some synaptic functions of DYRK1A. For instance, it has been found that DYRK1A phosphorylates and modulates the interaction of several components of the endocytic protein complex machinery (Dynamin 1, Amphiphysin, and Synaptojanin), suggesting a role in synaptic vesicle recycling. In addition, a polymorphism (SNP) in DYRK1A was found to be associated with HIV-1 replication in monocyte-derived macrophages, as well as with progression to AIDS in two independent cohorts of HIV-1-infected individuals.

SUMMARY

The present disclosure provides methods and reagents, involving contacting a cell with an agent, such as an indazole compound, in a sufficient amount to antagonize a Wnt activity, e.g., to reverse or control an aberrant growth state or correct a genetic disorder due to mutations in Wnt signaling components.

This disclosure features the use of one or more indazole-3-carboxamide compounds or salts or analogs thereof, in the treatment of one or more diseases or conditions independently selected from the group consisting of a tendinopathy, dermatitis, psoriasis, morphea, ichthyosis, Raynaud's syndrome, and Darier's disease; and/or for promoting wound healing. The methods include administering to a subject (e.g., a subject in need thereof) a therapeutically effective amount of one or more indazole-3-carboxamide compounds or salts or analogs thereof as described anywhere herein.

The present disclosure also provides methods and reagents, involving contacting a cell with an agent, such as an indazole compound, in a sufficient amount to antagonize DYRK1A activity, e.g., i) to normalize prenatal and early postnatal brain development; ii) to improve cognitive function in youth and adulthood; and/or iii) to attenuate Alzheimer's-type neurodegeneration.

Some embodiments disclosed herein include Wnt and/or DYRK1A inhibitors containing an indazole core. Other embodiments disclosed herein include pharmaceutical compositions and methods of treatment using these compounds.

One embodiment disclosed herein includes a compound having the structure of Formula I:

I

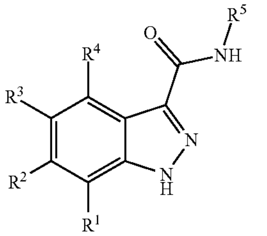

as well as prodrugs and pharmaceutically acceptable salts thereof.

In some embodiments of Formula (I):

$R^1$, $R^2$, and $R^4$ are independently selected from the group consisting of H and halide;

$R^3$ is selected from the group consisting of:

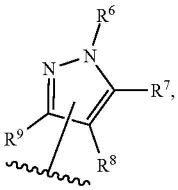
,
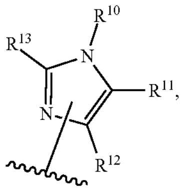
,
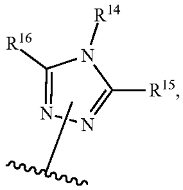
,
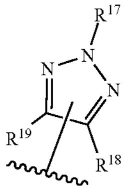
,
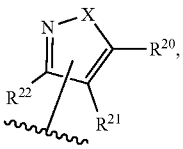
, and
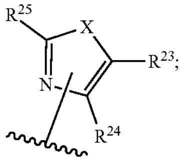
;

wherein each of $R^6$-$R^{25}$ is, independently, a substituent as defined anywhere herein or a single bond connecting $R^3$ to the indazole ring; wherein only one of $R^6$-$R^9$ (when present) is a bond, only one of $R^{10}$-$R^{13}$ (when present) is a bond, only one of $R^{14}$-$R^{16}$ (when present) is a bond, only one of $R^{17}$-$R^{19}$ (when present) is a bond, only one of $R^{20}$-$R^{22}$ is a bond, and only one of $R^{23}$-$R^{25}$ (when present) is a bond; for purposes of clarification, any one of the nitrogen atoms attached to $R^6$, $R^{10}$, $R^{14}$, or $R^{17}$ can serve as the point of attachment of $R^3$ to the indazole ring; likewise, any one of the carbon atoms attached to $R^7$, $R^8$, $R^9$, $R^{11}$, $R^{12}$, $R^{13}$, $R^{15}$, $R^{16}$, $R^{18}$, $R^{19}$, $R^{20}$, $R^{21}$, $R^{22}$, $R^{23}$, $R^{24}$, $R^{25}$ can serve as the point of attachment of $R^3$ to the indazole ring; accordingly:

when the nitrogen atom to which $R^6$ is attached serves as the point of attachment of $R^3$ to the indazole ring, then $R^6$ is a single bond connecting $R^3$ to the indazole ring;

when the carbon atom to which 127 is attached serves as the point of attachment of $R^3$ to the indazole ring, then $R^7$ is a single bond connecting $R^3$ to the indazole ring;

when the carbon atom to which $R^8$ is attached serves as the point of attachment of $R^3$ to the indazole ring, then $R^8$ is a single bond connecting $R^3$ to the indazole ring;

when the carbon atom to which $R^9$ is attached serves as the point of attachment of $R^3$ to the indazole ring, then $R^9$ is a single bond connecting $R^3$ to the indazole ring;

when the nitrogen atom to which $R^{10}$ is attached serves as the point of attachment of $R^3$ to the indazole ring, then $R^{10}$ is a single bond connecting $R^3$ to the indazole ring;

when the carbon atom to which $R^{11}$ is attached serves as the point of attachment of $R^3$ to the indazole ring, then $R^{11}$ is a single bond connecting $R^3$ to the indazole ring;

when the carbon atom to which $R^{12}$ is attached serves as the point of attachment of $R^3$ to the indazole ring, then $R^{12}$ is a single bond connecting $R^3$ to the indazole ring;

when the carbon atom to which $R^{13}$ is attached serves as the point of attachment of $R^3$ to the indazole ring, then $R^{13}$ is a single bond connecting $R^3$ to the indazole ring;

when the nitrogen atom to which $R^{14}$ is attached serves as the point of attachment of $R^3$ to the indazole ring, then $R^{14}$ is a single bond connecting $R^3$ to the indazole ring;

when the carbon atom to which $R^{15}$ is attached serves as the point of attachment of $R^3$ to the indazole ring, then $R^{15}$ is a single bond connecting $R^3$ to the indazole ring;

when the carbon atom to which $R^{16}$ is attached serves as the point of attachment of $R^3$ to the indazole ring, then $R^{16}$ is a single bond connecting $R^3$ to the indazole ring;

when the nitrogen to which $R^{17}$ is attached serves as the point of attachment of $R^3$ to the indazole ring, then $R^{17}$ is a single bond connecting $R^3$ to the indazole ring;

when the carbon atom to which $R^{18}$ is attached serves as the point of attachment of $R^3$ to the indazole ring, then $R^{18}$ is a single bond connecting $R^3$ to the indazole ring;

when the carbon atom to which $R^{19}$ is attached is instead attached to the indazole ring then $R^{19}$ is a single bond connecting $R^3$ to the indazole ring;

when the carbon atom to which $R^{20}$ is attached serves as the point of attachment of $R^3$ to the indazole ring, then $R^{20}$ is a single bond connecting $R^3$ to the indazole ring;

when the carbon atom to which $R^{21}$ is attached serves as the point of attachment of $R^3$ to the indazole ring, then $R^{21}$ is a single bond connecting $R^3$ to the indazole ring;

when the carbon atom to which $R^{22}$ is attached serves as the point of attachment of $R^3$ to the indazole ring, then $R^{22}$ is a single bond connecting $R^3$ to the indazole ring;

when the carbon atom to which $R^{23}$ is attached serves as the point of attachment of $R^3$ to the indazole ring, then $R^{23}$ is a single bond connecting $R^3$ to the indazole ring;

when the carbon atom to which $R^{24}$ is attached serves as the point of attachment of $R^3$ to the indazole ring, then $R^{24}$ is a single bond connecting $R^3$ to the indazole ring;

when the carbon to which $R^{25}$ is attached serves as the point of attachment of $R^3$ to the indazole ring, then $R^{25}$ is a single bond connecting $R^3$ to the indazole ring;

$R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heteroaryl substituted with 1-4 $R^{26}$, a monocyclic —($C_{1-4}$ alkylene)$_p$heterocyclyl optionally substituted with 1-10 $R^{27}$, a spirocyclic heterocyclyl optionally substituted with 1-10 $R^{27}$, —($C_{1-4}$ alkylene)$_p$carbocyclyl optionally substituted with 1-12 $R^{28}$, and -aryl optionally substituted with 1-5 $R^{29}$; wherein each —($C_{1-4}$ alkylene) is, independently, optionally substituted with a substituent as defined anywhere herein;

$R^6$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with a substituent as defined anywhere herein;

$R^7$, $R^8$, and $R^9$ are independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OH, and —($C_{1-4}$ alkylene)$_p$heterocyclyl optionally substituted with 1-10 $R^{27}$; wherein each —($C_{1-4}$ alkylene) is, independently, optionally substituted with a substituent as defined anywhere herein;

alternatively, one of $R^6$ and $R^7$, $R^7$ and $R^8$, or $R^8$ and $R^9$ are taken together to form a ring which is selected from the group consisting of -heterocyclyl optionally substituted with 1-10 $R^{32}$ and carbocyclyl optionally substituted with 1-12 $R^{33}$;

$R^{10}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and carbocyclyl optionally substituted with 1-12 $R^{31}$; wherein —($C_{1-4}$ alkylene) is, optionally substituted with a substituent as defined anywhere herein;

$R^{11}$, $R^{12}$, and $R^{13}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{10}$ and $R^{11}$, $R^{11}$ and $R^{12}$, or $R^{13}$ and $R^{10}$ are taken together to form a ring which is selected from the group consisting of -heterocyclyl optionally substituted with 1-10 $R^{32}$ and -carbocyclyl optionally substituted with 1-12 $R^{33}$;

$R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), ($C_{1-4}$ alkylene)$_p$heterocyclyl optionally substituted with 1-10 $R^{30}$, and carbocyclyl optionally substituted with 1-12 $R^{31}$; wherein —($C_{1-4}$ alkylene) is, optionally substituted with a substituent as defined anywhere herein;

$R^{15}$ and $R^{16}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{14}$ and $R^{15}$ or $R^{16}$ and $R^{14}$ are taken together to form a heterocyclyl optionally substituted with 1-10 $R^{32}$;

$R^{17}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and carbocyclyl optionally substituted with 1-12 $R^{31}$; wherein —($C_{1-4}$ alkylene) is, optionally substituted with a substituent as defined anywhere herein;

$R^{18}$ and $R^{19}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{18}$ and $R^{19}$ are taken together to form a ring which is selected from the group consisting of -heterocyclyl optionally substituted with 1-10 $R^{32}$ and -carbocyclyl optionally substituted with 1-12 $R^{33}$;

$R^{20}$, $R^{21}$, and $R^{22}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{20}$ and $R^{21}$ or $R^{21}$ and $R^{22}$ are taken together to form a ring which is selected from the group consisting of -heterocyclyl optionally substituted with 1-10 $R^{32}$ and -carbocyclyl optionally substituted with 1-12 $R^{33}$;

$R^{23}$, $R^{24}$, and $R^{25}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{23}$ and $R^{24}$ are taken together to form a ring which is selected from the group consisting of -heterocyclyl optionally substituted with 1-10 $R^{32}$ and -carbocyclyl optionally substituted with 1-12 $R^{33}$;

each $R^{26}$ is independently selected from the group consisting of halide, —$OR^{34}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —C(C═O)N($R^{41}$)$_2$, —($C_{1-4}$ alkylene)$_p$heterocyclyl optionally substituted with 1-10 $R^{35}$, and —O($C_{1-4}$alkylene)$_p$heterocyclyl optionally substituted with 1-10 $R^{36}$; wherein each —($C_{1-4}$ alkylene) is, independently, optionally substituted with a substituent as defined anywhere herein;

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), carbocyclyl optionally substituted with 1-12 $R^{28}$, and aryl optionally substituted with 1-5 $R^{46}$;

each $R^{28}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-4}$ alkylene)$_p$ heterocyclyl optionally substituted with 1-10 $R^{37}$; wherein —($C_{1-4}$ alkylene) is, optionally substituted with a substituent as defined anywhere herein;

each $R^{29}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$alkylene)$_p$heterocyclyl optionally substituted with 1-10 $R^{39}$, —NHheterocyclyl optionally substituted with 1-10 $R^{40}$, and —O($C_{1-4}$ alkylene)$_p$heterocyclyl optionally substituted with 1-10 $R^{40}$; wherein —($C_{1-4}$ alkylene) is, optionally substituted with a substituent as defined anywhere herein;

each $R^{30}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{31}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{32}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{33}$ is independently selected from the group consisting of unsubstituted —($C_{1-4}$ alkyl), unsubstituted —($C_{2-4}$ alkenyl), unsubstituted —($C_{2-4}$alkynyl), unsubstituted —($C_{1-4}$ haloalkyl), halide, and —CN;

each $R^{34}$ is independently selected from the group consisting of unsubstituted —($C_{1-4}$alkyl), unsubstituted —($C_{2-4}$ alkenyl), unsubstituted —($C_{2-4}$alkynyl), and unsubstituted —($C_{1-4}$ haloalkyl);

each $R^{35}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{36}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{37}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{38}$ is independently selected from the group consisting of H, unsubstituted —($C_{1-4}$ alkyl), unsubstituted —($C_{2-4}$ alkenyl), unsubstituted —($C_{2-4}$ alkynyl), and unsubstituted —($C_{1-4}$ haloalkyl);

each $R^{39}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$haloalkyl), halide, and —CN;

each $R^{40}$ independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$haloalkyl), halide, and —CN;

each $R^{41}$ is independently selected from the group consisting of H and —($C_{1-9}$ alkyl); each $R^{46}$ is independently selected from the group consisting of unsubstituted —($C_{1-4}$ alkyl), unsubstituted —($C_{2-4}$ alkenyl), unsubstituted —($C_{2-4}$ alkenyl), unsubstituted —($C_{1-4}$haloalkyl), halide, and —CN;

each X is O or S;

each p is independently 0 or 1; and with the proviso that Formula I is not a structure selected from the group consisting of:

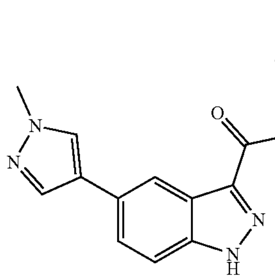

.

In some embodiments of Formula (I):

$R^1$, $R^2$, and $R^4$ are independently selected from the group consisting of H and halide;

$R^3$ is selected from the group consisting of:

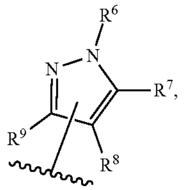
,
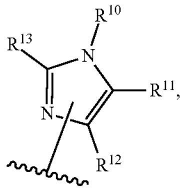
,
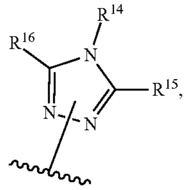
,
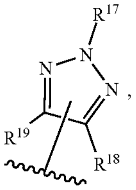
,
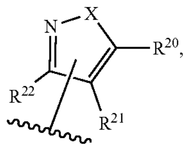
, and
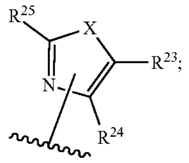
;

wherein each of $R^6$-$R^{25}$ is, independently, a substituent as defined anywhere herein or a single bond connecting $R^3$ to the indazole ring; wherein only one of $R^6$-$R^9$ (when present) is a bond, only one of $R^{10}$-$R^{13}$ (when present) is a bond, only one of $R^{14}$-$R^{16}$ (when present) is a bond, only one of $R^{17}$-$R^{19}$ (when present) is a bond, only one of $R^{20}$-$R^{22}$ is a bond, and only one of $R^{23}$-$R^{25}$ (when present) is a bond; for purposes of clarification, any one of the nitrogen atoms attached to $R^6$, $R^{10}$, $R^{14}$, or $R^{17}$ can serve as the point of attachment of $R^3$ to the indazole ring; likewise, any one of the carbon atoms attached to $R^7$, $R^8$, $R^9$, $R^{11}$, $R^{12}$, $R^{13}$, $R^{15}$, $R^{16}$, $R^{18}$, $R^{19}$, $R^{20}$, $R^{21}$, $R^{22}$, $R^{23}$, $R^{24}$, $R^{25}$ can serve as the point of attachment of $R^3$ to the indazole ring; accordingly:

when the nitrogen atom to which $R^6$ is attached serves as the point of attachment of $R^3$ to the indazole ring, then $R^6$ is a single bond connecting $R^3$ to the indazole ring;

when the carbon atom to which $R^7$ is attached serves as the point of attachment of $R^3$ to the indazole ring, then $R^7$ is a single bond connecting $R^3$ to the indazole ring;

when the carbon atom to which $R^8$ is attached serves as the point of attachment of $R^3$ to the indazole ring, then $R^8$ is a single bond connecting $R^3$ to the indazole ring;

when the carbon atom to which $R^9$ is attached serves as the point of attachment of $R^3$ to the indazole ring, then $R^9$ is a single bond connecting $R^3$ to the indazole ring;

when the nitrogen atom to which $R^{10}$ is attached serves as the point of attachment of $R^3$ to the indazole ring, then $R^{10}$ is a single bond connecting $R^3$ to the indazole ring;

when the carbon atom to which $R^{11}$ is attached serves as the point of attachment of $R^3$ to the indazole ring, then $R^{11}$ is a single bond connecting $R^3$ to the indazole ring;

when the carbon atom to which $R^{13}$ is attached serves as the point of attachment of $R^3$ to the indazole ring, then $R^{13}$ is a single bond connecting $R^3$ to the indazole ring;

when the carbon atom to which $R^{13}$ is attached serves as the point of attachment of $R^3$ to the indazole ring, then $R^{11}$ is a single bond connecting $R^3$ to the indazole ring;

when the nitrogen atom to which $R^{14}$ is attached serves as the point of attachment of $R^3$ to the indazole ring, then $R^{14}$ is a single bond connecting $R^3$ to the indazole ring;

when the carbon atom to which $R^{15}$ is attached serves as the point of attachment of $R^3$ to the indazole ring, then $R^{15}$ is a single bond connecting $R^3$ to the indazole ring;

when the carbon atom to which $R^{16}$ is attached serves as the point of attachment of $R^3$ to the indazole ring, then $R^{16}$ is a single bond connecting $R^3$ to the indazole ring;

when the nitrogen to which $R^{17}$ is attached serves as the point of attachment of $R^3$ to the indazole ring, then $R^{17}$ is a single bond connecting $R^3$ to the indazole ring;

when the carbon atom to which $R^{18}$ is attached serves as the point of attachment of $R^3$ to the indazole ring, then $R^{18}$ is a single bond connecting $R^3$ to the indazole ring;

when the carbon atom to which $R^{19}$ is attached is instead attached to the indazole ring then $R^{19}$ is a single bond connecting $R^3$ to the indazole ring;

when the carbon atom to which $R^{20}$ is attached serves as the point of attachment of $R^3$ to the indazole ring, then $R^{20}$ is a single bond connecting $R^3$ to the indazole ring;

when the carbon atom to which $R^{21}$ is attached serves as the point of attachment of $R^3$ to the indazole ring, then $R^{21}$ is a single bond connecting $R^3$ to the indazole ring;

when the carbon atom to which $R^{22}$ is attached serves as the point of attachment of $R^3$ to the indazole ring, then $R^{22}$ is a single bond connecting $R^3$ to the indazole ring;

when the carbon atom to which $R^{23}$ is attached serves as the point of attachment of $R^3$ to the indazole ring, then $R^{23}$ is a single bond connecting $R^3$ to the indazole ring;

when the carbon atom to which $R^{24}$ is attached serves as the point of attachment of $R^3$ to the indazole ring, then $R^{24}$ is a single bond connecting $R^3$ to the indazole ring;

when the carbon to which $R^{25}$ is attached serves as the point of attachment of $R^3$ to the indazole ring, then $R^{25}$ is a single bond connecting $R^3$ to the indazole ring;

$R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), heteroaryl substituted with 1-4 $R^{26}$, a monocyclic —($C_{1-4}$alkylene)$_p$heterocyclyl optionally substituted with 1-10 $R^{27}$, a spirocyclic heterocyclyl optionally substituted with 1-10 $R^{27}$, —($C_{1-4}$alkylene)$_p$carbocyclyl optionally substituted with 1-12 $R^{28}$, and aryl optionally substituted with 1-5 $R^{29}$; wherein each ($C_{1-4}$alkylene) is, independently, optionally substituted with a substituent as defined anywhere herein;

$R^6$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and carbocyclyl optionally substituted with 1-12 $R^{31}$; wherein —($C_{1-4}$alkylene) is, optionally substituted with a substituent as defined anywhere herein;

$R^7$, $R^8$, and $R^9$ are independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$alkylene)$_p$OH, and —($C_{1-4}$alkylene)$_p$heterocyclyl optionally substituted with 1-10 $R^{27}$; wherein each —($C_{1-4}$alkylene) is, independently, optionally substituted with a substituent as defined anywhere herein;

alternatively, one of $R^6$ and $R^7$, $R^7$ and $R^8$, or $R^8$ and $R^9$ are taken together to form a ring which is selected from the group consisting of -heterocyclyl optionally substituted with 1-10 $R^{32}$ and carbocyclyl optionally substituted with 1-12 $R^{33}$;

$R^{10}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$alkylene)$_p$heterocyclyl optionally substituted with 1-10 $R^{30}$, and carbocyclyl optionally substituted with 1-12 $R^{31}$; wherein —($C_{1-4}$alkylene) is, optionally substituted with a substituent as defined anywhere herein;

$R^{11}$, $R^{12}$, and $R^{13}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{10}$ and $R^{11}$, $R^{11}$ and $R^{12}$, or $R^{13}$ and $R^{10}$ are taken together to form a ring which is selected from the group consisting of -heterocyclyl optionally substituted with 1-10 $R^{32}$ and -carbocyclyl optionally substituted with 1-12 $R^{33}$;

$R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with a substituent as defined anywhere herein;

$R^{15}$ and $R^{16}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{14}$ and $R^{15}$ or $R^{16}$ and $R^{14}$ are taken together to form a heterocyclyl optionally substituted with 1-10 $R^{32}$;

$R^{17}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{30}$, and carbocyclyl optionally substituted with 1-12 $R^{31}$; wherein —($C_{1-4}$ alkylene) is, optionally substituted with a substituent as defined anywhere herein;

$R^{18}$ and $R^{19}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{18}$ and $R^{19}$ are taken together to form a ring which is selected from the group consisting of -heterocyclyl optionally substituted with 1-10 $R^{32}$ and -carbocyclyl optionally substituted with 1-12 $R^{33}$;

$R^{20}$, $R^{21}$, and $R^{22}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{20}$ and $R^{21}$ or $R^{21}$ and $R^{22}$ are taken together to form a ring which is selected from the group consisting of -heterocyclyl optionally substituted with 1-10 $R^{32}$ and -carbocyclyl optionally substituted with 1-12 $R^{33}$;

$R^{23}$, $R^{24}$, and $R^{25}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{23}$ and $R^{24}$ are taken together to form a ring which is selected from the group consisting of -heterocyclyl optionally substituted with 1-10 $R^{32}$ and -carbocyclyl optionally substituted with 1-12 $R^{33}$;

each $R^{26}$ is independently selected from the group consisting of halide, —$OR^{34}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —C(C═O)N($R^{41}$)$_2$, —($C_{1-4}$alkylene)$_p$heterocyclyl optionally substituted with 1-10 $R^{35}$, and —O($C_{1-4}$ alkylene)$_p$heterocyclyl optionally substituted with 1-10 $R^{36}$; wherein each —($C_{1-4}$alkylene) is, independently, optionally substituted with a substituent as defined anywhere herein;

each $R^{27}$ is independently selected from the group consisting of halide, unsubstituted ($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{28}$;

each $R^{28}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-4}$ alkylene)$_p$ heterocyclyl optionally substituted with 1-10 $R^{37}$; wherein —($C_{1-4}$ alkylene) is, optionally substituted with a substituent as defined anywhere herein;

each $R^{29}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$ heterocyclyl optionally substituted with 1-10 $R^{39}$, —NHheterocyclyl optionally substituted with 1-10 $R^{40}$, and —Oheterocyclyl optionally substituted with 1-10 $R^{40}$; wherein —($C_{1-4}$alkylene) is, optionally substituted with a substituent as defined anywhere herein;

each $R^{30}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{31}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{32}$ is independently selected from the group consisting of unsubstituted —($C_{1-4}$alkyl), unsubstituted —($C_{2-4}$ alkenyl), unsubstituted —($C_{2-4}$ alkynyl), unsubstituted ($C_{1-4}$ haloalkyl), halide, and —CN;

each $R^{33}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{34}$ is independently selected from the group consisting of unsubstituted —($C_{1-4}$alkyl), unsubstituted —($C_{2-4}$ alkenyl), unsubstituted —($C_{2-4}$alkynyl), and unsubstituted —($C_{1-4}$ haloalkyl);

each $R^{35}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{36}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{37}$ is independently selected from the group consisting of unsubstituted —($C_{1-4}$alkyl), unsubstituted —($C_{2-4}$ alkenyl), unsubstituted —($C_{2-4}$ alkynyl), unsubstituted —($C_{1-4}$ haloalkyl), halide, and —CN;

each $R^{38}$ is independently selected from the group consisting of H, unsubstituted —($C_{1-4}$ alkyl), unsubstituted —($C_{2-4}$ alkenyl), unsubstituted —($C_{2-4}$ alkynyl), and unsubstituted —($C_{1-4}$ haloalkyl);

each $R^{39}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{40}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{41}$ is independently selected from the group consisting of H and —($C_{1-9}$ alkyl);

each X is O or S;

each p is independently 0 or 1; and with the proviso that Formula I is not a structure selected from the group consisting of:

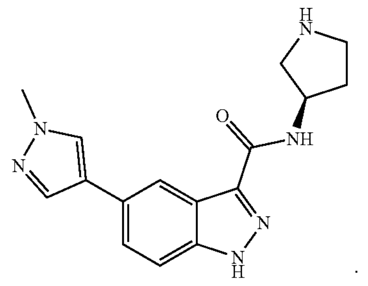 [SMILES: Cn1cc(-c2ccc3[nH]nc(C(=O)N[C@@H]4CCNC4)c3c2)cn1]

In another embodiment of Formula (I):

$R^1$, $R^2$, and $R^4$ are independently selected from the group consisting of H and halide;

$R^3$ is a 5-membered heteroaryl ring optionally substituted as defined anywhere herein, e.g., $R^3$ is a 5-membered heteroaryl ring optionally substituted with from 1-4 $R^{42}$;

$R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), heteroaryl substituted with 1-4 $R^{26}$, a monocyclic —($C_{1-4}$alkylene)$_p$heterocyclyl optionally substituted with 1-10 $R^{27}$, a spirocyclic heterocyclyl optionally substituted with 1-10 $R^{27}$, —($C_{1-4}$alkylene)$_p$carbocyclyl optionally substituted with 1-12 $R^{28}$, and aryl optionally substituted with 1-5 $R^{29}$; wherein each ($C_{1-4}$alkylene) is, independently, optionally substituted with a substituent as defined anywhere herein;

each $R^{26}$ is independently selected from the group consisting of halide, —$OR^{34}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —C(C=O)N($R^{41}$)$_2$, —($C_{1-4}$alkylene)$_p$heterocyclyl optionally substituted with 1-10 $R^{35}$, and —O($C_{1-4}$ alkylene)$_p$heterocyclyl optionally substituted with 1-10 $R^{36}$; wherein each —($C_{1-4}$ alkylene) is, independently, optionally substituted with a substituent as defined anywhere herein;

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), carbocyclyl optionally substituted with 1-12 $R^{28}$, and aryl optionally substituted with 1-5 $R^{46}$;

each $R^{28}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-4}$alkylene)$_p$ heterocyclyl optionally substituted with 1-10 $R^{37}$; wherein —($C_{1-4}$alkylene) is, optionally substituted with a substituent as defined anywhere herein;

each $R^{29}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{39}$, —NHheterocyclyl optionally substituted with 1-10 $R^{40}$, and —O($C_{1-4}$ alkylene)$_p$heterocyclyl optionally substituted with 1-10 $R^{40}$; wherein each —($C_{1-4}$ alkylene) is, independently, optionally substituted with a substituent as defined anywhere herein;

each $R^{34}$ is independently selected from the group consisting of unsubstituted —($C_{1-4}$alkyl), unsubstituted —($C_{2-4}$ alkenyl), unsubstituted —($C_{2-4}$ alkynyl), and unsubstituted ($C_{1-4}$ haloalkyl);

each $R^{35}$ is independently selected from the group consisting of unsubstituted —($C_{1-4}$ alkyl), unsubstituted —($C_{2-4}$ alkenyl), unsubstituted —($C_{2-4}$ alkynyl), unsubstituted ($C_{1-4}$ haloalkyl), halide, and —CN;

each $R^{36}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{37}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{38}$ is independently selected from the group consisting of H, unsubstituted —($C_{1-4}$ alkyl), unsubstituted —($C_{2-4}$alkenyl), unsubstituted —($C_{2-4}$alkynyl), and unsubstituted —($C_{1-4}$haloalkyl);

each $R^{39}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{40}$ is independently selected from the group consisting of unsubstituted —($C_{1-4}$alkyl), unsubstituted —($C_{2-4}$ alkenyl), unsubstituted —($C_{2-4}$ alkynyl), unsubstituted —($C_{1-4}$ haloalkyl), halide, and —CN;

each $R^{41}$ is independently selected from the group consisting of H and —($C_{1-9}$ alkyl);

each $R^{42}$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OH, —($C_{1-4}$ alkylene)$_p$heterocyclyl optionally substituted with 1-10 $R^{43}$, and carbocyclyl optionally substituted with 1-12 $R^{44}$; wherein each —($C_{1-4}$alkylene) is, independently, optionally substituted with a substituent as defined anywhere herein;

alternatively, two adjacent $R^{42}$ groups are taken together to form a ring which is selected from the group consisting of -heterocyclyl optionally substituted with 1-10 $R^{45}$ and carbocyclyl optionally substituted with 1-12 $R^{46}$;

each $R^{43}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{44}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{45}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{46}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each p is independently 0 or 1; and with the proviso that Formula I is not a structure selected from the group consisting of:

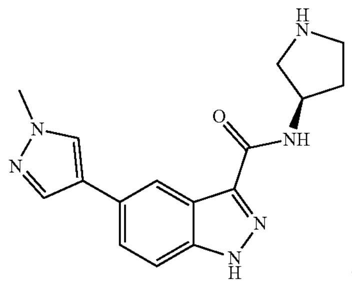

In another embodiment of Formula (I):

$R^1$, $R^2$, and $R^4$ are independently selected from the group consisting of H and halide;

$R^3$ is a 5-membered heteroaryl ring optionally substituted as defined anywhere herein, e.g., $R^3$ is a 5-membered heteroaryl ring optionally substituted with from 1-4 $R^{42}$;

$R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), heteroaryl substituted with 1-4 $R^{26}$, a monocyclic —($C_{1-4}$ alkylene)$_p$heterocyclyl optionally substituted with 1-10 $R^{27}$, a spirocyclic heterocyclyl optionally substituted with 1-10 $R^{27}$, —($C_{1-4}$ alkylene)$_p$carbocyclyl optionally substituted with 1-12 $R^{28}$, and aryl optionally substituted with 1-5 $R^{29}$; wherein each —($C_{1-4}$alkylene) is, independently, optionally substituted with a substituent as defined anywhere herein;

each $R^{26}$ is independently selected from the group consisting of halide, —$OR^{34}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —C(C═O)N($R^{41}$)$_2$, —($C_{1-4}$alkylene)$_p$heterocyclyl optionally substituted with 1-10 $R^{35}$, and —O($C_{1-4}$ alkylene)$_p$heterocyclyl optionally substituted with 1-10 $R^{36}$; wherein each —($C_{1-4}$alkylene) is, independently, optionally substituted with a substituent as defined anywhere herein;

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and carbocyclyl optionally substituted with 1-12 $R^{28}$;

each $R^{28}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-4}$ alkylene)$_p$ heterocyclyl optionally substituted with 1-10 $R^{37}$; wherein —($C_{1-4}$alkylene) is, optionally substituted with a substituent as defined anywhere herein;

each $R^{29}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$alkylene)$_p$heterocyclyl optionally substituted with 1-10 $R^{39}$, —NHheterocyclyl optionally substituted with 1-10 $R^{40}$, and —Oheterocyclyl optionally substituted with 1-10 $R^{40}$; wherein each —($C_{1-4}$alkylene) is, independently, optionally substituted with a substituent as defined anywhere herein;

each $R^{34}$ is independently selected from the group consisting of unsubstituted —($C_{1-4}$alkyl), unsubstituted —($C_{2-4}$ alkenyl), unsubstituted —($C_{2-4}$alkynyl), and unsubstituted —($C_{1-4}$ haloalkyl);

each $R^{35}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{36}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{37}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{38}$ is independently selected from the group consisting of H, unsubstituted —($C_{1-4}$alkyl), unsubstituted —($C_{2-4}$alkenyl), unsubstituted —($C_{2-4}$alkynyl), and unsubstituted —($C_{1-4}$haloalkyl);

each $R^{39}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{40}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{41}$ is independently selected from the group consisting of H and —($C_{1-9}$ alkyl);

each $R^{42}$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OH, —($C_{1-4}$ alkylene)$_p$heterocyclyl optionally substituted with 1-10 $R^{43}$, and carbocyclyl optionally substituted with 1-12 $R^{44}$; wherein each —($C_{1-4}$ alkylene) is, independently, optionally substituted with a substituent as defined anywhere herein;

alternatively, two adjacent $R^{42}$ groups are taken together to form a ring which is selected from the group consisting of -heterocyclyl optionally substituted with 1-10 $R^{45}$ and carbocyclyl optionally substituted with 1-12 $R^{46}$;

each $R^{43}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{44}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$haloalkyl), halide, and —CN;

each $R^{45}$ is independently selected from the group consisting of unsubstituted —($C_{1-4}$alkyl), unsubstituted —($C_{2-4}$ alkenyl), unsubstituted —($C_{2-4}$alkynyl), unsubstituted —($C_{1-4}$ haloalkyl), halide, and —CN;

each $R^{46}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each p is independently 0 or 1; and with the proviso that Formula I is not a structure selected from the group consisting of:

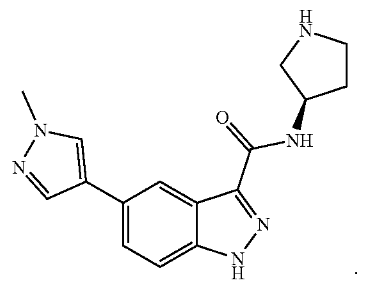 [SMILES: Cn1cc(-c2ccc3[nH]nc(C(=O)N[C@@H]4CCNC4)c3c2)cn1]

Some embodiments include administering stereoisomers and pharmaceutically acceptable salts of a compound of general Formula (I).

Some embodiments include administering pro-drugs of a compound of general Formula (I).

Some embodiments include administering pharmaceutical compositions comprising a compound of general Formula (I) or in a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Other embodiments disclosed herein include methods of inhibiting DYRK1A by administering to a patient affected by a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor and Stroke.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the disclosure, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 13/614,296; 14/019,229; and 14/664,517, all of which are incorporated by reference in their entirety herein.

Provided herein are compositions and methods for inhibiting DYRK1A. Other DYRK1A inhibitors and methods for using the same are disclosed in U.S. application Ser. No. 14/664,517, which is incorporated by reference in its entirety herein.

Some embodiments provided herein relate to a method for treating a disease including, but not limited to, neurological diseases or disorders, cancers, chronic inflammation, diabetic retinopathy, pulmonary fibrosis, rheumatoid arthritis, sepsis, ankylosing spondylitis, psoriasis, scleroderma, mycotic and viral infections, bone and cartilage diseases, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, osteoarthritis, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, non-limiting examples of a neurological disease or disorder associated with tau protein, amyloid or alpha-synuclein pathology which can be treated with the compounds and compositions provided herein include, but are not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, non-limiting examples of diseases in which chronic inflammation is involved which can be treated with the compounds and compositions provided herein include eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, non-limiting examples of cancers which can be treated with the compounds and compositions provided herein include colon, ovarian, pancreatic, breast, liver, prostate, and hematologic cancers.

In some embodiments, pharmaceutical compositions are provided that are effective for treatment of a disease of an animal, e.g., a mammal, caused by either the pathological activation or mutations of the Wnt pathway or DYRK1A overexpression. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, isobutyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

"Exocyclic double bond" means a carbon-carbon double bond connected to and hence external to, a ring structure.

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "haloalkoxy" means a haloalkyl-O— group in which the haloalkyl group is as described herein. Exemplary haloalkoxy groups include fluoromethoxy, difluoromethoxy, trifluoromethoxy, and also the linear or branched positional isomers thereof.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-a]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyl include 2-azaspiro[2.2]pentane, 4-azaspiro[2.5]octane, 1-azaspiro [3.5]nonane, 2-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R''; —NRR'; —C(O)NRR'; —C(NR)NR'R''; —C(NR')R''; a cyano; a nitro; an azido; —SH; —S—R; —$OSO_2$(OR); a sulfonate [such as —$SO_2$(OH) and —$SO_2$(OR)]; —$SO_2$NR'R''; and —$SO_2$R; in which each occurrence of R, R' and $R^{11}$ are independently selected from H; —($C_{1-9}$ alkyl); $C_{6-10}$ aryl optionally substituted with from 1-3 R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and a compound as provided herein or a salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Morphea" as used herein refers to a skin condition wherein discolored and/or hardened patches appear on the skin (e.g., one or more outer layers of the skin) resulting from excessive collagen deposition.

"Raynaud's syndrome" as used herein refers to a disease in which certain parts of the body (e.g., fingers and/or toes) feel numb and/or cold in response to various stimuli (e.g., cold temperatures and/or stress) due to arterial narrowing.

"Darier's disease" as used herein refers to an autosomal dominant disorder characterized by the appearance of dark crusty patches on the skin (e.g., keratotic papules, keratosis follicularis or dyskeratosis follicularis) that may contain pus.

"Wound healing" as used herein refers to a process by which skin and/or other bodily tissue repairs itself after experiencing, for example, damage and/or trauma.

"Ichthyosis" as used herein refers to a group of genetic skin disorders characterized by the presence of dry, scaly, cracked, and/or flaky skin.

"Tendinopathy" as used herein refers to a disease or disorder of a tendon characterized by inflammation, deterioration, and/or injury of the tendon and/or tissue contacting, near, or associated with the tendon. Tendinopathy includes, for example, inflammation of the tendon (e.g., tendonitis), non-inflammatory degeneration of, for example, the structure and/or composition of a tendon (e.g., tendinosis), inflammation of the paratenon near or in contact with a tendon (e.g., paratenonitis), micro-trauma to the tendon, and rupture of the tendon (e.g., acute, chronic, partial and/or complete rupture). The term also encompasses tenosynovitis, a tendinopathy of the outer lining of the tendon which occurs in certain tendons such as flexor tendons and the Achilles tendon. Symptoms of tendinopathy include pain at rest, upon palpation of the tendon, and/or with movement of, for example, the tendon, tissue, joint, or bone near or associated with the tendon; joint stiffness; difficulty moving; weakness of the joint or muscles surrounding the tendon; redness of the skin near the tendon; swelling of the tendon and/or of tissue near the tendon; and/or crepitus.

"Tendinosis" as used herein, refers to a non-inflammatory injury to the tendon characterized by intratendinous degeneration of the tendon typically in the form of microtears in the tissue in and around the tendon caused by overuse, leading to an increase in the number of tendon repair cells around the area of damage. Degeneration of the tendon is caused by damage to or disorganization of the collagen fibers, cells, and vascular components of the tendon, which can reduce the tendon's tensile strength and can lead to tendon rupture if not treated.

"Tendinitis" as used herein refers to an inflammatory injury to the tendon, characterized by degeneration like that observed in tendinosis, but also accompanied by inflammation of the tendon, vascular disruption and an inflammatory repair response. Tendinitis is often associated with fibroblastic and myofibroblastic proliferation, as well as hemorrhage and organizing granulation tissue. Generally, tendinitis is referred to by the body part involved, such as Achilles tendinitis (affecting the Achilles tendon), or patellar tendinitis (also known as "jumper's knee," affecting the patellar tendon), though there are certain exceptions, such as lateral epicondylitis (also known as "tennis elbow," affecting the Extensor Carpi Radialis Brevis tendon). Symptoms can vary from aches or pains and local stiffness to a burning sensation surrounding the entire joint around the inflamed tendon. In some cases, tendonitis is characterized by swelling, sometimes accompanied by heat and redness; there may also be visible knots surrounding the joint. For many patients, the pain is usually worse during and after activity, and the tendon and joint area can become stiffer the following day as muscles tighten from the movement of the tendon.

"Psoriasis" as used herein refers to an autoimmune disease in which skin cells build up and causes raised, red, scaly patches to appear on the skin.

"Dermatitis" (also known as eczema) as used herein refers to generic inflammation of the skin. Specific types of dermatitis include atopic, contact, nummular, photo-induced, and stasis dermatitis. These diseases are characterized by itchiness, red skin, and a rash.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

The compounds and compositions described herein can be used to inhibit DYRK1A for treating a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Some embodiments of the present disclosure include compounds of Formula I:

I

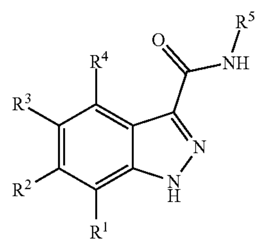

or salts, pharmaceutically acceptable salts, or prodrugs thereof.

In some embodiments, $R^1$, $R^2$, and $R^4$ are independently selected from the group consisting of H and halide.

In some embodiments, $R^3$ is a 5-membered heteroaryl ring optionally substituted as defined anywhere herein.

In some embodiments, $R^3$ is 5-membered heteroaryl ring optionally substituted with 1-4 (e.g., 1-3, 1-2, 1) $R^{42}$;

In some embodiments, $R^3$ is selected from the group consisting of: furanyl optionally substituted with 1-4 (e.g., 1-3, 1-2, 1) $R^{42}$, thiophenyl optionally substituted with 1-4 (e.g., 1-3, 1-2, 1) $R^{42}$, pyrrolyl optionally substituted with 1-4 (e.g., 1-3, 1-2, 1) $R^{42}$,

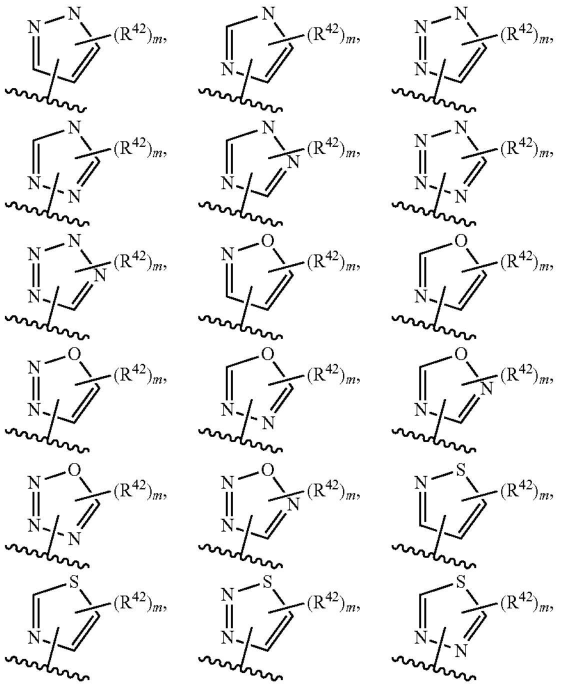

-continued

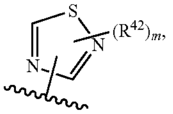 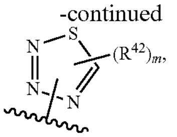 and 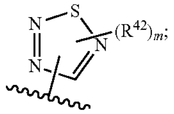

wherein each m is independently 1 to 4 (e.g., 1-3, 1-2, 1).

In some embodiments, $R^3$ is selected from the group consisting of:

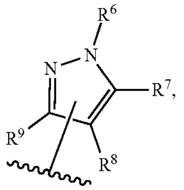 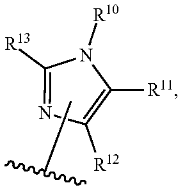

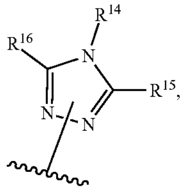 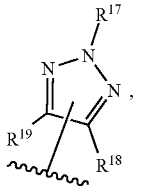

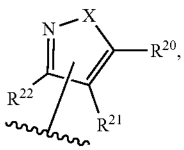 and 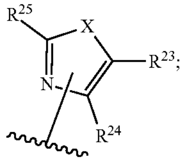

wherein each of $R^6$-$R^{25}$ is, independently, a substituent as defined anywhere herein or a single bond connecting $R^3$ to the indazole ring; wherein only one of $R^6$-$R^9$ (when present) is a bond, only one of $R^{16}$-$R^{13}$ (when present) is a bond, only one of $R^{14}$-$R^{16}$ (when present) is a bond, only one of $R^{17}$-$R^{19}$ (when present) is a bond, only one of $R^{20}$-$R^{22}$ is a bond, and only one of $R^{23}$-$R^{25}$ (when present) is a bond; for purposes of clarification, any one of the nitrogen atoms attached to $R^6$, $R^{10}$, $R^{14}$, or $R^{17}$ can serve as the point of attachment of $R^3$ to the indazole ring; likewise, any one of the carbon atoms attached to $R^7$, $R^8$, $R^9$, $R^{10}$, $R^{11}$, $R^{12}$, $R^{13}$, $R^{15}$, $R^{16}$, $R^{18}$, $R^{19}$, $R^{20}$, $R^{21}$, $R^{22}$, $R^{23}$, $R^{24}$, $R^{25}$ can serve as the point of attachment of $R^3$ to the indazole ring.

In some embodiment, —($C_{1-4}$ alkylene) is, optionally substituted with one or more substituents as defined anywhere herein.

In some embodiment, —($C_{1-4}$ alkylene) is, optionally substituted with one or more halides (e.g., F, Cl, Br, I) or one or more unsubstituted —($C_{1-3}$ alkyl) (e.g., $C_{2-3,\ 1-2,\ 1}$ alkyl).

In some embodiment, —($C_{1-4}$ alkylene) is, optionally substituted with one or more halides (e.g., F, Cl, Br, I) and one or more unsubstituted —($C_{1-3}$ alkyl) (e.g., $C_{2-3,\ 1-2,\ 1}$ alkyl).

In some embodiment, —($C_{1-4}$ alkylene) is, optionally substituted with one or more F or one or more Me.

In some embodiment, —($C_{1-4}$ alkylene) is, optionally substituted with one or more F and one or more Me.

In some embodiment, —($C_{1-4}$ alkylene) is —$CH_2$—.

In some embodiment, —($C_{1-4}$ alkylene) is —$CH_2CH_2$—.

In some embodiment, —($C_{1-4}$ alkylene) is —$CH_2CH_2CH_2$—.

In some embodiments, $R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heteroaryl substituted with 1-4 (e.g., 1-3, 1-2, 1) $R^{26}$, a monocyclic —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{27}$, a spirocyclic-heterocyclyl optionally substituted with 1-10 (e.g., 1-9, 1-8, 1-7, 1-6, 1-5, 1-4, 1-3, 1-2, 1) $R^{27}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{28}$, and -aryl optionally substituted with 1-5 (e.g., 1-4, 1-3, 1-2, 1) $R^{29}$; wherein each —($C_{1-4}$ alkylene) is, independently, optionally substituted with a substituent as defined anywhere herein.

In another embodiment, $R^5$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heteroaryl substituted with 1-4 (e.g., 1-3, 1-2, 1) $R^{26}$, a 6-membered monocyclic —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{27}$, a spirocyclic-heterocyclyl optionally substituted with 1-10 (e.g., 1-9, 1-8, 1-7, 1-6, 1-5, 1-4, 1-3, 1-2, 1) $R^{27}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{28}$, and -aryl optionally substituted with 1-5 (e.g., 1-4, 1-3, 1-2, 1) $R^{29}$; wherein each —($C_{1-4}$ alkylene) is, independently, optionally substituted with a substituent as defined anywhere herein.

In some embodiments, $R^6$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$haloalkyl), —($C_{1-4}$alkylene)$_p$heterocyclyl optionally substituted with 1-10 (e.g., 1-9, 1-8, 1-7, 1-6, 1-5, 1-4, 1-3, 1-2, 1) $R^{30}$, and -carbocyclyl optionally substituted with 1-12 (e.g., 1-11, 1-10, 1-9, 1-8, 1-7, 1-6, 1-5, 1-4, 1-3, 1-2, 1) $R^{31}$; wherein —($C_{1-4}$ alkylene) is, optionally substituted with a substituent as defined anywhere herein.

In some embodiments, $R^7$, $R^8$, and $R^9$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$haloalkyl), —($C_{1-4}$ alkylene)$_p$OH, and —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{27}$; wherein each —($C_{1-4}$ alkylene) is, independently, optionally substituted with a substituent as defined anywhere herein.

In some embodiments, one of $R^6$ and $R^7$, $R^7$ and $R^8$, or $R^8$ and $R^9$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^6$ and $R^7$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^7$ and $R^8$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^8$ and $R^9$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{10}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{30}$, and -carbocyclyl optionally substituted with 1-12 (e.g., 1-11, 1-10, 1-9, 1-8, 1-7, 1-6, 1-5, 1-4, 1-3, 1-2, 1) $R^{31}$; wherein —($C_{1-4}$ alkylene) is, optionally substituted with a substituent as defined anywhere herein.

In some embodiments, $R^{11}$, $R^{12}$, and $R^{13}$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$haloalkyl).

In some embodiments, one of $R^{10}$ and $R^{11}$, $R^{11}$ and $R^{12}$, or $R^{13}$ and $R^{10}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{10}$ and $R^{11}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11. 1-10. 1-9. 1-8. 1-7. 1-6. 1-5. 1-4. 1-3. 1-2. 1) $R^{33}$.

In some embodiments, $R^{11}$ and $R^{12}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{13}$ and $R^{16}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{30}$, and -carbocyclyl optionally substituted with 1-12 (e.g., 1-11, 1-10, 1-9, 1-8, 1-7, 1-6, 1-5, 1-4, 1-3, 1-2, 1) $R^{31}$; wherein —($C_{1-4}$ alkylene) is, optionally substituted with a substituent as defined anywhere herein.

In some embodiments, $R^{15}$ and $R^{16}$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$haloalkyl).

In some embodiments, one of $R^{14}$ and $R^{15}$ or $R^{16}$ and $R^{14}$ are taken together to form a heterocyclyl optionally substituted with 1-10 (e.g., 1-9, 1-8, 1-7, 1-6, 1-5, 1-4, 1-3, 1-2, 1) $R^{32}$.

In some embodiments, $R^{14}$ and $R^{15}$ are taken together to form a heterocyclyl optionally substituted with 1-10 (e.g., 1-9, 1-8, 1-7, 1-6, 1-5, 1-4, 1-3, 1-2, 1) $R^{32}$.

In some embodiments, $R^{16}$ and $R^{14}$ are taken together to form a heterocyclyl optionally substituted with 1-10 (e.g., 1-9, 1-8, 1-7, 1-6, 1-5, 1-4, 1-3, 1-2, 1) $R^{32}$.

In some embodiments, $R^{17}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$haloalkyl), —($C_{1-4}$alkylene)$_p$heterocyclyl optionally substituted with 1-10 (e.g., 1-9, 1-8, 1-7, 1-6, 1-5, 1-4, 1-3, 1-2, 1) $R^{30}$, and -carbocyclyl optionally substituted with 1-12 (e.g., 1-11, 1-10, 1-9, 1-8, 1-7, 1-6, 1-5, 1-4, 1-3, 1-2, 1) $R^{31}$; wherein —($C_{1-4}$ alkylene) is, optionally substituted with a substituent as defined anywhere herein.

In some embodiments, $R^{18}$ and $R^{19}$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$haloalkyl).

In some embodiments, $R^{18}$ and $R^{19}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{20}$, $R^{21}$, and $R^{22}$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$haloalkyl).

In some embodiments, one of $R^{20}$ and $R^{21}$ or $R^{21}$ and $R^{22}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{20}$ and $R^{21}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{21}$ and $R^{22}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, $R^{23}$, $R^{24}$, and $R^{25}$ are independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments, $R^{23}$ and $R^{24}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, each $R^{26}$ is independently selected from the group consisting of halide (e.g., F, Cl, Br, I), —$OR^{34}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —C(C═O)N($R^{41}$)$_2$, —($C_{1-4}$ alkylene)$_p$ heterocyclyl optionally substituted with 1-10 (e.g., 1-9, 1-8, 1-7, 1-6, 1-5, 1-4, 1-3, 1-2, 1) $R^{35}$, and —O($C_{1-4}$ alkylene)$_p$ heterocyclyl optionally substituted with 1-10 (e.g., 1-9. 1-8. 1-7. 1-6. 1-5. 1-4. 1-3. 1-2. 1) $R^{36}$; wherein each —($C_{1-4}$ alkylene) is, independently, optionally substituted with a substituent as defined anywhere herein.

In some embodiments, each $R^{27}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 (e.g., 1-11, 1-10, 1-9, 1-8, 1-7, 1-6, 1-5, 1-4, 1-3, 1-2, 1) $R^{28}$.

In some embodiments, each $R^{27}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -carbocyclyl optionally substituted with 1-12 (e.g., 1-11, 1-10, 1-9, 1-8, 1-7, 1-6, 1-5, 1-4, 1-3, 1-2, 1) $R^{28}$, and -aryl optionally substituted with 1-5 (e.g., 1-4, 1-3, 1-2, 1) $R^{46}$.

In some embodiments, each $R^{28}$ is independently selected from the group consisting of halide (e.g., F, Cl, Br, I), —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{37}$; wherein —($C_{1-4}$ alkylene) is, optionally substituted with a substituent as defined anywhere herein.

In some embodiments, each $R^{29}$ is independently selected from the group consisting of halide (e.g., F, Cl, Br, I), —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 14, 1-3, 1-2, 1) $R^{39}$, —NHheterocyclyl optionally substituted with 1-10 (e.g., 1-9, 1-8, 1-7, 1-6, 1-5, 1-4, 1-3, 1-2, 1) $R^{40}$, and —Oheterocyclyl optionally substituted with 1-10 (e.g., 1-9, 1-8, 1-7, 1-6, 1-5, 1-4, 1-3, 1-2, 1) $R^{40}$; wherein —($C_{1-4}$ alkylene) is, optionally substituted with a substituent as defined anywhere herein.

In some embodiments, each $R^{29}$ is independently selected from the group consisting of halide (e.g., F, Cl, Br, I), —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{39}$, —NHheterocyclyl optionally substituted with 1-10 (e.g., 1-9, 1-8, 1-7, 1-6, 1-5, 1-4, 1-3, 1-2, 1) $R^{40}$, and —O($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{40}$; wherein —($C_{1-4}$ alkylene) is, optionally substituted with a substituent as defined anywhere herein.

In some embodiments, each $R^{30}$ is independently selected from the group consisting of unsubstituted —($C_{1-4}$ alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2,\ 1}$ haloalkyl), halide (e.g., F, Cl, Br, I), and —CN.

In some embodiments, each $R^{31}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl), halide (e.g., F, Cl, Br, I), and —CN.

In some embodiments, each $R^{32}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2,\ 1}$ haloalkyl), halide (e.g., F, Cl, Br, I), and —CN.

In some embodiments, each $R^{33}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2,\ 1}$ haloalkyl), halide (e.g., F, Cl, Br, I), and —CN.

In some embodiments, each $R^{34}$ is independently selected from the group consisting of unsubstituted —($C_{1-4}$ alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), and unsubstituted —($C_{1-4}$ haloalkyl) (e.g., $C_{2-4,\ 3-4,\ 2-3,\ 1-3,\ 1-2,\ 1}$ haloalkyl).

In some embodiments, each $R^{35}$ is independently selected from the group consisting of unsubstituted —($C_{1-4}$alkyl) (e.g., $C_{2-4,\ 34,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{36}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{37}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{38}$ is independently selected from the group consisting of H, unsubstituted —($C_{1-4}$ alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), and unsubstituted —($C_{1-4}$ haloalkyl) (e.g., $C_{2-4,\ 3-4,\ 2-3,\ 1-3,\ 1-2,\ 1}$ haloalkyl).

In some embodiments, each $R^{39}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{40}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{41}$ is independently selected from the group consisting of H and —($C_{1-9}$ alkyl).

In some embodiments, each $R^{42}$ is independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$alkylene)$_p$OH, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{30}$, and -carbocyclyl optionally substituted with 1-12 (e.g., 1-11, 1-10, 1-9, 1-8, 1-7, 1-6, 1-5, 1-4, 1-3, 1-2, 1) $R^{31}$; wherein each —($C_{1-4}$ alkylene) is, independently, optionally substituted with a substituent as defined anywhere herein.

In some embodiments, two adjacent $R^{42}$ groups are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{32}$ and -carbocyclyl optionally substituted with 1-12 (e.g., 1-11, 1-10, 1-9, 1-8, 1-7, 1-6, 1-5, 1-4, 1-3, 1-2, 1) $R^{33}$.

In some embodiments, each $R^{43}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$ haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{44}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl), unsubstituted —($C_{2-4}$alkynyl) (e.g., $C_{2-4,\ 3-4,\ 2-3,\ 1-3}$ alkynyl), unsubstituted —($C_{1-4}$ haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{45}$ is independently selected from the group consisting of unsubstituted —($C_{1-4}$ alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$ haloalkyl) (e.g., $C_{2-4,\ 3-4,\ 2-3,\ 1-3,\ 1-2}$, haloalkyl), halide (e.g., F, Cl, Br, I), and —CN.

In some embodiments, each $R^{46}$ is independently selected from the group consisting of unsubstituted —($C_{1-4}$alkyl) (e.g., $C_{2-4,\ 3-4,\ 2-3,\ 1-3,\ 1-2,\ 1}$ alkyl), unsubstituted —($C_{2-4}$ alkenyl) (e.g., $C_{2-4,\ 3-4,\ 2-3,\ 1-3}$ alkenyl), unsubstituted —($C_{2-4}$ alkynyl) (e.g., $C_{2-4,\ 3-4,\ 2-3,\ 1-3}$ alkynyl), unsubstituted —($C_{1-4}$ haloalkyl) (e.g., $C_{2-4,\ 3-4,\ 2-3,\ 1-3,\ 1-2}$, haloalkyl), halide (e.g., F, Cl, Br, I), and —CN.

In some embodiments, each X is O or S.

In some embodiments, each p is independently 0 or 1.

In some embodiments, each m is independently 1 to 4.

In some embodiments, there is the proviso that Formula I is not a structure selected from the group consisting of:

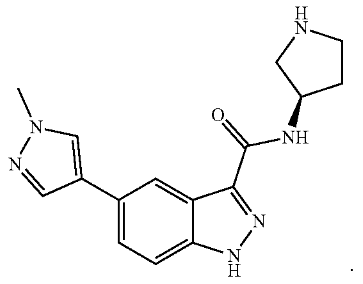 [SMILES: Cn1cc(-c2ccc3[nH]nc(C(=O)N[C@@H]4CCNC4)c3c2)cn1]

In some embodiments, $R^1$, $R^2$ and $R^4$ are H.

In some embodiments, $R^1$ and $R^4$ are H, and $R^2$ is F.

In some embodiments, $R^1$ and $R^2$ are H, and $R^4$ is F.

In some embodiments, $R^2$ and $R^4$ are H, and $R^1$ is F.

In some embodiments, $R^3$ is

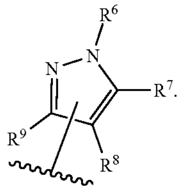

In certain embodiments, $R^8$ is a single bond connecting $R^3$ to the indazole ring, i.e., $R^3$ has the following formula:

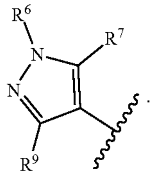

In some embodiments, $R^3$ is

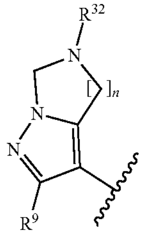

and n is 1 to 3.

In some embodiments, $R^6$ is selected from the group consisting of H, unsubstituted —($C_{1-3}$ alkyl) (e.g., $C_{2-3,\ 1-2,\ 1}$ alkyl), unsubstituted —($C_{1-2}$ haloalkyl), and —($C_{3-4}$ carbocyclyl) optionally substituted with 1-2 $R^{31}$.

In some embodiments, $R^6$ is selected from the group consisting of H, methyl, —$CF_3$, and cyclopropyl optionally substituted with 1-2 $R^{31}$.

In some embodiments, 127 is selected from the group consisting of H, halide, unsubstituted —($C_{1-2}$ alkyl) (e.g., $C_1$ alkyl), and unsubstituted —($C_{1-2}$ haloalkyl).

In some embodiments, $R^7$ is selected from the group consisting of H, F, methyl, and —$CF_3$.

In some embodiments, $R^9$ is selected from the group consisting of H and halide.

In some embodiments, $R^9$ is selected from the group consisting of H and F.

In some embodiments, $R^3$ is

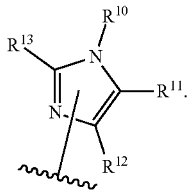

In certain embodiments, $R^{11}$ is a single bond connecting $R^3$ to the indazole ring, i.e., $R^3$ has the following formula:

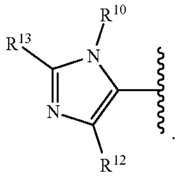

In some embodiments, $R^3$ is

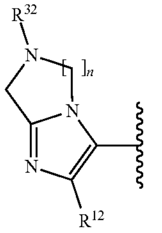

and n is 1 to 3.

In some embodiments, $R^{10}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{31}$.

In some embodiments, $R^{10}$ is selected from the group consisting of H, methyl, —$CF_3$, and cyclopropyl optionally substituted with 1-2 $R^{31}$.

In some embodiments, $R^{12}$ is selected from the group consisting of H and halide.

In some embodiments, $R^{12}$ is selected from the group consisting of H and F.

In some embodiments, $R^{13}$ is selected from the group consisting of H, halide, unsubstituted —($C_{1-2}$ alkyl) (e.g., $C_1$ alkyl), and unsubstituted —($C_{1-2}$ haloalkyl) (e.g., $C_1$ haloalkyl).

In some embodiments, $R^{13}$ is selected from the group consisting of H, F, methyl, and —$CF_3$.

In some embodiments, $R^3$ is

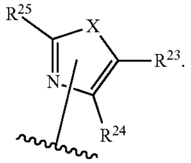

In some embodiments, $R^3$ is

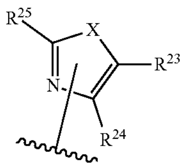

and X is S.

In some embodiments, $R^3$ is

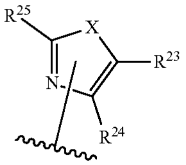

and X is O.

In certain embodiments, $R^{23}$ is a single bond connecting $R^3$ to the indazole ring, i.e., $R^3$ has the following formula:

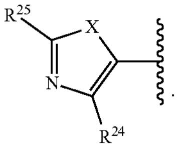

In some embodiments, $R^3$ is

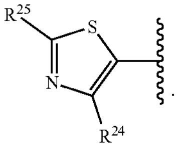

In some embodiments, $R^3$ is

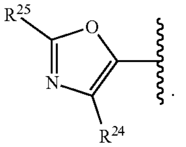

In some embodiments, $R^{24}$ is selected from the group consisting of H and halide.

In some embodiments, $R^{24}$ is selected from the group consisting of H and F.

In some embodiments, $R^{25}$ is selected from the group consisting of H, halide, unsubstituted —($C_{1-2}$ alkyl) (e.g., $C_1$ alkyl), and unsubstituted —($C_{1-2}$ haloalkyl) (e.g., $C_1$ haloalkyl).

In some embodiments, $R^{25}$ is selected from the group consisting of H, F, methyl, and —$CF_3$.

In some embodiments, $R^3$ is

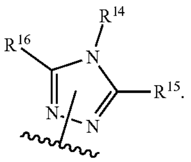

In certain embodiments, $R^{15}$ is a single bond connecting $R^3$ to the indazole ring, i.e., $R^3$ has the following formula:

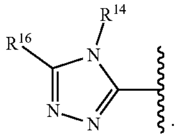

In some embodiments, $R^3$ is

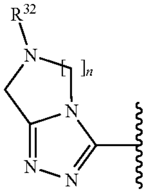

and n is 1 to 3.

In some embodiments, $R^{14}$ is selected from the group consisting of H, unsubstituted —($C_{1-3}$ alkyl) (e.g., $C_{2-3,\ 1-2,\ 1}$ alkyl), unsubstituted —($C_{1-2}$ haloalkyl), and —($C_{3-4}$ carbocyclyl) optionally substituted with 1-2 $R^{31}$.

In some embodiments, $R^{14}$ is selected from the group consisting of H, methyl, —$CF_3$, and cyclopropyl optionally substituted with 1-2 $R^{31}$.

In some embodiments, $R^{16}$ is selected from the group consisting of H, halide, unsubstituted —($C_{1-2}$ alkyl) (e.g., $C_1$ alkyl), and unsubstituted —($C_{1-2}$ haloalkyl) (e.g., $C_1$ haloalkyl).

In some embodiments, $R^{16}$ is selected from the group consisting of H, F, methyl, and —$CF_3$.

In some embodiments, $R^{31}$ is selected from the group consisting of halide, unsubstituted —($C_{1-3}$ alkyl) (e.g., $C_{2-3,\ 1-2,\ 1}$ alkyl), and unsubstituted —($C_{1-2}$ haloalkyl).

In some embodiments, $R^{31}$ is selected from the group consisting of F, methyl, and —$CF_3$.

In some embodiments, $R^{32}$ is selected from the group consisting of H and unsubstituted —($C_{1-2}$ alkyl) (e.g., $C_1$ alkyl).

In some embodiments, $R^{32}$ is selected from the group consisting of H and methyl.

In some embodiments, $R^5$ is selected from the group consisting of unsubstituted —($C_{1-5}$ alkyl) (e.g., $C_{2-5,\ 3-5,\ 4-5,\ 2-4,\ 3-4,\ 2-3,\ 1-4,\ 1-3,\ 1-2,\ 1}$ alkyl), unsubstituted —($C_{1-4}$ haloalkyl), -heteroaryl substituted with 1-2 $R^{26}$, a monocyclic —($C_{1-4}$ alkylene)$_p$heterocyclyl optionally substituted with 1-3 $R^{27}$, a spirocyclic-heterocyclyl optionally substituted with 1-3 $R^{27}$, —($C_{1-4}$ alkylene)$_p$carbocyclyl optionally substituted with 1-12 $R^{28}$, and -aryl optionally substituted with 1-2 $R^{29}$; wherein each —($C_{1-4}$ alkylene) is, independently, optionally substituted with a substituent as defined anywhere herein.

In some embodiments, $R^5$ is selected from the group consisting of unsubstituted —($C_{1-5}$ alkyl) (e.g., $C_{2-5,\ 3-5,\ 4-5,\ 2-4,\ 3-4,\ 2-3,\ 14,\ 1-3,\ 1-2,\ 1}$ alkyl), unsubstituted —($C_{1-4}$haloalkyl), -heteroaryl substituted with 1-2 $R^{26}$, a 6-membered monocyclic —($C_{1-4}$ alkylene)$_p$heterocyclyl optionally substituted with 1-3 $R^{27}$, a spirocyclic-heterocyclyl optionally substituted with 1-3 $R^{27}$, —($C_{1-4}$ alkylene)$_p$ carbocyclyl optionally substituted with 1-12 $R^{28}$, and -aryl optionally substituted with 1-2 $R^{29}$; wherein each —($C_{1-4}$ alkylene) is, independently, optionally substituted with a substituent as defined anywhere herein.

In some embodiments, $R^5$ is selected from the group consisting of unsubstituted —($C_{1-4}$ alkyl) (e.g., $C_{2-4,\ 34,\ 2-3,\ 1-3,\ 1-2,\ 1}$ alkyl) and unsubstituted —($C_{1-3}$ fluoroalkyl) (e.g., $C_{2-3,\ 1-2,\ 1}$ fluoroalkyl).

In some embodiments, $R^5$ is selected from the group consisting of -pyridinyl substituted with 1 $R^{26}$ and -thiazolyl substituted with 1 $R^{26}$.

In some embodiments, $R^5$ is selected from the group consisting of a monocyclic-heterocyclyl optionally substituted with 1-2 $R^{27}$ and a spirocyclic-heterocyclyl optionally substituted with 1 $R^{27}$.

In some embodiments, $R^5$ is selected from the group consisting of a 6-membered monocyclic-heterocyclyl optionally substituted with 1-2 $R^{27}$ and a spirocyclic-heterocyclyl optionally substituted with 1 $R^{27}$.

In some embodiments, $R^5$ is selected from the group consisting of -carbocyclyl optionally substituted with 1-2 $R^{28}$ and —$CH_2$carbocyclyl optionally substituted with 1-2 $R^{28}$.

In some embodiments, $R^5$ is -phenyl substituted with 1-2 $R^{29}$.

In some embodiments, $R^{26}$ is selected from the group consisting of halide, —O($C_{1-2}$ fluoroalkyl), unsubstituted —($C_{1-3}$ alkyl) (e.g., $C_{2-3,\ 1-2,\ 1}$ alkyl), unsubstituted —($C_{1-3}$ fluoroalkyl) (e.g., $C_{2-3,\ 12,\ 1}$ fluoroalkyl), -heterocyclyl optionally substituted with 1-2 $R^{35}$, and —Oheterocyclyl optionally substituted with 1-2 $R^{36}$.

In some embodiments, $R^{26}$ is selected from the group consisting of F, —$OCHF_2$, —$OCF_3$, methyl, —$CF_3$,

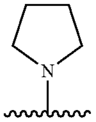, 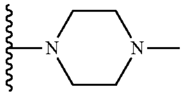, and

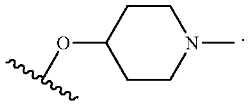.

In some embodiments, $R^{27}$ is selected from the group consisting of halide, unsubstituted —($C_{1-4}$alkyl) (e.g., $C_{2-4,\ 3-4,\ 2-3,\ 1-3,\ 1-2,\ 1}$ alkyl), unsubstituted —($C_{1-4}$haloalkyl) (e.g., $C_{2-4,\ 3-4,\ 2-3,\ 1-3,\ 12,\ 1}$ haloalkyl), and —($C_{3-4}$ carbocyclyl) optionally substituted with 1-2 $R^{28}$.

In some embodiments, $R^{27}$ is selected from the group consisting of F, unsubstituted —($C_{1-4}$alkyl) (e.g., $C_{2-4,\ 3-4,\ 2-3,\ 13,\ 1-2,\ 1}$ alkyl), unsubstituted —($C_{1-4}$ fluoroalkyl) (e.g., $C_{2-4,\ 3-4,\ 2-3,\ 1-3,\ 1-2,\ 1}$ fluoroalkyl), and -cyclopropyl.

In some embodiments, $R^{28}$ is selected from the group consisting of halide, —O($C_{1-3}$ alkyl) (e.g., $C_{2-3,\ 1-2,\ 1}$ alkyl), unsubstituted —($C_{1-3}$ alkyl) (e.g., $C_{2-3,\ 1-2,\ 1}$ alkyl), unsubstituted —($C_{1-3}$ haloalkyl) (e.g., $C_{2-3,\ 12,\ 1}$ haloalkyl), and —$CH_2$heterocyclyl optionally substituted with 1-2 $R^{37}$.

In some embodiments, $R^{28}$ is selected from the group consisting of F, —OMe,

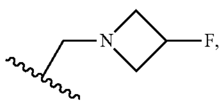, and 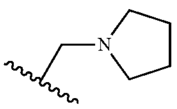.

In some embodiments, $R^{29}$ is independently selected from the group consisting of halide, —OH, —O($C_{1-3}$ haloalkyl)

(e.g., $C_{2-3, 12, 1}$ haloalkyl), unsubstituted —($C_{1-3}$ alkyl) (e.g., $C_{2-3, 1-2, 1}$ alkyl), unsubstituted —($C_{1-3}$ haloalkyl) (e.g., $C_{2-3, 1-2, 1}$ haloalkyl), -heterocyclyl optionally substituted with 1-2 $R^{39}$, —$CH_2$heterocyclyl optionally substituted with 1-2 $R^{39}$, —NHheterocyclyl optionally substituted with 1-2 $R^{40}$, and —Oheterocyclyl optionally substituted with 1-2 $R^{40}$.

In some embodiments, $R^{29}$ is independently selected from the group consisting of F, —OH, —$OCHF_2$, —$OCF_3$, methyl, —$CF_3$,

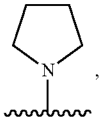, 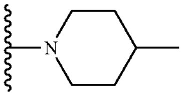, 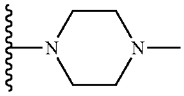,
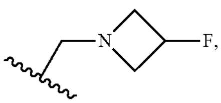 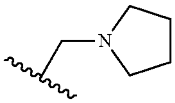,
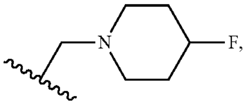 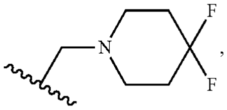,
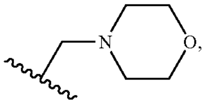 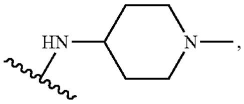, and
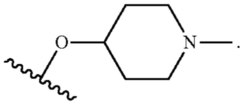.

In some embodiments, $R^{29}$ is independently selected from the group consisting of halide, —OH, —O($C_{1-3}$ haloalkyl) (e.g., $C_{2-3, 1-2, 1}$ haloalkyl), unsubstituted —($C_{1-3}$ alkyl) (e.g., $C_{2-3, 1-2, 1}$ alkyl), unsubstituted —($C_{1-3}$ haloalkyl) (e.g., $C_{2-3, 1-2, 1}$ haloalkyl), heterocyclyl optionally substituted with 1-2 $R^{39}$, —$CH_2$heterocyclyl optionally substituted with 1-2 $R^{39}$, —NHheterocyclyl optionally substituted with 1-2 $R^{40}$, and —O($C_{1-4}$ alkylene)$_p$heterocyclyl optionally substituted with 1-2 $R^{40}$.

In some embodiments, $R^{29}$ is independently selected from the group consisting of F, —OH, —$OCHF_2$, —$OCF_3$, methyl, —$CF_3$,

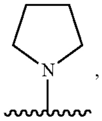, 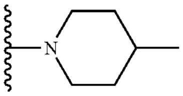, 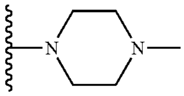,
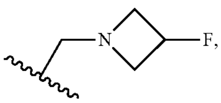 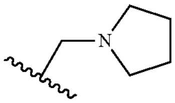,
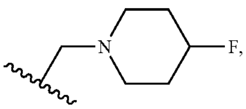 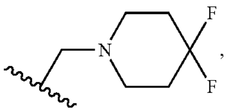,
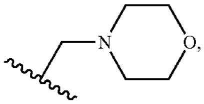 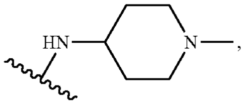, -continued

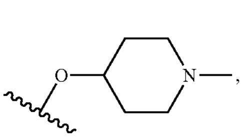, and 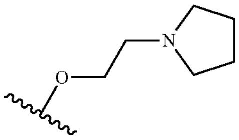.

Illustrative compounds of Formula (I) are shown in Table 1.

TABLE 1

| | |
|---|---|
| 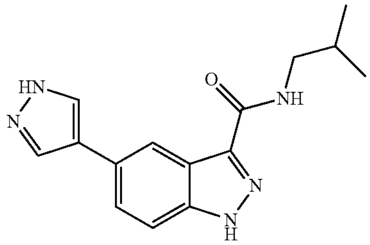 [SMILES: CC(C)CNC(=O)c1n[nH]c2ccc(-c3cn[nH]c3)cc12] | 1 |
| 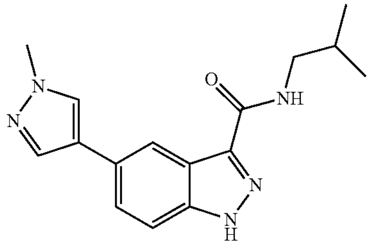 [SMILES: CC(C)CNC(=O)c1n[nH]c2ccc(-c3cnn(C)c3)cc12] | 2 |
| 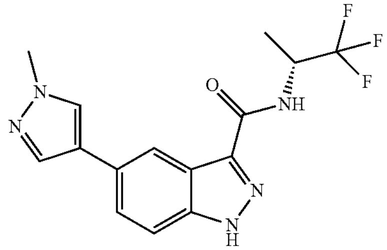 [SMILES: C[C@@H](NC(=O)c1n[nH]c2ccc(-c3cnn(C)c3)cc12)C(F)(F)F] | 3 |
| 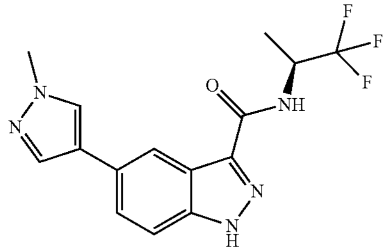 [SMILES: C[C@H](NC(=O)c1n[nH]c2ccc(-c3cnn(C)c3)cc12)C(F)(F)F] | 4 |
| 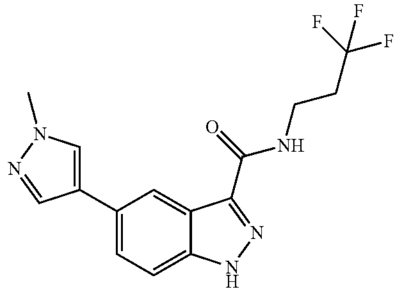 [SMILES: Cn1cc(-c2ccc3[nH]nc(C(=O)NCCC(F)(F)F)c3c2)cn1] | 5 |

TABLE 1-continued
6
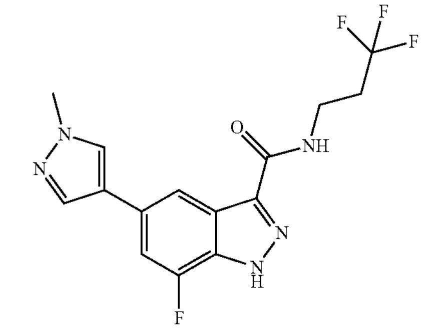 [SMILES: Cn1cc(-c2cc(F)c3[nH]nc(C(=O)NCCC(F)(F)F)c3c2)cn1]
7
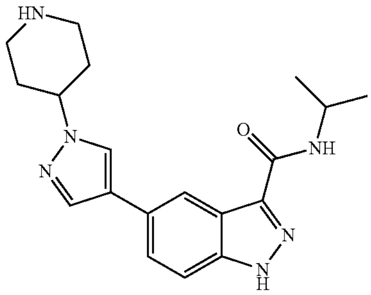 [SMILES: CC(C)NC(=O)c1n[nH]c2ccc(-c3cnn(C4CCNCC4)c3)cc12]
8
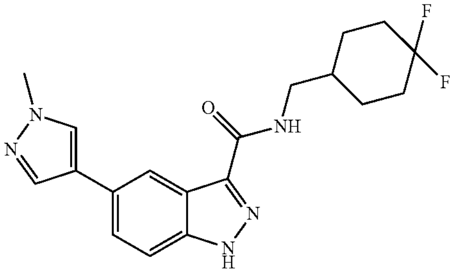 [SMILES: Cn1cc(-c2ccc3[nH]nc(C(=O)NCC4CCC(F)(F)CC4)c3c2)cn1]
9
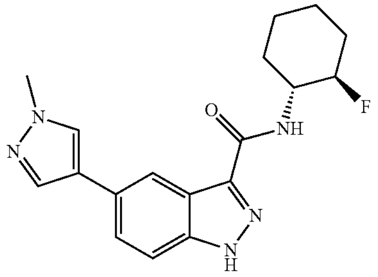 [SMILES: Cn1cc(-c2ccc3[nH]nc(C(=O)N[C@@H]4CCCC[C@H]4F)c3c2)cn1]
10
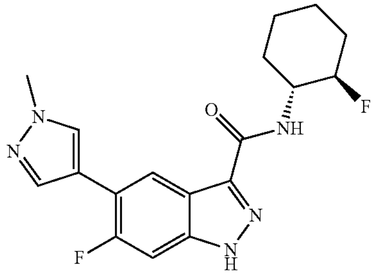 [SMILES: Cn1cc(-c2cc3c(C(=O)N[C@@H]4CCCC[C@H]4F)n[nH]c3cc2F)cn1]
TABLE 1-continued
11
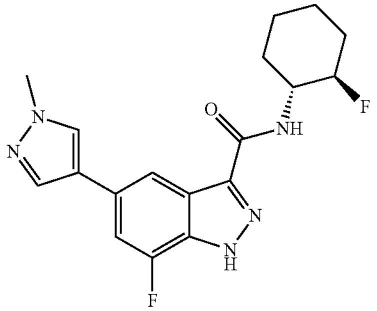 [SMILES: Cn1cc(-c2cc(F)c3[nH]nc(C(=O)N[C@@H]4CCCC[C@H]4F)c3c2)cn1]
12
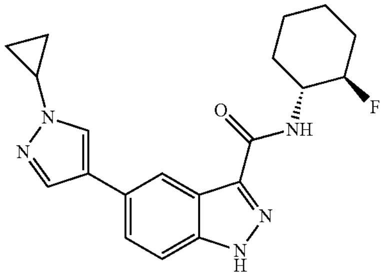 [SMILES: O=C(N[C@@H]1CCCC[C@H]1F)c1n[nH]c2ccc(-c3cnn(C4CC4)c3)cc12]
13
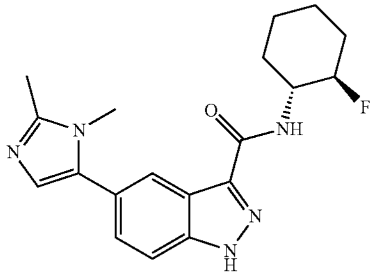 [SMILES: Cc1ncc(-c2ccc3[nH]nc(C(=O)N[C@@H]4CCCC[C@H]4F)c3c2)n1C]
14
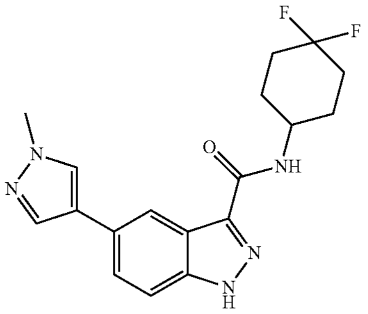 [SMILES: Cn1cc(-c2ccc3[nH]nc(C(=O)NC4CCC(F)(F)CC4)c3c2)cn1]
15
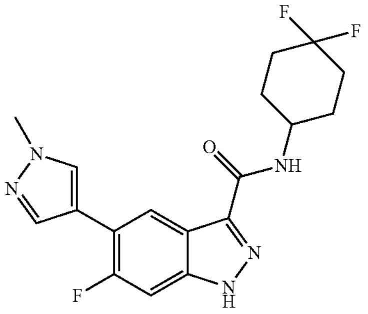 [SMILES: Cn1cc(-c2cc3c(C(=O)NC4CCC(F)(F)CC4)n[nH]c3cc2F)cn1]

16
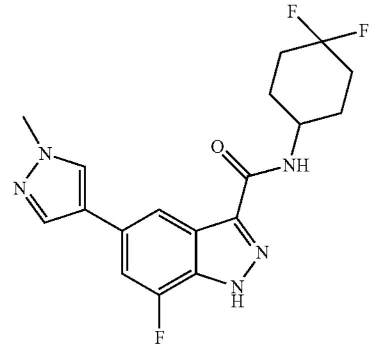 [SMILES: Cn1cc(-c2cc(F)c3[nH]nc(C(=O)NC4CCC(F)(F)CC4)c3c2)cn1]
17
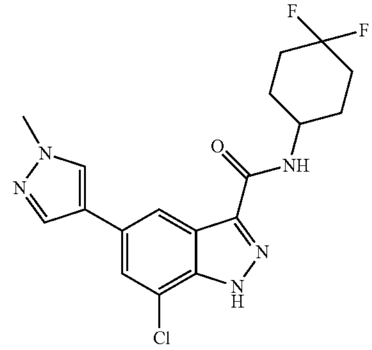 [SMILES: Cn1cc(-c2cc(Cl)c3[nH]nc(C(=O)NC4CCC(F)(F)CC4)c3c2)cn1]
18
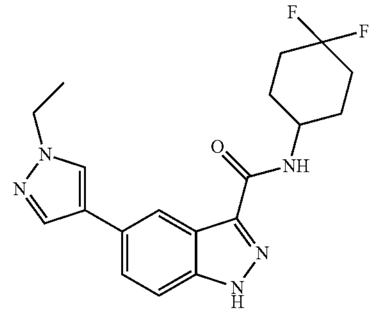 [SMILES: CCn1cc(-c2ccc3[nH]nc(C(=O)NC4CCC(F)(F)CC4)c3c2)cn1]
19
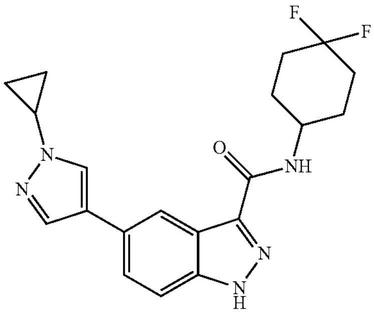 [SMILES: O=C(NC1CCC(F)(F)CC1)c1n[nH]c2ccc(-c3cnn(C4CC4)c3)cc12]
20
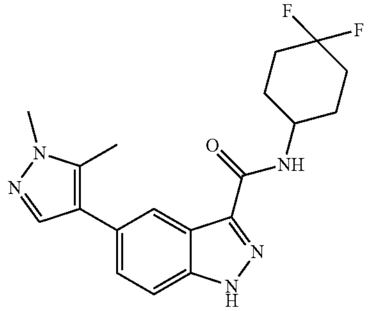 [SMILES: Cc1c(-c2ccc3[nH]nc(C(=O)NC4CCC(F)(F)CC4)c3c2)cnn1C]
21
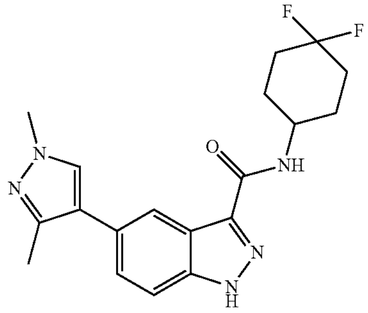 [SMILES: Cc1nn(C)cc1-c1ccc2[nH]nc(C(=O)NC3CCC(F)(F)CC3)c2c1]
22
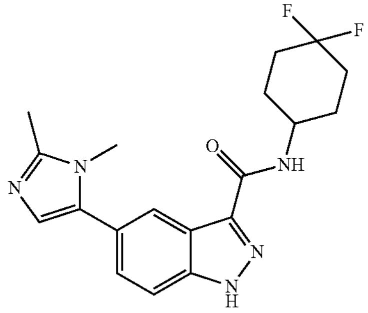 [SMILES: Cc1ncc(-c2ccc3[nH]nc(C(=O)NC4CCC(F)(F)CC4)c3c2)n1C]
23
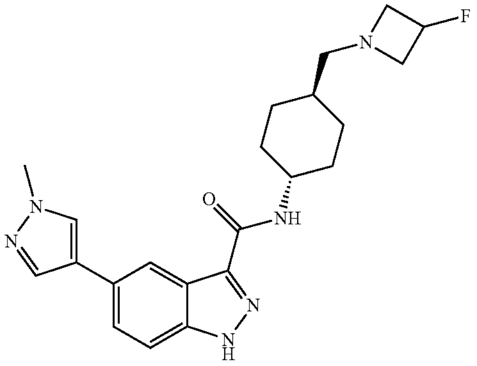 [SMILES: Cn1cc(-c2ccc3[nH]nc(C(=O)N[C@H]4CC[C@H](CN5CC(F)C5)CC4)c3c2)cn1]

TABLE 1-continued
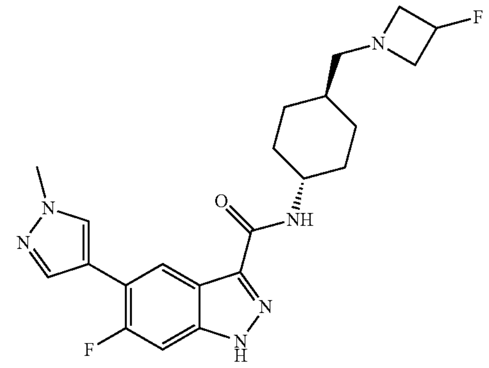 [SMILES: Cn1cc(-c2cc3c(C(=O)N[C@H]4CC[C@H](CN5CC(F)C5)CC4)n[nH]c3cc2F)cn1]
24
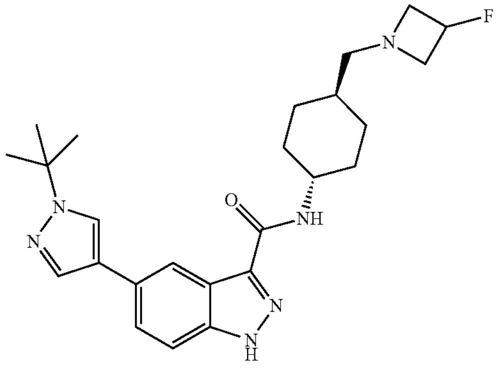 [SMILES: CC(C)(C)n1cc(-c2ccc3[nH]nc(C(=O)N[C@H]4CC[C@H](CN5CC(F)C5)CC4)c3c2)cn1]
25
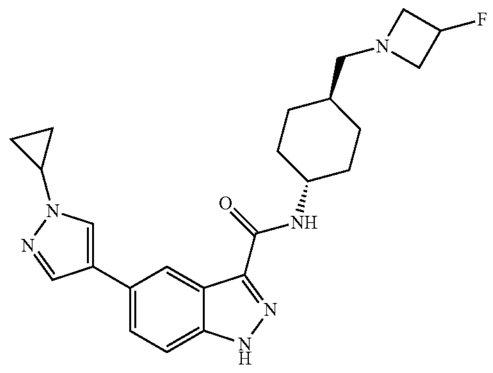 [SMILES: O=C(N[C@H]1CC[C@H](CN2CC(F)C2)CC1)c1n[nH]c2ccc(-c3cnn(C4CC4)c3)cc12]
26
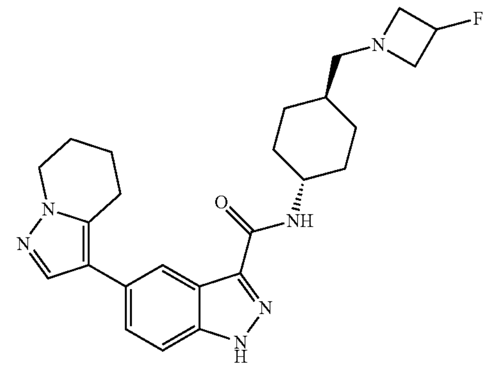 [SMILES: O=C(N[C@H]1CC[C@H](CN2CC(F)C2)CC1)c1n[nH]c2ccc(-c3cnn4c3CCCC4)cc12]
27
TABLE 1-continued
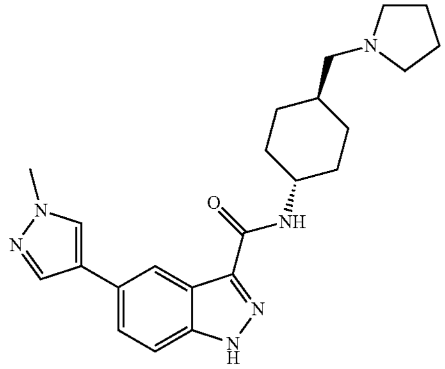 [SMILES: Cn1cc(-c2ccc3[nH]nc(C(=O)N[C@H]4CC[C@H](CN5CCCC5)CC4)c3c2)cn1]
28
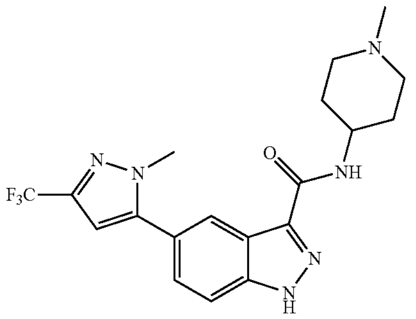 [SMILES: CN1CCC(NC(=O)c2n[nH]c3ccc(-c4cc(C(F)(F)F)nn4C)cc23)CC1]
29
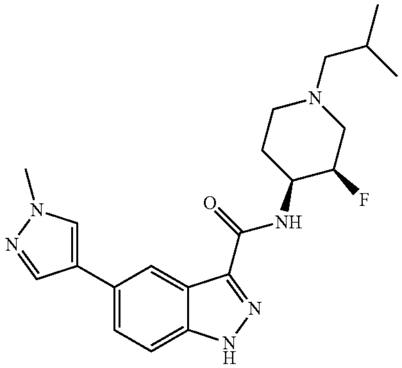 [SMILES: CC(C)CN1CC[C@H](NC(=O)c2n[nH]c3ccc(-c4cnn(C)c4)cc23)[C@H](F)C1]
30
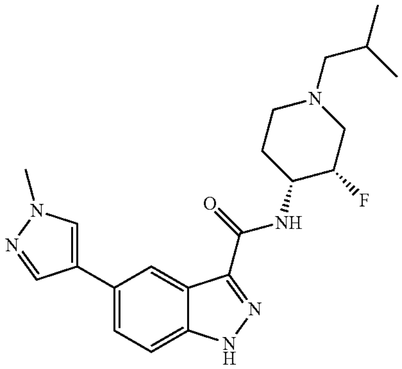 [SMILES: CC(C)CN1CC[C@@H](NC(=O)c2n[nH]c3ccc(-c4cnn(C)c4)cc23)[C@@H](F)C1]
31

TABLE 1-continued
32
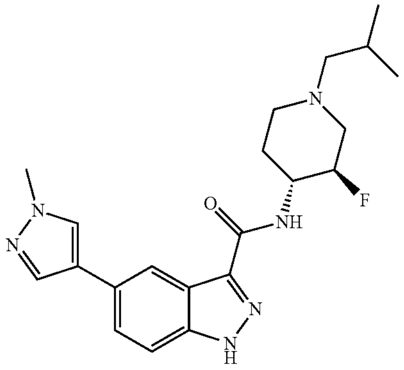 [SMILES: CC(C)CN1CC[C@@H](NC(=O)c2n[nH]c3ccc(-c4cnn(C)c4)cc23)[C@H](F)C1]
33
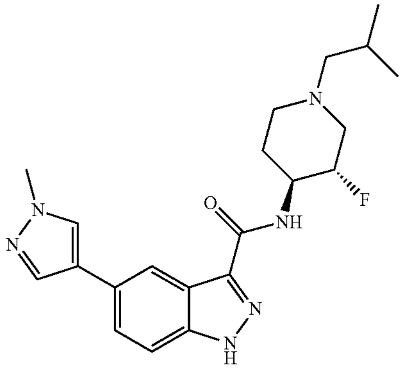 [SMILES: CC(C)CN1CC[C@H](NC(=O)c2n[nH]c3ccc(-c4cnn(C)c4)cc23)[C@@H](F)C1]
34
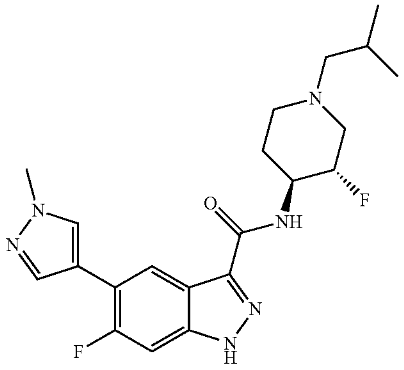 [SMILES: CC(C)CN1CC[C@H](NC(=O)c2n[nH]c3cc(F)c(-c4cnn(C)c4)cc23)[C@@H](F)C1]
35
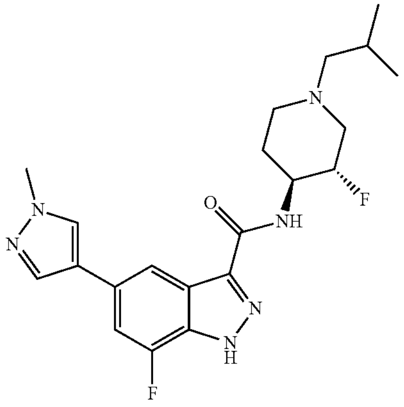 [SMILES: CC(C)CN1CC[C@H](NC(=O)c2n[nH]c3c(F)cc(-c4cnn(C)c4)cc23)[C@@H](F)C1]
TABLE 1-continued
36
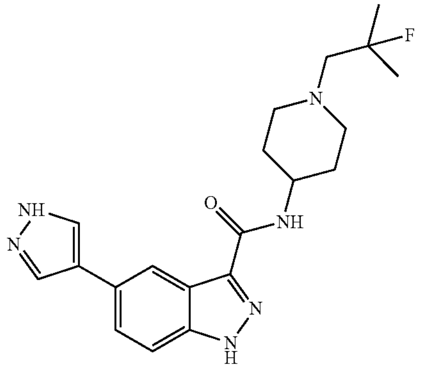 [SMILES: CC(C)(F)CN1CCC(NC(=O)c2n[nH]c3ccc(-c4cn[nH]c4)cc23)CC1]
37
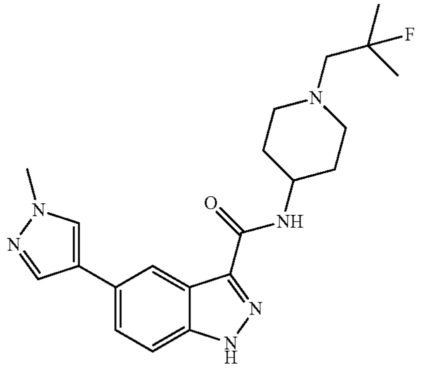 [SMILES: Cn1cc(-c2ccc3[nH]nc(C(=O)NC4CCN(CC(C)(C)F)CC4)c3c2)cn1]
38
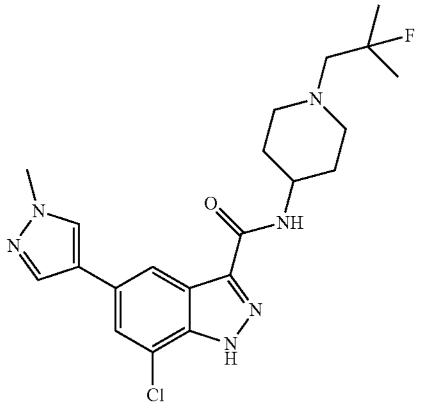 [SMILES: Cn1cc(-c2cc(Cl)c3[nH]nc(C(=O)NC4CCN(CC(C)(C)F)CC4)c3c2)cn1]
39
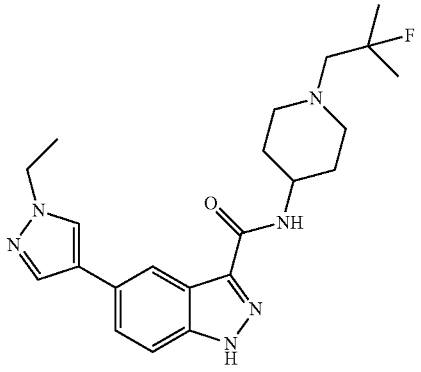 [SMILES: CCn1cc(-c2ccc3[nH]nc(C(=O)NC4CCN(CC(C)(C)F)CC4)c3c2)cn1]

TABLE 1-continued
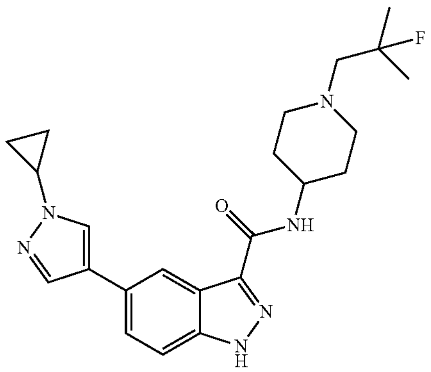 [SMILES: CC(C)(F)CN1CCC(NC(=O)c2n[nH]c3ccc(-c4cnn(C5CC5)c4)cc23)CC1]
40
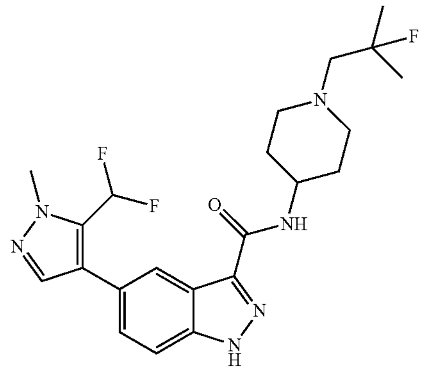 [SMILES: Cn1ncc(-c2ccc3[nH]nc(C(=O)NC4CCN(CC(C)(C)F)CC4)c3c2)c1C(F)F]
41
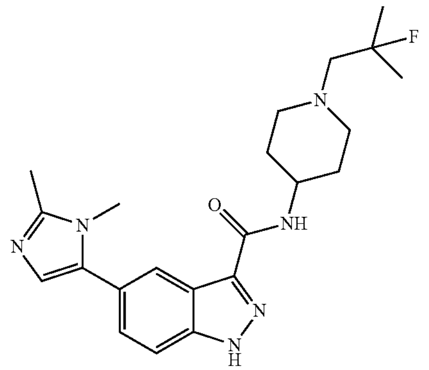 [SMILES: Cc1ncc(-c2ccc3[nH]nc(C(=O)NC4CCN(CC(C)(C)F)CC4)c3c2)n1C]
42
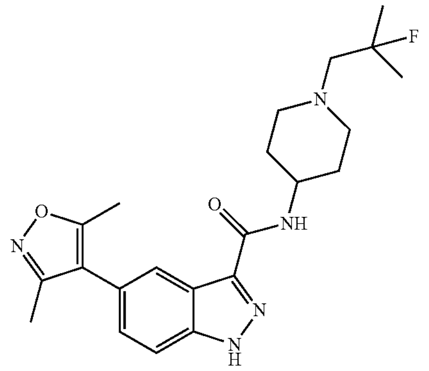 [SMILES: Cc1noc(C)c1-c1ccc2[nH]nc(C(=O)NC3CCN(CC(C)(C)F)CC3)c2c1]
43
TABLE 1-continued
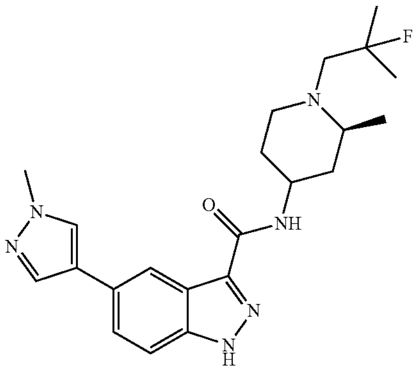 [SMILES: C[C@H]1CC(NC(=O)c2n[nH]c3ccc(-c4cnn(C)c4)cc23)CCN1CC(C)(C)F]
44
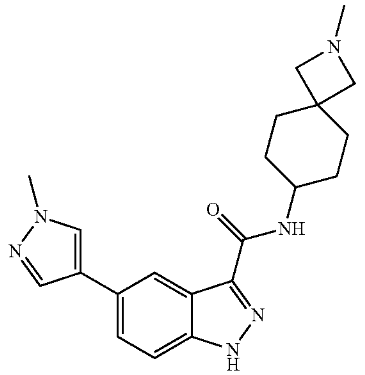 [SMILES: CN1CC2(CCC(NC(=O)c3n[nH]c4ccc(-c5cnn(C)c5)cc34)CC2)C1]
45
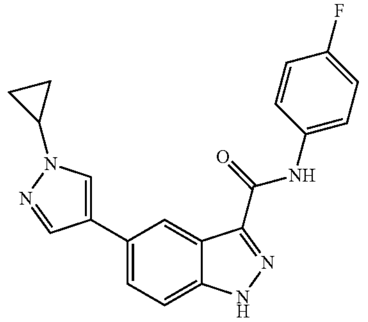 [SMILES: O=C(Nc1ccc(F)cc1)c1n[nH]c2ccc(-c3cnn(C4CC4)c3)cc12]
46
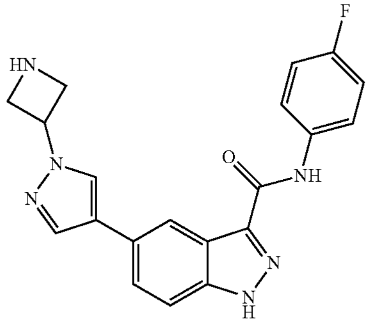 [SMILES: O=C(Nc1ccc(F)cc1)c1n[nH]c2ccc(-c3cnn(C4CNC4)c3)cc12]
47

TABLE 1-continued
48
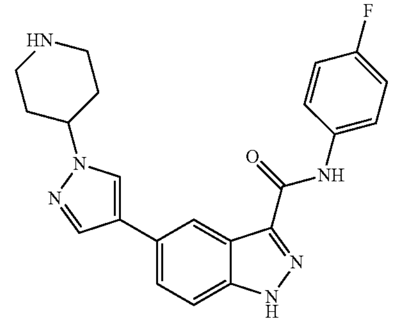 [SMILES: O=C(Nc1ccc(F)cc1)c1n[nH]c2ccc(-c3cnn(C4CCNCC4)c3)cc12]
49
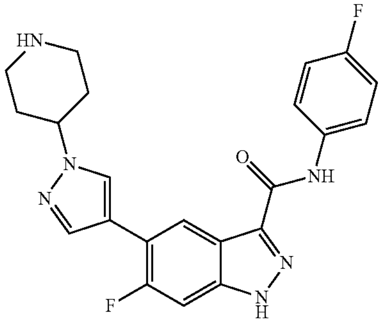 [SMILES: O=C(Nc1ccc(F)cc1)c1n[nH]c2cc(F)c(-c3cnn(C4CCNCC4)c3)cc12]
50
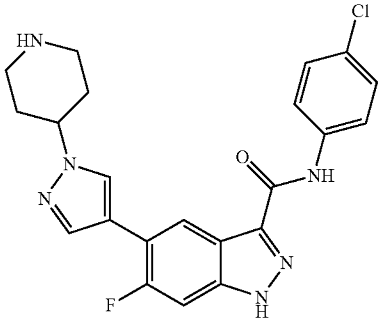 [SMILES: O=C(Nc1ccc(Cl)cc1)c1n[nH]c2cc(F)c(-c3cnn(C4CCNCC4)c3)cc12]
51
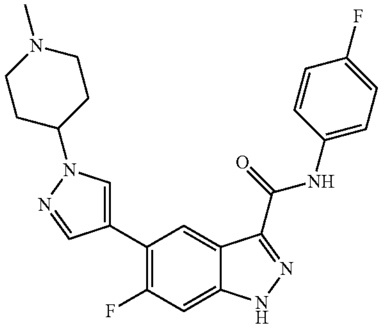 [SMILES: CN1CCC(n2cc(-c3cc4c(C(=O)Nc5ccc(F)cc5)n[nH]c4cc3F)cn2)CC1]
52
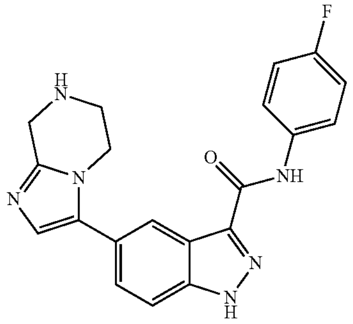 [SMILES: O=C(Nc1ccc(F)cc1)c1n[nH]c2ccc(-c3cnc4n3CCNC4)cc12]
TABLE 1-continued
53
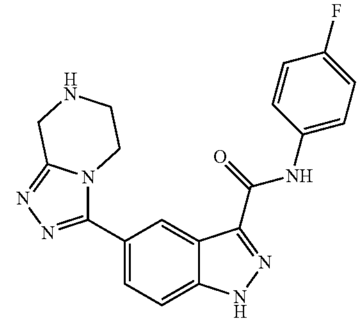 [SMILES: O=C(Nc1ccc(F)cc1)c1n[nH]c2ccc(-c3nnc4n3CCNC4)cc12]
54
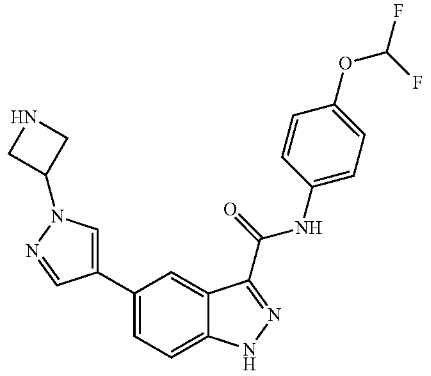
55
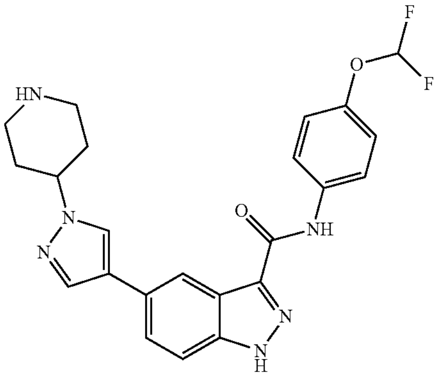 [SMILES: O=C(Nc1ccc(OC(F)F)cc1)c1n[nH]c2ccc(-c3cnn(C4CCNCC4)c3)cc12]
56
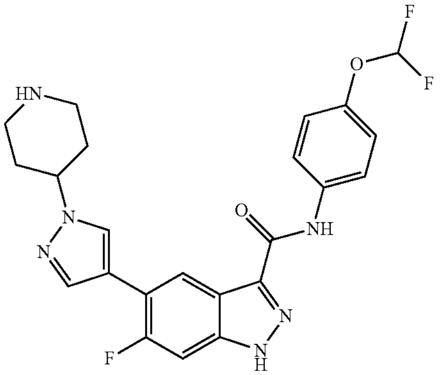 [SMILES: O=C(Nc1ccc(OC(F)F)cc1)c1n[nH]c2cc(F)c(-c3cnn(C4CCNCC4)c3)cc12]

TABLE 1-continued
57
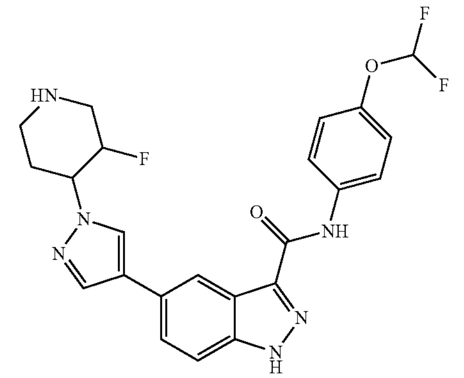 [SMILES: O=C(Nc1ccc(OC(F)F)cc1)c1n[nH]c2ccc(-c3cnn(C4CCNCC4F)c3)cc12]
58
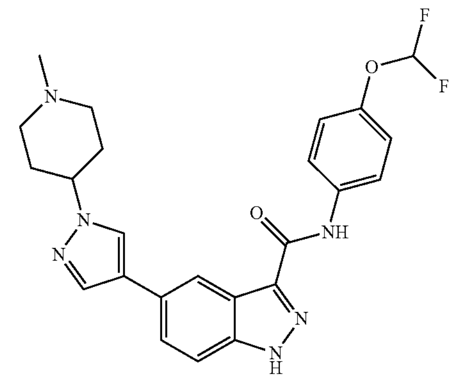 [SMILES: CN1CCC(n2cc(-c3ccc4[nH]nc(C(=O)Nc5ccc(OC(F)F)cc5)c4c3)cn2)CC1]
59
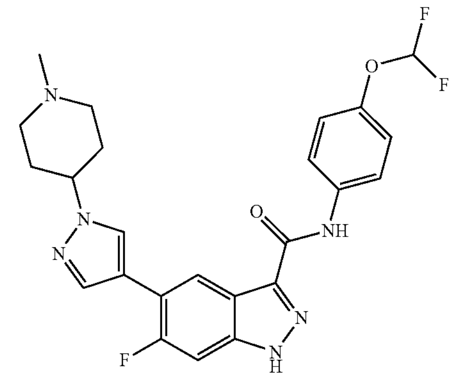 [SMILES: CN1CCC(n2cc(-c3cc4c(C(=O)Nc5ccc(OC(F)F)cc5)n[nH]c4cc3F)cn2)CC1]
60
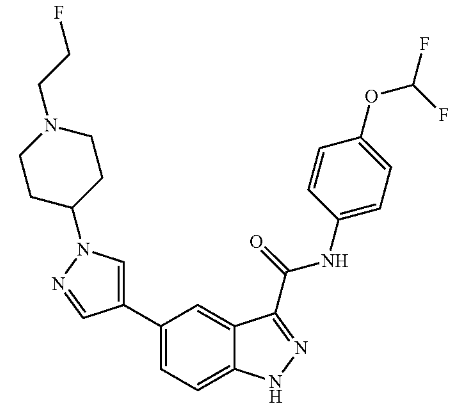 [SMILES: O=C(Nc1ccc(OC(F)F)cc1)c1n[nH]c2ccc(-c3cnn(C4CCN(CCF)CC4)c3)cc12]
TABLE 1-continued
61
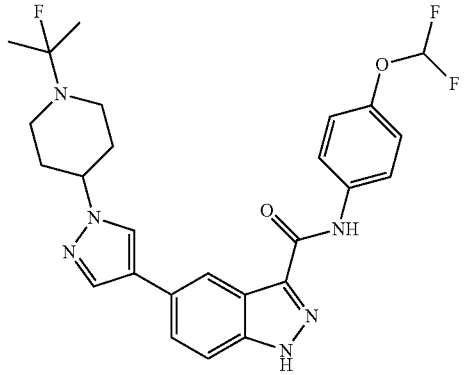 [SMILES: CC(C)(F)N1CCC(n2cc(-c3ccc4[nH]nc(C(=O)Nc5ccc(OC(F)F)cc5)c4c3)cn2)CC1]
62
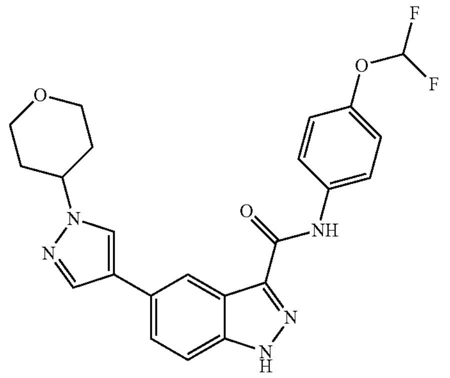 [SMILES: O=C(Nc1ccc(OC(F)F)cc1)c1n[nH]c2ccc(-c3cnn(C4CCOCC4)c3)cc12]
63
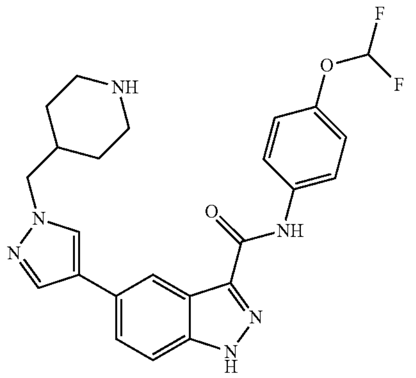 [SMILES: O=C(Nc1ccc(OC(F)F)cc1)c1n[nH]c2ccc(-c3cnn(CC4CCNCC4)c3)cc12]
64
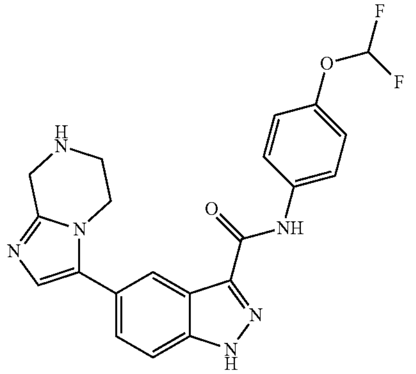 [SMILES: O=C(Nc1ccc(OC(F)F)cc1)c1n[nH]c2ccc(-c3cnc4n3CCNC4)cc12]

TABLE 1-continued
65
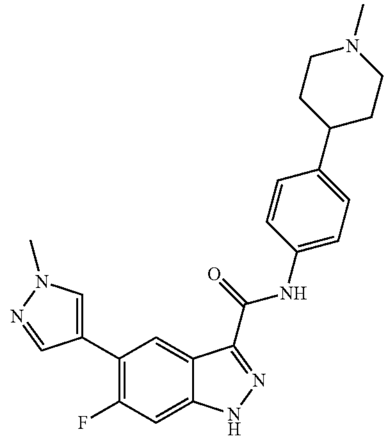 [SMILES: CN1CCC(c2ccc(NC(=O)c3n[nH]c4cc(F)c(-c5cnn(C)c5)cc34)cc2)CC1]
66
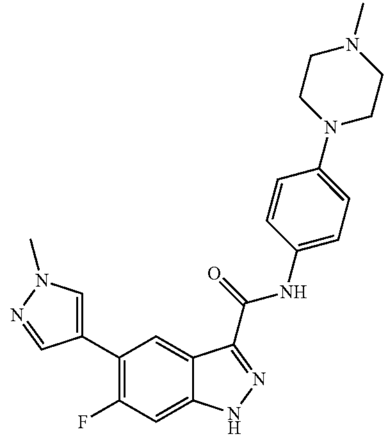 [SMILES: CN1CCN(c2ccc(NC(=O)c3n[nH]c4cc(F)c(-c5cnn(C)c5)cc34)cc2)CC1]
67
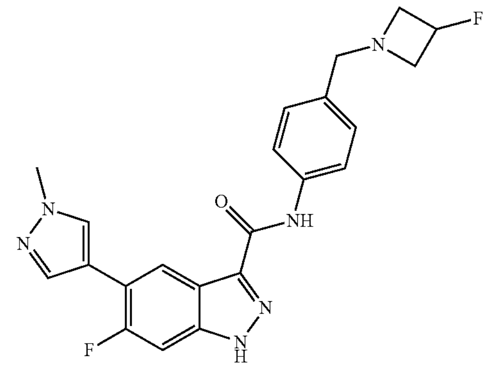 [SMILES: Cn1cc(-c2cc3c(C(=O)Nc4ccc(CN5CC(F)C5)cc4)n[nH]c3cc2F)cn1]
68
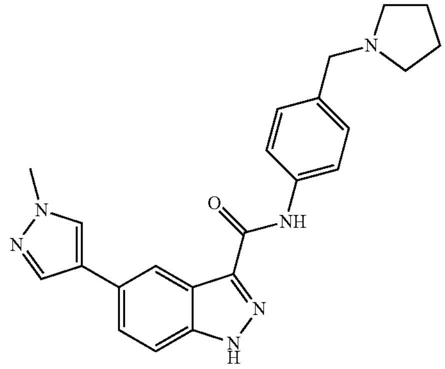 [SMILES: Cn1cc(-c2ccc3[nH]nc(C(=O)Nc4ccc(CN5CCCC5)cc4)c3c2)cn1]
TABLE 1-continued
69
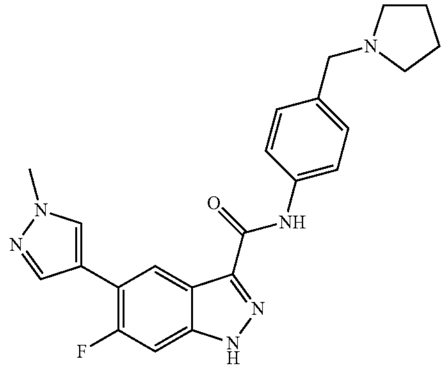 [SMILES: Cn1cc(-c2cc3c(C(=O)Nc4ccc(CN5CCCC5)cc4)n[nH]c3cc2F)cn1]
70
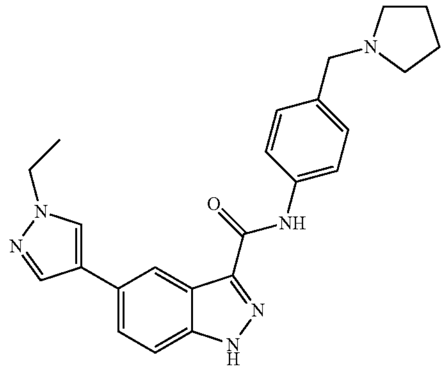 [SMILES: CCn1cc(-c2ccc3[nH]nc(C(=O)Nc4ccc(CN5CCCC5)cc4)c3c2)cn1]
71
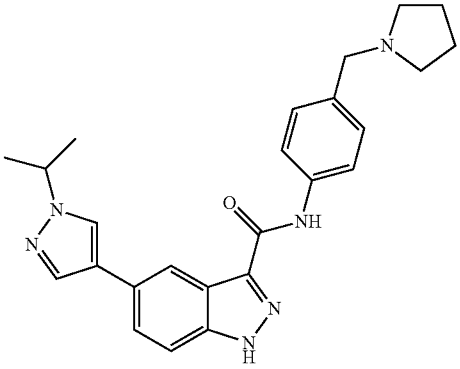 [SMILES: CC(C)n1cc(-c2ccc3[nH]nc(C(=O)Nc4ccc(CN5CCCC5)cc4)c3c2)cn1]
72
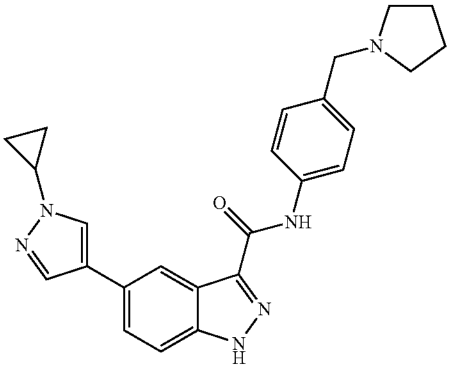 [SMILES: O=C(Nc1ccc(CN2CCCC2)cc1)c1n[nH]c2ccc(-c3cnn(C4CC4)c3)cc12]

TABLE 1-continued
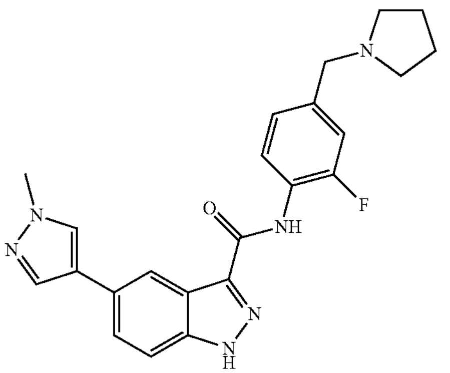 [SMILES: Cn1cc(-c2ccc3[nH]nc(C(=O)Nc4ccc(CN5CCCC5)cc4F)c3c2)cn1]
73
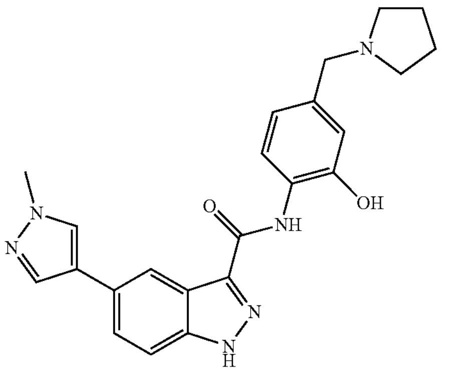 [SMILES: Cn1cc(-c2ccc3[nH]nc(C(=O)Nc4ccc(CN5CCCC5)cc4O)c3c2)cn1]
74
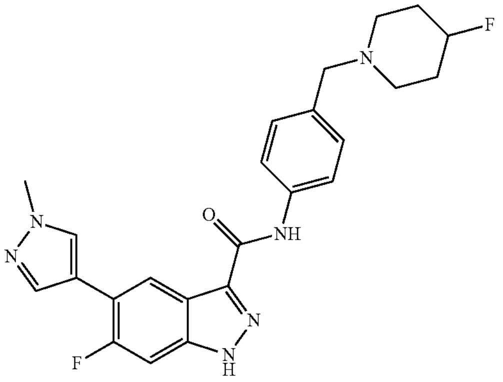 [SMILES: Cn1cc(-c2cc3c(C(=O)Nc4ccc(CN5CCC(F)CC5)cc4)n[nH]c3cc2F)cn1]
75
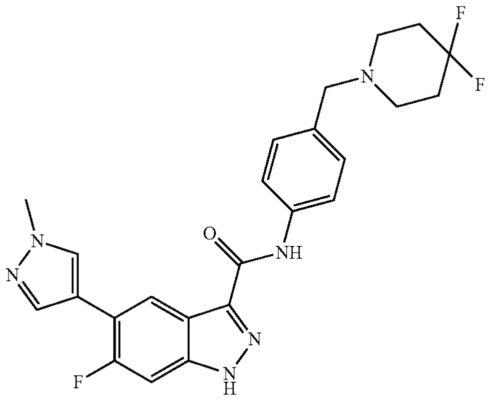 [SMILES: Cn1cc(-c2cc3c(C(=O)Nc4ccc(CN5CCC(F)(F)CC5)cc4)n[nH]c3cc2F)cn1]
76
TABLE 1-continued
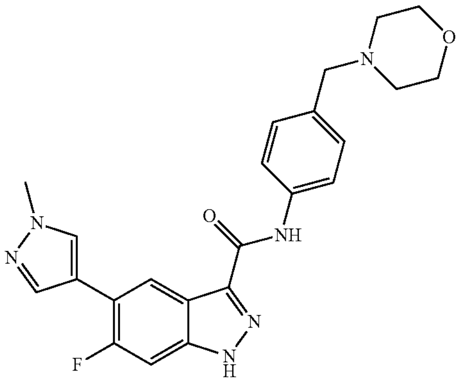 [SMILES: Cn1cc(-c2cc3c(C(=O)Nc4ccc(CN5CCOCC5)cc4)n[nH]c3cc2F)cn1]
77
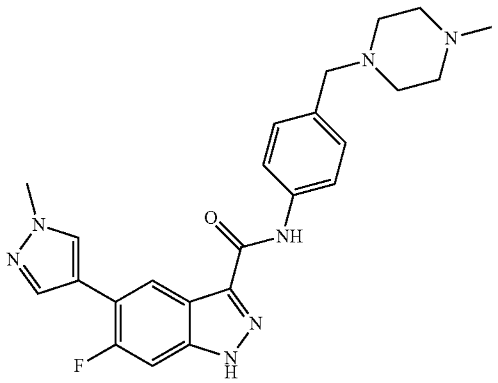 [SMILES: CN1CCN(Cc2ccc(NC(=O)c3n[nH]c4cc(F)c(-c5cnn(C)c5)cc34)cc2)CC1]
78
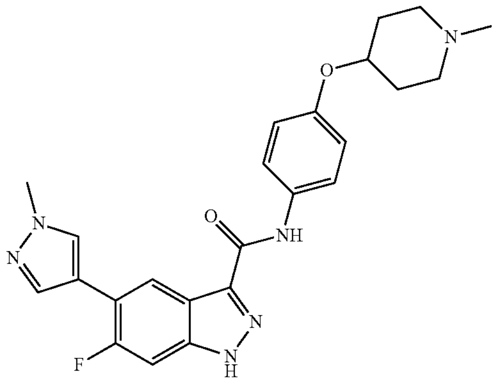 [SMILES: CN1CCC(Oc2ccc(NC(=O)c3n[nH]c4cc(F)c(-c5cnn(C)c5)cc34)cc2)CC1]
79
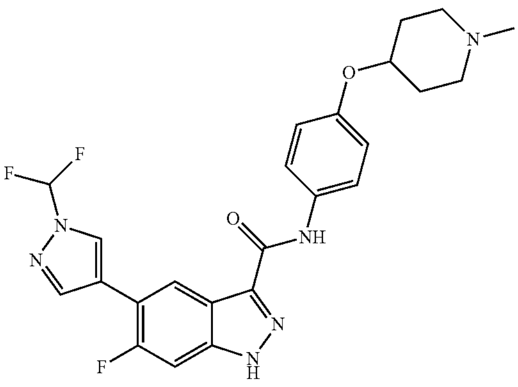 [SMILES: CN1CCC(Oc2ccc(NC(=O)c3n[nH]c4cc(F)c(-c5cnn(C(F)F)c5)cc34)cc2)CC1]
80

TABLE 1-continued
81
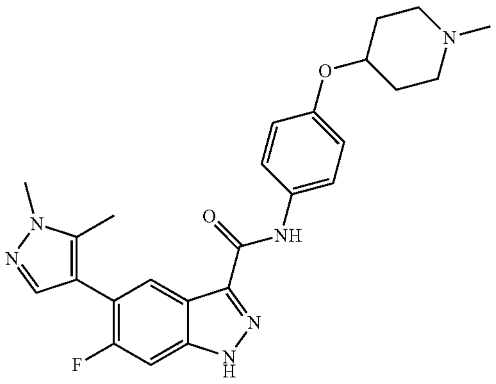 [SMILES: Cc1c(-c2cc3c(C(=O)Nc4ccc(OC5CCN(C)CC5)cc4)n[nH]c3cc2F)cnn1C]
82
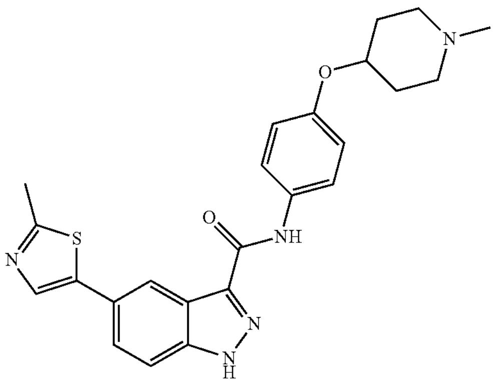 [SMILES: Cc1ncc(-c2ccc3[nH]nc(C(=O)Nc4ccc(OC5CCN(C)CC5)cc4)c3c2)s1]
83
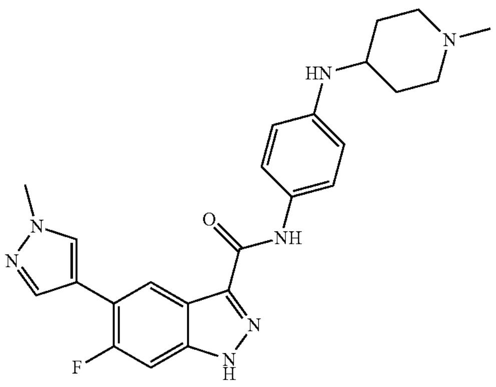 [SMILES: CN1CCC(Nc2ccc(NC(=O)c3n[nH]c4cc(F)c(-c5cnn(C)c5)cc34)cc2)CC1]
84
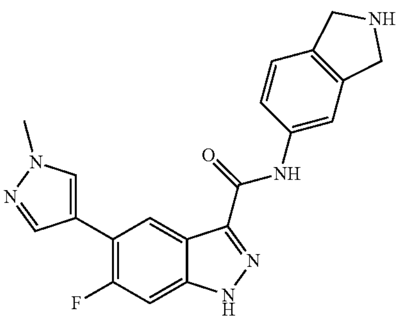 [SMILES: Cn1cc(-c2cc3c(C(=O)Nc4ccc5c(c4)CNC5)n[nH]c3cc2F)cn1]
TABLE 1-continued
85
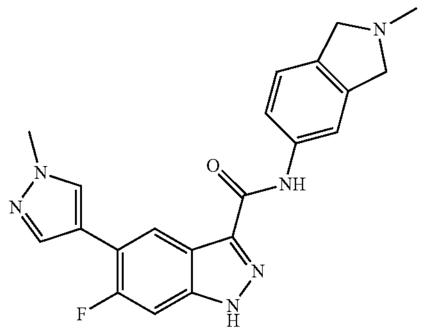 [SMILES: CN1Cc2ccc(NC(=O)c3n[nH]c4cc(F)c(-c5cnn(C)c5)cc34)cc2C1]
86
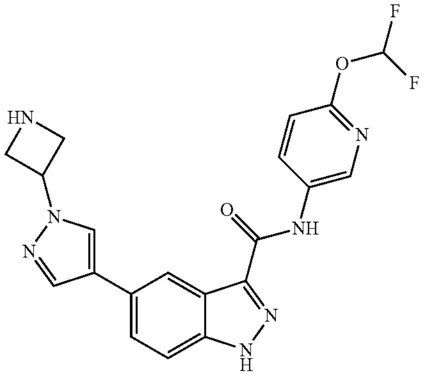 [SMILES: O=C(Nc1ccc(OC(F)F)nc1)c1n[nH]c2ccc(-c3cnn(C4CNC4)c3)cc12]
87
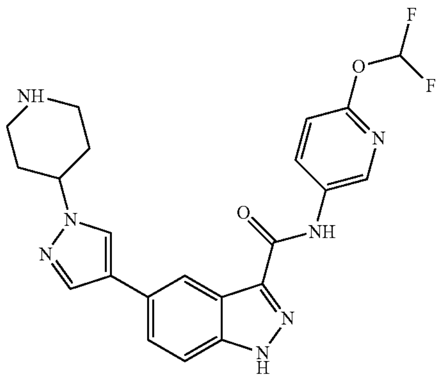 [SMILES: O=C(Nc1ccc(OC(F)F)nc1)c1n[nH]c2ccc(-c3cnn(C4CCNCC4)c3)cc12]
88
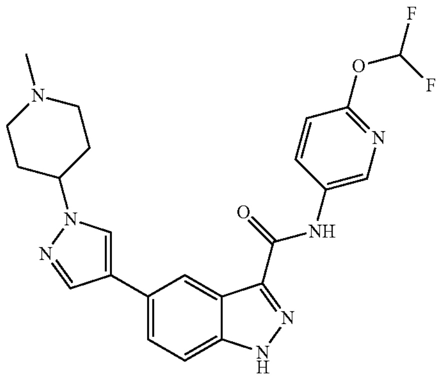 [SMILES: CN1CCC(n2cc(-c3ccc4[nH]nc(C(=O)Nc5ccc(OC(F)F)nc5)c4c3)cn2)CC1]

TABLE 1-continued
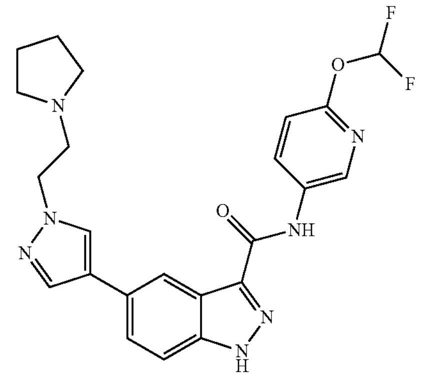 [SMILES: O=C(Nc1ccc(OC(F)F)nc1)c1n[nH]c2ccc(-c3cnn(CCN4CCCC4)c3)cc12]
89
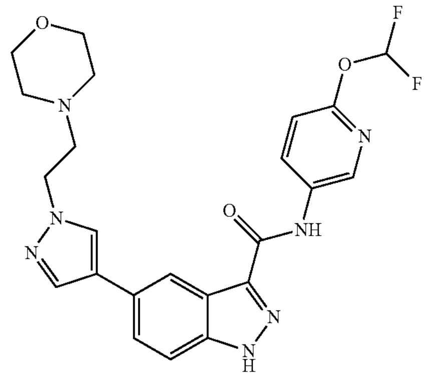 [SMILES: O=C(Nc1ccc(OC(F)F)nc1)c1n[nH]c2ccc(-c3cnn(CCN4CCOCC4)c3)cc12]
90
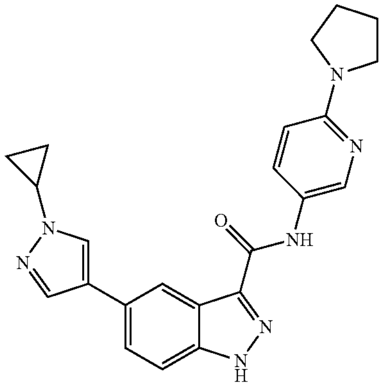 [SMILES: O=C(Nc1ccc(N2CCCC2)nc1)c1n[nH]c2ccc(-c3cnn(C4CC4)c3)cc12]
91
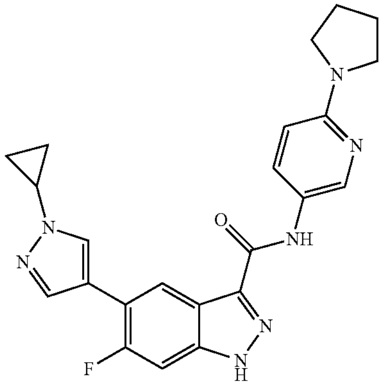 [SMILES: O=C(Nc1ccc(N2CCCC2)nc1)c1n[nH]c2cc(F)c(-c3cnn(C4CC4)c3)cc12]
92
TABLE 1-continued
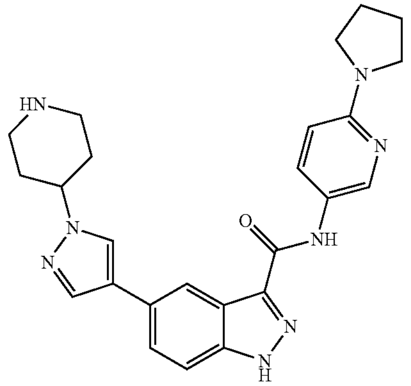 [SMILES: O=C(Nc1ccc(N2CCCC2)nc1)c1n[nH]c2ccc(-c3cnn(C4CCNCC4)c3)cc12]
93
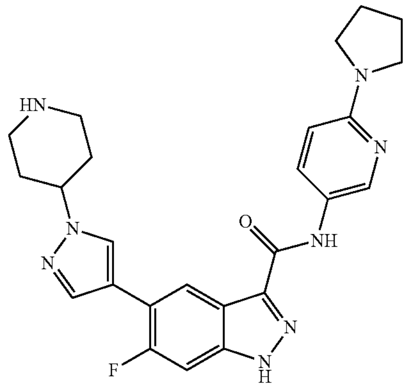 [SMILES: O=C(Nc1ccc(N2CCCC2)nc1)c1n[nH]c2cc(F)c(-c3cnn(C4CCNCC4)c3)cc12]
94
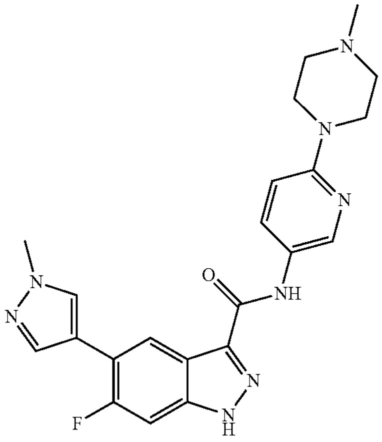 [SMILES: CN1CCN(c2ccc(NC(=O)c3n[nH]c4cc(F)c(-c5cnn(C)c5)cc34)cn2)CC1]
95
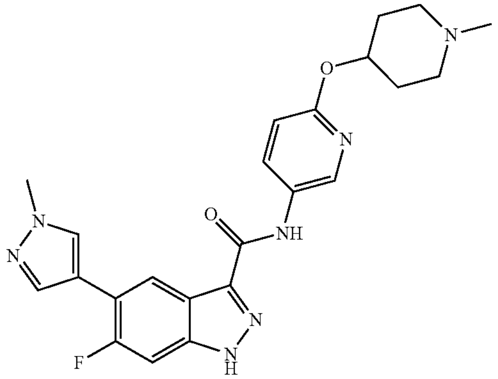 [SMILES: CN1CCC(Oc2ccc(NC(=O)c3n[nH]c4cc(F)c(-c5cnn(C)c5)cc34)cn2)CC1]
96

TABLE 1-continued
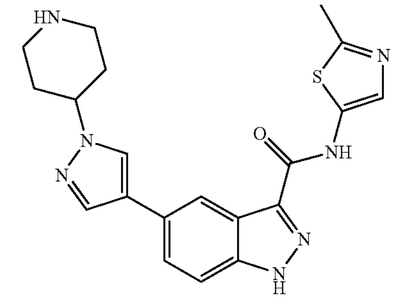 [SMILES: Cc1ncc(NC(=O)c2n[nH]c3ccc(-c4cnn(C5CCNCC5)c4)cc23)s1]
97
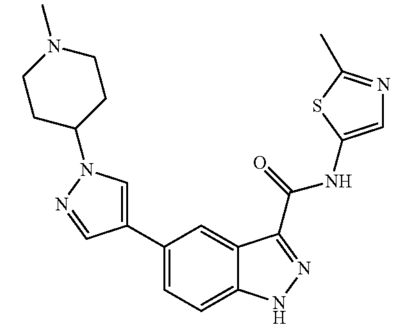 [SMILES: Cc1ncc(NC(=O)c2n[nH]c3ccc(-c4cnn(C5CCN(C)CC5)c4)cc23)s1]
98
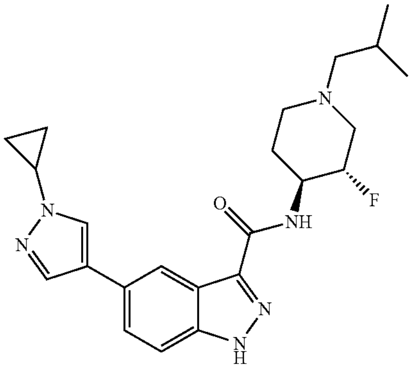 [SMILES: CC(C)CN1CC[C@H](NC(=O)c2n[nH]c3ccc(-c4cnn(C5CC5)c4)cc23)[C@@H](F)C1]
99
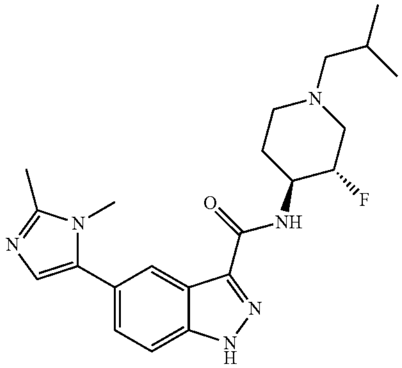 [SMILES: Cc1ncc(-c2ccc3[nH]nc(C(=O)N[C@H]4CCN(CC(C)C)C[C@@H]4F)c3c2)n1C]
100
TABLE 1-continued
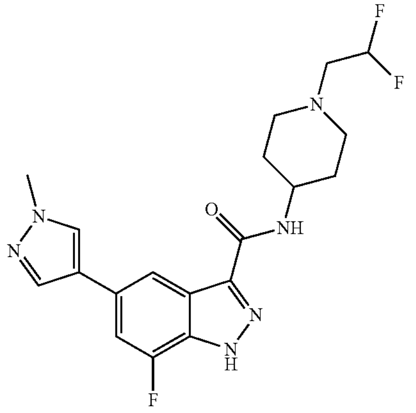 [SMILES: Cn1cc(-c2cc(F)c3[nH]nc(C(=O)NC4CCN(CC(F)F)CC4)c3c2)cn1]
101
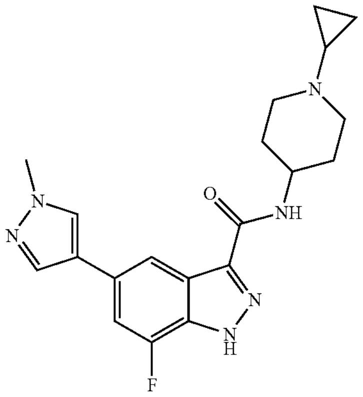 [SMILES: Cn1cc(-c2cc(F)c3[nH]nc(C(=O)NC4CCN(C5CC5)CC4)c3c2)cn1]
102
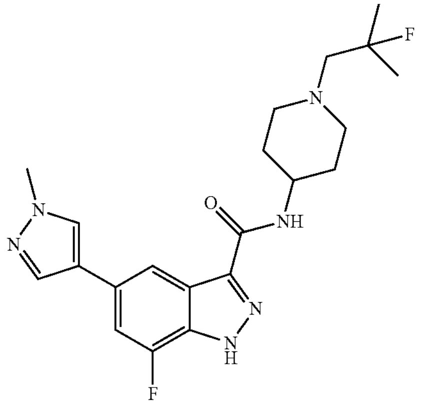 [SMILES: Cn1cc(-c2cc(F)c3[nH]nc(C(=O)NC4CCN(CC(C)(C)F)CC4)c3c2)cn1]
103
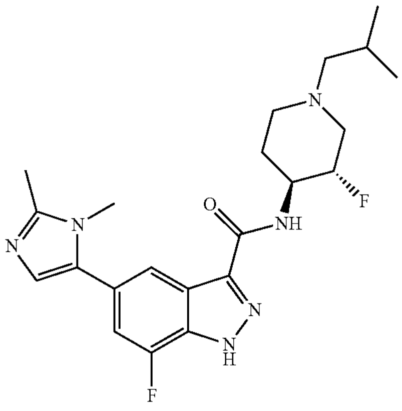 [SMILES: Cc1ncc(-c2cc(F)c3[nH]nc(C(=O)N[C@H]4CCN(CC(C)C)C[C@@H]4F)c3c2)n1C]
104

TABLE 1-continued
105
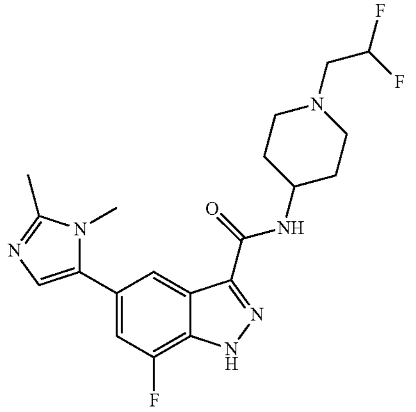 [SMILES: Cc1ncc(-c2cc(F)c3[nH]nc(C(=O)NC4CCN(CC(F)F)CC4)c3c2)n1C]
106
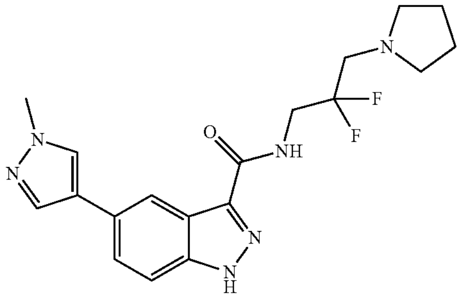 [SMILES: Cn1cc(-c2ccc3[nH]nc(C(=O)NCC(F)(F)CN4CCCC4)c3c2)cn1]
107
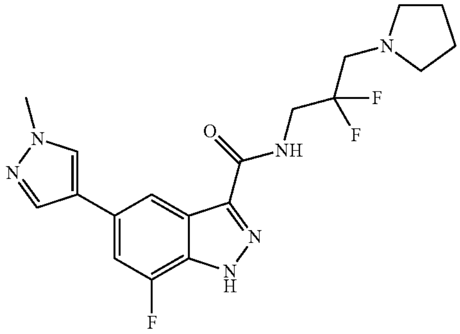 [SMILES: Cn1cc(-c2cc(F)c3[nH]nc(C(=O)NCC(F)(F)CN4CCCC4)c3c2)cn1]
108
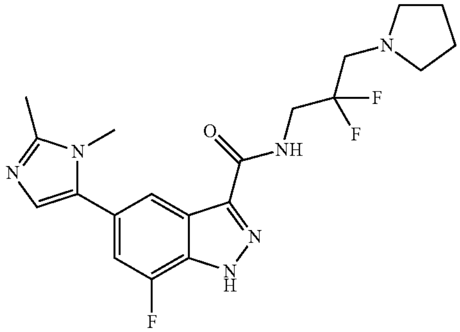 [SMILES: Cc1ncc(-c2cc(F)c3[nH]nc(C(=O)NCC(F)(F)CN4CCCC4)c3c2)n1C]
TABLE 1-continued
109
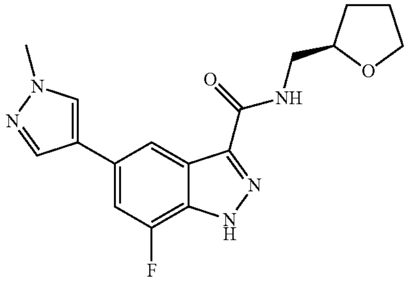 [SMILES: Cn1cc(-c2cc(F)c3[nH]nc(C(=O)NC[C@H]4CCCO4)c3c2)cn1]
110
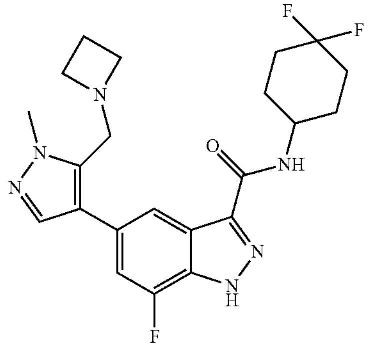 [SMILES: Cn1ncc(-c2cc(F)c3[nH]nc(C(=O)NC4CCC(F)(F)CC4)c3c2)c1CN1CCC1]
111
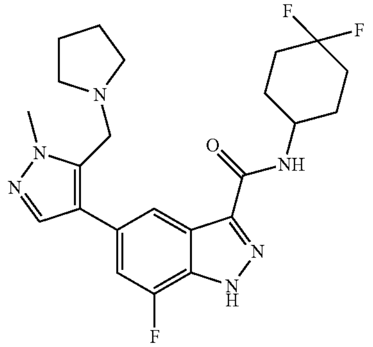 [SMILES: Cn1ncc(-c2cc(F)c3[nH]nc(C(=O)NC4CCC(F)(F)CC4)c3c2)c1CN1CCCC1]
112
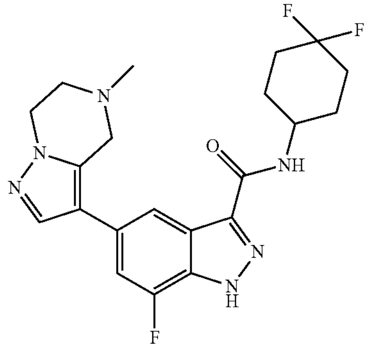 [SMILES: CN1CCn2ncc(-c3cc(F)c4[nH]nc(C(=O)NC5CCC(F)(F)CC5)c4c3)c2C1]
113
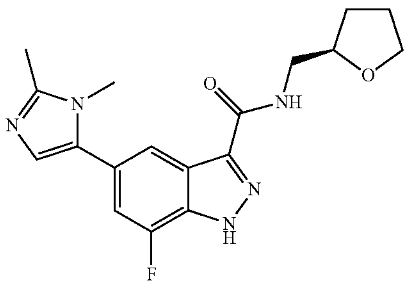 [SMILES: Cc1ncc(-c2cc(F)c3[nH]nc(C(=O)NC[C@H]4CCCO4)c3c2)n1C]

TABLE 1-continued
114
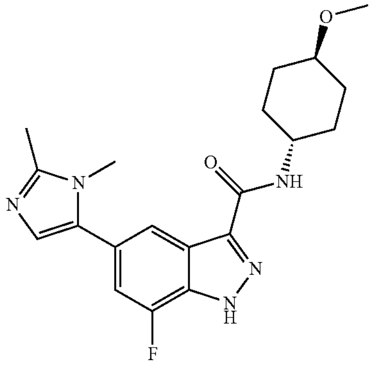 [SMILES: CO[C@H]1CC[C@H](NC(=O)c2n[nH]c3c(F)cc(-c4cnc(C)n4C)cc23)CC1]
115
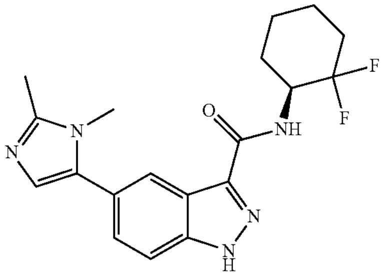 [SMILES: Cc1ncc(-c2ccc3[nH]nc(C(=O)N[C@H]4CCCCC4(F)F)c3c2)n1C]
116
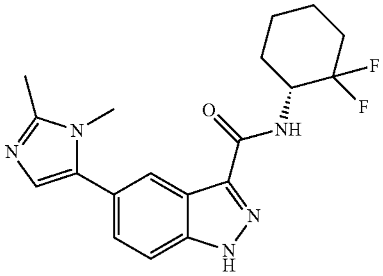 [SMILES: Cc1ncc(-c2ccc3[nH]nc(C(=O)N[C@@H]4CCCCC4(F)F)c3c2)n1C]
117
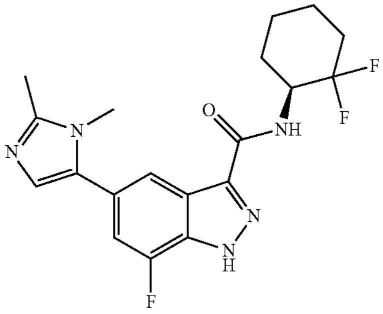 [SMILES: Cc1ncc(-c2cc(F)c3[nH]nc(C(=O)N[C@H]4CCCCC4(F)F)c3c2)n1C]
118
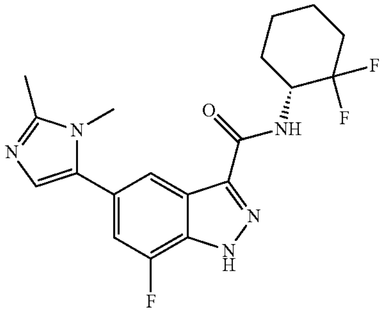 [SMILES: Cc1ncc(-c2cc(F)c3[nH]nc(C(=O)N[C@@H]4CCCCC4(F)F)c3c2)n1C]
TABLE 1-continued
119
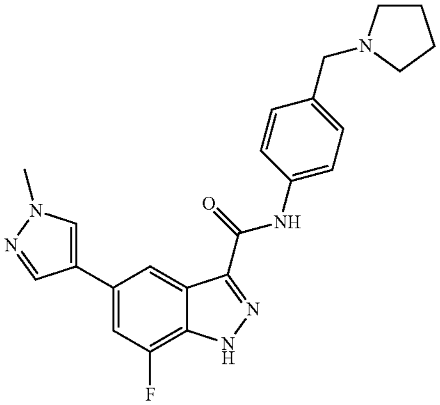 [SMILES: Cn1cc(-c2cc(F)c3[nH]nc(C(=O)Nc4ccc(CN5CCCC5)cc4)c3c2)cn1]
120
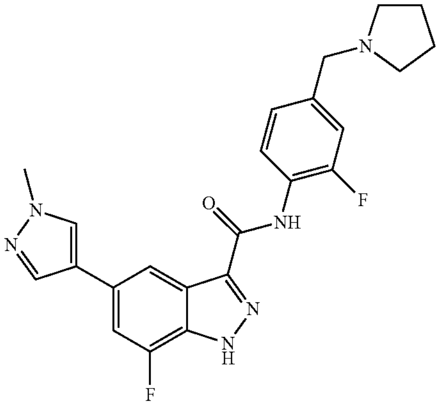 [SMILES: Cn1cc(-c2cc(F)c3[nH]nc(C(=O)Nc4ccc(CN5CCCC5)cc4F)c3c2)cn1]
121
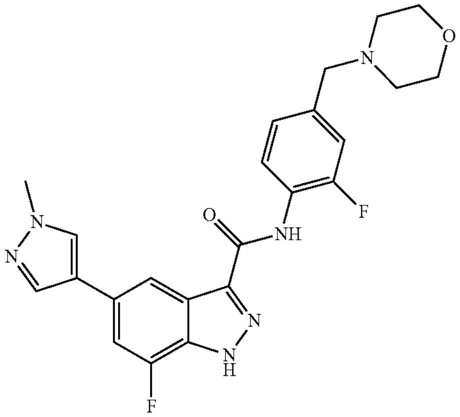 [SMILES: Cn1cc(-c2cc(F)c3[nH]nc(C(=O)Nc4ccc(CN5CCOCC5)cc4F)c3c2)cn1]
122
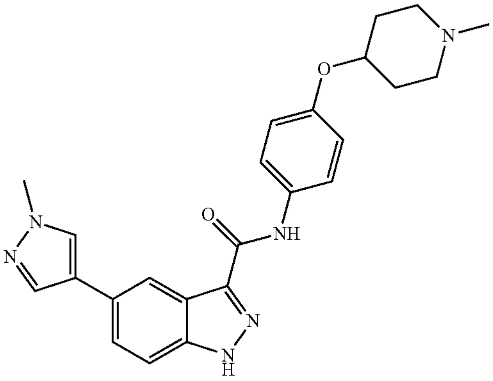 [SMILES: CN1CCC(Oc2ccc(NC(=O)c3n[nH]c4ccc(-c5cnn(C)c5)cc34)cc2)CC1]

TABLE 1-continued
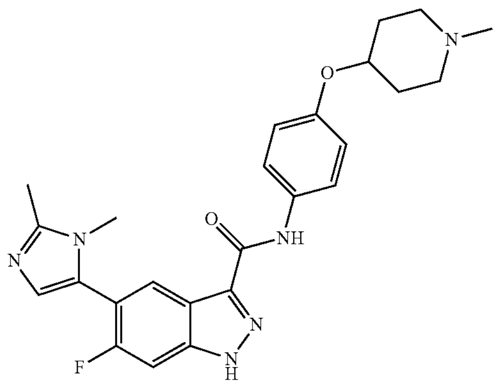 [SMILES: Cc1ncc(-c2cc3c(C(=O)Nc4ccc(OC5CCN(C)CC5)cc4)n[nH]c3cc2F)n1C]
123
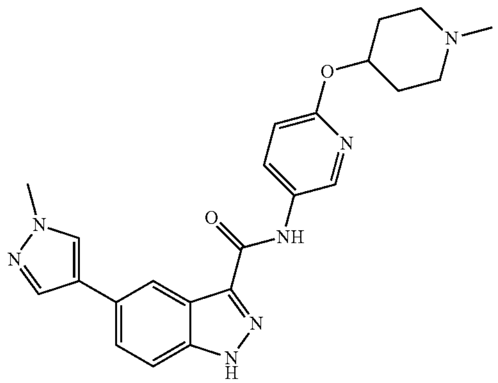 [SMILES: CN1CCC(Oc2ccc(NC(=O)c3n[nH]c4ccc(-c5cnn(C)c5)cc34)cn2)CC1]
124
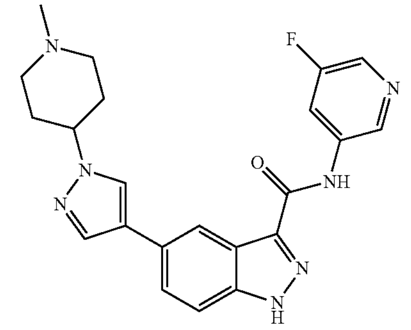 [SMILES: CN1CCC(n2cc(-c3ccc4[nH]nc(C(=O)Nc5cncc(F)c5)c4c3)cn2)CC1]
125
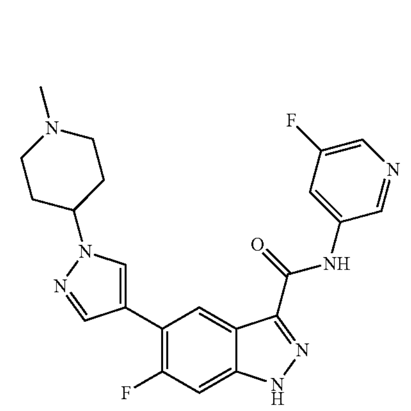 [SMILES: CN1CCC(n2cc(-c3cc4c(C(=O)Nc5cncc(F)c5)n[nH]c4cc3F)cn2)CC1]
126
TABLE 1-continued
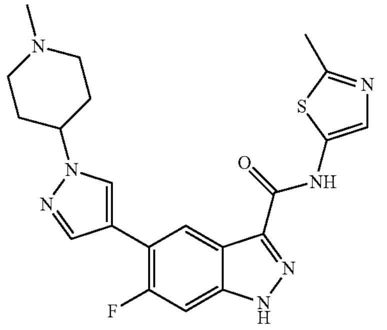 [SMILES: Cc1ncc(NC(=O)c2n[nH]c3cc(F)c(-c4cnn(C5CCN(C)CC5)c4)cc23)s1]
127
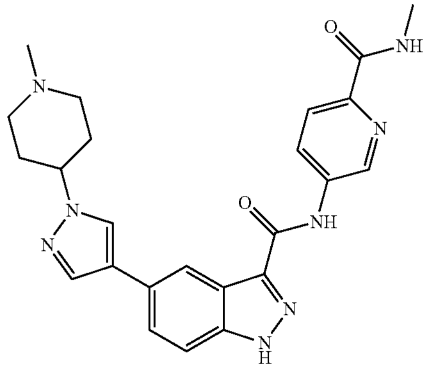 [SMILES: CNC(=O)c1ccc(NC(=O)c2n[nH]c3ccc(-c4cnn(C5CCN(C)CC5)c4)cc23)cn1]
128
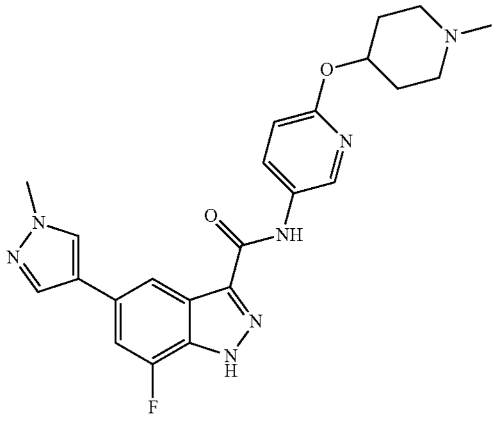 [SMILES: CN1CCC(Oc2ccc(NC(=O)c3n[nH]c4c(F)cc(-c5cnn(C)c5)cc34)cn2)CC1]
129
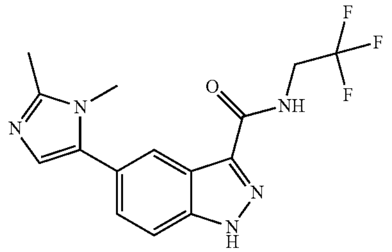 [SMILES: Cc1ncc(-c2ccc3[nH]nc(C(=O)NCC(F)(F)F)c3c2)n1C]
130
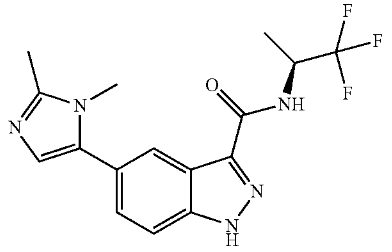 [SMILES: Cc1ncc(-c2ccc3[nH]nc(C(=O)N[C@@H](C)C(F)(F)F)c3c2)n1C]
131

TABLE 1-continued
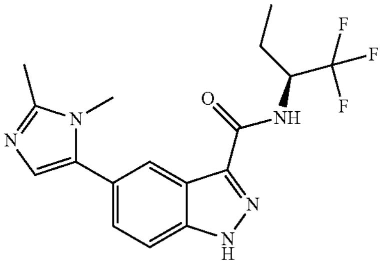 [SMILES: CC[C@H](NC(=O)c1n[nH]c2ccc(-c3cnc(C)n3C)cc12)C(F)(F)F]
132
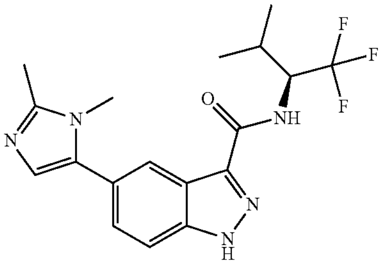 [SMILES: Cc1ncc(-c2ccc3[nH]nc(C(=O)N[C@@H](C(C)C)C(F)(F)F)c3c2)n1C]
133
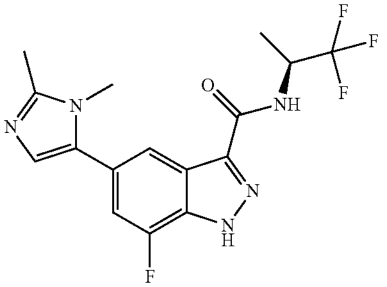 [SMILES: Cc1ncc(-c2cc(F)c3[nH]nc(C(=O)N[C@@H](C)C(F)(F)F)c3c2)n1C]
134
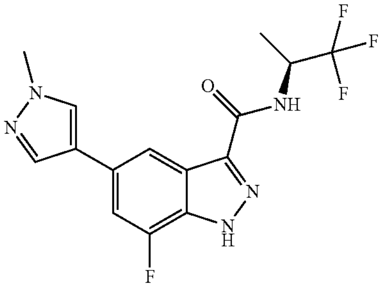 [SMILES: C[C@H](NC(=O)c1n[nH]c2c(F)cc(-c3cnn(C)c3)cc12)C(F)(F)F]
135
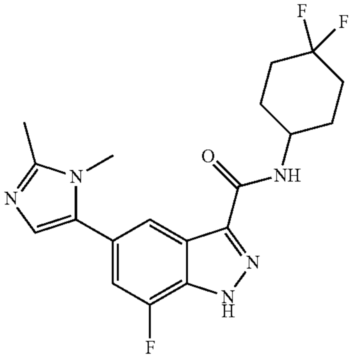 [SMILES: Cc1ncc(-c2cc(F)c3[nH]nc(C(=O)NC4CCC(F)(F)CC4)c3c2)n1C]
136
TABLE 1-continued
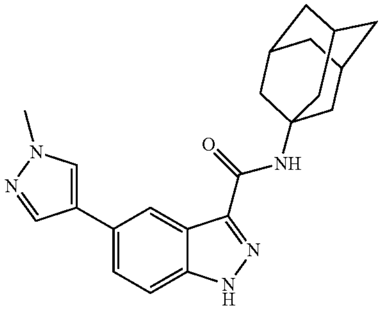 [SMILES: Cn1cc(-c2ccc3[nH]nc(C(=O)NC45CC6CC(CC(C6)C4)C5)c3c2)cn1]
137
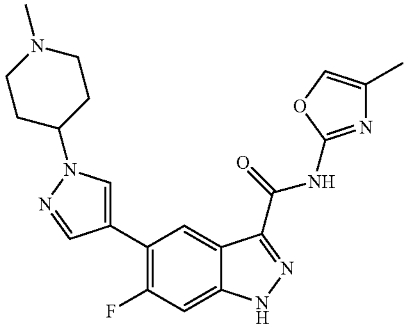 [SMILES: Cc1coc(NC(=O)c2n[nH]c3cc(F)c(-c4cnn(C5CCN(C)CC5)c4)cc23)n1]
138
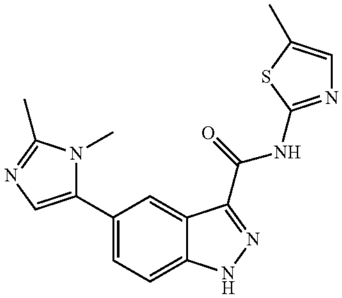 [SMILES: Cc1cnc(NC(=O)c2n[nH]c3ccc(-c4cnc(C)n4C)cc23)s1]
139
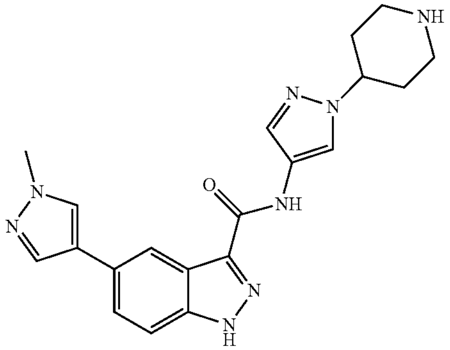 [SMILES: Cn1cc(-c2ccc3[nH]nc(C(=O)Nc4cnn(C5CCNCC5)c4)c3c2)cn1]
140

TABLE 1-continued
141
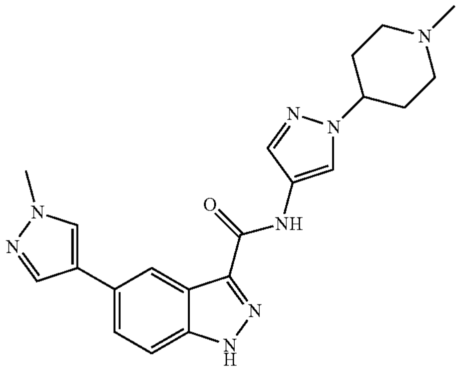 [SMILES: CN1CCC(n2cc(NC(=O)c3n[nH]c4ccc(-c5cnn(C)c5)cc34)cn2)CC1]
142
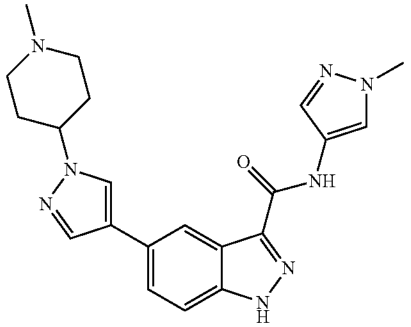 [SMILES: CN1CCC(n2cc(-c3ccc4[nH]nc(C(=O)Nc5cnn(C)c5)c4c3)cn2)CC1]
143
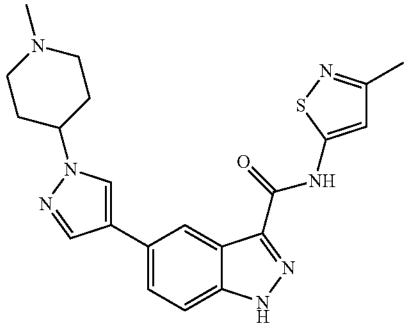 [SMILES: Cc1cc(NC(=O)c2n[nH]c3ccc(-c4cnn(C5CCN(C)CC5)c4)cc23)sn1]
144
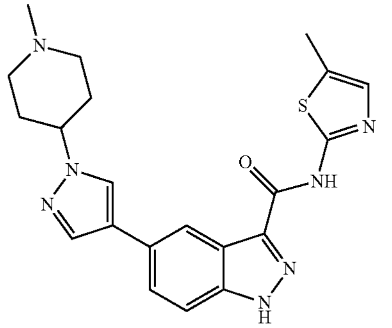 [SMILES: Cc1cnc(NC(=O)c2n[nH]c3ccc(-c4cnn(C5CCN(C)CC5)c4)cc23)s1]
TABLE 1-continued
145
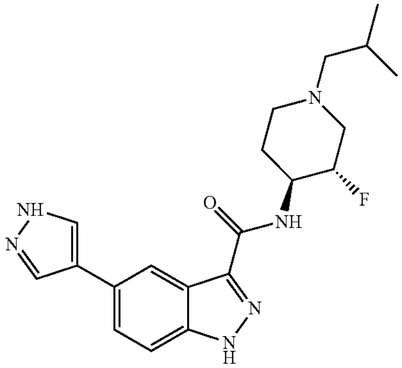 [SMILES: CC(C)CN1CC[C@H](NC(=O)c2n[nH]c3ccc(-c4cn[nH]c4)cc23)[C@@H](F)C1]
146
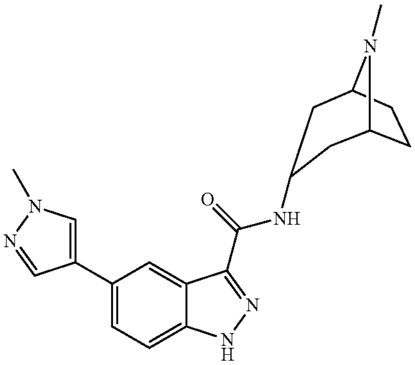 [SMILES: CN1C2CCC1CC(NC(=O)c1n[nH]c3ccc(-c4cnn(C)c4)cc13)C2]
147
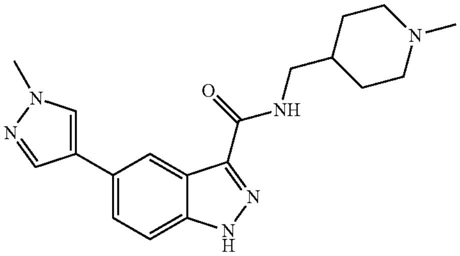 [SMILES: CN1CCC(CNC(=O)c2n[nH]c3ccc(-c4cnn(C)c4)cc23)CC1]
148
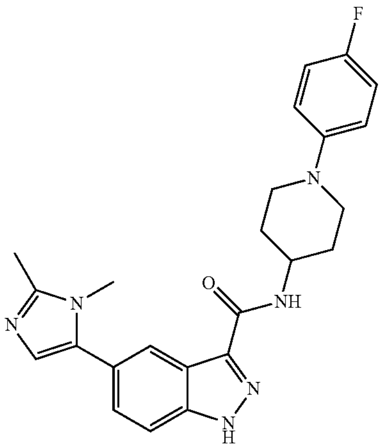 [SMILES: Cc1ncc(-c2ccc3[nH]nc(C(=O)NC4CCN(c5ccc(F)cc5)CC4)c3c2)n1C]

TABLE 1-continued
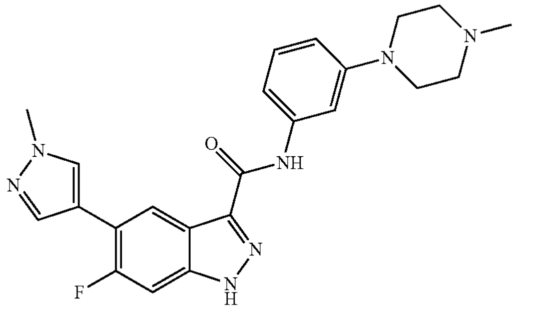 [SMILES: CN1CCN(c2cccc(NC(=O)c3n[nH]c4cc(F)c(-c5cnn(C)c5)cc34)c2)CC1]
149
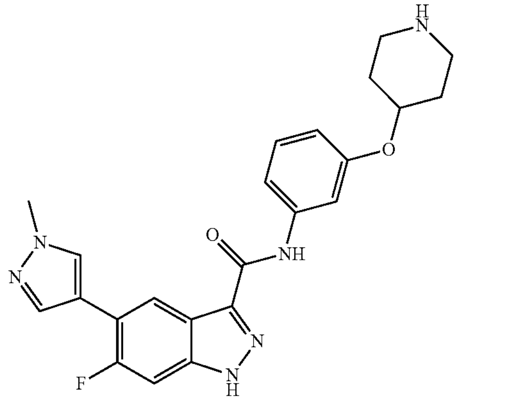 [SMILES: Cn1cc(-c2cc3c(C(=O)Nc4cccc(OC5CCNCC5)c4)n[nH]c3cc2F)cn1]
150
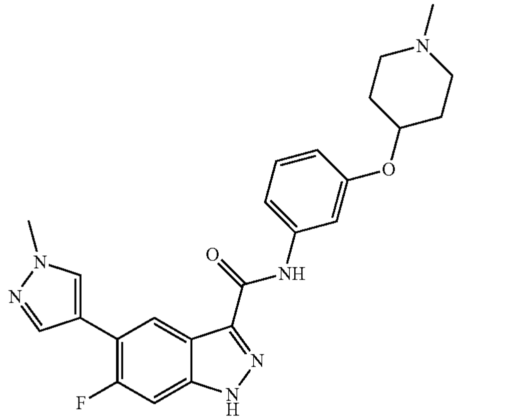 [SMILES: CN1CCC(Oc2cccc(NC(=O)c3n[nH]c4cc(F)c(-c5cnn(C)c5)cc34)c2)CC1]
151
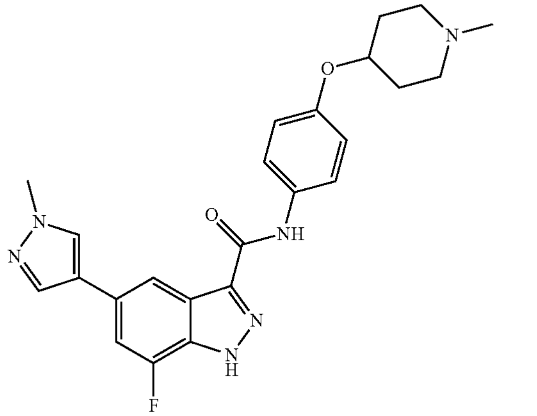 [SMILES: CN1CCC(Oc2ccc(NC(=O)c3n[nH]c4c(F)cc(-c5cnn(C)c5)cc34)cc2)CC1]
152
TABLE 1-continued
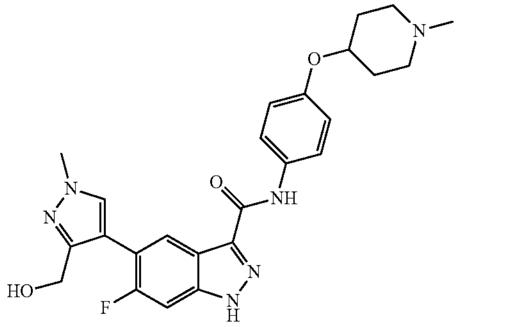 [SMILES: CN1CCC(Oc2ccc(NC(=O)c3n[nH]c4cc(F)c(-c5cn(C)nc5CO)cc34)cc2)CC1]
153
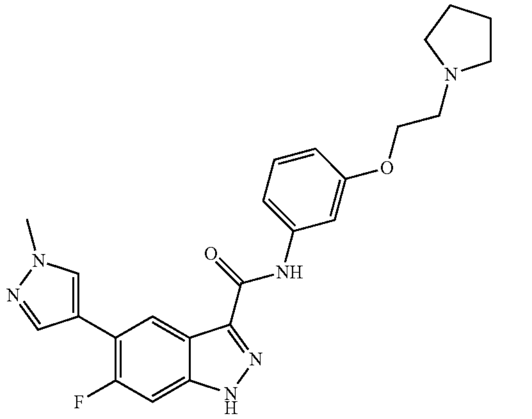 [SMILES: Cn1cc(-c2cc3c(C(=O)Nc4cccc(OCCN5CCCC5)c4)n[nH]c3cc2F)cn1]
154
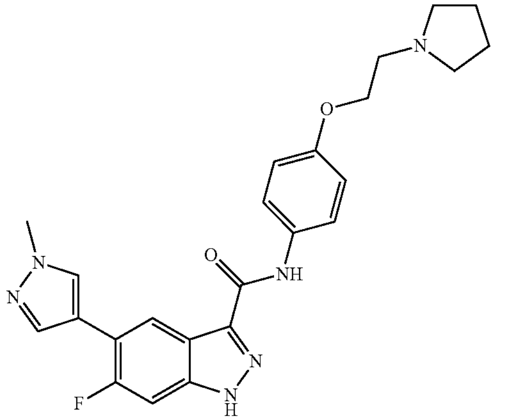 [SMILES: Cn1cc(-c2cc3c(C(=O)Nc4ccc(OCCN5CCCC5)cc4)n[nH]c3cc2F)cn1]
155
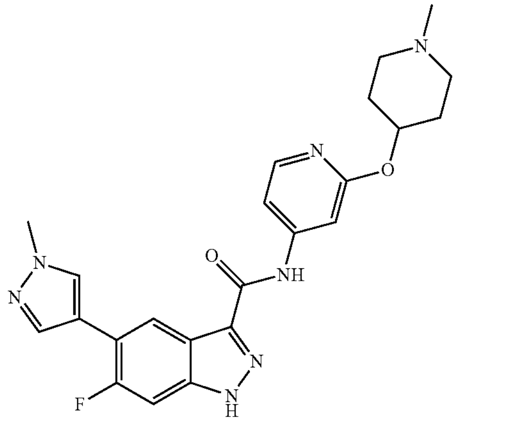 [SMILES: CN1CCC(Oc2cc(NC(=O)c3n[nH]c4cc(F)c(-c5cnn(C)c5)cc34)ccn2)CC1]
156

TABLE 1-continued
157
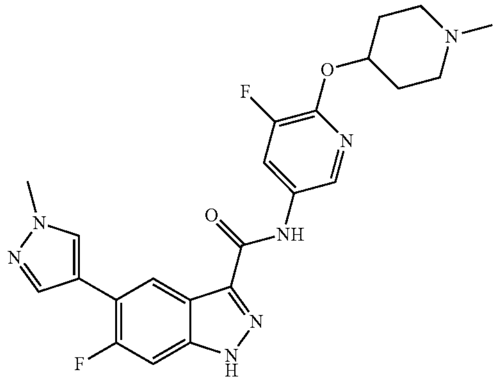 [SMILES: CN1CCC(Oc2ncc(NC(=O)c3n[nH]c4cc(F)c(-c5cnn(C)c5)cc34)cc2F)CC1]
158
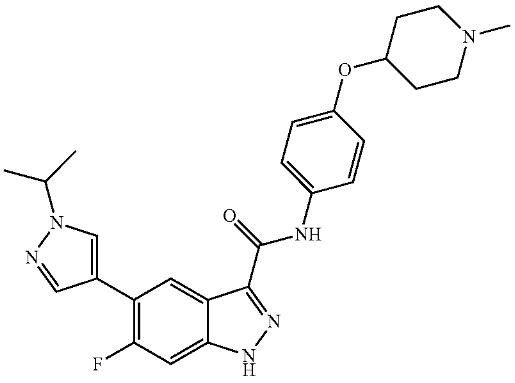 [SMILES: CC(C)n1cc(-c2cc3c(C(=O)Nc4ccc(OC5CCN(C)CC5)cc4)n[nH]c3cc2F)cn1]
159
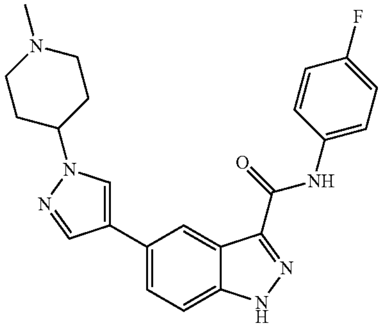 [SMILES: CN1CCC(n2cc(-c3ccc4[nH]nc(C(=O)Nc5ccc(F)cc5)c4c3)cn2)CC1]
160
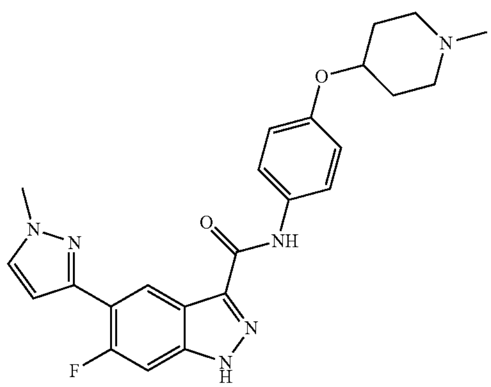 [SMILES: CN1CCC(Oc2ccc(NC(=O)c3n[nH]c4cc(F)c(-c5ccn(C)n5)cc34)cc2)CC1]
161
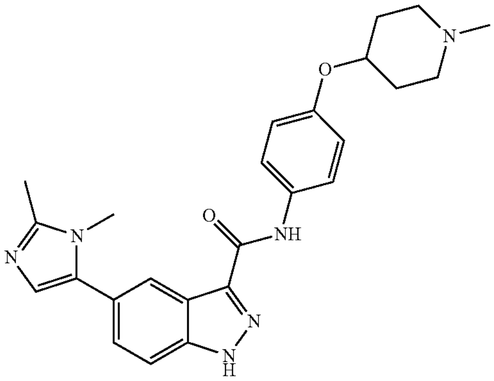 [SMILES: Cc1ncc(-c2ccc3[nH]nc(C(=O)Nc4ccc(OC5CCN(C)CC5)cc4)c3c2)n1C]
162
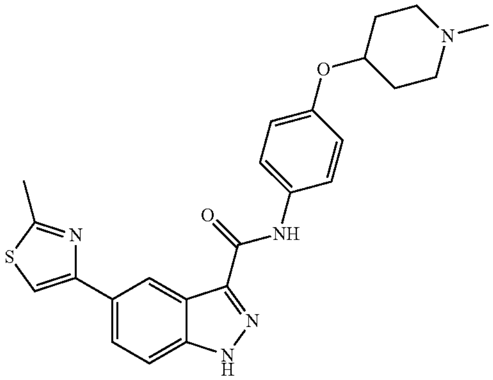 [SMILES: Cc1nc(-c2ccc3[nH]nc(C(=O)Nc4ccc(OC5CCN(C)CC5)cc4)c3c2)cs1]
163
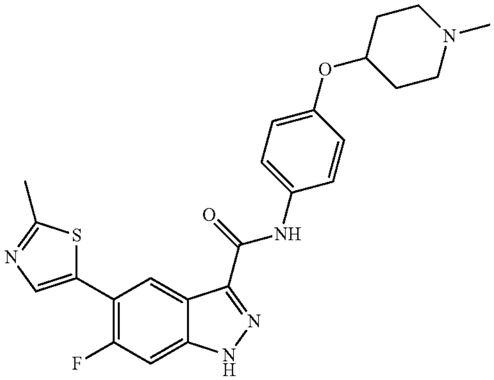 [SMILES: Cc1ncc(-c2cc3c(C(=O)Nc4ccc(OC5CCN(C)CC5)cc4)n[nH]c3cc2F)s1]
164
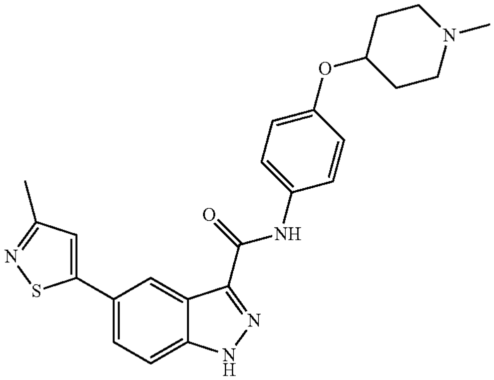 [SMILES: Cc1cc(-c2ccc3[nH]nc(C(=O)Nc4ccc(OC5CCN(C)CC5)cc4)c3c2)sn1]
Administration and Pharmaceutical Compositions
Some embodiments include administration of the compounds described herein as pharmaceutical compositions comprising: (a) a safe and therapeutically effective amount of the indazole-3-carboxamide, or its corresponding enantiomer, diastereoisomer or tautomer, or pharmaceutically acceptable salt; and (b) a pharmaceutically acceptable carrier.

In some embodiments, the methods described herein further include administering the compounds of this invention in combination (administered together or sequentially) with other known agents.

Non-limiting examples of diseases which can be treated with a combination of a compound of Formula (I) and other another active agent are colorectal cancer, ovarian cancer, chronic inflammation, diabetic retinopathy, pulmonary fibrosis, and osteoarthritis. For example, a compound of Formula (I) can be combined with one or more chemotherapeutic compounds.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELOD®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIC), Gemcitabine (GEMZAR®), Cyclophosphamide)(CYTOXAN®, Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZ S-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™) vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or more typically in combination with a conventional pharmaceutical carrier, excipient or the like. The term “excipient” is used herein to describe any ingredient other than the compound(s) of the disclosure. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, UK. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG’s, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

In some embodiments, the compositions can be administered by transdermal patch.

Other modes of deliveries include using biodegradable or non-biodegradable scaffolds.

It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome. In another embodiment, the kit can include a compound or composition as described herein and a label that indicates that the contents are to be administered to a patient with one or more diseases or conditions independently selected from the group consisting of a tendinopathy, dermatitis, psoriasis, morphea, ichthyosis, Raynaud's syndrome, and Darier's disease; and/or for promoting wound healing.

The actual dose of the active compounds of the present invention depends on the specific compound, and on the condition to be treated; the selection of the appropriate dose is well within the knowledge of the skilled artisan.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated.

Non-limiting examples include one or more diseases or conditions independently selected from the group consisting of a tendinopathy, dermatitis, psoriasis, morphea, ichthyosis, Raynaud's syndrome, and Darier's disease. In certain embodiments, the compounds and compositions provided herein can be used for promoting wound healing.

In some embodiments, the methods further include administering to a patient in need of such treatment an effective amount of one or more of the compounds of Formula (I), in combination (simultaneously or sequentially) with at least one other agent.

In some embodiments, the methods further include administering a pharmaceutical composition that includes a therapeutically effective amount of a compound of Formula (I), or a pharmaceutically acceptable salt thereof, and a pharmaceutically acceptable excipient and optionally at least one other agent.

In some embodiments, the one or more diseases or conditions is a tendinopathy. In certain embodiments, the tendinopathy is tendinosis. In certain embodiments, the tendinopathy is tendinitis. In certain embodiments, the tendinopathy is tenosynovitis.

A tendon is a band of fibrous connective tissue that usually connects muscle to bone. Healthy tendons include parallel arrays of type I collagen fibers closely packed together, but also include a small amount of elastin and of proteoglycans. Tendons can be slow to heal if injured, and sometimes do not regain their original strength. Partial tears heal by the rapid production of disorganized type-III collagen, which is weaker than normal tendon. Recurrence of injury in the damaged region of tendon is common.

Tendons which may be treated by the methods of the invention include any tendon of the human or mammalian body. Non-limiting examples of tendons include the patellar tendon, the anterior tibialis tendon, the Achilles tendon, the hamstring tendon, the semitendinosus tendon, the gracilis tendon, the abductor tendon, the adductor tendon, the supraspinatus tendon, the infraspinatus tendon, the subscapularis tendon, the teres minor tendon, the flexor tendon, the rectus femoris tendon, the tibialis posterior tendon, and the quadriceps femoris tendon.

In some embodiments, the tendon is a tendon of the foot or ankle; e.g., the extensor hallucis longus, the flexor hallucis longus, the extensor digitorum longus, the extensor digitorum brevis, the peroneus longus, the peroneus brevis, the flexor hallucis brevis, the flexor digitorum longus, the posterior tibialis, the Achilles tendon, and the plantar fascia.

In some embodiments, the tendon is a tendon of the leg; e.g., the patellar tendon, the anterior tibialis tendon, the Achilles tendon, the hamstring tendon, the semitendinosus tendon, the gracilis tendon, the abductor tendon, the adductor tendon, the flexor tendon, the rectus femoris tendon, the tibialis posterior tendon, and the quadriceps femoris tendon.

In some embodiments, the tendon is a tendon of the shoulder; e.g., the supraspinatus tendon, the infraspinatus tendon, the subscapularis tendon, and the teres minor tendon (rotator cuff complex).

In some embodiments, the tendon is a tendon of the elbow; e.g., the biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris and the digitorum superficialis. In some embodiments, the tendon is a tendon of the wrist. In some embodiments, the tendon of the wrist is selected from the group consisting of biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris, the digitorum superficialis, the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus. In some embodiments, the tendon is a tendon of the hand. In some embodiments, the tendon of the hand is selected from the group consisting of the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus.

Non-limiting examples of tendinopathies include: clavicular or patellar tendinopathy, patellar tendonitis; medial tibial stress syndrome; Achilles tendinopathy, lateral epicondylitis or "tennis elbow;" medial epicondylitis or "golfer's elbow;" plantar fasciitis; and rotator cuff tendinopathy.

In some embodiments, the tendinopathy is rotator cuff tendinopathy; e.g., supraspinatus tendinopathy, infraspinatus tendinopathy, subscapularis tendinopathy, and teres minor tendinopathy.

In some embodiments, the tendinopathy is lateral epicondylitis or "tennis elbow" at the extensor muscle group origin at the lateral humeral condyle insertion, principally in the extensor carpi radialis brevis (ECRB) tendon. In some embodiments, the tendinopathy is medial epicondylitis or "golfer's elbow" at the interface between the pronator teres and flexor carpi radialis origin of the medial humeral condyle.

In some embodiments, the tendinopathy is patellar tendinopathy. In some embodiments, the tendinopathy is Achilles tendinopathy. In some embodiments, the tendinopathy is plantar fasciitis. In some embodiments, the tendinopathy is medial plantar fasciitis. In some embodiments, the tendinopathy is lateral plantar fasciitis.

In some embodiments, the tendinopathy is tendinosis. In some embodiments, the tendinosis is selected from the group consisting of extensor hallucis longus tendinosis, flexor hallucis longus tendinosis, extensor digitorum longus tendinosis, extensor digitorum brevis tendinosis, peroneus longus tendinosis, peroneus brevis tendinosis, flexor hallucis brevis tendinosis, flexor digitorum longus tendinosis, posterior tibialis tendinosis, Achilles tendon tendinosis, and plantar fascia tendinosis. In some embodiments, the tendinosis is selected from the group consisting of patellar tendinosis, the anterior tibialis tendinosis, the hamstring tendinosis, semitendinosus tendinosis, gracilis tendinosis, abductor tendinosis, and adductor tendinosis. In some embodiments, the tendinosis is selected from the group consisting of flexor tendinosis, rectus femoris tendinosis, tibialis posterior tendinosis, and quadriceps femoris tendinosis. In some embodiments, the tendinosis is selected from the group consisting of supraspinatus tendinosis, infraspinatus tendinosis, subscapularis tendinosis, and teres minor tendinosis.

In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis and digitorum superficialis tendinosis. In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis, digitorum superficialis tendinosis, flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis. In some embodiments, the tendinosis is selected from the group consisting of flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis.

In some embodiments, the tendinopathy is tendinitis. In some embodiments, the tendinitis is selected from the group consisting of extensor hallucis longus tendinitis, flexor hallucis longus tendinitis, extensor digitorum longus tendinitis, extensor digitorum brevis tendinitis, peroneus longus tendinitis, peroneus brevis tendinitis, flexor hallucis brevis tendinitis, flexor digitorum longus tendinitis, posterior tibialis tendinitis, Achilles tendon tendinitis, and plantar fascia tendinitis. In some embodiments, the tendinitis is selected from the group consisting of patellar tendinitis, the anterior tibialis tendinitis, the hamstring tendinitis, semitendinosus tendinitis, gracilis tendinitis, abductor tendinitis, and adductor tendinitis. In some embodiments, the tendinitis is selected from the group consisting of flexor tendinitis, rectus femoris tendinitis, tibialis posterior tendinitis, and quadriceps femoris tendinitis. In some embodiments, the tendinitis is selected from the group consisting of supraspinatus tendinitis, infraspinatus tendinitis, subscapularis tendinitis, and teres minor tendinitis.

In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis and digitorum superficialis tendinitis. In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis, digitorum superficialis tendinitis, flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, and extensor pollicis longus tendinitis. In some embodiments, the tendinitis is selected from the group consisting of flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, calcific tendinitis, and extensor pollicis longus tendinitis.

In some embodiments, the tendinitis is caused by chronic overuse injuries of tendon failed healing.

In some embodiments, the injury or damage is localized very near the muscle-tendon junction (myotendinous junction).

In some embodiments, the tendinitis leads to scarring and fibrosis.

The methods of the invention may result in improvement in one or more of the following: decreasing pain of the affected joint or limb, decreasing stiffness of the affected joint or limb, increasing mobility of the affected joint or limb, increasing strength of the affected joint or limb, decreasing the rate of tendinopathy progression, decreasing inflammation, increasing the strength of the tendon, or improving the rate of tendon strength recovery. Various methods for measuring effectiveness of the treatment include, but are not limited to: Disabilities of the Arm, Shoulder and Hand Score (DASH), Visual Analog Score (VAS), and grip strength testing.

In some embodiments, the treatment results in increased strength of the tendon. In some embodiments, the treatment results in a more rapid rate of tendon strength recovery. In some embodiments, the treatment results in an increase in tendon strength of about 30%, about 40%, about 50%, about 60%, about 70%, about 80%, about 90% within about 1, 2, 3, 4, 5, 6, 7, 8, 9, 10, 11, 12, 13, 14, 15, 16, 17, 18, 19, 20, or 21 days of administration of a compound of the invention, as compared to baseline.

The methods of the invention may include preventive treatments.

In some embodiments, the administering is by direct injection to the affected site. In some embodiments, the direct injection is accomplished using the "peppering technique" with or without ultrasound guidance. The "peppering technique" is an injection method whereby after the needle is inserted into the tender area, multiple small injections are performed by withdrawing, redirecting and reinserting the needle without emerging from the skin.

In some embodiments, the methods can further include administering one or more other therapeutic regimens and/or agents effective for treating a tendinopathy, e.g., palliative care, with treatment focusing on anti-inflammatory measures, including treatment with nonsteroidal anti-inflammatory drugs (NSAIDs), steroid injections, cortisone injections, platelet rich plasma (PRP) injections, physical therapy, shock wave therapy, low-level laser therapy (phototherapy), cell therapy, and sclerotherapy.

In some embodiments, the one or more diseases or conditions is psoriasis. Non-limiting examples include: psoriasis vulgaris (including nummular psoriasis and plaque psoriasis); generalized pustular psoriasis (including impetigo herpetiformis and von Zumbusch's disease); acrodermatitis continua; erythrodermic psoriasis; pustulosis palmaris et plantaris; guttate psoriasis; arthropathic psoriasis; other psoriasis (including inverse psoriasis).

In some embodiments, the one or more diseases or conditions is dermatitis. Non-limiting examples include: atopic dermatitis, contact dermatitis (e.g., allergic contact dermatitis, irritant contact dermatitis), stasis dermatitis, dermatitis that led up to steroid dermatitis, steroid-resistant dermatitis, dermatitis to which tacrolimus is not applicable, chronic dermatitis, erythroderma (e.g., erythroderma posteczematosa and erythroderma secondary to dermatoses, toxic erythroderma, infantile desquamative erythroderma, and paraneoplastic erythroderma), eczema, nummular eczema, dyshidrotic eczema, asteatotic eczema, seborrheic dermatitis, autosensitization dermatitis, stasis dermatitis, urticaria, drug eruption, dermal vasculitis, prurigo, pruritus cutaneus, erythema (e.g. nodosum or multiforme), rosacea, rosacea-like dermatitis, lichen planus, photo-induced dermatitis, or follicular keratosis. In certain embodiments, the dermatitis is contact dermatitis, e.g., allergic contact dermatitis, e.g., resulting from direct skin contact with a substance such as poison ivy, poison oak, or poison sumac.

In some embodiments, the one or more diseases or conditions is scleroderma. Non-limiting examples include: localized scleroderma (including morphea and linear scleroderma) and systemic scleroderma (systemic sclerosis) (including diffuse scleroderma and limited scleroderma (also known as CREST which includes calcinosis, Raynaud's phenomenon, esophageal dysfunction, sclerodactyly, and elangiectasia)).

In some embodiments, the one or more diseases or conditions is morphea.

In some embodiments, the one or more diseases or conditions is ichthyosis.

In some embodiments, the one or more diseases or conditions is Darier's disease.

In some embodiments, the methods can further include administering one or more other therapeutic regimens and/or agents effective in treating a skin disorder described herein, e.g., corticosteroids, immune modulators, vitamin D3 and its analogs, retinoic acids and their pharmaceutically active derivatives, or combinations thereof. Specific non-limiting examples of drugs include betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, prednisone, Benadryl, tacrolimus, picrolimus, tazarotene, isotretinoin, cyclosporin, anthralin, vitamin D3, cholecalciferol, calcitriol, calcipotriol, tacalcitol, calcipotriene, Gossypol, 4-hydroxyestradiol, 2-hydroxyestradiol, 2-hydroxyestrone, 2-benzimidazolylthioacetamide-N-ethyl-2-benzyl (KH7.102), an antibody, a nucleic acid, or combinations thereof.

In some embodiments, the one or more diseases or conditions is Raynaud's syndrome.

Other disorders and diseases in which aberrant Wnt signaling is implicated include cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

- a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.
- a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions provided herein have been found to possess immunomodulatory activities and are expected to control the innate immune system (e.g. macrophages and T cells) and suppress pro-inflammatory cytokine release (e.g. TNF, IL-6) which is well known to be involved in chronic inflammation in a wide variety of disease areas. Therefore compounds and compositions provided herein can used to treat chronic inflammation associated with disorders and diseases including but not limited to eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

The compounds and compositions provided herein can be used as inhibitors and/or modulators of the enzyme DYRK1A, and thus can be used to treat a variety of disorders and diseases associated with tau protein, amyloid or alpha-synuclein pathology including, but not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is the pain and inflammation associated with cancer.

In some embodiments, the disorder or disease is the pain and inflammation associated with a joint.

In some embodiments, the disorder or disease is the pain and inflammation associated with the knee.

In some embodiments, the disorder or disease is the pain and inflammation associated with the hip.

In some embodiments, the disorder or disease is the pain and inflammation associated with the shoulder.

In some embodiments, the disorder or disease is the pain and inflammation associated with arthritis.

In some embodiments, the disorder or disease is the pain and inflammation associated with gastrointestinal disorders.

In some embodiments, the disorder or disease is the pain and inflammation associated with pulmonary disorders.

In some embodiments, the disorder or disease is the pain and inflammation associated with allergies.

In some embodiments, the disorder or disease is the pain and inflammation associated with skin disorders.

In some embodiments, the disorder or disease is the pain and inflammation associated with diabetes.

In some embodiments, the disorder or disease is the pain and inflammation associated with pancreatitis.

In some embodiments, the disorder or disease is the pain and inflammation associated with tendonitis.

In some embodiments, the disorder or disease is the pain and inflammation associated with heart disease.

In some embodiments, the disorder or disease is the pain and inflammation associated with lupus.

In some embodiments, the disorder or disease is the pain and inflammation associated with a neurological disorder.

In some embodiments, the disorder or disease is the pain and inflammation associated with multiple sclerosis.

In some embodiments, the disorder or disease is the pain and inflammation associated with Parkinson's.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is degenerative disk disease.

In some embodiments, the disorder or disease is a neurological disorder.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the disorder or disease is a neurological disease or disorder associated with tau protein, amyloid or alpha-synuclein pathology.

In some embodiments, the disorder or disease is selected from the group consisting of: Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, a compound of Formula (I) inhibits DYRK1A.

In some embodiments, a compound of Formula (I) inhibits GSK3.

In some embodiments, a compound of Formula (I) inhibits GSK3β.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$. or $G_{.1}$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

In another example, in vitro assays for DYRK1A biological activity may be used, e.g. regulation of microtubule-associated protein tau (MAPT/Tau) phosphorylation in neuronal cell line such as the human SH-SY5Y neuroblastoma cell line. Assays for DYRK1A-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1A-regulated phosphorylation uses the SH-SY5Y cells cultured in a 96 well plate format for a period of time sufficient to stabilize microtubules and Tau phosphorylation, usually at least 2 days, then treated with a 1/3 serial dilution of compounds overnight and lysed. The cell lysate is resolved by SDS PAGE, then transferred to nitrocellulose and probed with an antibody specific for pSer396 Tau. The chemiluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by ELISA by adding the lysate mentioned above onto total Tau-coated plates and detected with a specific pSer396 antibody. Colorimetric detection of ELISA signal is performed by Cytation3 plate reader (Biotek).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations,* $2^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis,* 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:

brine=saturated aqueous sodium chloride
$CDCl_3$=deuterated chloroform
DAST=diethylaminosulfur trifluoride
DCE=dichloroethane
DCM=dichloromethane
DHP=3,4-dihydro-2H-pyran
DIBAL=diisobutylaluminium hydride
DIPEA=N,N-diisopropylethylamine
DMAP=4-dimethylaminopyridine
DMF=N,N-dimethylformamide
DMSO-$d_6$=deuterated dimethylsulfoxide
ESIMS=electron spray mass spectrometry
EtOAc=ethyl acetate
$Et_3SiH$=triethylsilane
HATU=1-[Bis(dimethylamino)methylene]-1H-1,2,3-triazolo[4,5-b]pyridinium 3-oxid hexafluorophosphate
HCl=hydrochloric acid
HOAc=acetic acid
KOAc=potassium acetate
$K_3PO_4$=potassium phosphate
LAH=lithium aluminum hydride
MeCN=acetonitrile
MeOH=methanol
$MgSO_4$=magnesium sulfate
MsCl=methanesulfonyl chloride (mesyl chloride)
MW=microwave irradiation
$NaBH_3CN$=sodium cyanoborohydride
$NaBH(OAc)_3$=sodium triacetoxy borohydride $NaHCO_3$=sodium bicarbonate NMR=nuclear magnetic resonance Pd/C=palladium on carbon $PdCl_2(dppf)_2$=1, 1'-bis(diphenylphosphino)ferrocene-palladium(II)dichloride $Pd(PPh_3)_2Cl_2$=dichloro-bis(triphenylphosphine)palladium (II)

$Pd(PPh_3)_4$=tetrakis(triphenylphosphine)palladium(0)

PPTS=pyridinium p-toluenesulfonate r.t.=room temperature

TEA=triethylamine

TFA=trifluoroacetic acid

THF=tetrahydrofuran

TLC=thin layer chromatography

Tr-Cl=triphenylmethyl chloride (trityl chloride)

TsCl=4-Toluenesulfonyl chloride (tosyl chloride)

The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formula I of the present disclosure can be prepared as depicted in Scheme 1.

Scheme 1

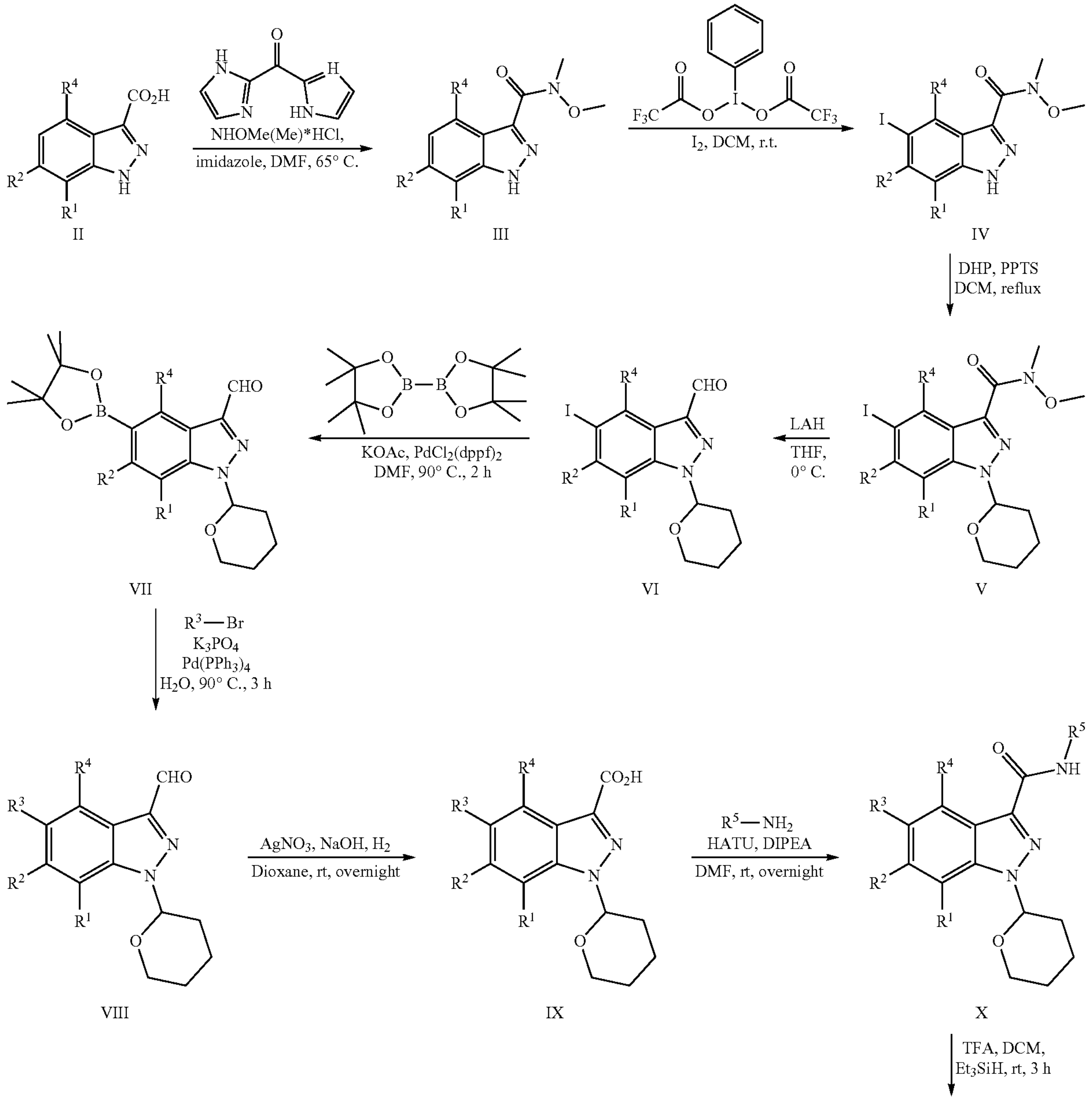

II III IV V VI VII VIII IX X

-continued

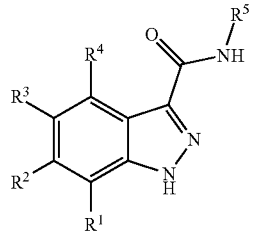

I

Scheme 1 describes a method for preparation of indazole-3-carboxamide derivatives (I) by first forming the Weinreb amide (III) of a 1H-indazole-3-carboxylic acid (II). The Weinreb amide (III) is reacted with (bis(trifluoroacetoxy) iodo)benzene to produce the 5-iodo-1H-indazole-3-carboxylic acid (IV) followed by THP protection of the indazole nitrogen. The Weinreb amide of protected indazole V is reduced to aldehyde VI followed by reaction with bis (pinacolato)diboron to give the pinacol ester (VII). Suzuki coupling with a variety of aromatic and nonaromatic bromides yields the $R^3$ substituted indazole VIII. Oxidation of the aldehyde to the acid (IX) followed by HATU mediated coupling of a variety of amines and sequent deprotection produces the desired indazole-3-carboxamide derivatives (I).

Compounds of Formula I of the present disclosure can also be prepared as depicted in Scheme 2.

Scheme 2

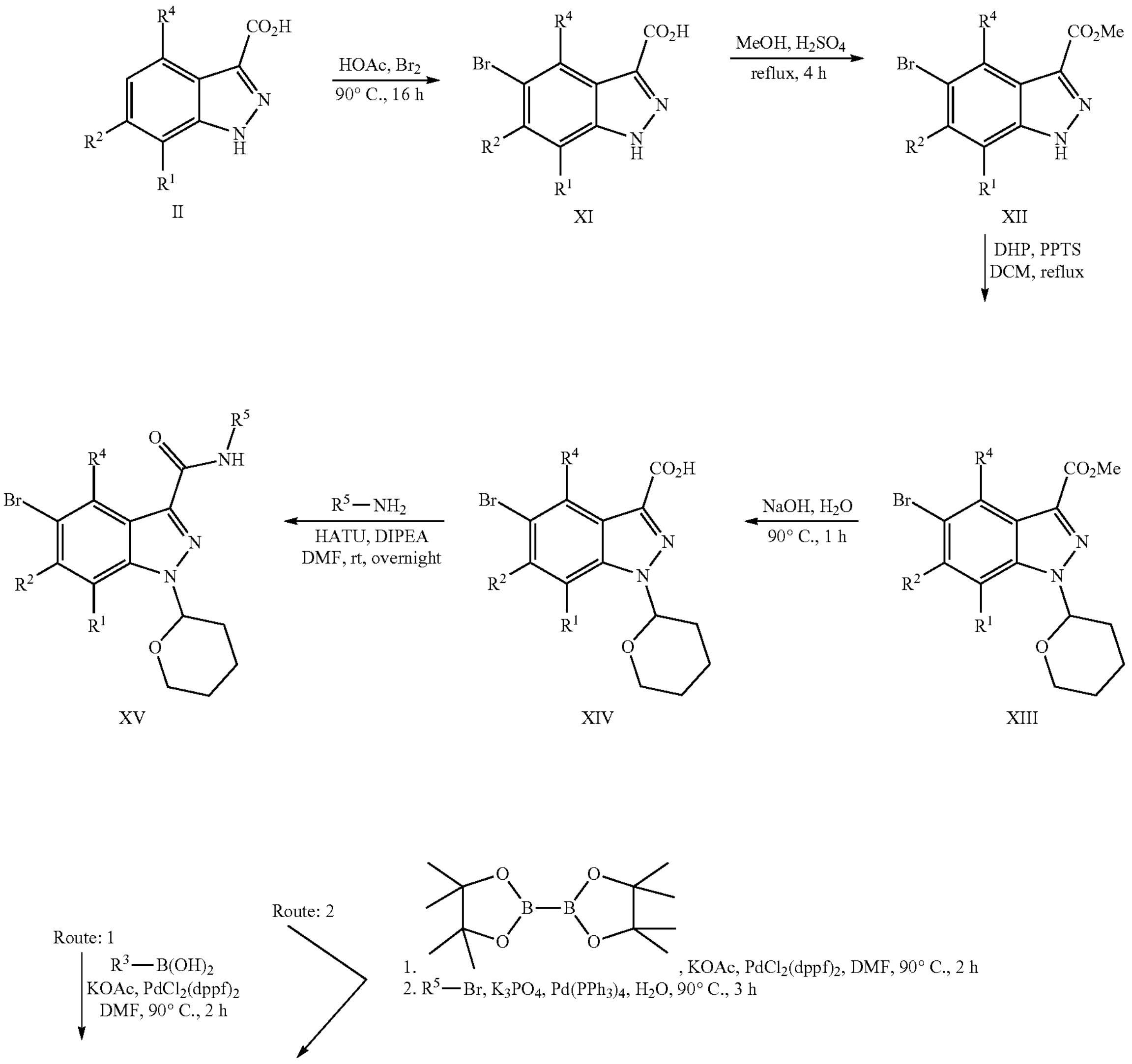

II XI XII XV XIV XIII

-continued

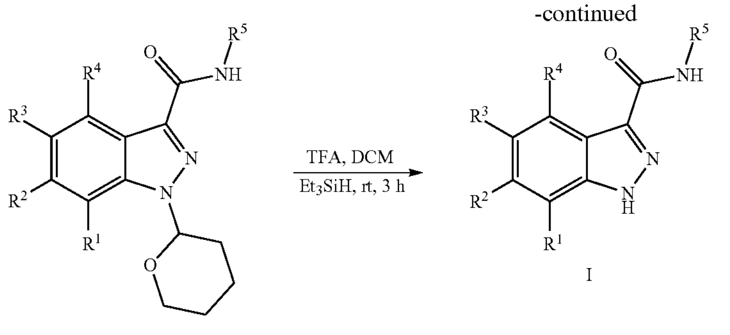

X

I

Scheme 2 describes an alternative method for preparation of indazole-3-carboxamide derivatives (I) by bromination of the indazole 5-position followed by esterification to form ester XII. The indazole nitrogen is THP protected and the ester is hydrolyzed to acid XIV. The acid is coupled with a variety of amines to produce amide XV which is then coupled with a variety of boronic acids (Route 1) to give X. Alternatively, XV can be converted to the boronate ester and then couple to a variety of bromides (Route 2) to yield X. Final deprotection of the indazole nitrogen yields the desired indazole-3-carboxamide derivatives (I).

Compounds of Formula I of the present disclosure can also be prepared as depicted in Scheme 3.

Scheme 3

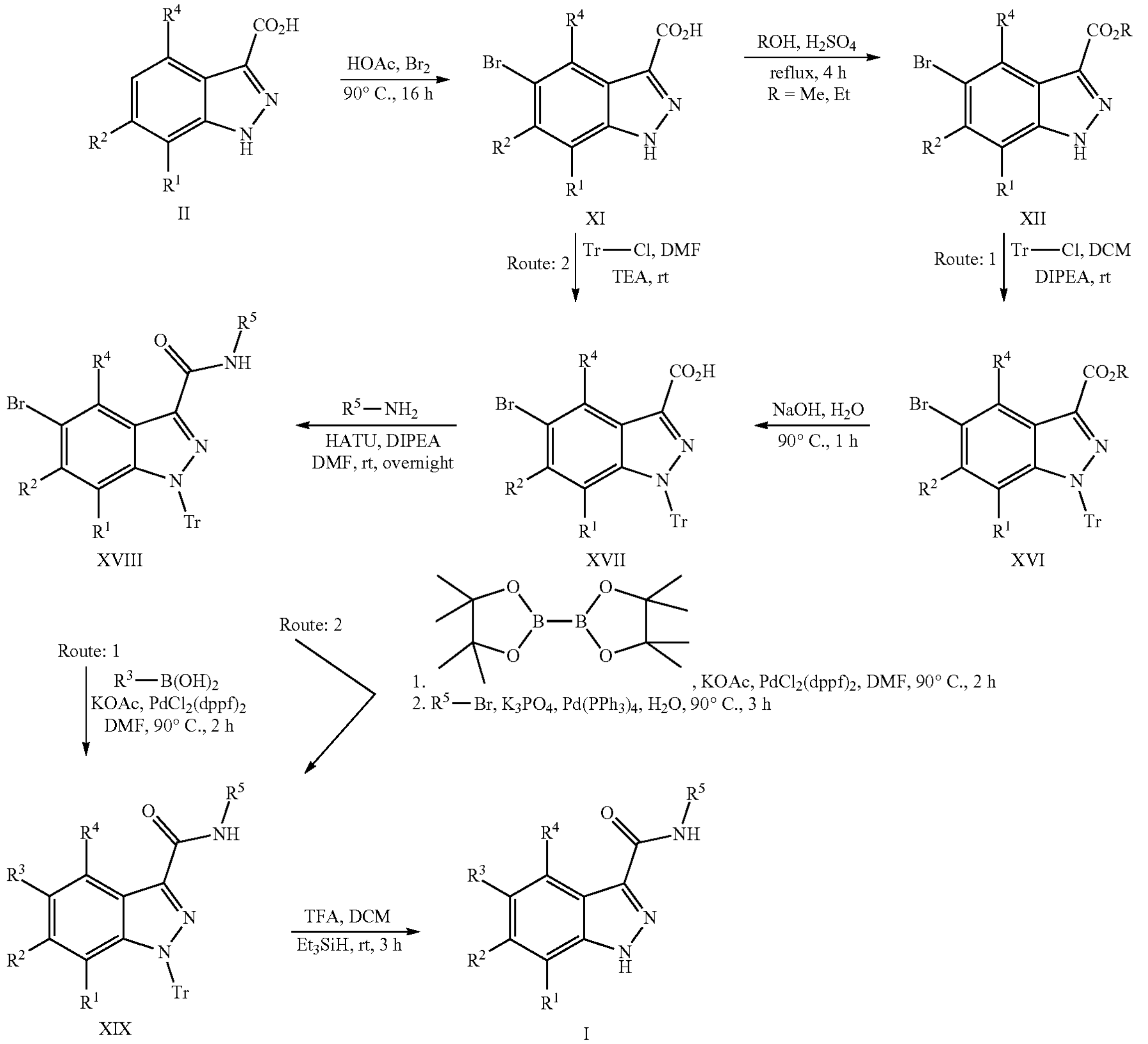

Scheme 3 describes another alternative method for preparation of indazole-3-carboxamide derivatives (I) by bromination of the indazole 5-position followed by either Route 1: esterification to form ester XII, then trityl protection of the indazole nitrogen and then finally hydrolyzed of the ester to acid XVII; or Route 2: trityl protection of the indazole nitrogen directly to acid XVII. The acid is coupled with a variety of amines to produce amide XVIII which is then coupled with a variety of boronic acids (Route 3) to give XIX. Alternatively, XVIII can be converted to the boronate ester and then couple to a variety of bromides (Route 4) to yield XIX. Final deprotection of the indazole nitrogen yields the desired indazole-3-carboxamide derivatives (I).

The following are commercially available intermediates.

XX

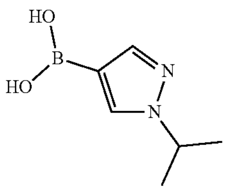

Combi Blocks Inc.

XXI

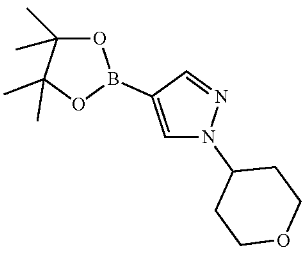

Combi Blocks Inc.

XXII

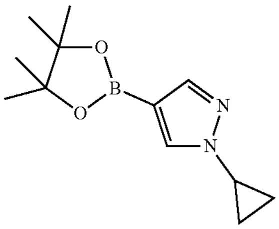

Combi Blocks Inc.

XXIII

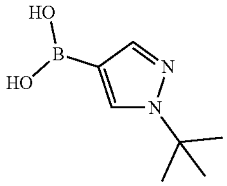

Combi Blocks Inc.

XXIIV

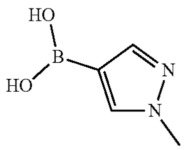

Combi Blocks Inc.

-continued

XXV

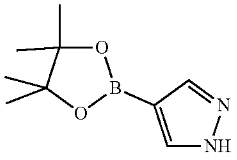

Combi Blocks Inc.

XXVI

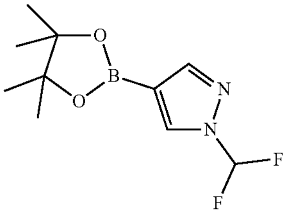

Combi Blocks Inc.

XXVII

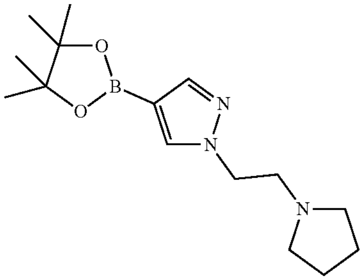

Combi Blocks Inc.

XXVIII

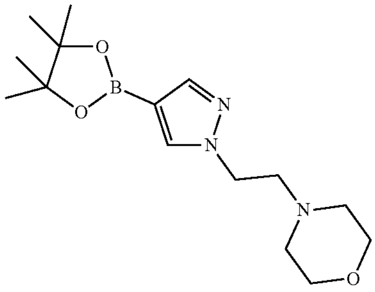

Combi Blocks Inc.

XXIX

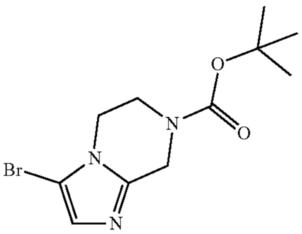

Combi Blocks Inc.

XXX

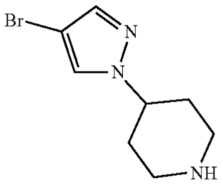

Combi Blocks Inc.

-continued
XXXI
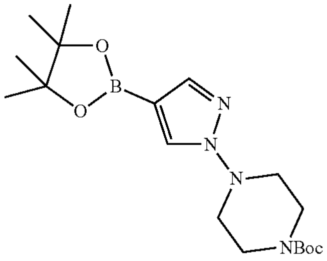
Advanced ChemBlocks, Inc.
XXXII
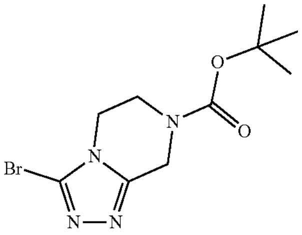
J&W Pharmlab LLC
XXXIII
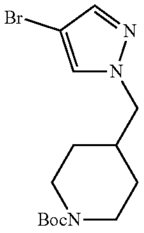
Enamine Ltd
XXXIX
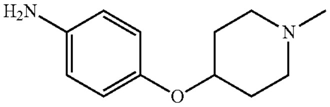
ChemBridge Corporation
XXXV
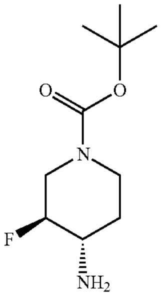
Synthonix
XXXVI
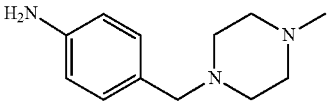
Combi Blocks Inc.
-continued
XXXVII
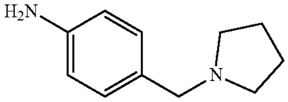
Combi Blocks Inc.
XXXVIII
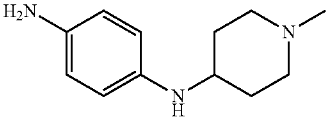
Aldrich
XXXIX
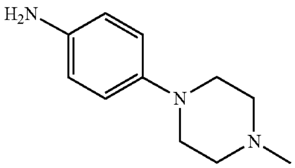
Combi Blocks Inc.
XL
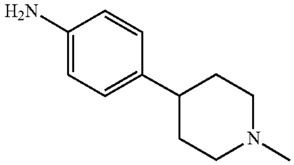
J&W Pharmlab LLC
XLI
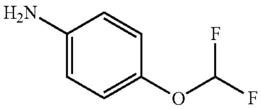
Combi Blocks Inc.
XLII
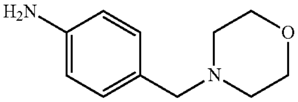
Combi Blocks Inc.
XLIII
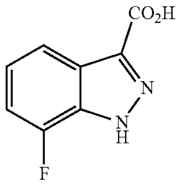
J&W Pharmlab LLC
XLIV
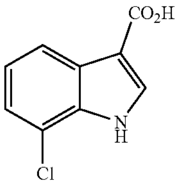
J&W Pharmlab LLC -continued

XLV

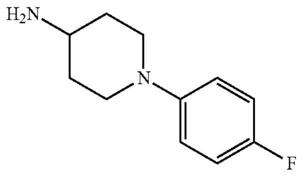

ChemBridge Corporation

XLVI

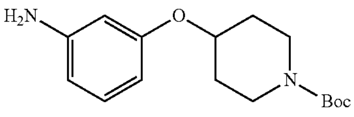

AstaTech Inc.

XLVII

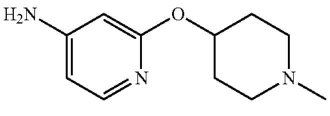

Enamine Ltd

XLVIII

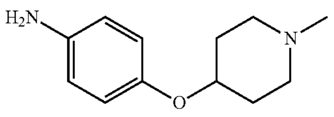

ChemBridge Corporation

Illustrative Compound Examples

Preparation of intermediate 5-bromo-1-(tetrahydro-2H-pyran-2-yl)-1H-indazole-3-carboxylic acid (LII) is depicted below in Scheme 4

Scheme 4

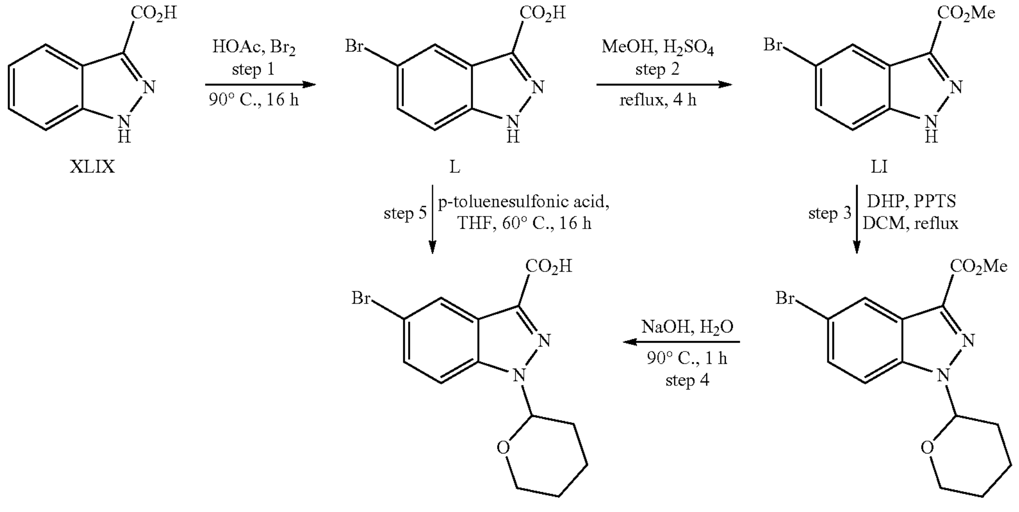

XLIX, L, LI, LII, LIII

Step 1

A suspension of indazole-3-carboxylic acid (XLIX) (1.0 g, 6.16 mmol) in glacial acetic acid (60 mL) was heated at 120° C. to get a clear solution. The solution was cooled to 90° C. A solution of bromine (0.633 mL, 12.33 mmol) in glacial acetic acid (2 mL) was added slowly to the solution while heating at 90° C. The solution was further heated 16 h at 90° C. The solution was cooled to room temperature, poured into ice water and further stirred at room temperature for 15 min. The solids formed were filtered, washed with cold water and dried under vacuum at room temperature to get 5-bromo-1H-indazole-3-carboxylic acid (L) as a white solid (1.30 g, 5.39 mmol, 87.5% yield). $^1H$ NMR (DMSO-$d_6$) δ ppm 13.95 (s, 1H), 13.18 (br s, 1H), 8.21 (d, J=1.2 Hz, 1H), 7.65 (d, J=7.0 Hz, 1H), 7.56 (dd, J=7.0, 1.2 Hz, 1H); ESIMS found for $C_8H_4BrN_2O_2$ m/z 242.0 (M+H).

Step 2

Concentrated sulfuric acid (1 mL) was added to a suspension of 5-bromo-1H-indazole-3-carboxylic acid (L) (1.30 g, 5.39 mmol) in dry MeOH (50 mL) and heated to reflux for 4 h under argon. The solution was cooled to room temperature and the MeOH was evaporated under vacuum. The residue was dissolved in EtOAc and washed with water. The organic phase was dried over $Na_2SO_4$, filtered and concentrated to afford methy 5-bromo-1H-indazole-3-carboxylate (LI) as a white solid (1.35 g, 5.29 mmol, 98% yield). $^1H$ NMR (DMSO-$d_6$) δ ppm 14.13 (s, 1H), 8.21 (d, J=1.6 Hz, 1H), 7.67 (d, J=7.2 Hz, 1H), 7.59 (dd, J=7.2, 1.2 Hz, 1H), 3.92 (s, 3H); ESIMS found for $C_9H_7BrN_2O_2$ m/z 256.0 (M+H).

Step 3

A suspension of methyl 5-bromo-1H-indazole-3-carboxylate (LI) (1.35 g, 5.29 mmol), pyridinium p-toluenesulfonate (0.143 g, 0.56 mmol) and 3,4 dihydro-2H-pyran (1.02 mL, 11.90 mmol) in anhydrous dichloroethane (20 mL) was refluxed 5 h under argon. The suspension was turned into the clear solution. The solution was cooled and the excess solvent was evaporated under vacuum. The residue was dissolved in EtOAc and washed with dilute $NaHCO_3$ solution (sat[d]. $NaHCO_3$ sol''/$H_2O$: 1:9). The organic layer was dried over $Na_2SO_4$, filtered and concentrated. The residue was purified by column chromatography (100% hexanes→5:95 EtOAc:hexanes) to get methyl 5-bromo-1-(tetrahydro-2H-pyran-2-yl)-1H-indazole-3-carboxylate (LIII) as a white solid (1.47 g, 4.34 mmol, 82% yield). $^1H$ NMR (DMSO-$d_6$) δ ppm 8.22 (d, J=1.4 Hz, 1H), 7.89 (d, J=7.2 Hz, 1H), 7.68 (dd, J=7.2, 1.6 Hz, 1H), 6.02 (dd, J=8.0, 2.4 Hz, 1H), 3.94 (s, 3H), 3.88 (m, 1H), 3.79 (m, 1H), 2.37-2.31 (m, 1H), 2.05-1.96 (m, 2H), 1.77-1.73 (m, 1H). 1.60-1.58 (m, 2H); ESIMS found for $C_{13}H_{15}BrN_2O_3$ m/z 340.0 (M+H).

Step 4

2 N Aqueous NaOH solution (10 mL) was added to a suspension of methyl 5-bromo-1-(tetrahydro-2H-pyran-2-yl)-1H-indazole-3-carboxylate (LIII) (1.30 g, 3.83 mmol) in water (20 mL) and heated at 90° C. for 1 h. The solution was cooled to room temperature, diluted with ice water and acidified to pH 3.0 with 10% aqueous HCl. The solids formed were filtered, washed with cold water and dried under vacuum at room temperature to get 5-bromo-1-(tetrahydro-2H-pyran-2-yl)-1H-indazole-3-carboxylic acid (LII) as a white solid (0.87 g, 2.68 mmol, 70% yield). ESIMS found for $C_{13}H_{13}BrN_2O_3$ m/z 326.0 (M+H).

Step 5

To a solution of 5-bromo-1H-indazole-3-carboxylic acid (L) (59.8 g, 248 mmol) in THF (800 mL) under argon was added 3,4 dihydro-2H-pyran (50.6 mL, 558 mmol) and p-TsOH (4.72 g, 24.8 mmol). The reaction was heated to reflux at 60° C. for 16 h. An additional portion of p-TsOH (0.025 eq) and 3,4 dihydro-2H-pyran (0.56 eq) was added and the reflux continued for 5 h. The solution was concentrated under vacuum. EtOAc was added to the residue and the suspension was filtered and dried under high vacuum overnight to produce 5-bromo-1-(tetrahydro-2H-pyran-2-yl)-1H-indazole-3-carboxylic acid (LII) as a white solid (49.07 g, 150.9 mmol, 60.8% yield). ESIMS found for $C_{13}H_{13}BrN_2O_3$ m/z 326.3 (M+H).

Preparation of intermediate 5-bromo-6-fluoro-1-(tetrahydro-2H-pyran-2-yl)-1H-indazole-3-carboxylic acid (LVIII) is depicted below in Scheme 5

2,2,2-trichloro-1-ethoxyethanol (LV) (6.11 g, 31.6 mmol, 1.21 eq) then the mixture was heated to 55° C. for 20 h. The solids were then filtered, washed with water and dried under vacuum at 60° C. for 3 h. The solids were then added batch wise to $H_2SO_4$ (15.5 mL) at 60° C. at such a rate as to keep the temperature below 70° C. This mixture was then heated to 80° C. for 20 min and then poured over ice. The solids were filtered, washed with water and dried over vacuum at 60° C. to produce 5-bromo-6-fluoro-indoline-2,3-dione (LVI) (5.33 g, 21.8 mmol, 83% yield) as a yellow solid. $^1H$ NMR (DMSO-$d_6$, 500 MHz) δ ppm 6.94 (d, J=8.78 Hz, 1H), 7.88 (d, J=7.14 Hz, 1H), 11.28 (s, 1H); ESIMS found for $C_8H_3BrFNO_2$ m/z 245.8 ($^{81}$BrM+H).

Step 2

5-Bromo-6-fluoro-indoline-2,3-dione (LVI) (4.34 g, 17.8 mmol, 1 eq) was added to 1N NaOH (19.5 mL) and heated to 50° C. for 1 h. The brownish mixture was then stirred at room temperature for 2 h. This mixture was then cooled to 0° C. and a solution of sodium nitrate (1.23 g, 17.8 mmol, 1 eq) in water (4.4 mL) was added and stirred at 0° C. for 20 min. This solution was added to a solution of $H_2SO_4$ (1.9 mL, 35.6 mmol, 2 eq) in water (37 mL) at 0° C. over 15 min, using a Pasteur pipette with the tip always below the surface of the solution. This solution was stirred at 0° C. for 30 min. Tin (II) chloride (8.1 g, 42.7 mmol, 2.4 eq) in conc. HCl (16.8 mL) was added at 0° C. over 30 min and the mixture was stirred for 2 h. The solids were filtered, washed with water and dried under vacuum to produce 5-bromo-6-fluoro-1H-indazole-3-carboxylic acid (LVII) (4.2 g, 91.1% yield) of a brown solid which was used without further purification. $^1H$ NMR (DMSO-$d_6$, 500 MHz) δ ppm 7.70 (d, J=8.78 Hz, 1H), 8.31 (d, J=6.59 Hz, 1H), 14.02 (brs, 1H); ESIMS found for $C_8H_4BrFN_2O_2$ m/z 258.6 ($^{79}$BrM+H).

Scheme 5

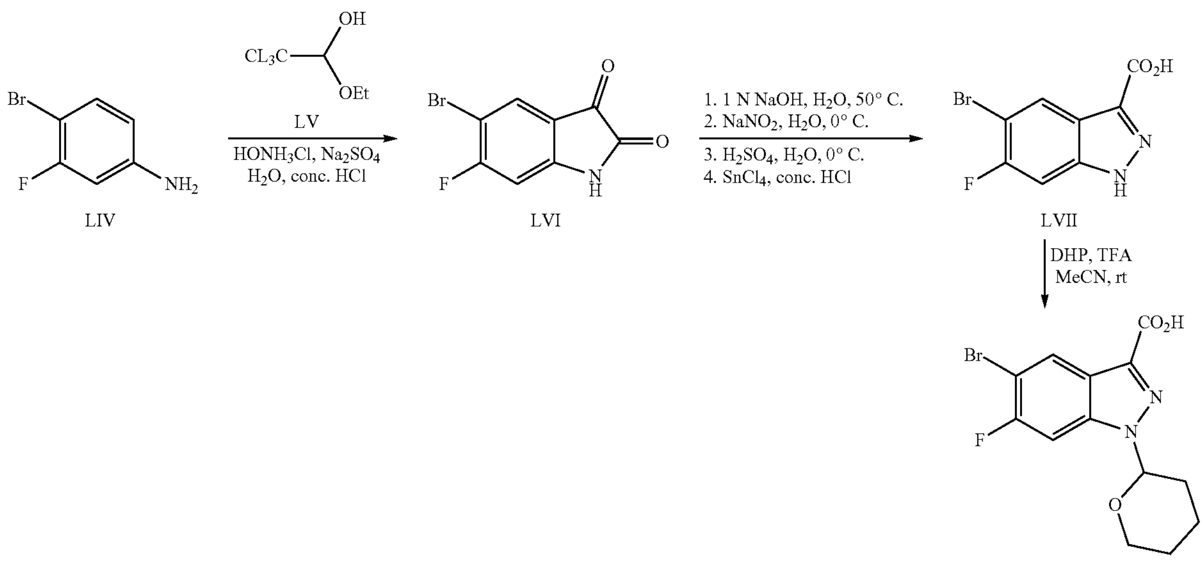

LIV LVI LVII LVIII

Step 1

To a solution of 4-bromo-3-fluoro-aniline (LIV) (5 g, 26.3 mmol, 1 eq), hydroxylamine hydrochloride (6.58 g, 94.7 mmol, 3.6 eq), sodium sulfate (29.9 mmol, 210.5 mmol, 8 eq), conc. HCl (1.49 mL) in water (180 mL) was added Step 3

To a solution of 5-bromo-6-fluoro-1H-indazole-3-carboxylic acid (LVII) (2.0 g, 7.72 mmol) in MeCN (12 mL) was added TFA (30 μL, 0.40 mmol) and DHP (2.2 mL, 15.44 mmol). The reaction was stirred at room temperature for 24 h. The solvent was removed under vacuum and the residue was purified on a silica gel column [100% $CHCl_3$ (0.1% TFA)→10% MeOH/$CHCl_3$ (0.1% TFA)] to give 5-bromo-6-fluoro-1-(tetrahydro-2H-pyran-2-yl)-1H-indazole-3-carboxylic acid (LVIII) as a yellow solid (2.11 g, 6.14 mmol, 79.5% yield). $^1H$ NMR (DMSO-$d_6$, 500 MHz) δ ppm 1.67-1.86 (m, 3H), 1.96-2.11 (m, 2H), 2.32-2.44 (m, 1H), 3.67-3.83 (m, 1H), 3.85-3.98 (m, 1H), 5.95 (dd, J=2.47 Hz, J=9.61 Hz, 1H), 7.99 (s, 1H), 8.32 (s, 1H).

Preparation of intermediate 1-(2-fluoroethyl)-4-(4-(4,4,5,5-tetramethyl-1,3,2-dioxaborolan-2-yl)-1H-pyrazol-1-yl)piperidine (LXII) is depicted below in Scheme 6.

Scheme 6

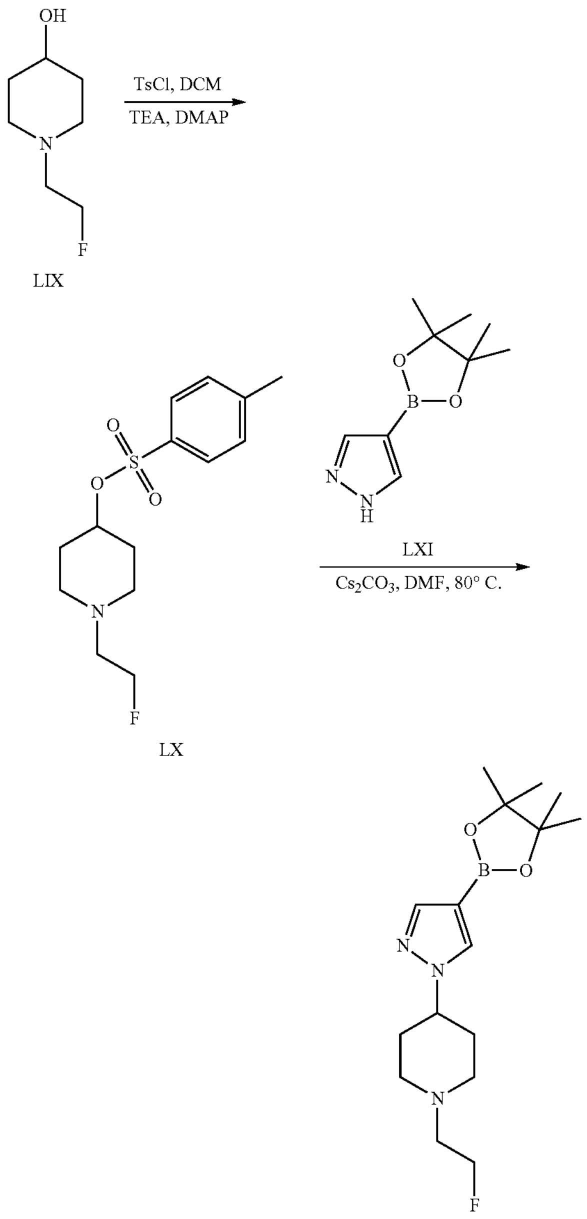

LIX

LX

LXII

Step 1

To a solution of TsCl (1.684 g, 8.83 mmol) in DCM (10 mL) at 0° C. was added triethylamine (1.420 mL, 10.19 mmol), DMAP (0.083 g, 0.679 mmol) followed by the dropwise addition of 1-(2-fluoroethyl)piperidin-4-ol (LIX) (1 g, 6.79 mmol) in DCM (10 mL). The reaction was brought to ambient temperature and stirred for 15 h. The mixture was poured into water and extracted with DCM. The organic layer was dried (sodium sulfate), concentrated in vacuo and the crude product purified on a silica column (100% hexanes→70% EtOAc/hexanes) to afford 1-(2-fluoroethyl)piperidin-4-yl 4-methylbenzenesulfonate (LX) as a brown oil (1.18 g, 3.92 mmol, 57.6% yield). ESIMS found for $C_{16}H_{27}BFN_3O_2$ m/z 302.1 (M+H).

Step 2

A mixture of 4-(4,4,5,5-tetramethyl-1,3,2-dioxaborolan-2-yl)-1H-pyrazole (LXI) (0.3 g, 1.546 mmol), 1-(2-fluoroethyl)piperidin-4-yl 4-methylbenzenesulfonate (LX) (0.513 g, 1.701 mmol) and $Cs_2CO_3$ (0.655 g, 2.010 mmol) in DMF (6 mL) was stirred at 80° C. for 6 h. The mixture was diluted with water and extracted with DCM. The organic layer was dried over anhydrous sodium sulfate and concentrated to give 1-(2-fluoroethyl)-4-(4-(4,4,5,5-tetramethyl-1,3,2-dioxaborolan-2-yl)-1H-pyrazol-1-yl)piperidine (LXII) as a brown oil (0.2 g, 0.619 mmol, 40.0% yield). Used in the next step without purification. ESIMS found for $C_{10}H_{16}N_4$ m/z 324.2 (M+H).

Preparation of intermediate tert-butyl 2-fluoro-4-(4-(4,4,5,5-tetramethyl-1,3,2-dioxaborolan-2-yl)-1H-pyrazol-1-yl)piperidine-1-carboxylate (LXV) is depicted below in Scheme 7.

Scheme 7

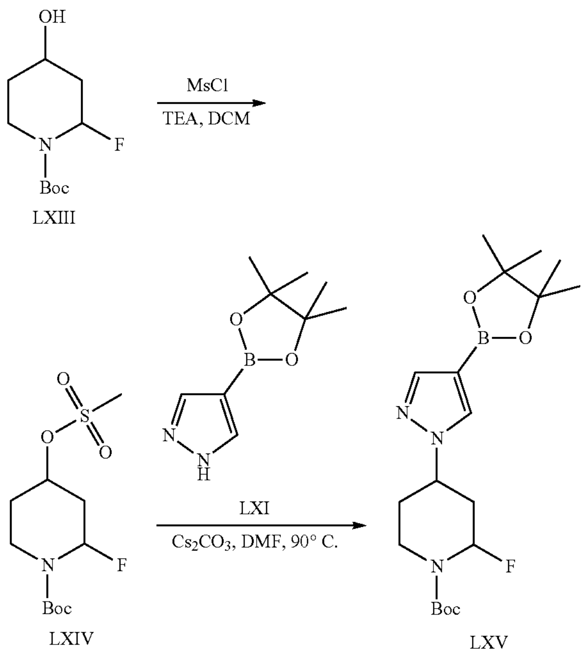

LXIII

LXIV

LXV

Step 1

To a solution of tert-butyl 3-fluoro-4-hydroxypiperidine-1-carboxylate (LXIII) (1 g, 4.56 mmol) in DCM (10 mL) and triethylamine (0.954 mL, 6.84 mmol) at 0° C. was added methanesulfonyl chloride (0.426 mL, 5.47 mmol) dropwise. The reaction was brought to ambient temperature and was stirred for 4 h. The mixture was concentrated in vacuo and diluted in EtOAc. The solution was washed with saturated aqueous sodium bicarbonate and brine. The organic layer was dried (sodium sulfate) and concentrated in vacuo to afford tert-butyl 3-fluoro-4-((methylsulfonyl)oxy)piperidine-1-carboxylate (LXIV) as a white solid (1.3 g, 4.37 mmol, 95.8% yield). $^1H$ NMR (DMSO-$d_6$, 500 MHz) δ ppm 1.36-1.44 (m, 9H), 1.77-1.96 (m, 2H), 2.88-3.12 (m, 1H), 3.13-3.23 (m, 1H), 3.25 (s, 3H), 3.87 (br s, 1H), 4.02-4.14 (m, 1H), 4.79-5.00 (m, 2H); ESIMS found for $C_{19}H_{31}BFN_3O_4$ m/z 298.1 (M+H).

Step 2

A mixture of 4-(4,4,5,5-tetramethyl-1,3,2-dioxaborolan-2-yl)-1H-pyrazole (LXI) (0.2 g, 1.031 mmol), tert-butyl 3-fluoro-4-((methylsulfonyl)oxy)piperidine-1-carboxylate (LXIV) (0.337 g, 1.134 mmol) and $Cs_2CO_3$ (0.470 g, 1.443 mmol) in DMF (4 mL) was heated at 90° C. for 16 h. The mixture was cooled to room temperature, diluted with water and extracted with EtOAc. The organic layer was washed with water, brine, and dried over anhydrous sodium sulfate and concentrated. The crude product was purified on a silica gel column (EtOAc/Hexanes 0%→100%) to give tert-butyl 3-fluoro-4-(4-(4,4,5,5-tetramethyl-1,3,2-dioxaborolan-2-yl)-1H-pyrazol-1-yl) piperidine-1-carboxylate (LXV) as a colorless oil (210 mg, 0.531 mmol, 51.5% yield). Used in the next step w/o further purification. ESIMS found for $C_{19}H_3O_3FN_3O_4$ m/z 396.2 (M+H).

The following intermediate was prepared in accordance with the procedure described in the above Scheme 7.

LXVI

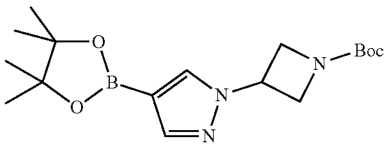

tert-Butyl 3-(4-(4,4,5,5-tetramethyl-1,3,2-dioxaborolan-2-yl)-1H-pyrazol-1-yl)azetidine-1-carboxylate (LXVI): Colorless oil (1.7 g, 4.87 mmol, 94.6% yield). ESIMS found for $C_{17}H_{28}BN_3O_4$ m/z 350.2 (M+H).

Preparation of intermediate 1-methyl-4-(4-(4,4,5,5-tetramethyl-1,3,2-dioxaborolan-2-yl)-1H-pyrazol-1-yl)piperidine (LXIX) is depicted below in Scheme 8.

Scheme 8

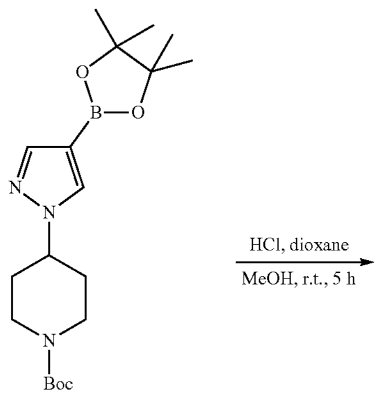

LXVII

-continued

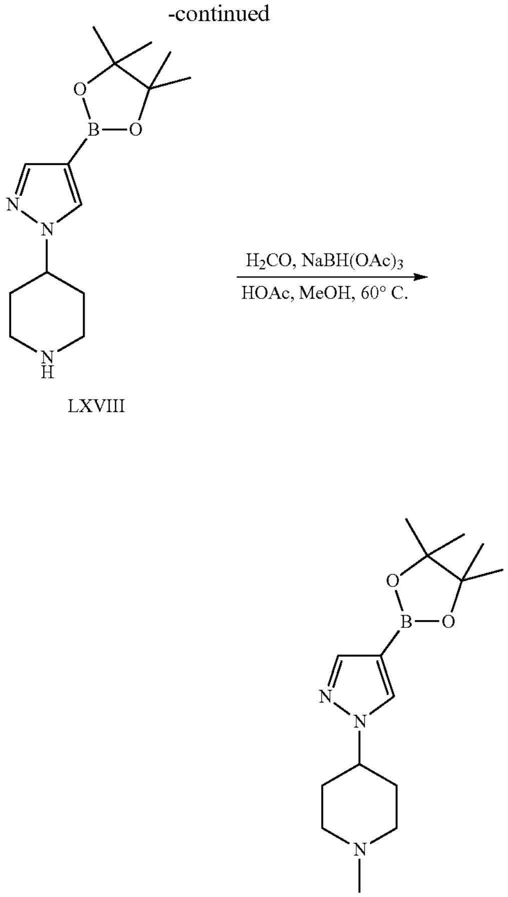

LXVIII

LXIX

Step 1

To a solution of tert-butyl 4-(4-(4,4,5,5-tetramethyl-1,3,2-dioxaborolan-2-yl)-1H-pyrazol-1-yl)piperidine-1-carboxylate (LXVII) (2.5 g, 6.63 mmol) in DCM (15 mL) was added 4 M HCl (4.97 mL, 19.88 mmol) in dioxane and the mixture stirred at room temperature for 16 h. The reaction was concentrated, re-suspended in $CHCl_3$ and washed with saturated aqueous $NaHCO_3$. The organic layer was separated and the aqueous layer was extracted with 20% iPA/$CHCl_3$ (2×). The combined organic layers were dried, filtered and concentrated to produce 4-(4-(4,4,5,5-tetramethyl-1,3,2-dioxaborolan-2-yl)-1H-pyrazol-1-yl)piperidine (LXVIII).

Step 2

To a solution of 4-(4-(4,4,5,5-tetramethyl-1,3,2-dioxaborolan-2-yl)-1H-pyrazol-1-yl)piperidine (LXVIII) in MeOH (15 mL) was added formaldehyde (0.493 mL, 6.63 mmol) and acetic acid (1.138 mL, 19.88 mmol) and the mixture stirred at room temperature for 15 min sodium triacetoxyborohydride (4.21 g, 19.88 mmol) was added and the mixture stirred at 60° C. for additional 2 h. The reaction was cooled and quenched with saturated aqueous $NaHCO_3$ until pH~7-8. The mixture was extracted with $CHCl_3$ (2×) and the combined organic layers were dried, filtered and concentrated to give 1-methyl-4-(4-(4,4,5,5-tetramethyl-1,3,2-dioxaborolan-2-yl)-1H-pyrazol-1-yl)piperidine (LXIX) as a white solid (0.32 g, 1.099 mmol, 16.58% yield). ESIMS found for $C_{15}H_{26}BN_3O_2$ m/z 292.0 (M+H).

Preparation of intermediate 4-(4-bromo-1H-pyrazol-1-yl)-1-(2-fluoro-2-methylpropyl)piperidine (LXXII) is depicted below in Scheme 9.

Scheme 9

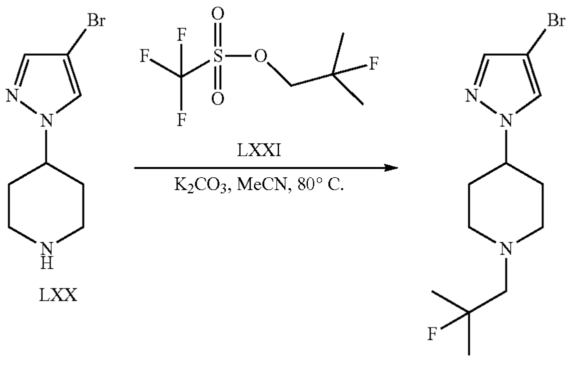

LXX

LXXII

Step 1

To a suspension of 4-(4-bromo-1H-pyrazol-1-yl)piperidine (0.5 g, 2.173 mmol) (LXX) and $K_2CO_3$ (0.901 g, 6.52 mmol) in acetonitrile (8 mL) was added 2-fluoro-2-methylpropyl trifluoromethanesulfonate (LXXI) (0.731 g, 3.26 mmol). The mixture was heated at 80° C. for 15 h and diluted with water. The mixture was extracted with EtOAc and the organic layer washed with brine; dried, filtered and concentrated to give 4-(4-bromo-1H-pyrazol-1-yl)-1-(2-fluoro-2-methylpropyl)piperidine (LXXII) as an off-white solid (0.65 g, 2.137 mmol, 98.3% yield). $^1H$ NMR (DMSO-$d_6$) δ ppm 1.31 (d, J=21.40 Hz, 6H), 1.89-1.96 (m, 4H), 2.21-2.28 (m, 2H), 2.46 (d, J=23.10 Hz, 2H), 2.96 (br d, J=12.35 Hz, 2H), 4.06-4.15 (m, 1H), 7.52 (s, 1H), 8.03 (s, 1H); ESIMS found for $C_{12}H_{19}BrFN_3$ m/z 306.1 (M+H).

Preparation of intermediate 4-bromo-5-(difluoromethyl)-1-methyl-1H-pyrazole (LXXV) is depicted below in Scheme 10.

Scheme 10

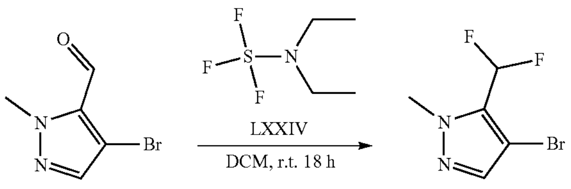

LXXIII

LXXV

Step 1

To a solution of 4-bromo-1-methyl-1H-pyrazole-5-carbaldehyde (LXXIII) (0.5 g, 2.65 mmol) in DCM (10 ml), under $N_2$ atmosphere, was added DAST (LXXIV) (0.874 ml, 6.61 mmol) at room temperature and the mixture was stirred for 18 h. LC-MS showed the completion of the starting material and a new product with higher retention time. The reaction mixture was carefully treated with saturated aqueous $NaHCO_3$ and diluted with DCM. The organic layer was separated and washed with water and brine. The organic layer was dried over anhydrous $Na_2SO_4$ and concentrated in vacuo to obtain 4-bromo-5-(difluoromethyl)-1-methyl-1H-pyrazole (LXXV) as a brown liquid (0.125 g, 0.592 mmol, 22.39% yield) which was used for next step without purification. ESIMS found for $C_5H_5BrF_2N_2$ m/z 211.1 (M+H).

Preparation of intermediate 6-(4-methylpiperazin-1-yl) pyridin-3-amine (LXXIX) is depicted below in Scheme 11.

Scheme 11

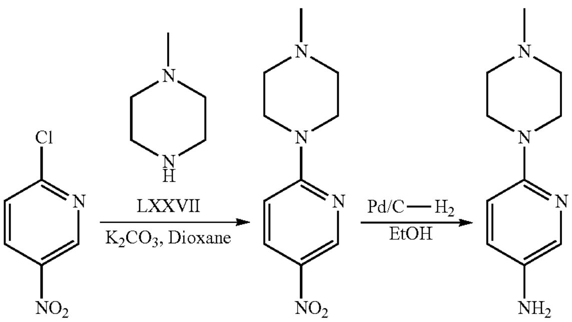

LXXVI LXXVIII LXXIX

Step 1

To a solution of 2-chloro-5-nitropyridine (LXXVI) (3.17 g, 20.0 mmol) in dioxane (50 mL) was added 1-methylpiperazine (LXXVII) (4.00 g, 40.0 mmol) and potassium carbonate. The reaction was refluxed overnight, cooled to room temperature and concentrated under vacuum. The residue was treated with water and sonicated followed by stirring for 30 min. The solid was filtered, washed with cold water and dried to give 1-methyl-4-(5-nitropyridin-2-yl)piperazine (LXXVIII) as a yellow solid (3.85 g, 17.3 mmol, 86.6% yield). ESIMS found for $C_{10}H_{14}N_4O_2$ m/z 223.1 (M+H).

Step 2

10% Palladium on carbon (40 mg) was added to a solution of 1-methyl-4-(5-nitropyridin-2-yl)piperazine (LXXVIII) (3.80 g, 17.09 mmol) in EtOH (50.0 mL). The flask was evacuated and replaced with a hydrogen atmosphere. The solution was stirred at room temperature for 6 h under hydrogen. The catalyst was filtered through a pad of Celite, and the solvent was removed under reduced pressure to afford 6-(4-methylpiperazin-1-yl)pyridin-3-amine (LXXIX) as a brown viscous oil which solidified under vacuum (3.30 g, 17.1 mmol, quantitative). ESIMS found for $C_{10}H_{16}N_4$ m/z 193.0 (M+H).

The following intermediates were prepared in accordance with the procedure described in the above Scheme 11.

LXXX

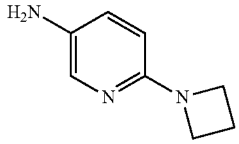

6-(Azetidin-1-yl)pyridin-3-amine (LXXX): Burgundy solid (1.45 g, 9.70 mmol, 99.3% yield). ESIMS found for $C_8H_{11}N_3$ m/z 149.0 (M+H).

LXXXI

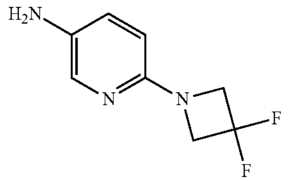

6-(3,3-Difluoroazetidin-1-yl)pyridin-3-amine (LXXXI): Purple solid (820 mg, 4.43 mmol, 89.9% yield). ESIMS found for $C_8H_9F_2N_3$ m/z 186.0 (M+H).

LXXXII

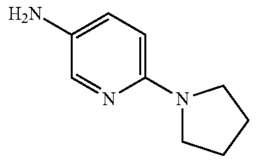

6-(Pyrrolidin-1-yl)pyridin-3-amine (LXXXII): Deep purple oil (1.43 g, 8.77 mmol, 100% yield). ESIMS found for $C_9H_{13}N_3$ m/z 164 (M+H).

LXXXIII

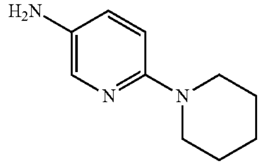

6-(Piperidin-1-yl)pyridin-3-amine (LXXXIII): Dark red viscous oil (4.93 g, 27.81 mmol, 95.9% yield). $^1H$ NMR (DMSO-$d_6$) δ ppm 1.48-1.71 (m, 8H), 3.42-3.53 (m, 2H), 4.48 (brs, 2H), 6.59 (d, J=9 Hz, 1H), 6.89 (dd, J=9 Hz, J=3 Hz, 1H), 7.58 (d, J=3 Hz, 1H); ESIMS found for $C_{10}H_{15}N_3$ m/z 178.0 (M+H).

LXXXIV

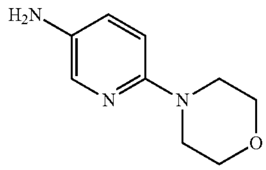

6-Morpholinopyridin-3-amine (LXXXIV): Purple solid (782 mg, 4.36 mmol, 95% yield). ESIMS found for $C_9H_{13}N_3O$ m/z 180 (M+H).

Preparation of intermediate 4-(2-(pyrrolidin-1-yl)ethoxy) aniline (LXXXVIII) is depicted below in Scheme 12.

Scheme 12

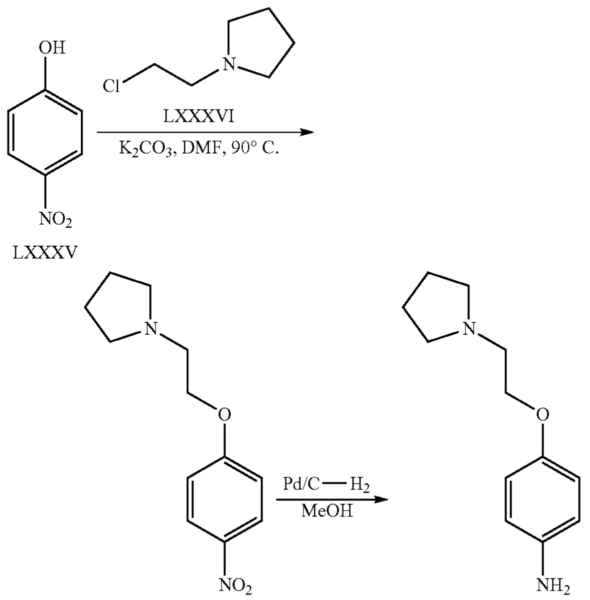

LXXXV

LXXXVII

LXXXVIII

Step 1

To a solution of 4-nitrophenol (LXXXV) (2.8 g, 20.0 mmol) in DMF (50 mL) was added 1-(2-chloroethyl)pyrrolidine HCl (LXXXVI) (3.4 g, 20.0 mmol) and potassium carbonate (8.3 g, 60 mmol). The reaction was heated at 90° C. overnight, cooled to room temperature and concentrated under vacuum. The residue was extracted with EtOAc, washed with brine and dried over $Na_2SO_4$. The organic layer was concentrated. The residue was purified on an ISCO silica column (50% EtOAC/hexanes→100% EtOAc) to yield 1-(2-(4-nitrophenoxy)ethyl)pyrrolidine (LXXXVII) as a yellow solid (0.65 g, 2.75 mmol, 13.8% yield). ESIMS found for $C_{12}H_{16}N_2O_3$ m/z 237.1 (M+H).

Step 2

10% Palladium on carbon (~7 mg) was added to a solution of 1-(2-(4-nitrophenoxy)ethyl)pyrrolidine (LXXXVII) (0.65 g, 2.75 mmol) in MeOH (10.0 mL). The flask was evacuated and replaced with a hydrogen atmosphere. The solution was stirred at room temperature overnight under hydrogen. The catalyst was filtered through a pad of Celite, and the solvent was removed under reduced pressure to afford 4-(2-(pyrrolidin-1-yl)ethoxy)aniline (LXXXVIII) as a yellow oil (500 mg, 2.42 mmol, 88.1% yield). ESIMS found for $C_{12}H_{18}N_2O$ m/z 207.0 (M+H).

The following intermediate was prepared in accordance with the procedure described in the above Scheme 12.

LXXXIX

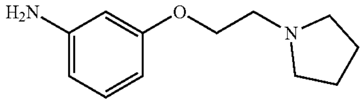

3-(2-(pyrrolidin-1-yl)ethoxy)aniline (LXXXIX): Yellow oil (2.19 g, 10.6 mmol, 66.1% yield). ESIMS found for $C_{12}H_{18}N_2O$ m/z 207.1 (M+H).

Preparation of intermediate tert-butyl 4-(5-aminopyridin-2-yl)piperazine-1-carboxylate (XCII) is depicted below in Scheme 13.

Scheme 13

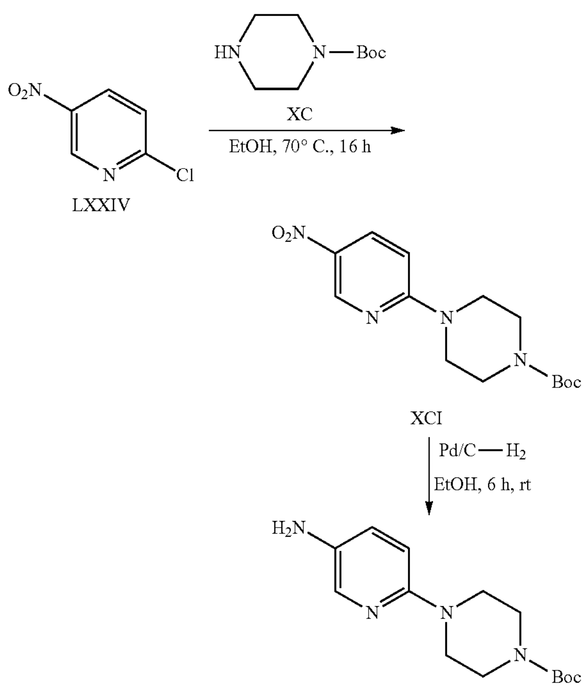

LXXIV
XC
XCI
XCII

Step 1

To a solution of 2-chloro-5-nitropyridine (LXXIV) (2.0 g, 12.6 mmol) in EtOH (20 mL) was added tert-butyl piperazine-1-carboxylate (XC) (7.05 g, 37.9 mmol). The reaction was headed at 70° C. for 16 h. The reaction was concentrated under vacuum and then dissolved in EtOAc. The EtOAc was washed with 1 M NaOH, brine and then dried over $MgSO_4$ to give tert-butyl 4-(5-nitropyridin-2-yl)piperazine-1-carboxylate (XCI) as a yellow solid (4.94 g). ESIMS found for $C_{14}H_{20}N_4O_4$ m/z 309.0 (M+H).

Step 2

Preparation of intermediate tert-butyl 4-(5-aminopyridin-2-yl)piperazine-1-carboxylate (XCII) was performed following the procedure listed in Scheme 11, Step 2. Purple solid (990 mg, 3.56 mmol, quantitative). ESIMS found for $C_{14}H_{22}N_4O_2$ m/z 278.8 (M+H).

Preparation of intermediate 6-isopropoxypyridin-3-amine (XCV) is depicted below in Scheme 14.

Scheme 14

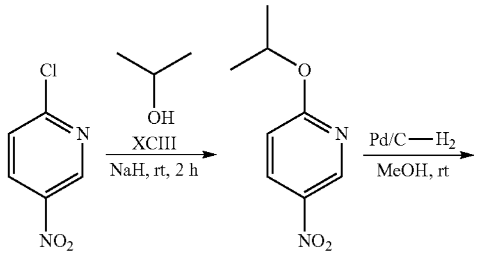

LXXIV
XCIII
XCIV

-continued

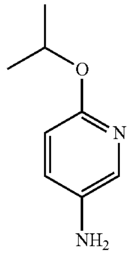
XCV

Step 1

To a suspension of 2-chloro-5-nitropyridine (LXXIV) (1.58 g, 10.0 mmol) in isopropanol (XCIII) (20 mL) was added NaH (60% in mineral oil) (800 mg, 20 mmol) in portions. The solution was stirred under Ar at room temperature for 2 h. The reaction was then quenched by adding dropwise addition of water. The solution was concentrated under vacuum and the residue was partitioned between $CHCl_3$ and water. The organic layer was separated and the aqueous phase was washed with $CHCl_3$. The combined $CHCl_3$ were washed with water, brine, dried over $MgSO_4$ and concentrated under vacuum. The residue was purified on a silica column (5:1 EtOAc:hexane) to yield 2-chloro-5-nitropyridine (XCIV) as a yellow solid (880 mg, 4.83 mmol, 48.3% yield). $^1H$ NMR (DMSO-$d_6$, 500 MHz) δ ppm 1.34 (d, J=6.5 Hz, 6H), 5.38 (sep, J=6.5 Hz, 1H), 6.96 (d, J=9.5 Hz, 1H), 8.44 (dd, J=2.5 Hz, J=9 Hz, 1H), 9.07 (d, J=3 Hz, 1H); ESIMS found for $C_8H_{10}N_2O_3$ m/z 183.1 (M+H).

Step 2

Preparation of intermediate 6-isopropoxypyridin-3-amine (XCV) was performed following the procedure listed in Scheme 11, Step 2. Brown oil (735 mg, 4.83 mmol, 100% yield). $^1H$ NMR (DMSO-$d_6$, 500 MHz) δ ppm 1.21 (d, J=6 Hz, 6H), 4.68 (s, 2H), 5.01 (sep, J=6 Hz, 1H), 6.45 (d, J=8.5 Hz, 1H), 6.97 (dd, J=2.5 Hz, J=8.5 Hz, 1H), 7.48 (d, J=3 Hz, 1H); ESIMS found for $C_8H_{12}N_2O$ m/z 153.1 (M+H).

The following intermediates were prepared in accordance with the procedure described in the above Scheme 14.

XCVI

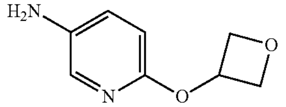

6-(Oxetan-3-yloxy)pyridin-3-amine (XCVI): Yellow solid (1.69 g, 10.0 mmol, 100% yield). $^1H$ NMR (DMSO-$d_6$, 500 MHz) δ ppm 4.49 (dd, J=5.5 Hz, J=7.5 Hz, 2H), 4.75-4.85 (m, 4H), 5.38 (quin, J=5.5 Hz, 1H), 6.60 (d, J=8.5 Hz, 1H), 7.02 (dd, J=2.5 Hz, J=8.5 Hz, 1H), 7.42 (d, J=2.5 Hz, 1H); ESIMS found for $C_8H_{10}N_2O_2$ m/z 167.0 (M+H).

XCVII

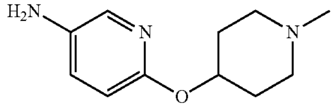

6-((1-Methylpiperidin-4-yl)oxy)pyridin-3-amine (XCVII): Light grey solid (2.99 g, 14.4 mmol, 96.0% yield). $^1H$ NMR (DMSO-$d_6$, 500 MHz) δ ppm 1.58 (dtd, J=12.62, 9.19, 9.19, 3.84 Hz, 2H), 1.84-1.92 (m, 2H), 2.11 (br t, J=9.61 Hz, 2H), 2.16 (s, 3H), 2.58-2.65 (m, 2H), 4.69 (s, 2H), 4.74 (tt, J=8.75, 4.15 Hz, 1H), 6.49 (d, J=8.51 Hz, 1H), 6.97 (dd, J=8.78, 3.02 Hz, 1H), 7.47 (d, J=2.74 Hz, 1H); ESIMS found for $C_{11}H_{17}N_3O$ m/z 208.1 (M+H).

Preparation of intermediate 6-(difluoromethoxy)pyridin-3-amine (CI) is depicted below in Scheme 15.

Scheme 15

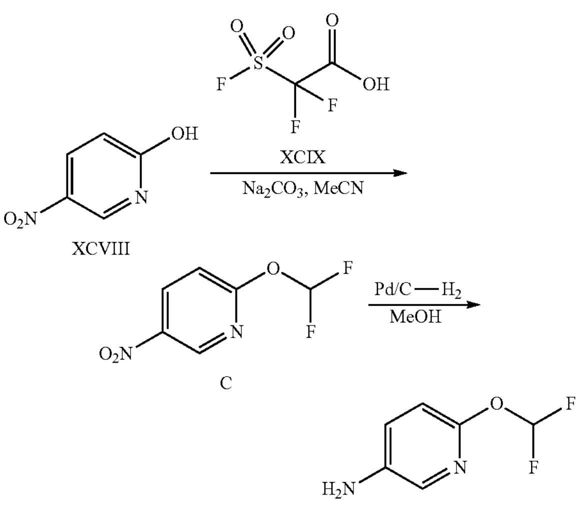

XCVIII C CI

Step 1

To a solution of 5-nitropyridin-2-ol (XCVIII) (1 g, 7.14 mmol) in acetonitrile (10 mL) at 0° C. was added sodium carbonate (1.513 g, 14.28 mmol), and 2,2-difluoro-2-(fluorosulfonyl)acetic acid (XCIX) (1.107 mL, 10.71 mmol). The reaction was allowed to stir from 0° C. to room temperature over 16 h. The reaction was quenched with saturated aqueous sodium bicarbonate and extracted with EtOAc, washed with brine, dried over sodium sulfate, filtered and concentrated in vacuo. The crude product was purified on a silica gel column (0%→10% EtOAc/hexane) to give 2-(difluoromethoxy)-5-nitropyridine (C) as a light brown oil (1.01 g, 5.31 mmol, 74.4% yield). $^1H$ NMR (DMSO-$d_6$, 500 MHz) δ ppm 7.36 (d, J=9.61 Hz, 1H), 7.82 (t, J=71.70 Hz, 1H), 8.70 (dd, J=9.06, 2.74 Hz, 1H), 9.15 (d, J=2.74 Hz, 1H); ESIMS found for $C_6H_4F_2N_2O_3$ m/z 191.0 (M+H).

Step 2

Preparation of intermediate 6-(difluoromethoxy)pyridin-3-amine (CI) was performed following the procedure listed in Scheme 11, Step 2. Brown oil (0.82 g, 5.12 mmol, 97.3% yield). ESIMS found for $C_6H_6F_2N_2O$ m/z 161.1 (M+H).

Preparation of intermediate 6-(pyrrolidin-1-ylmethyl) pyridin-3-amine (CV) is depicted below in Scheme 16.

Scheme 16

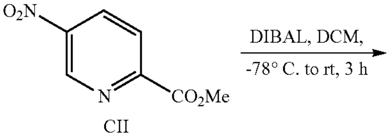

CII

-continued

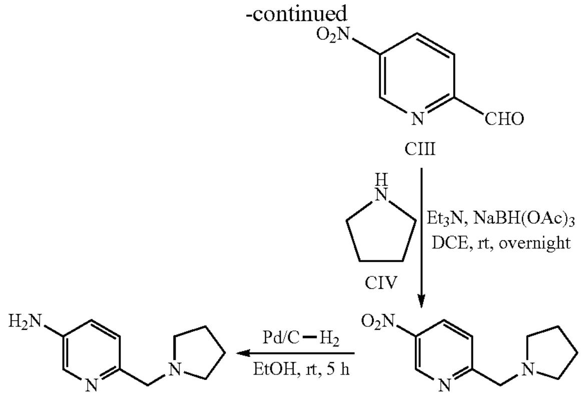

CIII CIV CVI CV

Step 1

To a suspension of methyl 5-nitropicolinate (CII) (1.282 g, 7.03 mmol) in DCM (25 mL) stirred at −78° C. under argon was slowly added DIBAL (1M in toluene) (9.14 mL, 9.14 mmol). The solution was allowed to warm to room temperature over 3 h. An aqueous solution of potassium sodium tartrate was added, diluted further with water and DCM. The solution was stirred at room temperature for another 30 min before the organic layer was separated. The aqueous layer was extracted 2×DCM, combined with the organic layer, dried over $MgSO_4$, filtered and evaporated under reduced pressure. The residue was purified by column chromatography to produce 5-nitropicolinaldehyde (CIII) as a brown oil (0.64 g, 4.2 mmol, 60% yield). $^1H$ NMR (DMSO-$d_6$) δ ppm 8.17 (d, J=9 Hz, 1H), 8.81 (dd, J=9 Hz, J=2 Hz, 1H), 9.56 (d, J=2 Hz, 1H), 10.08 (s, 1H).

Step 2

Preparation of 5-nitro-2-(pyrrolidin-1-ylmethyl)pyridine (CV) was performed following the procedure listed in Scheme 21, Step 1. Purple oil (0.41 g, 1.98 mmol, 86% yield). $^1H$ NMR (DMSO-$d_6$) δ ppm 9.28 (d, J=3 Hz, 1H), 8.56 (dd, J=11 Hz, 3 Hz, 1H), 7.72 (d, J=11 Hz, 1H), 3.85 (s, 2H), 2.53-2.50 (m, 4H), 1.75-1.70 (m, 4H).

Step 3

Preparation of intermediate 6-(pyrrolidin-1-ylmethyl) pyridin-3-amine (CVI) was performed following the procedure listed in Scheme 11, Step 2. Dark brown oil (0.35 g, 1.97 mmol, quantitative). ESIMS found for $C_{10}H_{15}N_3$ m/z 178 (M+H).

The following intermediates were prepared in accordance with the procedure described in the above Scheme 16.

CVII

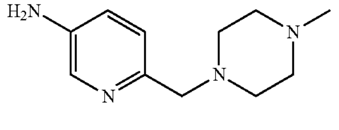

6-((4-Methylpiperazin-1-yl)methyl)pyridin-3-amine (CVII): Brown oil (120 mg, 0.58 mmol, 100% yield). ESIMS found for $C_{11}H_{18}N_4$ m/z 207.0 (M+H).

CVIII

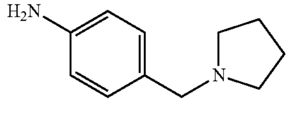

4-(Pyrrolidin-1-ylmethyl)aniline (CVIII): Light brown oil (1.64 g, 9.30 mmol, 101% yield). ESIMS found for $C_{11}H_{16}N_2$ m/z 177.1 (M+H).

CIX

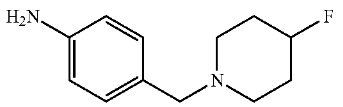

4-((4-Fluoropiperidin-1-yl)methyl)aniline (CIX): Light brown oil (0.78 g, 3.75 mmol, 74.4% yield). ESIMS found for $C_{12}H_{17}FN_2$ m/z 209.1 (M+H).

Preparation of intermediate 2-chloro-5-(pyrrolidin-1-ylmethyl)aniline (CXII) is depicted below in Scheme 17.

Scheme 17

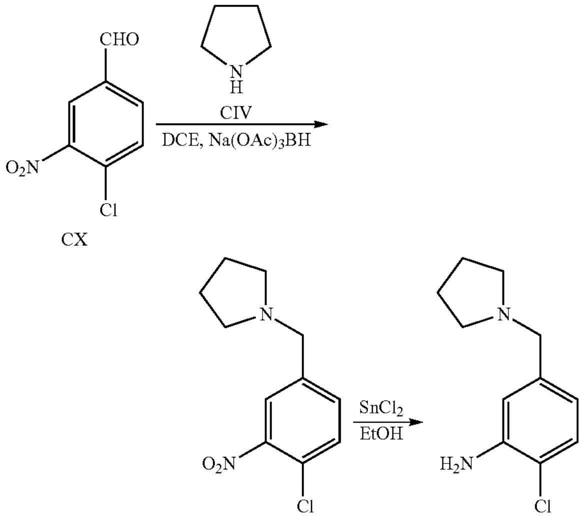

CX

CXI CXII

Step 1

To a stirring solution of 4-chloro-3-nitrobenzaldehyde (CX) (1.5 g, 8.08 mmol) in DCE (40 mL) was added pyrrolidine (CIV) (0.664 ml, 8.08 mmol) and the mixture was stirred for 10 min. Sodium triacetoxyborohydride (3.43 g, 16.17 mmol) was then added portion wise and the mixture was stirred at room temperature for 20 h. The reaction was quenched with aq. sat. $NaHCO_3$, diluted with DCM, organic layer separated and washed sequentially with aq. sat. $NaHCO_3$, $H_2O$ and aq. sat. NaCl. The organic layer was dried over anhydrous $Na_2SO_4$ and concentrated in vacuo. The crude product was purified by silica gel column (100% hexanes→hexanes:EtOAc 2.5:1) to obtain 1-(4-chloro-3-nitrobenzyl)pyrrolidine (CXI) (1.39 g, 5.78 mmol, 71.4% yield). ESIMS found for $C_{11}H_{13}ClN_2O_2$ m/z 241.0 (M+H).

Step 2

A mixture of 1-(4-chloro-3-nitrobenzyl)pyrrolidine (CXI) (1.39 g, 5.78 mmol) and tin(II) chloride (5.48 g, 28.9 mmol) in EtOH (30 mL) was heated to reflux overnight. The solvents were concentrated in vacuo, the residue taken in water, basified with 1N NaOH and extracted with chloroform. The organic layer was washed with water, aq. sat. NaCl, dried over anhydrous $Na_2SO_4$ and dried in high vacuo to obtain 2-chloro-5-(pyrrolidin-1-ylmethyl)aniline (CXII) (0.61 g, 2.90 mmol, 50.1% yield) which was used for next step without purification. ESIMS found for $C_{11}H_{15}ClN_2$ m/z 211.0 (M+H).

The following intermediates were prepared in accordance with the procedure described in the above Scheme 17.

CXIII

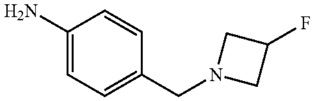

4-((3-Fluoroazetidin-1-yl)methyl)aniline (CXIII): Brown oil (226 mg, 1.254 mmol, 23.96% yield). ESIMS found for $C_{10}H_{13}FN_2$ m/z 181.0 (M+H).

CXIV

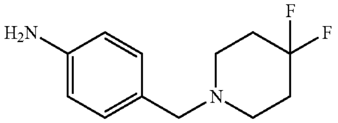

4-((4,4-Difluoropiperidin-1-yl)methyl)aniline (CXIV): Brown oil (0.16 g, 0.707 mmol, 12.33% yield). $^1H$ NMR (DMSO-$d_6$, 500 MHz) δ ppm 1.91 (ddd, J=19.90, 14.13, 5.76 Hz, 4H), 2.41 (br s, 4H), 3.33 (s, 2H), 4.94 (s, 2H), 6.50 (d, J=8.23 Hz, 2H), 6.92 (d, J=8.23 Hz, 2H); ESIMS found for $C_{12}H_{16}F_2N_2$ m/z 227.1 (M+H).

Preparation of intermediate 2-fluoro-4-(pyrrolidin-1-ylmethyl)aniline (CXVII) is depicted below in Scheme 18

Scheme 18

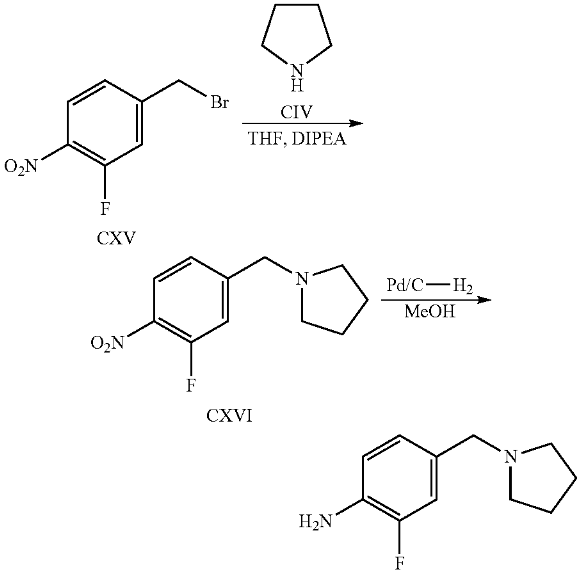

CXV

CXVI

CXVII

Step 1

To a solution of 4-(bromomethyl)-2-fluoro-1-nitrobenzene (CXV) (0.404 g, 1.726 mmol) in THF (15 mL) was added DIPEA (0.452 mL, 2.59 mmol) at 0° C. Pyrrolidine (CIV) (0.157 ml, 1.899 mmol) in THF (5 mL) was slowly added. The reaction mixture was allowed to warm to room temperature and stirred for 4 h. The reaction was concentrated under vacuum and purified via silica gel column (50%→100% EtOAc/Hexanes) to yield 1-(3-fluoro-4-nitrobenzyl)pyrrolidine (CXVI) as a yellow oil (0.220 g, 0.981 mmol, 56.8% yield). ESIMS found for $C_{11}H_{13}FN_2O_2$ m/z 225.1 (M+H).

Step 2

Preparation of intermediate 2-fluoro-4-(pyrrolidin-1-ylmethyl)aniline (CXVII) was performed following the procedure listed in Scheme 11, Step 2. Amber colored oil (0.212 g, 1.091 mmol, 100% yield). ESIMS found for $C_{11}H_{15}FN_2$ m/z 195 (M+H).

Preparation of intermediate 1-(2-fluoro-2-methylpropyl) piperidin-4-amine (CXX) is depicted below in Scheme 19.

Scheme 19

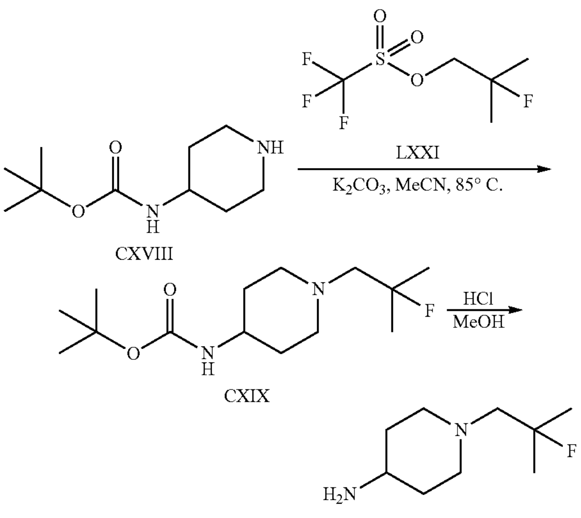

CXVIII

CXIX

CXX

Step 1

A mixture of tert-butyl piperidin-4-ylcarbamate (CXVIII) (50.0 g, 250 mmol), 2-fluoro-2-methylpropyl trifluoromethanesulfonate (LXXI) (84 g, 374 mmol) and potassium carbonate (69.0 g, 499 mmol) in acetonitrile (480 mL) was heated to 85° C. overnight. The solvent was removed in vacuo, the residue partitioned between EtOAc/water, the organic layer was separated, washed with brine, dried over anhydrous $Na_2SO_4$, solvents removed in vacuo and the crude was purified by column chromatography using EtOAc/hexanes to obtain tert-butyl (1-(2-fluoro-2-methylpropyl)piperidin-4-yl)carbamate (CXIX) (72.9 g, 266 mmol, 106% yield) as yellow white solid. ESIMS found for $C_{14}H_{27}FN_2O_2$ m/z 274.9 (M+H).

Step 2 tert-Butyl (1-(2-fluoro-2-methylpropyl)piperidin-4-yl) carbamate (CXIX) (68.5 g, 250 mmol) was added to a solution of 12 N hydrochloric acid in MeOH (41.6 mL, 499 mmol). The reaction mixture was capped and stirred at room temperature overnight. The solvent was removed under nigh vacuum to recover a quantitative yield of 1-(2-fluoro-2-methylpropyl)piperidin-4-amine (CXX), 2HCl (62.1 g, 251 mmol, 101% yield). Carried onto next step without further purification. ESIMS found for $C_9H_{19}FN_2$ m/z 175.1 (M+H).

The following intermediate was prepared in accordance with the procedure described in the above Scheme 19.

CXXI

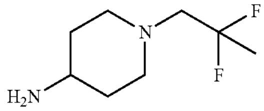

1-(2,2-Difluoropropyl)piperidin-4-amine (CXXI): Brown oil (1.685 g, 6.71 mmol, 74.7% yield). ESIMS found for $C_8H_{16}F_2N_2$ m/z 179.1 (M+H).

Preparation of intermediate 1-(2-fluoroethyl)piperidin-4-amine (CXXIV) is depicted below in Scheme 20.

Scheme 20

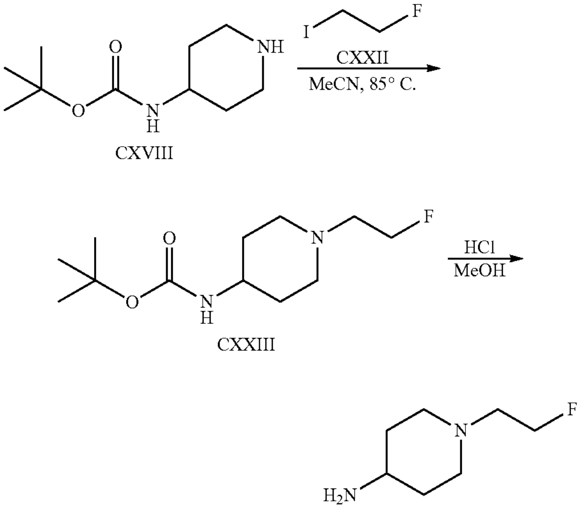

CXVIII

CXXIII

CXXIV

Step 1

A mixture of tert-butyl piperidin-4-ylcarbamate (CXVIII) (959 mg, 4.79 mmol), 1-fluoro-2-iodoethane (CXXII) (1.0 g, 5.75 mmol), and potassium carbonate (3.32 g, 23.95 mmol) in in acetonitrile (20 mL) was heated to 85° C. overnight. The solvent was removed in vacuo, the residue partitioned between EtOAc/water, the organic layer was separated, washed with brine, dried over anhydrous $Na_2SO_4$, solvents removed in vacuo and the crude was purified by column chromatography using EtOAc/hexanes to obtain tert-butyl (1-(2-fluoroethyl)piperidin-4-yl)carbamate (CXXIII) (1.24 g, 5.0 mmol, 105% yield) as yellow white solid. ESIMS found for $C_{12}H_{23}FN_2O_2$ m/z 247.0 (M+H).

Step 2 tert-Butyl (1-(2-fluoroethyl)piperidin-4-yl)carbamate (CXXIII) (1.24 g, 4.79 mmol) was added to a solution of 4 N hydrochloric acid in dioxane (10 mL, 40 mmol). The reaction mixture was capped and stirred at room temperature overnight. The solvent was removed under nigh vacuum to recover a quantitative yield of 1-(2-fluoroethyl)piperidin-4-amine*2HCl (CXXIV)(1.2 g, 5.47 mmol, 114% yield). Carried onto next step without further purification. ESIMS found for $C_7H_{15}FN_2$ m/z 147.0 (M+H).

The following intermediates were prepared in accordance with the procedure described in the above Scheme 20.

CXXV

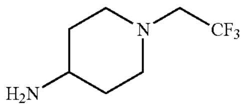

1-(2,2,2-Trifluoroethyl)piperidin-4-amine (CXXV): Brown oil (2.1 g, 11.5 mmol). ESIMS found for $C_7H_{13}F_3N_2$ m/z 183.1 (M+H).

CXXVI

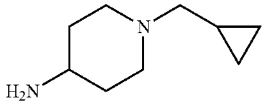

1-(Cyclopropylmethyl)piperidin-4-amine (CXXVI): Brown oil (1.96 g, 12.6 mmol). ESIMS found for $C_9H_{18}N_2$ m/z 155.0 (M+H).

CXXVII

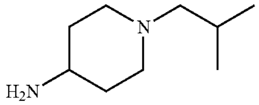

1-Isobutylpiperidin-4-amine (CXXVII): White solid (14.48 g, 92.7 mmol). ESIMS found for $C_9H_{20}N_2$ m/z 156.5 (M+H).

CXXVIII

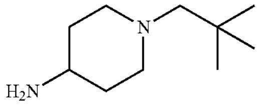

1-Neopentylpiperidin-4-amine (CXXVIII): Orange solid (600 mg, 3.52 mmol). ESIMS found for $C_{10}H_{22}N_2$ m/z 170.9 (M+H).

CXXIX

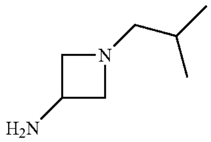

1-Isobutylazetidin-3-amine (CXXIX): White solid (0.524 g, 3.18 mmol). ESIMS found for $C_7H_{16}N_2$ m/z 129.2 (M+H).

Preparation of intermediate (1r,4r)-4-((3-fluoroazetidin-1-yl)methyl)cyclohexan-1-amine (CXXXIII) is depicted below in Scheme 21

Scheme 21

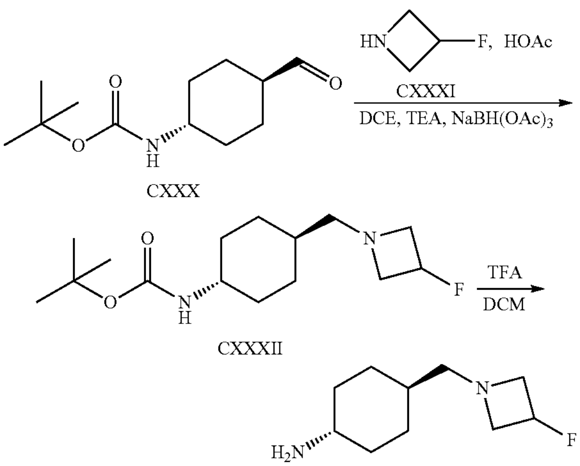

CXXX

CXXXII

CXXXIII

Step 1

To a solution of tert-butyl-trans-4-formylcyclohexyl)carbamate (CXXX) (2.0 g, 8.8 mmol) in DCE (50 mL) was added 3-fluoroazetidine, HCl (CXXXI) (1.227 g, 11.0 mmol) [pretreated with HOAc (1.511 mL, 26.4 mmol)] followed by the addition of triethylamine (1.533 mL, 11.0 mmol). After 15 min, sodium triacetoxyborohydride (3.73 g, 17.6 mmol) was added and the mixture was stirred at room temperature for overnight. The mixture was diluted with DCM, washed with saturated aqueous $NaHCO_3$, water and brine solution. The organic layer was dried over anhydrous $Na_2SO_4$, solvents were concentrated in vacuo to yield the crude tert-butyl-trans-4-((3-fluoroazetidin-1-yl)methyl) cyclohexyl)carbamate (CXXXII) as a white solid (2.091 g, 7.3 mmol, 83.0% yield). Used for next step without purification. $^1H$ NMR (DMSO-$d_6$, 500 MHz) δ ppm 0.79-0.91 (m, 1H), 1.02-1.14 (m, 1H), 1.37 (d, J=3.84 Hz, 12H), 1.41 (br d, J=4.94 Hz, 2H), 1.65-1.78 (m, 2H), 2.24 (d, J=6.86 Hz, 1H), 2.31 (br d, J=4.67 Hz, 1H), 2.95-3.06 (m, 2H), 3.10 (br s, 1H), 3.40 (br s, 1H), 3.46-3.58 (m, 2H), 5.10 (dsxt, J=58.00, 5.20 Hz, 1H); ESIMS found for $C_{15}H_{27}FN_2O_2$ m/z 287.2 (M+H).

Step 2

To a solution of tert-butyl-trans-4-((3-fluoroazetidin-1-yl) methyl)cyclohexyl) carbamate (CXXXII) (0.859 g, 3 mmol) in DCM (6 ml) was added TFA (6 ml, 78 mmol) dropwise and the mixture was stirred at room temperature for 3 hr. The solvents were concentrated in vacuo and the residue was dried under high vacuo. The crude (1r,4r)-4-((3-fluoroazetidin-1-yl)methyl)cyclohexan-1-amine (CXXXIII) was used for next step without purification. ESIMS found for $C_{10}H_{19}FN_2$ m/z 187.1 (M+H).

Preparation of intermediate 5-bromo-N-((1r,4r)-4-(pyrrolidin-1-ylmethyl)cyclohexyl)-1-(tetrahydro-2H-pyran-2-yl)-1H-indazole-3-carboxamide (CXXXVII) is depicted below in Scheme 22.

Scheme 22

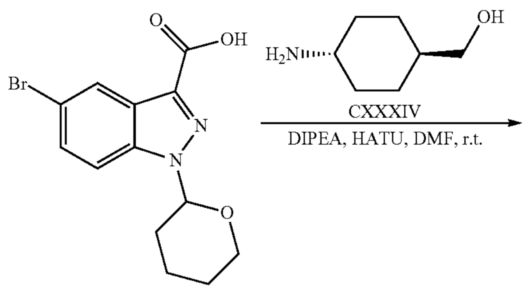

LII

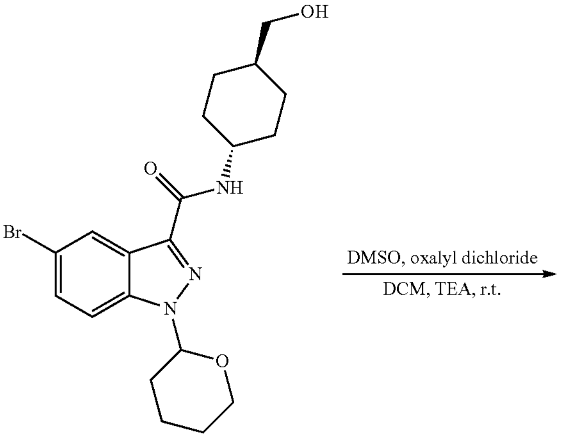

CXXXV

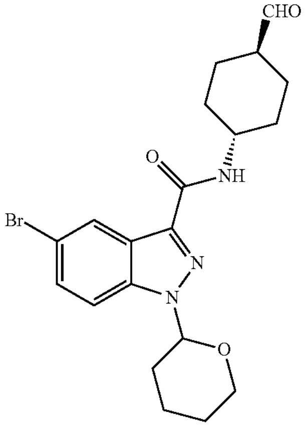

CXXXVI

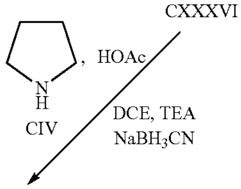

-continued

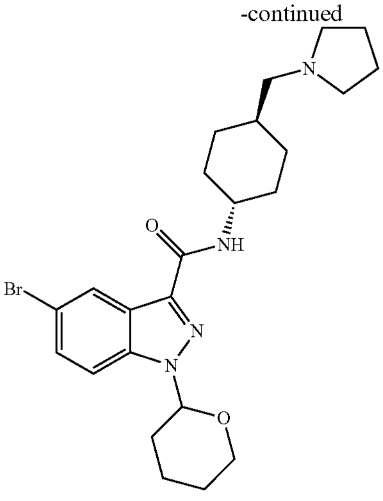

CXXXVII

Step 1

To a solution of trans-4-aminocyclohexyl)methanol (CXXXIV) (1.0 g, 6.04 mmol) and HATU (2.78 g, 7.30 mmol) in DMF (15 mL) was added DIPEA (4.03 mL, 23.07 mmol) and the mixture was stirred for 10 min. Then, 5-bromo-1-(tetrahydro-2H-pyran-2-yl)-1H-indazole-3-carboxylic acid (LII) (2.5 g, 7.69 mmol) was added and the mixture was stirred at room temperature for 18 h. The LC-MS of mixture showed near completion of the starting material. The solvents were concentrated in vacuo, the residue partitioned between EtOAc and saturated aqueous $NaHCO_3$, organic layer was separated, washed with water and brine. The organic layer was dried over anhydrous $Na_2SO_4$, solvents removed in vacuo and the crude product was purified by column chromatography using (90→100% EtOAc/hexanes) to obtain 5-bromo-N-trans-4-(hydroxymethyl)cyclohexyl)-1-(tetrahydro-2H-pyran-2-yl)-1H-indazole-3-carboxamide (CXXXV) as a white solid (2.06 g, 4.72 mmol, 61.4% yield). ESIMS found for $C_{20}H_{26}BrN_3O_3$ m/z 438.1 (M+H).

Step 2

To a solution of DMSO (0.464 mL, 6.53 mmol) in DCM (3 mL) at room temperature under Ar was added dropwise oxalyl dichloride (0.285 ml, 3.27 mmol) in DCM (3.00 mL). After 15 min, 5-bromo-N-trans-4-(hydroxymethyl) cyclohexyl)-1-(tetrahydro-2H-pyran-2-yl)-1H-indazole-3-carboxamide (CXXXV) (0.95 g, 2.177 mmol) in DCM (5.00 mL) was added and the mixture was stirred at room temperature for 1 h. Then, triethylamine (0.910 mL, 6.53 mmol) was added dropwise and the mixture was continued to stir at room temperature for 1 h. LC-MS showed complete conversion of the starting material into the product. The reaction mixture was diluted with $H_2O$ and DCM, organic layer separated, washed with brine, dried over anhydrous $Na_2SO_4$ and the solvents were concentrated in vacuo to obtain trans-5-bromo-N-(4-formylcyclohexyl)-1-(tetrahydro-2H-pyran-2-yl)-1H-indazole-3-carboxamide (CXXXVI) as a white puffy solid (0.875 g, 2.015 mmol, 93% yield). Used for next step without purification. ESIMS found for $C_{20}H_{24}BrN_3O_3$ m/z 434.1 (M+H).

Step 3

To a solution of trans-5-bromo-N-(4-formylcyclohexyl)-1-(tetrahydro-2H-pyran-2-yl)-1H-indazole-3-carboxamide (CXXXVI) (0.434 g, 1 mmol) in DCE (5 mL) was added pyrrolidine (CIV) (0.249 ml, 3.0 mmol) followed by the addition of acetic acid (0.286 mL, 5.0 mmol). After 15 min, sodium cyanoborohydride (0.126 g, 2.0 mmol) was added and the mixture was stirred at room temperature for 18 h. The mixture was diluted with DCM, washed with saturated aqueous $NaHCO_3$, water and brine solution. The organic layer was dried over anhydrous $Na_2SO_4$, solvents were concentrated in vacuo to produce the crude trans-5-bromo-N-(4-(pyrrolidin-1-ylmethyl)cyclohexyl)-1-(tetrahydro-2H-pyran-2-yl)-1H-indazole-3-carboxamide (CXXXVII) as a gummy solid (0.489 g, 1.0 mmol, 100% yield). Used for next step without purification. ESIMS found for $C_{24}H_{33}BrN_4O_2$ m/z 489.2 (M+H).

Example 1

Preparation of N-((2S,4R)-1-(2-fluoro-2-methylpropyl)-2-methylpiperidin-4-yl)-5-(1-methyl-1H-pyrazol-4-yl)-1H-indazole-3-carboxamide (44) is depicted below in Scheme 23.

Scheme 23

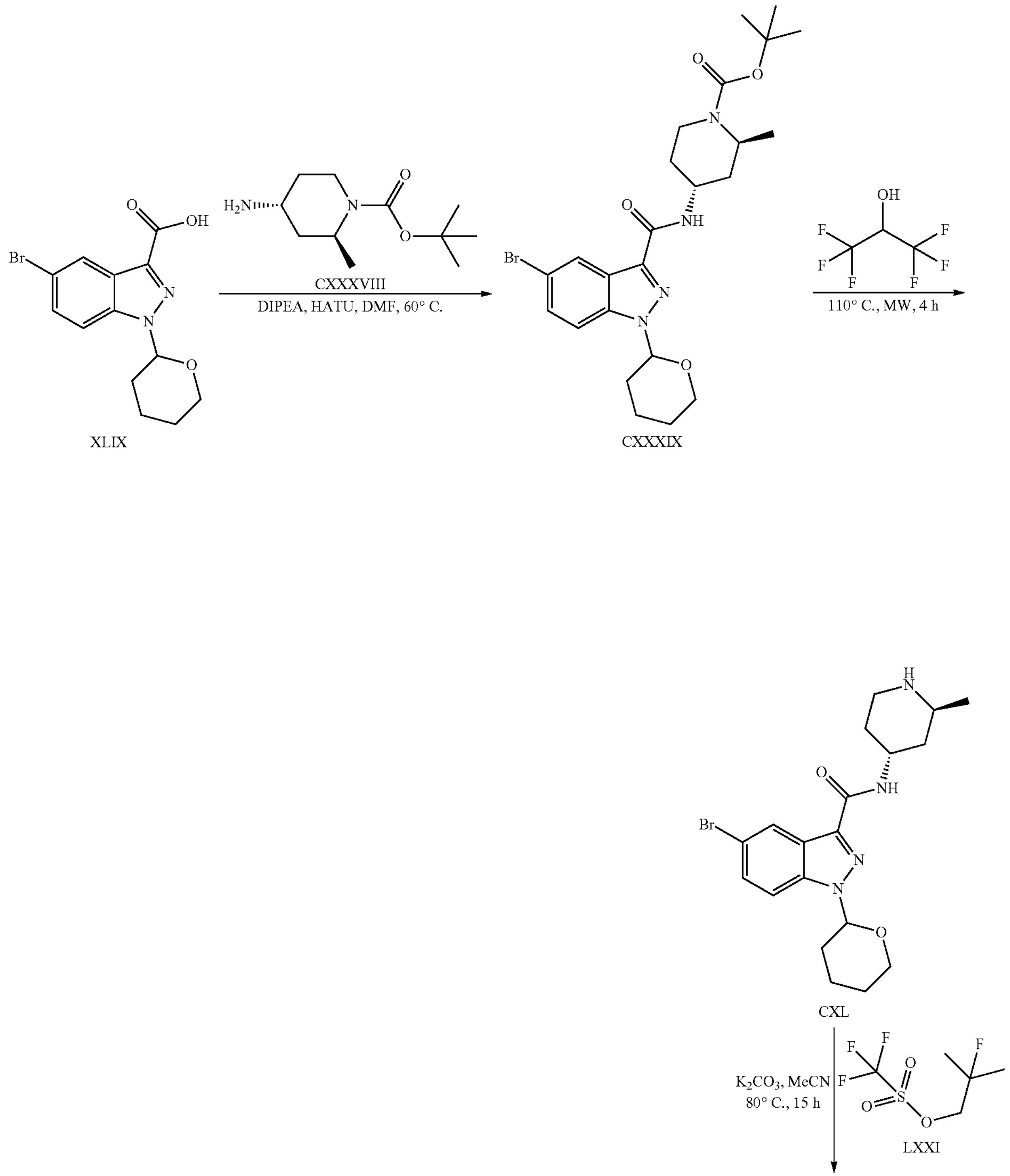

XLIX, CXXXIX, CXL, LXXI

-continued

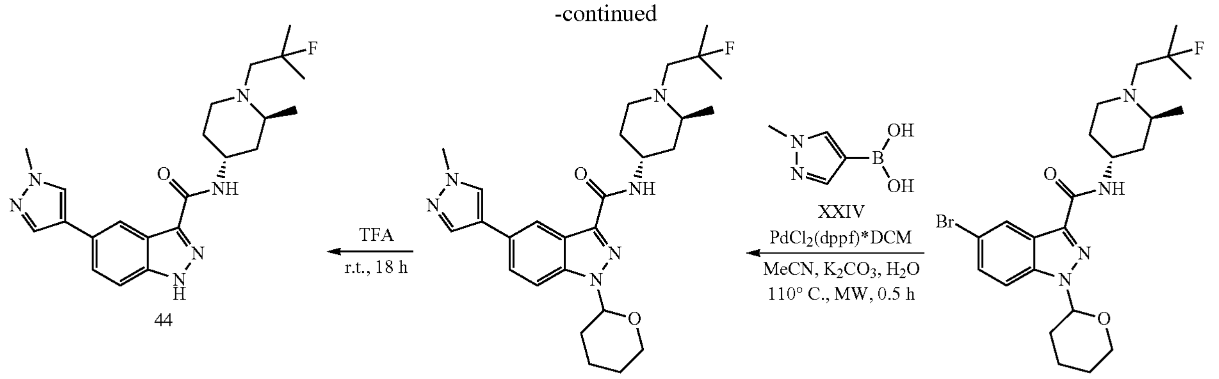

44 CXLII CXLI

Step 1

To a solution of 5-bromo-1-(tetrahydro-2H-pyran-2-yl)-1H-indazole-3-carboxylic acid (XLIX) (0.745 g, 2.29 mmol) and HATU (0.827 g, 2.176 mmol) in DMF (8 mL) was added DIPEA (0.80 mL, 4.58 mmol) and the mixture was stirred for 10 min. Then, trans-tert-butyl 4-amino-2-methylpiperidine-1-carboxylate (CXXXVIII) (0.5 g, 2.33 mmol) was added and the mixture was heated to 60° C. for 4 h. The LC-MS of mixture showed near completion of the starting material. The solvents were concentrated in vacuo, the residue partitioned between EtOAc and saturated aqueous $NaHCO_3$, the organic layer was separated, washed with water and brine. The organic layer was dried over anhydrous $Na_2SO_4$, solvents removed in vacuo and the crude was purified by silica gel column chromatography (0→50% EtOAc/hexanes) to obtain trans-tert-butyl 4-(5-bromo-1-(tetrahydro-2H-pyran-2-yl)-1H-indazole-3-carboxamido)-2-methylpiperidine-1-carboxylate (CXXXIX) as a white solid (1.194 g, 2.290 mmol, 100% yield). ESIMS found $C_{24}H_{33}BrN_4O_4$ m/z 544.4 (M+Na).

Step 2

A solution of trans-tert-butyl 4-(5-bromo-1-(tetrahydro-2H-pyran-2-yl)-1H-indazole-3-carboxamido)-2-methylpiperidine-1-carboxylate (CXXXIX) (1.19 g, 2.282 mmol) in 1,1,1,3,3,3-hexafluoropropan-2-ol (10 mL, 2.282 mmol) was heated to 110° C. for 4 h with microwave irradiation. The solvents were concentrated and the crude was purified by column chromatography (0→30% 7N $NH_3$/MeOH/$CHCl_3$) to obtain 5-bromo-N-((2S,4R)-2-methylpiperidin-4-yl)-1-(tetrahydro-2H-pyran-2-yl)-1H-indazole-3-carboxamide (CXL) as a white solid (0.576 g, 1.367 mmol, 59.9% yield). ESIMS found for $C_{19}H_{25}BrN_4O_2$ m/z 422.2 (M+H).

Step 3

To a solution of trans-5-bromo-2-methylpiperidin-4-yl-1-(tetrahydro-2H-pyran-2-yl)-1H-indazole-3-carboxamide (CXL) (0.576 g, 1.367 mmol) in acetonitrile (5 mL) was added potassium carbonate (0.567 g, 4.10 mmol) followed by the addition of 2-fluoro-2-methylpropyl trifluoromethanesulfonate (LXXI) (0.383 g, 1.709 mmol). The mixture was heated to 80° C. for 15 h. The solvents were concentrated, the residue partitioned between EtOAc and water, the organic layer separated and washed with brine. The organic layer was dried over anhydrous $Na_2SO_4$, solvents removed in vacuo and dried under high vacuo to obtain 5-bromo-N-((2S,4R)-1-(2-fluoro-2-methylpropyl)-2-methylpiperidin-4-yl)-1-(tetrahydro-2H-pyran-2-yl)-1H-indazole-3-carboxamide (CXLI) (0.67 g, 1.352 mmol, 98.9% yield). Used for next step without purification. ESIMS found for $C_{23}H_{32}BrFN_4O_2$ m/z 496.2 (M+1).

Step 4

To a solution of trans-5-bromo-N-(1-(2-fluoro-2-methylpropyl)-2-methylpiperidin-4-yl)-1-(tetrahydro-2H-pyran-2-yl)-1H-indazole-3-carboxamide (CXLI) (0.22 g, 0.444 mmol), (1-methyl-1H-pyrazol-4-yl)boronic acid (XXIV) (0.084 g, 0.666 mmol), and Pd(dppf)$Cl_2$-DCM adduct (0.018 g, 0.022 mmol) in acetonitrile (2 mL). 2 M solution of potassium carbonate (0.666 mL, 1.332 mmol) was added and $N_2$ gas was bubbled into the mixture for 10 min. The mixture was then heated to 110° C. for 0.5 h with microwave irradiation. The mixture was cooled, the organic layer separated, absorbed on silica and purified by column chromatography (0→70% EtOAc/hexanes) to obtain N-((2S,4R)-1-(2-fluoro-2-methylpropyl)-2-methylpiperidin-4-yl)-5-(1-methyl-1H-pyrazol-4-yl)-1-(tetrahydro-2H-pyran-2-yl)-1H-indazole-3-carboxamide (CXLII) as a white solid (0.1 g, 0.201 mmol, 45.3% yield). ESIMS found for $C_{27}H_{37}FN_6O_2$ m/z 497.3 (M+1).

Step 5

To a solution of trans-N-(1-(2-fluoro-2-methylpropyl)-2-methylpiperidin-4-yl)-5-(1-methyl-1H-pyrazol-4-yl)-1-(tetrahydro-2H-pyran-2-yl)-1H-indazole-3-carboxamide (CXLII) (0.1 g, 0.201 mmol) in DCM (0.75 mL) was added TFA (0.776 mL, 10.07 mmol) and the mixture was stirred at room temperature for 18 h. The solvents were removed in vacuo, the residue treated with 7 N $NH_3$/MeOH, solvents removed in vacuo and the crude was purified by preparative TLC using 6% of 7 N $NH_3$/MeOH/$CHCl_3$ to obtain N-((2S,4R)-1-(2-fluoro-2-methylpropyl)-2-methylpiperidin-4-yl)-5-(1-methyl-1H-pyrazol-4-yl)-1H-indazole-3-carboxamide (44) as an off-white solid (0.035 g, 0.085 mmol, 42.1% yield). $^1H$ NMR (DMSO-$d_6$, 500 MHz) δ ppm 1.05 (3H, d, J=6.59 Hz), 1.30 (6H, dd, J=21.40, 4.70 Hz), 1.61 (1H, br d, J=12.62 Hz), 1.64-1.75 (2H, m), 1.81-1.90 (1H, m), 2.51-2.56 (2H, m), 2.59-2.66 (1H, m), 2.72-2.80 (1H, m), 3.02 (1H, br d, J=6.31 Hz), 3.88 (3H, s), 4.08-4.21 (1H, m), 7.56-7.65 (2H, m), 7.83 (1H, s), 7.97 (1H, br d, J=7.96 Hz), 8.14 (1H, s), 8.26 (1H, s), 13.49 (1H, br s); ESIMS found for $C_{22}H_{29}FN_6O$ m/z 413.3 (M+1).

Example 2

Preparation of N-(4-(difluoromethoxy)phenyl)-5-(1-(1-(2-fluoro-2-methylpropyl)piperidin-4-yl)-1H-pyrazol-4-yl)-1H-indazole-3-carboxamide (61) is depicted below in Scheme 24.

Scheme 24

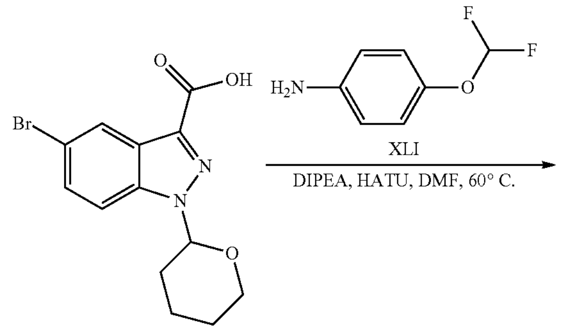

XLI

XLIX

-continued

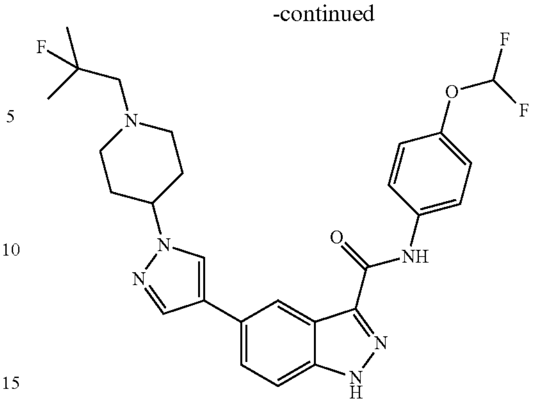

61

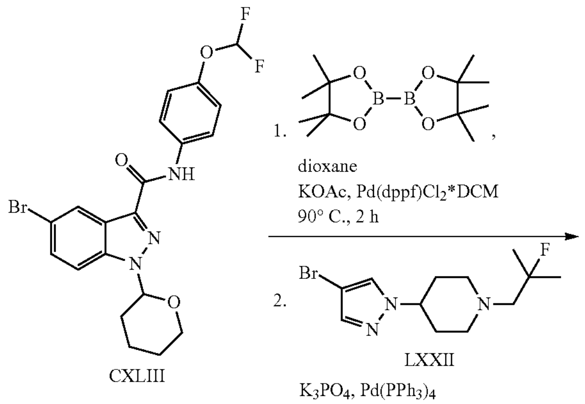

LXXII

CXLIII

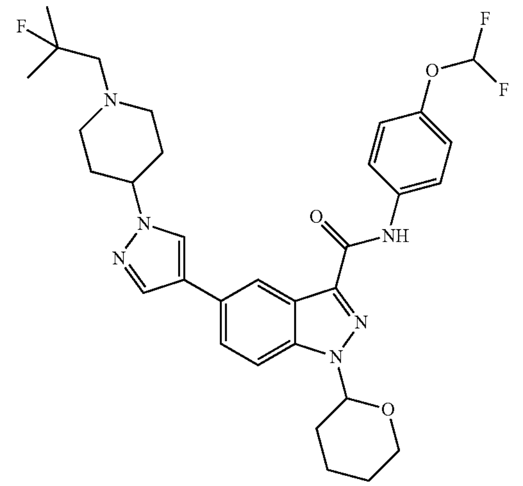

CXLIV

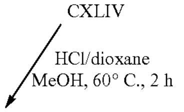

Step 1

To a solution of 5-bromo-1-(tetrahydro-2H-pyran-2-yl)-1H-indazole-3-carboxylic acid (XLIX) (1 g, 3.08 mmol), 4-(difluoromethoxy)aniline (XLI) (0.420 mL, 3.38 mmol) and HATU (1.286 g, 3.38 mmol) in DMF (10 mL) was added DIPEA (1.343 mL, 7.69 mmol). The reaction mixture was stirred at 60° C. for 2 h. Water was then added to the reaction mixture and extracted with EtOAc. The organic layer was washed with water, saturated aqueous $NaHCO_3$ and brine. The organic layer was dried, filtered and concentrated. The crude product was triturated in MeOH and the resulting solid filtered to give 5-bromo-N-(4-(difluoromethoxy)phenyl)-1-(tetrahydro-2H-pyran-2-yl)-1H-indazole-3-carboxamide as a white solid (CXLIII) (1.26 g, 2.70 mmol, 88% yield). ESIMS found $C_{20}H_{18}BrF_2N_3O_3$ m/z 466.1 (M+H).

Step 2-3

To a solution of 5-bromo-N-(4-(difluoromethoxy)phenyl)-1-(tetrahydro-2H-pyran-2-yl)-1H-indazole-3-carboxamide (CXLIII) (100 mg, 0.214 mmol) and 4,4,4',4',5,5,5',5'-octamethyl-2,2'-bi(1,3,2-dioxaborolane) (65.4 mg, 0.257 mmol) in dioxane (5 mL) were added potassium acetate (63.1 mg, 0.643 mmol) and Pd(dppf)$Cl_2$-DCM adduct (17.51 mg, 0.021 mmol). The mixture was bubbled with nitrogen and the reaction sealed and heated at 90° C. for 2 h. The reaction was cooled to room temperature and to it was added 4-(4-bromo-1H-pyrazol-1-yl)-1-(2-fluoro-2-methylpropyl)piperidine (LXXII) (71.8 mg, 0.236 mmol), $K_3PO_4$ (2 M in water) (0.268 ml, 0.536 mmol) and $Pd(PPh_3)_4$ (24.78 mg, 0.021 mmol). The mixture was bubbled with nitrogen and the reaction heated in a sealed tube at 90° C. for 6 h. The reaction was cooled to room temperature, filtered and concentrated. The crude product was purified on a silica gel column (0%→90% EtOAc/hexanes) to give N-(4-(difluoromethoxy)phenyl)-5-(1-(1-(2-fluoro-2-methylpropyl)piperidin-4-yl)-1H-pyrazol-4-yl)-1-(tetrahydro-2H-pyran-2-yl)-1H-indazole-3-carboxamide (CXLIV) as a white foam (41 mg, 0.067 mmol, 31.3% yield). ESIMS found for $C_{32}H_{37}F_3N_6O_3$ m/z 611.3 (M+H).

Step 4

To a solution of N-(4-(difluoromethoxy)phenyl)-5-(1-(1-(2-fluoro-2-methylpropyl)piperidin-4-yl)-1H-pyrazol-4-yl)-1-(tetrahydro-2H-pyran-2-yl)-1H-indazole-3-carboxamide (CXLIV) (40 mg, 0.066 mmol) in MeOH (3 mL) was added with HCl (0.164 mL, 0.655 mmol) (4 M in dioxane). The mixture was heated at 60° C. for 2 h and concentrated. The crude product was purified on a silica gel column (0%→5% 7N $NH_3$ in MeOH/$CHCl_3$). The fractions containing the product were combined, concentrated, and triturated in ether. The resulting solid was filtered to give N-(4-(difluoromethoxy)phenyl)-5-(1-(1-(2-fluoro-2-methylpropyl) piperidin-4-yl)-1H-pyrazol-4-yl)-1H-indazole-3-carboxamide (61) as a white solid (20 mg, 0.038 mmol, 58.0% yield). $^1$H NMR (DMSO-$d_6$, 500 MHz) δ ppm 1.34 (6H, d, J=21.40 Hz), 1.97-2.10 (4H, m), 2.29 (2H, td, J=11.53, 3.29 Hz), 3.01 (2H, br d, J=12.08 Hz), 4.15 (1H, tt, J=10.60, 5.18 Hz), 7.18 (1H, t, J=74.40 Hz), 7.16-7.20 (1H, m), 7.65 (1H, dd, J=8.78, 0.82 Hz), 7.69-7.73 (1H, m), 7.89 (1H, d, J=0.82 Hz), 7.94-7.98 (2H, m), 8.33 (1H, d, J=0.82 Hz), 8.34-8.36 (1H, m), 10.44 (1H, s), 13.75 (1H, br s); ESIMS found for $C_{27}H_{29}F_3N_6O_2$ m/z 527.2 (M+1).

The following compounds were prepared in accordance with the procedures described in the above Examples 1 and 2.

1

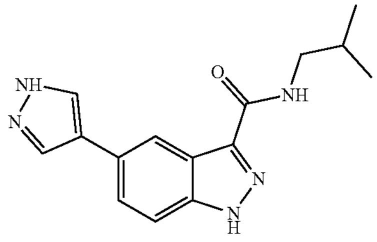

N-Isobutyl-5-(1H-pyrazol-4-yl)-1H-indazole-3-carboxamide 1

White solid (45.5 mg, 0.161 mmol, 25.9% yield). $^1$H NMR (DMSO-$d_6$, 500 MHz) δ ppm 0.91 (d, J=6.86 Hz, 6H), 1.90 (dquin, J=13.45, 6.72, 6.72, 6.72, 6.72 Hz, 1H), 3.14 (t, J=6.59 Hz, 2H), 7.58 (d, J=8.78 Hz, 1H), 7.67 (dd, J=8.51, 1.65 Hz, 1H), 7.91 (br s, 1H), 8.17 (br s, 1H), 8.28-8.33 (m, 2H), 12.92 (br s, 1H), 13.47 (br s, 1H); ESIMS found for $C_{15}H_{17}N_5O$ m/z 284.2 (M+1).

2

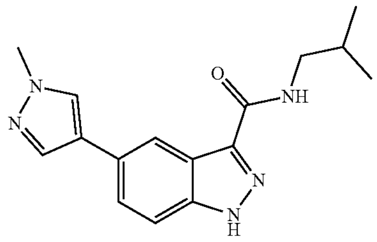

N-Isobutyl-5-(1-methyl-1H-pyrazol-4-yl)-1H-indazole-3-carboxamide 2

White solid (25.5 mg, 0.086 mmol, 14.87% yield). $^1$H NMR (DMSO-$d_6$, 500 MHz) δ ppm 0.90 (d, J=6.59 Hz, 6H), 1.90 (dquin, J=13.62, 6.75, 6.75, 6.75, 6.75 Hz, 1H), 3.14 (t, J=6.59 Hz, 2H), 3.88 (s, 3H), 7.57-7.60 (m, 1H), 7.61-7.65 (m, 1H), 7.83 (s, 1H), 8.14 (s, 1H), 8.27 (s, 1H), 8.30 (br t, J=6.04 Hz, 1H), 13.48 (br s, 1H); ESIMS found for $C_{16}H_{19}N_5O$ m/z 298.2 (M+1).

3

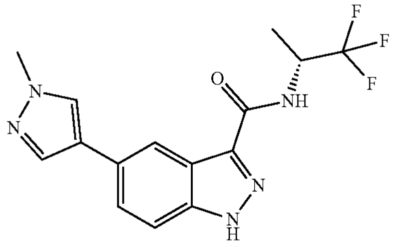

(R)-5-(1-Methyl-1H-pyrazol-4-yl)-N-(1,1,1-trifluoropropan-2-yl)-1H-indazole-3-carboxamide 3

White solid (27.6 mg, 0.082 mmol, 26.5% yield). $^1$H NMR (DMSO-$d_6$, 500 MHz) δ ppm 1.41 (d, J=7.14 Hz, 3H), 3.88 (s, 3H), 4.85-4.96 (m, 1H), 7.60-7.69 (m, 2H), 7.85 (s, 1H), 8.17 (s, 1H), 8.25 (s, 1H), 8.86 (d, J=9.06 Hz, 1H), 13.69 (br s, 1H); ESIMS found for $C_{15}H_{14}F_3N_5O$ m/z 338.1 (M+1).

4

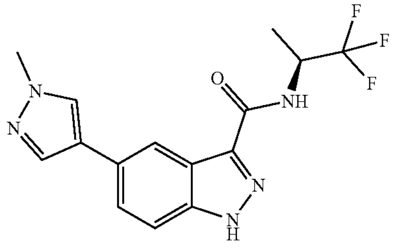

(S)-5-(1-Methyl-1H-pyrazol-4-yl)-N-(1,1,1-trifluoropropan-2-yl)-1H-indazole-3-carboxamide 4

White solid (35.5 mg, 0.105 mmol, 34.4% yield). $^1$H NMR (DMSO-$d_6$, 500 MHz) δ ppm 1.41 (d, J=7.14 Hz, 3H), 3.88 (s, 3H), 4.90 (dq, J=15.75, 7.83 Hz, 1H), 7.59-7.69 (m, 2H), 7.85 (s, 1H), 8.17 (s, 1H), 8.25 (s, 1H), 8.85 (d, J=9.06 Hz, 1H), 13.67 (br s, 1H); ESIMS found for $C_{15}H_{14}F_3N_5O$ m/z 338.1 (M+1).

5

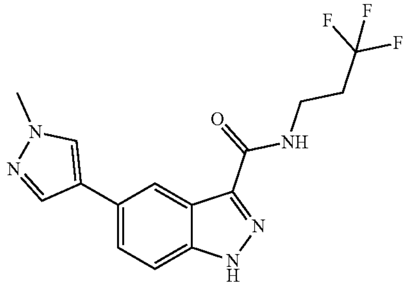

5-(1-Methyl-1H-pyrazol-4-yl)-N-(3,3,3-trifluoropropyl)-1H-indazole-3-carboxamide 5

White solid (34.2 mg, 0.101 mmol, 31.7% yield). $^1$H NMR (DMSO-$d_6$, 500 MHz) δ ppm 2.54-2.66 (m, 2H), 3.56

(q, J=6.86 Hz, 2H), 3.88 (s, 3H), 7.58-7.66 (m, 2H), 7.84 (s, 1H), 8.16 (s, 1H), 8.27 (s, 1H), 8.57 (t, J=5.90 Hz, 1H), 13.57 (br s, 1H); ESIMS found for $C_{15}H_{14}F_3N_5O$ m/z 338.1 (M+1).

6

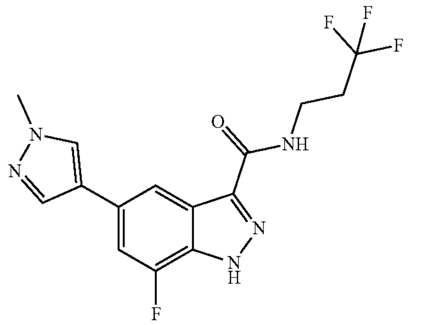

7-Fluoro-5-(1-methyl-1H-pyrazol-4-yl)-N-(3,3,3-trifluoropropyl)-1H-indazole-3-carboxamide 6

White solid (47 mg, 0.132 mmol, 45.4% yield). $^1$H NMR (DMSO-$d_6$, 500 MHz) δ ppm 2.54-2.66 (2H, m), 3.56 (2H, q, J=6.77 Hz), 3.87 (3H, s), 7.55 (1H, dd, J=12.62, 1.10 Hz), 7.89 (1H, s), 8.09 (1H, d, J=0.82 Hz), 8.22 (1H, s), 8.67 (1H, t, J=5.90 Hz), 14.14 (1H, br s); ESIMS found for $C_{15}H_{13}F_4N_5O$ m/z 356.1 (M+1).

7

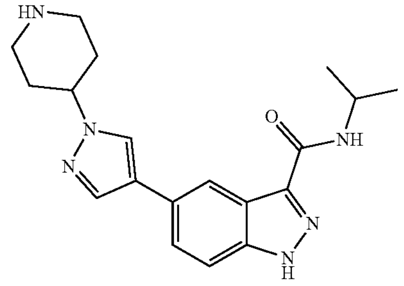

N-Isopropyl-5-(1-(piperidin-4-yl)-1H-pyrazol-4-yl)-1H-indazole-3-carboxamide 7

White solid (289 mg, 0.082 mmol, 41.2% yield). $^1$H NMR (DMSO-$d_6$, 500 MHz) δ ppm 1.21 (d, J=6.59 Hz, 6H), 1.83 (qd, J=12.03, 3.98 Hz, 2H), 1.94-2.04 (m, 2H), 2.60 (br t, J=11.25 Hz, 2H), 3.05 (br d, J=12.35 Hz, 2H), 4.13-4.26 (m, 2H), 7.55-7.60 (m, 1H), 7.63-7.68 (m, 1H), 7.85 (s, 1H), 8.02 (d, J=8.23 Hz, 1H), 8.22 (s, 1H), 8.28 (s, 1H), 13.46 (br s, 1H); ESIMS found for $C_{19}H_{24}N_6O$ m/z 353.2 (M+1).

8

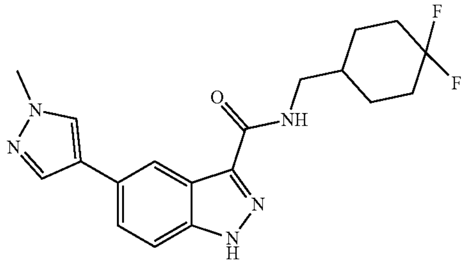

N-((4,4-Difluorocyclohexyl)methyl)-5-(1-methyl-1H-pyrazol-4-yl)-1H-indazole-3-carboxamide 8

White solid (14.4 mg, 0.039 mmol, 11.61% yield). $^1$H NMR (DMSO-$d_6$, 500 MHz) δ ppm 1.18-1.30 (m, 2H), 1.70-1.86 (m, 5H), 2.01 (br d, J=9.33 Hz, 2H), 3.23 (t, J=6.45 Hz, 2H), 3.88 (s, 3H), 7.57-7.65 (m, 2H), 7.83 (s, 1H), 8.15 (s, 1H), 8.26 (d, J=0.82 Hz, 1H), 8.45 (t, J=6.18 Hz, 1H), 13.52 (br s, 1H); ESIMS found for $C_{19}H_{21}F_2N_5O$ m/z 374.1 (M+1).

9

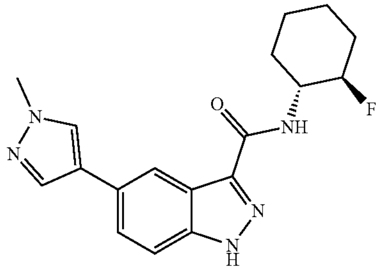

N-((1R,2R)-2-Fluorocyclohexyl)-5-(1-methyl-1H-pyrazol-4-yl)-1H-indazole-3-carboxamide 9

White solid (28 mg, 0.082 mmol, 35.6% yield). $^1$H NMR (DMSO-$d_6$, 500 MHz) δ ppm 1.20-1.35 (m, 2H), 1.42-1.55 (m, 2H), 1.65 (br d, J=10.98 Hz, 1H), 1.74 (br d, J=9.06 Hz, 1H), 1.81-1.89 (m, 1H), 2.07-2.16 (m, 1H), 3.88 (s, 3H), 3.98-4.09 (m, 1H), 4.53-4.71 (m, 1H), 7.61 (qd, J=8.55, 1.23 Hz, 2H), 7.83 (s, 1H), 8.14 (s, 1H), 8.26 (d, J=0.82 Hz, 1H), 8.39 (d, J=9.06 Hz, 1H), 13.54 (br s, 1H); ESIMS found for $C_{18}H_{20}FN_5O$ m/z 342.1 (M+1).

10

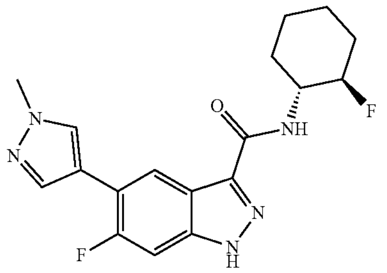

6-Fluoro-N-((1R,2R)-2-fluorocyclohexyl)-5-(1-methyl-1H-pyrazol-4-yl)-1H-indazole-3-carboxamide 10

Light brown solid (15 mg, 0.042 mmol, 24.68% yield). $^1$H NMR (DMSO-$d_6$, 500 MHz) δ ppm 1.18-1.35 (2H, m), 1.41-1.53 (2H, m), 1.65 (1H, br d, J=10.70 Hz), 1.73 (1H, br d, J=9.33 Hz), 1.84 (1H, br d, J=9.88 Hz), 2.08-2.16 (1H, m), 3.91 (3H, s), 3.97-4.08 (1H, m), 4.61 (1H, dtd, J=50.30, 10.20, 4.10 Hz), 7.50 (1H, d, J=11.25 Hz), 7.81 (1H, s), 8.12 (1H, d, J=2.20 Hz), 8.34 (1H, d, J=7.41 Hz), 8.47 (1H, d, J=8.78 Hz), 13.63 (1H, br s); ESIMS found for $C_{15}H_{19}F_2N_5O$ m/z 360.2 (M+1).

11

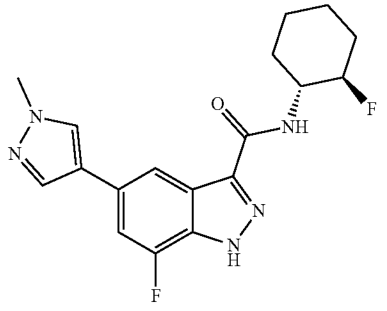

7-Fluoro-N-((1R,2R)-2-fluorocyclohexyl)-5-(1-methyl-1H-pyrazol-4-yl)-1H-indazole-3-carboxamide 11

White solid (61 mg, 0.170 mmol, 58.4% yield). $^1$H NMR (DMSO-$d_6$, 500 MHz) δ ppm 1.20-1.35 (2H, m), 1.42-1.54 (2H, m), 1.65 (1H, br d, J=11.25 Hz), 1.74 (1H, br d, J=9.33 Hz), 1.85 (1H, br d, J=9.33 Hz), 2.12 (1H, br d, J=4.39 Hz), 3.87 (3H, s), 3.97-4.09 (1H, m), 4.62 (1H, dtd, J=50.00, 10.20, 4.20 Hz), 7.54 (1H, dd, J=12.35, 0.82 Hz), 7.88 (1H, s), 8.09 (1H, d, J=0.82 Hz), 8.20 (1H, s), 8.51 (1H, d, J=8.78 Hz), 14.10 (1H, br s); ESIMS found for $C_{18}H_{19}F_2N_5O$ m/z 360.1 (M+1).

12

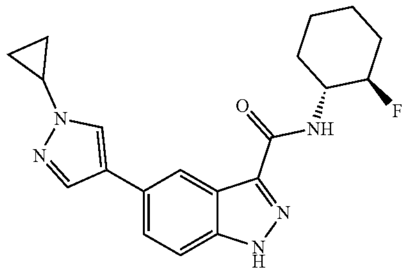

5-(1-Cyclopropyl-1H-pyrazol-4-yl)-N-((1R,2R)-2-fluorocyclohexyl)-1H-indazole-3-carboxamide 12

White solid (64 mg, 0.174 mmol, 46.3% yield). $^1$H NMR (DMSO-$d_6$, 500 MHz) δ ppm 0.95-1.01 (2H, m), 1.08-1.14 (2H, m), 1.20-1.36 (2H, m), 1.41-1.54 (2H, m), 1.65 (1H, br d, J=9.61 Hz), 1.74 (1H, br d, J=9.33 Hz), 1.85 (1H, br d, J=8.78 Hz), 2.12 (1H, br d, J=4.67 Hz), 3.75 (1H, tt, J=7.38, 3.88 Hz), 3.97-4.09 (1H, m), 4.62 (1H, dtd, J=50.00, 10.40, 4.70 Hz), 7.56-7.61 (1H, m), 7.63-7.68 (1H, m), 7.83 (1H, s), 8.24 (1H, s), 8.28 (1H, s), 8.39 (1H, d, J=9.06 Hz), 13.54 (1H, br s); ESIMS found for $C_{20}H_{22}FN_5O$ m/z 368.2 (M+1).

13

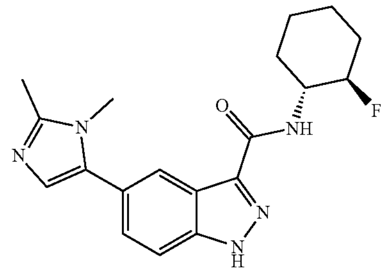

5-(1,2-Dimethyl-1H-imidazol-5-yl)-N-((1R,2R)-2-fluorocyclohexyl)-1H-indazole-3-carboxamide 13

Light brown solid (17 mg, 0.048 mmol, 24.73% yield). $^1$H NMR (DMSO-$d_6$, 500 MHz) δ ppm 1.20-1.34 (2H, m), 1.42-1.54 (2H, m), 1.65 (1H, br d, J=10.98 Hz), 1.73 (1H, br d, J=9.06 Hz), 1.84 (1H, br d, J=5.76 Hz), 2.12 (1H, br d, J=4.94 Hz), 2.36 (3H, s), 3.52 (3H, s), 3.96-4.09 (2H, m), 4.61 (1H, dtd, J=50.30, 9.90, 4.40 Hz), 6.86 (1H, s), 7.46 (1H, dd, J=8.64, 1.51 Hz), 7.69 (1H, d, J=8.51 Hz), 8.15 (1H, s), 8.46 (1H, d, J=8.78 Hz), 13.68 (1H, br s); ESIMS found for $C_{19}H_{22}FN_5O$ m/z 356.1 (M+1).

14

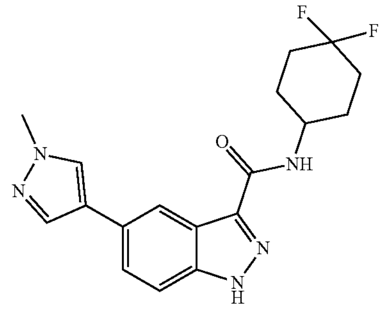

N-(4,4-Difluorocyclohexyl)-5-(1-methyl-1H-pyrazol-4-yl)-1H-indazole-3-carboxamide 14

White solid (2.26 g, 6.29 mmol, 43.9%). $^1$H NMR (DMSO-$d_6$, 500 MHz) δ ppm 1.69-1.80 (m, 2H), 1.89 (br d, J=13.72 Hz, 2H), 1.92-2.12 (m, 4H), 3.88 (s, 3H), 3.99-4.09 (m, 1H), 7.57-7.65 (m, 2H), 7.83 (s, 1H), 8.14 (s, 1H), 8.25 (s, 1H), 8.29 (d, J=8.23 Hz, 1H), 13.52 (br s, 1H); ESIMS found for $C_{18}H_{19}F_2N_5O$ m/z 360.1 (M+1).

15

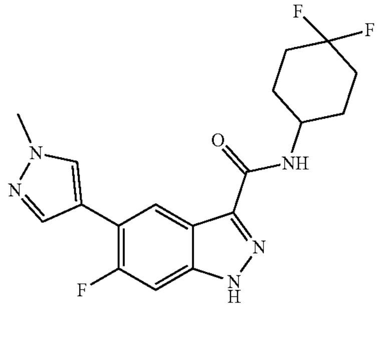

N-(4,4-Difluorocyclohexyl)-6-fluoro-5-(1-methyl-1H-pyrazol-4-yl)-1H-indazole-3-carboxamide 15

White solid (54 mg, 0.143 mmol, 48.9% yield). $^1$H NMR (DMSO-$d_6$, 500 MHz) δ ppm 1.68-1.81 (2H, m), 1.88 (2H, br d, J=14.55 Hz), 1.91-2.13 (4H, m), 3.90 (3H, s), 3.98-4.09 (1H, m), 7.50 (1H, d, J=11.25 Hz), 7.81 (1H, s), 8.12 (1H, d, J=1.92 Hz), 8.28-8.34 (1H, m), 8.37 (1H, d, J=7.96 Hz), 13.60 (1H, br s); ESIMS found for $C_{15}H_{18}F_3N_5O$ m/z 378.1 (M+1).

16

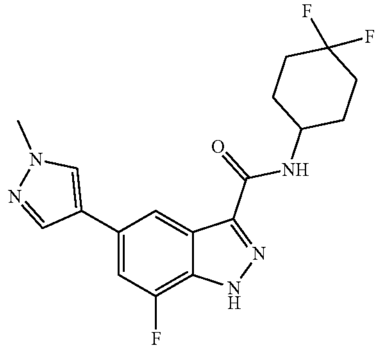

N-(4,4-Difluorocyclohexyl)-7-fluoro-5-(1-methyl-1H-pyrazol-4-yl)-1H-indazole-3-carboxamide 16

White solid (64 mg, 0.170 mmol, 58.4% yield). $^1$H NMR (DMSO-$d_6$, 500 MHz) δ ppm 1.70-1.81 (2H, m), 1.88 (2H, br d, J=14.82 Hz), 1.91-2.12 (4H, m), 3.87 (3H, s), 3.99-4.09 (1H, m), 7.53 (1H, d, J=12.62 Hz), 7.88 (1H, s), 8.07 (1H, s), 8.20 (1H, s), 8.41 (1H, d, J=8.23 Hz), 14.08 (1H, br s); ESIMS found for $C_{15}H_{18}F_3N_5O$ m/z 378.1 (M+1).

17

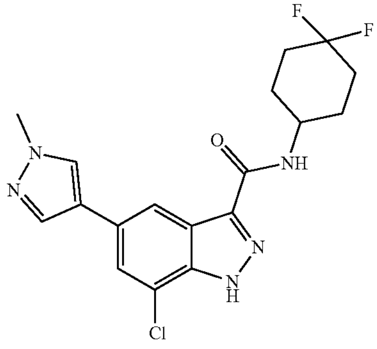

7-Chloro-N-(4,4-difluorocyclohexyl)-5-(1-methyl-1H-pyrazol-4-yl)-1H-indazole-3-carboxamide 17

White solid (44 mg, 0.112 mmol, 59.3% yield). $^1$H NMR (DMSO-$d_6$, 500 MHz) δ ppm 1.71-1.81 (2H, m), 1.89 (2H, br d, J=14.82 Hz), 1.92-2.12 (4H, m), 3.87 (3H, s), 3.99-4.09 (1H, m), 7.77 (1H, d, J=1.37 Hz), 7.89 (1H, s), 8.20-8.23 (2H, m), 8.39 (1H, d, J=8.23 Hz), 13.98 (1H, br s); ESIMS found for $C_{18}H_{18}ClF_2N_5O$ m/z 394.1 (M+1).

18

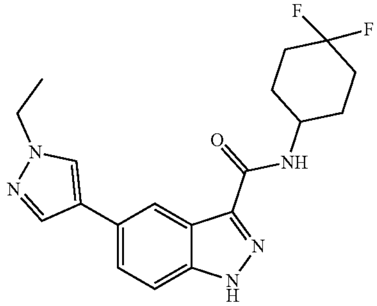

N-(4,4-Difluorocyclohexyl)-5-(1-ethyl-1H-pyrazol-4-yl)-1H-indazole-3-carboxamide 18

White solid (52 mg, 0.139 mmol, 49.4% yield). $^1$H NMR (DMSO-$d_6$, 500 MHz) δ ppm 1.42 (3H, t, J=7.27 Hz), 1.70-1.81 (2H, m), 1.89 (2H, br d, J=14.00 Hz), 1.91-2.12 (4H, m), 3.99-4.09 (1H, m), 4.16 (2H, q, J=7.14 Hz), 7.56-7.61 (1H, m), 7.62-7.67 (1H, m), 7.84 (1H, s), 8.19 (1H, s), 8.26 (1H, s), 8.29 (1H, d, J=8.23 Hz), 13.51 (1H, br s); ESIMS found for $C_{19}H_{21}F_2N_5O$ m/z 374.1 (M+1).

19

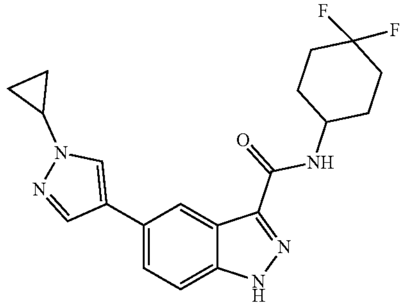

5-(1-Cyclopropyl-1H-pyrazol-4-yl)-N-(4,4-difluorocyclohexyl)-1H-indazole-3-carboxamide 19

White solid (78 mg, 0.202 mmol, 55.9% yield). $^1H$ NMR ($DMSO-d_6$, 500 MHz) δ ppm 0.95-1.01 (2H, m), 1.08-1.13 (2H, m), 1.69-1.80 (2H, m), 1.89 (2H, br d, J=14.55 Hz), 1.91-2.13 (4H, m), 3.75 (1H, tt, J=7.44, 3.81 Hz), 3.98-4.09 (1H, m), 7.55-7.60 (1H, m), 7.63-7.67 (1H, m), 7.83 (1H, s), 8.23 (1H, s), 8.26 (1H, s), 8.29 (1H, d, J=7.96 Hz), 13.51 (1H, br s); ESIMS found for $C_{20}H_{21}F_2N_5O$ m/z 386.1 (M+1).

20

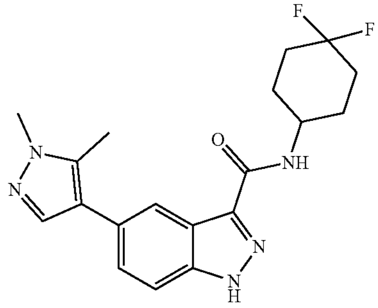

N-(4,4-Difluorocyclohexyl)-5-(1,5-dimethyl-1H-pyrazol-4-yl)-1H-indazole-3-carboxamide 20

White solid (25.4 mg, 0.068 mmol, 44.5% yield). $^1H$ NMR ($DMSO-d_6$, 500 MHz) δ ppm 1.69-1.80 (m, 2H), 1.88 (br d, J=14.27 Hz, 2H), 1.91-2.12 (m, 4H), 2.39 (s, 3H), 3.80 (s, 3H), 3.99-4.10 (m, 1H), 7.46 (dd, J=8.78, 1.65 Hz, 1H), 7.57 (s, 1H), 7.63 (d, J=9.33 Hz, 1H), 8.12 (s, 1H), 8.31 (d, J=8.23 Hz, 1H), 13.56 (br s, 1H); ESIMS found for $C_{19}H_{21}F_2N_5O$ m/z 374.2 (M+1).

21

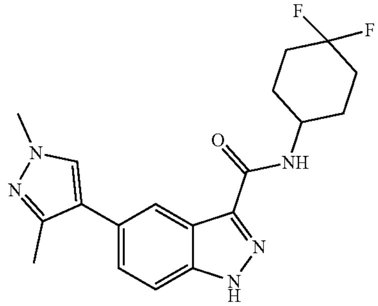

N-(4,4-Difluorocyclohexyl)-5-(1,3-dimethyl-1H-pyrazol-4-yl)-1H-indazole-3-carboxamide 21

White solid (25.4 mg, 0.068 mmol, 41.5% yield). $^1H$ NMR ($DMSO-d_6$, 500 MHz) δ ppm 1.69-1.80 (m, 2H), 1.88 (br d, J=14.00 Hz, 2H), 1.91-2.11 (m, 4H), 2.31 (s, 3H), 3.80 (s, 3H), 3.99-4.10 (m, 1H), 7.48 (dd, J=8.64, 1.51 Hz, 1H), 7.61 (d, J=8.51 Hz, 1H), 7.89 (s, 1H), 8.17 (d, J=0.82 Hz, 1H), 8.30 (d, J=8.23 Hz, 1H), 13.54 (br s, 1H); ESIMS found for $C_{19}H_{21}F_2N_5O$ m/z 374.2 (M+1).

22

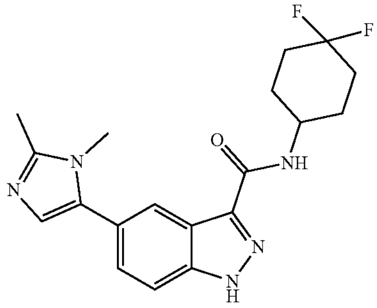

N-(4,4-Difluorocyclohexyl)-5-(1,2-dimethyl-1H-imidazol-5-yl)-1H-indazole-3-carboxamide 22

White solid (88 mg, 0.236 mmol, 53.9% yield). $^1H$ NMR ($DMSO-d_6$, 500 MHz) δ ppm 1.69-1.80 (m, 2H), 1.88 (br d, J=14.00 Hz, 2H), 1.91-2.13 (m, 4H), 2.36 (s, 3H), 3.52 (s, 3H), 3.98-4.10 (m, 1H), 6.86 (s, 1H), 7.46 (dd, J=8.78, 1.65 Hz, 1H), 7.68 (d, J=8.51 Hz, 1H), 8.14 (d, J=0.82 Hz, 1H), 8.34 (d, J=8.23 Hz, 1H), 13.66 (br s, 1H); ESIMS found for $C_{19}H_{21}F_2N_{50}$ m/z 374.2 (M+1).

23

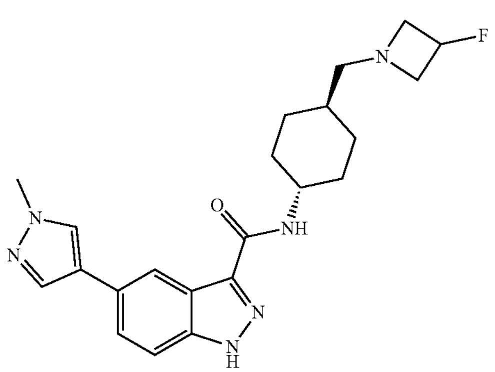

N-((1R,4R)-4-((3-Fluoroazetidin-1-yl)methyl)cyclohexyl)-5-(1-methyl-1H-pyrazol-4-yl)-1H-indazole-3-carboxamide 23

Off-white solid (37 mg, 0.090 mmol, 28.8% yield). $^1H$ NMR ($DMSO-d_6$, 500 MHz) δ ppm 0.93-1.04 (2H, m), 1.23 (1H, br s), 1.34-1.45 (2H, m), 1.46-1.61 (1H, m), 1.77 (2H, br d, J=11.53 Hz), 1.85 (2H, br d, J=9.88 Hz), 2.31 (1H, br s), 2.96-3.14 (2H, m), 3.56 (2H, br s), 3.72-3.83 (1H, m), 3.88 (3H, s), 5.03-5.22 (1H, m), 7.55-7.64 (2H, m), 7.82 (1H, d, J=0.82 Hz), 8.01 (1H, d, J=8.51 Hz), 8.12-8.15 (1H, m), 8.25 (1H, s), 13.47 (1H, s); ESIMS found for $C_{22}H_{27}FN_6O$ m/z 411.3 (M+1).

24

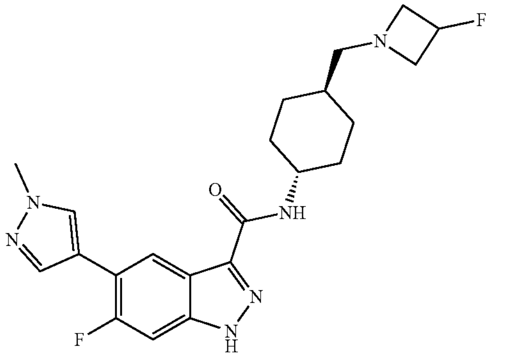

6-fluoro-N-((1R,4R)-4-((3-fluoroazetidin-1-yl) methyl)cyclohexyl)-5-(1-methyl-1H-pyrazol-4-yl)-1H-indazole-3-carboxamide 24

White solid (45 mg, 0.105 mmol, 41.4% yield). $^1$H NMR (DMSO-$d_6$, 500 MHz) δ ppm 0.92-1.03 (1H, m), 1.35-1.60 (5H, m), 1.67 (1H, br d, J=11.80 Hz), 1.77 (1H, br d, J=12.90 Hz), 1.84 (1H, br d, J=10.70 Hz), 2.29 (1H, d, J=6.86 Hz), 2.42 (1H, br d, J=4.94 Hz), 2.97-3.07 (2H, m), 3.50-3.59 (2H, m), 3.90 (3H, s), 5.03-5.22 (1H, m), 7.49 (1H, dd, J=10.98, 6.04 Hz), 7.81 (1H, s), 7.91 (1H, d, J=7.96 Hz), 8.12 (1H, br d, J=2.47 Hz), 8.32 (1H, dd, J=7.55, 3.70 Hz), 13.57 (1H, br s); ESIMS found for $C_{22}H_{26}F_2N_6O$ m/z 429.2 (M+1).

25

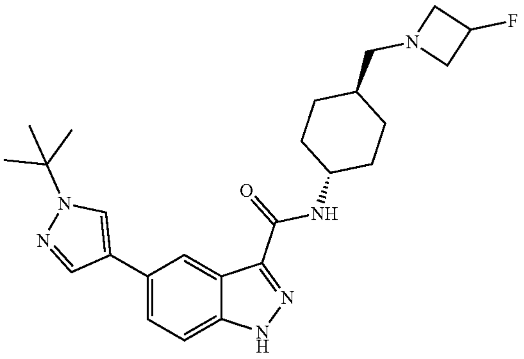

5-(1-(tert-Butyl)-1H-pyrazol-4-yl)-N-((1R,4R)-4-((3-fluoroazetidin-1-yl) methyl)cyclohexyl)-1H-indazole-3-carboxamide 25

White solid (39 mg, 0.086 mmol, 66.1% yield). $^1$H NMR (DMSO-$d_6$, 500 MHz) δ ppm 0.93-1.03 (2H, m), 1.18-1.28 (2H, m), 1.35-1.53 (3H, m), 1.57 (9H, s), 1.78 (1H, br d, J=11.80 Hz), 1.86 (1H, br d, J=9.61 Hz), 2.29 (2H, d, J=6.86 Hz), 2.98-3.08 (2H, m), 3.50-3.59 (2H, m), 3.72-3.82 (1H, m), 5.12 (1H, dquin, J=58.00, 4.90, 4.90, 4.90, 4.90 Hz), 7.57 (1H, d, J=8.51 Hz), 7.68 (1H, dd, J=8.64, 1.51 Hz), 7.84 (1H, s), 8.00 (1H, d, J=8.23 Hz), 8.24-8.27 (1H, m), 8.29 (1H, s), 13.45 (1H, br s); ESIMS found for $C_{25}H_{33}FN_6O$ m/z 453.3 (M+1).

26

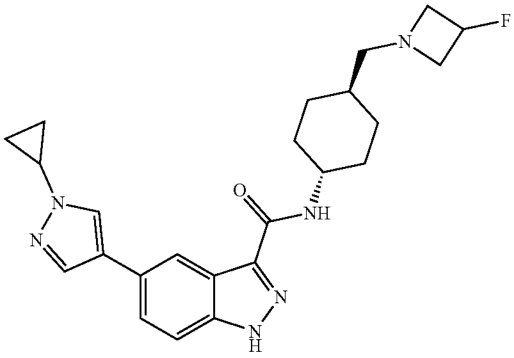

5-(1-Cyclopropyl-1H-pyrazol-4-yl)-N-((1R,4R)-4-((3-fluoroazetidin-1-yl) methyl)cyclohexyl)-1H-indazole-3-carboxamide 26

White solid (76 mg, 0.174 mmol, 63.8% yield). $^1$H NMR (DMSO-$d_6$, 500 MHz) δ ppm 0.96-1.01 (3H, m), 1.08-1.14 (2H, m), 1.23 (1H, br s), 1.35-1.60 (4H, m), 1.68 (1H, br d, J=11.25 Hz), 1.77 (1H, br d, J=11.53 Hz), 1.85 (1H, br d, J=10.43 Hz), 2.29 (1H, d, J=6.86 Hz), 2.42 (1H, br d, J=5.76 Hz), 2.98-3.07 (2H, m), 3.50-3.59 (2H, m), 3.75 (1H, tt, J=7.34, 3.77 Hz), 3.97 (1H, br d, J=4.12 Hz), 5.03-5.22 (1H, m), 7.55-7.60 (1H, m), 7.62-7.66 (1H, m), 7.82 (1H, d, J=1.92 Hz), 8.03 (1H, d, J=8.51 Hz), 8.23 (1H, d, J=3.02 Hz), 8.26 (1H, br s), 13.48 (1H, br s); ESIMS found for $C_{24}H_{29}FN_6O$ m/z 437.2 (M+1).

27

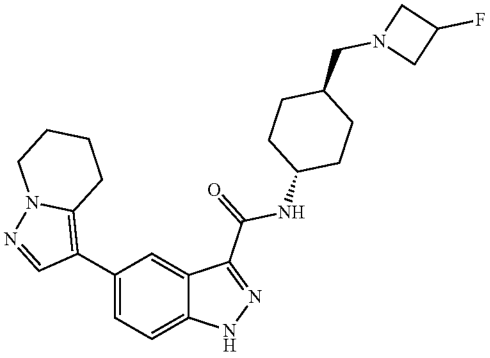

N-((1R,4R)-4-((3-Fluoroazetidin-1-yl)methyl)cyclohexyl)-5-(4,5,6,7-tetrahydropyrazolo[1,5-a]pyridin-3-yl)-1H-indazole-3-carboxamide 27

White solid (7 mg, 0.016 mmol, 14.32% yield). $^1$H NMR (DMSO-$d_6$, 500 MHz) δ ppm 0.92-1.03 (1H, m), 1.23 (1H, s), 1.35-1.59 (5H, m), 1.67 (1H, br s), 1.74-1.88 (2H, m), 2.27-2.44 (2H, m), 2.96-3.07 (2H, m), 3.16 (2H, br t, J=5.35 Hz), 3.50-3.59 (2H, m), 3.73-4.01 (2H, m), 4.04 (2H, br t, J=5.21 Hz), 4.09 (2H, s), 5.04-5.22 (1H, m), 7.51 (1H, br d, J=8.78 Hz), 7.61 (1H, dd, J=8.78, 5.21 Hz), 7.75 (1H, s), 7.84-8.06 (1H, m), 8.07 (1H, br d, J=4.39 Hz), 13.51 (1H, br s); ESIMS found for $C_{25}H_{31}FN_6O$ m/z 451.2 (M+1).

28

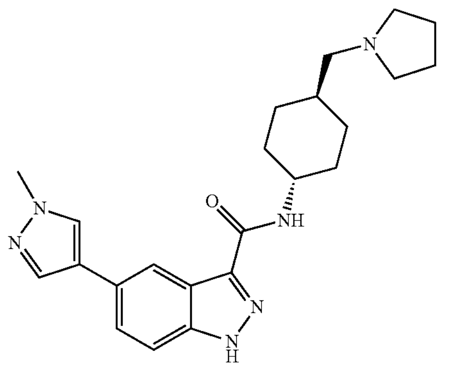

5-(1-Methyl-1H-pyrazol-4-yl)-N-((1R,4R)-4-(pyrrolidin-1-ylmethyl) cyclohexyl)-1H-indazole-3-carboxamide 28

Light brown solid (33 mg, 0.081 mmol, 31.9% yield). $^1H$ NMR (DMSO-$d_6$, 500 MHz) δ ppm 0.91-1.02 (1H, m), 1.34-1.52 (3H, m), 1.53-1.62 (1H, m), 1.68 (5H, br d, J=3.29 Hz), 1.82-1.90 (3H, m), 2.23 (1H, br d, J=6.86 Hz), 2.34-2.44 (5H, m), 3.74-3.84 (1H, m), 3.88 (3H, s), 7.55-7.66 (2H, m), 7.81-7.84 (1H, m), 8.00 (1H, d, J=8.23 Hz), 8.12-8.15 (1H, m), 8.26 (1H, d, J=0.82 Hz), 13.47 (1H, br s); ESIMS found for $C_{23}H_{30}N_6O$ m/z 407.3 (M+1).

29

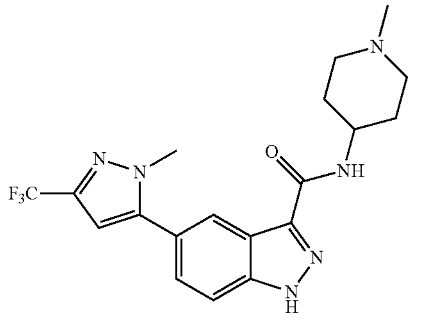

5-(1-Methyl-3-(trifluoromethyl)-1H-pyrazol-5-yl)-N-(1-methylpiperidin-4-yl)-1H-indazole-3-carboxamide 29

White solid (10.8 mg, 0.03 mmol, 24.2% yield). $^1H$ NMR (DMSO-$d_6$, 500 MHz) δ ppm 1.64-1.79 (4H, m), 1.92-2.00 (2H, m), 2.17 (3H, s), 2.76 (2H, br d, J=11.53 Hz), 3.75-3.86 (1H, m), 3.92 (3H, s), 6.92 (1H, s), 7.61 (1H, dd, J=8.78, 1.65 Hz), 7.76 (1H, d, J=8.51 Hz), 8.24 (1H, d, J=8.23 Hz), 8.30 (1H, s), 13.78 (1H, br s); ESIMS found for $C_{19}H_{21}F_3N_6O$ m/z 406.8 (M+1).

30

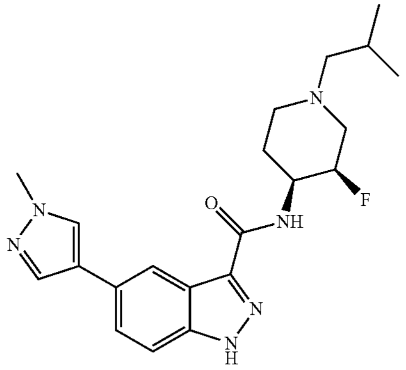

N-((3R,4S)-3-Fluoro-1-isobutylpiperidin-4-yl)-5-(1-methyl-1H-pyrazol-4-yl)-1H-indazole-3-carboxamide 30

White solid (121.2 mg, 0.304 mmol, 35.8% yield). $^1H$ NMR (DMSO-$d_6$, 500 MHz) δ ppm 0.86 (br d, J=6.31 Hz, 5H), 1.70 (br d, J=10.43 Hz, 1H), 1.73-1.81 (m, 1H), 1.92-2.02 (m, 1H), 2.03-2.13 (m, 3H), 2.21 (dd, J=38.20, 12.90 Hz, 1H), 2.85 (br d, J=11.25 Hz, 1H), 3.10 (br t, J=10.84 Hz, 1H), 3.88 (s, 3H), 3.98-4.13 (m, 1H), 4.81 (d, J=49.80 Hz, 1H), 7.59-7.67 (m, 2H), 7.83 (d, J=0.82 Hz, 1H), 7.85 (d, J=8.30 Hz, 1H), 8.15 (s, 1H), 8.25 (s, 1H), 13.59 (s, 1H); ESIMS found for $C_{21}H_{27}FN_6O$ m/z 399.2 (M+1).

31

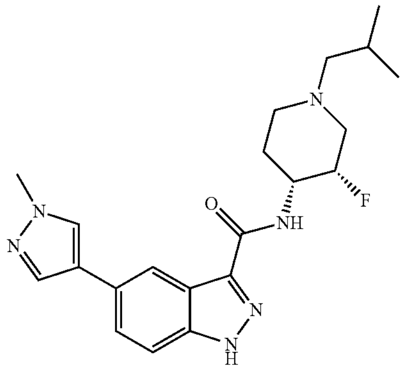

N-((3 S,4R)-3-Fluoro-1-isobutylpiperidin-4-yl)-5-(1-methyl-1H-pyrazol-4-yl)-1H-indazole-3-carboxamide 31

White solid (26.9 mg, 0.068 mmol, 52.5% yield). $^1H$ NMR (DMSO-$d_6$, 500 MHz) δ ppm 0.86 (d, J=6.31 Hz, 6H), 1.70 (br d, J=10.15 Hz, 1H), 1.73-1.82 (m, 1H), 1.97 (qd, J=12.12, 3.70 Hz, 1H), 2.03-2.13 (m, 3H), 2.21 (dd, J=38.20, 12.70 Hz, 1H), 2.85 (br d, J=10.15 Hz, 1H), 3.07-3.15 (m, 1H), 3.88 (s, 3H), 3.98-4.13 (m, 1H), 4.81 (d, J=49.80 Hz, 1H), 7.58-7.67 (m, 2H), 7.83 (d, J=0.82 Hz, 1H), 7.85 (d, J=8.23 Hz, 1H), 8.15 (s, 1H), 8.24 (s, 1H), 13.58 (br s, 1H); ESIMS found for $C_{21}H_{27}FN_6O$ m/z 399.2 (M+1).

32

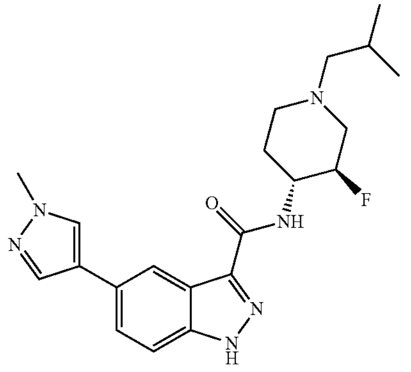

N-((3R,4R)-3-Fluoro-1-isobutylpiperidin-4-yl)-5-(1-methyl-1H-pyrazol-4-yl)-1H-indazole-3-carboxamide 32

White solid (22.4 mg, 0.056 mmol, 39.9% yield). $^1H$ NMR (DMSO-$d_6$, 500 MHz) δ ppm 0.86 (d, J=6.59 Hz, 6H), 1.63-1.86 (m, 3H), 1.93-2.04 (m, 2H), 2.12 (dd, J=7.55, 3.70 Hz, 2H), 2.78 (br d, J=10.98 Hz, 1H), 3.14-3.21 (m, 1H), 3.88 (s, 3H), 3.96-4.08 (m, 1H), 4.70 (dtd, J=50.00, 9.70, 9.70, 5.00 Hz, 1H), 7.57-7.66 (m, 2H), 7.83 (s, 1H), 8.14 (s, 1H), 8.26 (s, 1H), 8.51 (d, J=8.78 Hz, 1H), 13.56 (br s, 1H); ESIMS found for $C_{21}H_{27}FN_6O$ m/z 399.2 (M+1).

33

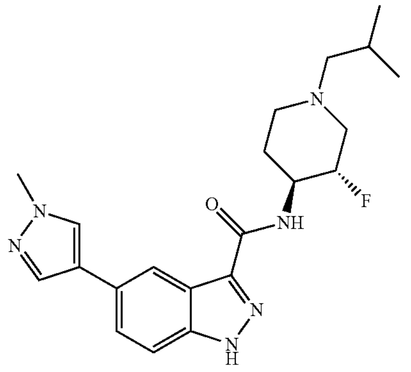

N-((3S,4S)-3-Fluoro-1-isobutylpiperidin-4-yl)-5-(1-methyl-1H-pyrazol-4-yl)-1H-indazole-3-carboxamide 33

Off-white solid (25 mg, 0.063 mmol, 37.4% yield). $^1H$ NMR (DMSO-$d_6$, 500 MHz) δ ppm 0.86 (6H, d, J=6.31 Hz), 1.64-1.88 (3H, m), 1.94-2.05 (2H, m), 2.08-2.18 (2H, m), 2.79 (1H, br d, J=9.61 Hz), 3.14-3.20 (1H, m), 3.88 (3H, s), 3.96-4.08 (1H, m), 4.62-4.80 (1H, m), 7.57-7.67 (2H, m), 7.83 (1H, s), 8.14 (1H, s), 8.26 (1H, s), 8.49 (1H, d, J=8.78 Hz), 13.54 (1H, s); ESIMS found for $C_{21}H_{27}FN_6O$ m/z 399.3 (M+1).

34

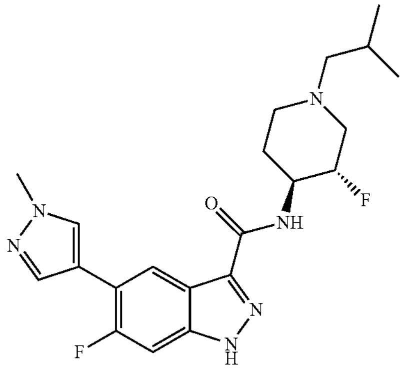

6-Fluoro-N-((3S,4S)-3-fluoro-1-isobutylpiperidin-4-yl)-5-(1-methyl-1H-pyrazol-4-yl)-1H-indazole-3-carboxamide 34

White solid (27 mg, 0.065 mmol, 25.4% yield). $^1H$ NMR (DMSO-$d_6$, 500 MHz) δ ppm 0.86 (6H, d, J=6.59 Hz), 1.64-1.73 (1H, m), 1.73-1.86 (2H, m), 1.93-2.04 (2H, m), 2.08-2.17 (2H, m), 2.78 (1H, br d, J=10.15 Hz), 3.14-3.21 (1H, m), 3.90 (3H, s), 3.95-4.08 (1H, m), 4.70 (1H, dtd, J=50.00, 9.70, 4.70 Hz), 7.51 (1H, d, J=10.98 Hz), 7.81 (1H, s), 8.12 (1H, d, J=2.20 Hz), 8.34 (1H, d, J=7.41 Hz), 8.57 (1H, d, J=8.78 Hz), 13.65 (1H, s); ESIMS found for $C_{21}H_{26}F_2N_6O$ m/z 417.2 (M+1).

35

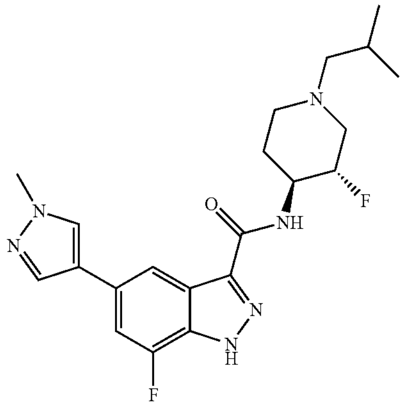

7-Fluoro-N-((3S,4S)-3-fluoro-1-isobutylpiperidin-4-yl)-5-(1-methyl-1H-pyrazol-4-yl)-1H-indazole-3-carboxamide 35

White solid (51 mg, 0.122 mmol, 34.1% yield). $^1H$ NMR (DMSO-$d_6$, 500 MHz) δ ppm 0.86 (6H, d, J=6.59 Hz), 1.64-1.86 (3H, m), 1.94-2.04 (2H, m), 2.07-2.17 (2H, m), 2.79 (1H, br d, J=10.15 Hz), 3.14-3.20 (1H, m), 3.87 (3H, s), 3.96-4.08 (1H, m), 4.71 (1H, dtd, J=50.00, 9.70, 4.70 Hz), 7.54 (1H, dd, J=12.35, 0.82 Hz), 7.88 (1H, s), 8.08 (1H, d, J=0.82 Hz), 8.20 (1H, s), 8.61 (1H, d, J=8.78 Hz), 14.12 (1H, br s); ESIMS found for $C_{21}H_{26}F_2N_6O$ m/z 417.2 (M+1).

36

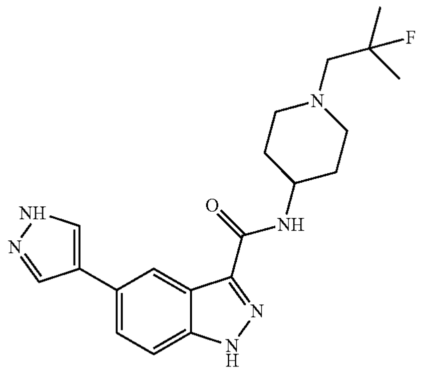

N-(1-(2-Fluoro-2-methylpropyl)piperidin-4-yl)-5-(1H-pyrazol-4-yl)-1H-indazole-3-carboxamide 36

White solid (17 mg, 0.044 mmol, 22.22% yield). $^1$H NMR (DMSO-$d_6$, 500 MHz) δ ppm 1.31 (6H, d, J=21.40 Hz), 1.65-1.80 (4H, m), 2.15-2.24 (2H, m), 2.44 (2H, d, J=23.10 Hz), 2.91 (2H, br d, J=12.08 Hz), 3.77-3.87 (1H, m), 7.49 (1H, ddd, J=7.00, 5.08, 1.65 Hz), 7.64 (1H, d, J=8.23 Hz), 7.74 (1H, d, J=8.78 Hz), 8.13-8.18 (1H, m), 8.20 (1H, d, J=8.23 Hz), 8.25 (1H, d, J=4.94 Hz), 8.38 (1H, s), 13.71 (1H, br s); ESIMS found for $C_{20}H_{25}FN_6O$ m/z 385.2 (M+1).

37

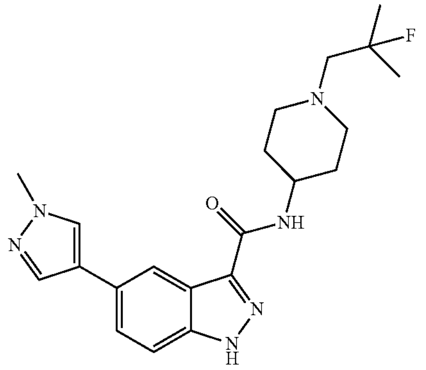

N-(1-(2-Fluoro-2-methylpropyl)piperidin-4-yl)-5-(1-methyl-1H-pyrazol-4-yl)-1H-indazole-3-carboxamide 37

White solid (38.2 mg, 0.096 mmol, 17.79% yield). $^1$H NMR (DMSO-$d_6$, 500 MHz) δ ppm 1.29 (s, 3H), 1.34 (s, 3H), 1.65-1.80 (m, 4H), 2.16-2.24 (m, 2H), 2.44 (d, J=23.10 Hz, 2H), 2.91 (br d, J=11.53 Hz, 2H), 3.76-3.84 (m, 1H), 3.88 (s, 3H), 7.56-7.60 (m, 1H), 7.60-7.64 (m, 1H), 7.82 (s, 1H), 8.08 (d, J=7.96 Hz, 1H), 8.13 (s, 1H), 8.25 (s, 1H), 13.49 (br s, 1H); ESIMS found for $C_{21}H_{27}FN_6O$ m/z 399.2 (M+1).

38

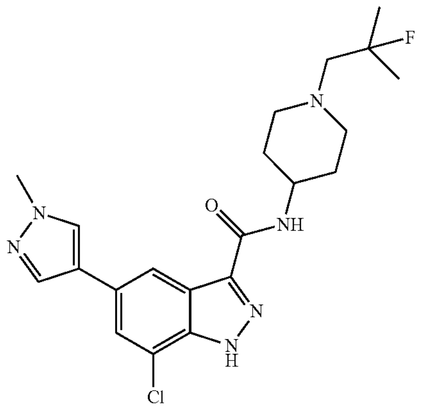

7-Chloro-N-(1-(2-fluoro-2-methylpropyl)piperidin-4-yl)-5-(1-methyl-1H-pyrazol-4-yl)-1H-indazole-3-carboxamide 38

White solid (0.036 g, 0.083 mmol, 61.4% yield). $^1$H NMR (DMSO-$d_6$, 500 MHz) δ ppm 1.32 (6H, d, J=21.40 Hz), 1.65-1.80 (4H, m), 2.19 (2H, td, J=11.60, 2.61 Hz), 2.44 (2H, d, J=22.90 Hz), 2.88-2.94 (2H, m), 3.76-3.85 (1H, m), 3.87 (3H, s), 7.77 (1H, d, J=1.37 Hz), 7.89 (1H, s), 8.19-8.24 (3H, m), 13.99 (1H, br s); ESIMS found for $C_{21}H_{26}ClFN_6O$ m/z 433.2 (M+1).

39

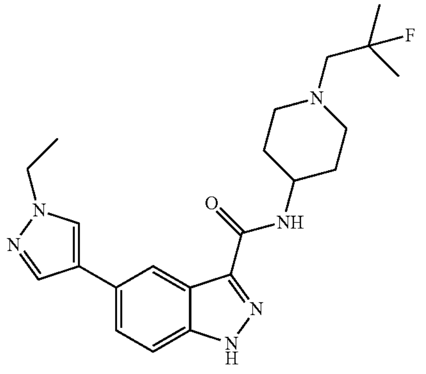

5-(1-Ethyl-1H-pyrazol-4-yl)-N-(1-(2-fluoro-2-methylpropyl)piperidin-4-yl)-1H-indazole-3-carboxamide 39

White solid (37 mg, 0.090 mmol, 40.5% yield). $^1$H NMR (DMSO-$d_6$, 500 MHz) δ ppm 1.32 (6H, d, J=21.40 Hz), 1.42 (3H, t, J=7.27 Hz), 1.64-1.81 (4H, m), 2.16-2.25 (2H, m), 2.44 (2H, d, J=23.10 Hz), 2.91 (2H, br d, J=11.80 Hz), 3.76-3.87 (1H, m), 4.16 (2H, q, J=7.41 Hz), 7.57-7.61 (1H, m), 7.62-7.66 (1H, m), 7.83 (1H, s), 8.09 (1H, d, J=7.96 Hz), 8.19 (1H, s), 8.27 (1H, s), 13.49 (1H, br s); ESIMS found for $C_{22}H_{29}FN_6O$ m/z 413.2 (M+1).

40

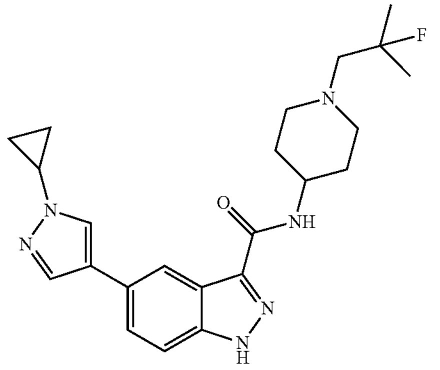

5-(1-Cyclopropyl-1H-pyrazol-4-yl)-N-(1-(2-fluoro-2-methylpropyl)piperidin-4-yl)-1H-indazole-3-carboxamide 40

White solid (22.5 mg, 0.053 mmol, 33.7% yield). $^1$H NMR (DMSO-$d_6$, 500 MHz) δ ppm 0.95-1.02 (2H, m), 1.07-1.13 (2H, m), 1.32 (6H, d, J=21.40 Hz), 1.64-1.82 (4H, m), 2.15-2.25 (2H, m), 2.44 (2H, d, J=22.90 Hz), 2.91 (2H, br d, J=12.08 Hz), 3.75 (1H, tt, J=7.34, 3.77 Hz), 3.78-3.87 (1H, m), 7.55-7.60 (1H, m), 7.62-7.67 (1H, m), 7.82 (1H, d, J=0.82 Hz), 8.08 (1H, br d, J=8.23 Hz), 8.23 (1H, s), 8.26 (1H, d, J=1.37 Hz), 13.49 (1H, br s); ESIMS found for $C_{23}H_{29}FN_6O$ m/z 425.3 (M+1).

41

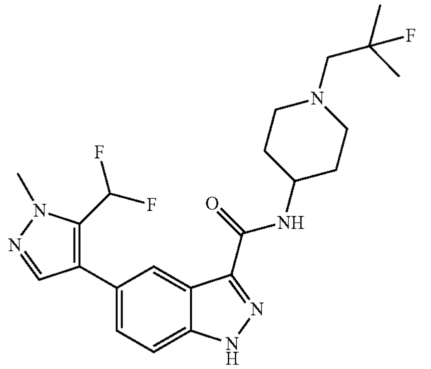

5-(5-(Difluoromethyl)-1-methyl-1H-pyrazol-4-yl)-N-(1-(2-fluoro-2-methylpropyl)piperidin-4-yl)-1H-indazole-3-carboxamide 41

Off-white solid (0.055 g, 0.123 mmol, 46.7% yield). $^1$H NMR (DMSO-$d_6$, 500 MHz) δ ppm 1.31 (6H, d, J=21.40 Hz), 1.64-1.80 (4H, m), 2.16-2.24 (2H, m), 2.44 (2H, d, J=23.10 Hz), 2.90 (2H, br d, J=12.08 Hz), 3.77-3.87 (1H, m), 4.02 (3H, s), 7.20 (1H, t, J=53.30 Hz), 7.43 (1H, dd, J=8.78, 1.65 Hz), 7.67 (1H, dd, J=8.51, 0.82 Hz), 7.73 (1H, s), 8.10-8.18 (2H, m), 13.63 (1H, br s); ESIMS found for $C_{22}H_{27}F_3N_6O$ m/z 449.2 (M+1).

42

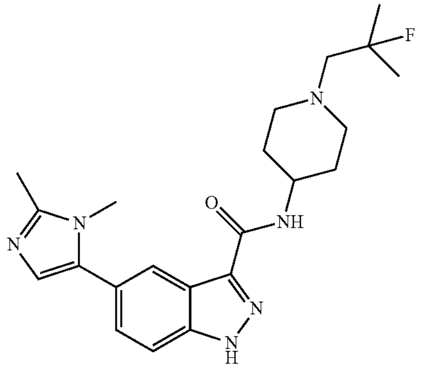

5-(1,2-Dimethyl-1H-imidazol-5-yl)-N-(1-(2-fluoro-2-methylpropyl)piperidin-4-yl)-1H-indazole-3-carboxamide 42

Brown solid (7 mg, 0.017 mmol, 16.85% yield). $^1$H NMR (DMSO-$d_6$, 500 MHz) δ 1.31 (4H, d, J=21.40 Hz), 1.65-1.80 (6H, m), 2.15-2.23 (2H, m), 2.36 (3H, s), 2.44 (2H, d, J=22.90 Hz), 2.84-2.95 (2H, m), 3.52 (3H, s), 3.76-3.87 (1H, m), 6.86 (1H, s), 7.45 (1H, dd, J=8.78, 1.65 Hz), 7.68 (1H, d, J=8.51 Hz), 8.12-8.18 (2H, m), 13.65 (1H, br s); ESIMS found for $C_{22}H_{29}FN_6O$ m/z 413.2 (M+1).

43

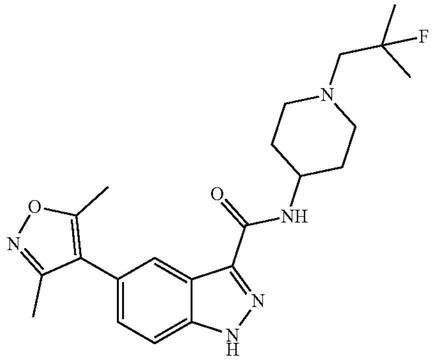

5-(3,5-Dimethylisoxazol-4-yl)-N-(1-(2-fluoro-2-methylpropyl)piperidin-4-yl)-1H-indazole-3-carboxamide 43

White solid (45 mg, 0.109 mmol, 54.2% yield). $^1$H NMR (DMSO-$d_6$, 500 MHz) δ ppm 1.31 (6H, d, J=21.40 Hz), 1.65-1.78 (4H, m), 2.15-2.21 (2H, m), 2.22 (3H, s), 2.40 (3H, s), 2.43 (2H, d, J=23.10 Hz), 2.90 (2H, br d, J=11.53 Hz), 3.76-3.86 (1H, m), 7.40 (1H, dd, J=8.51, 1.65 Hz), 7.70 (1H, d, J=8.78 Hz), 8.09 (1H, s), 8.17 (1H, d, J=7.96 Hz), 13.66 (1H, br s); ESIMS found for $C_{22}H_{28}FN_5O_2$ m/z 414.2 (M+1).

45

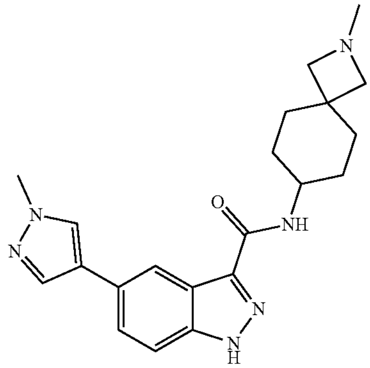

5-(1-Methyl-1H-pyrazol-4-yl)-N-(2-methyl-2-azaspiro[3.5]nonan-7-yl)-1H-indazole-3-carboxamide 45

Off-white solid (0.013 g, 0.034 mmol, 20.37% yield). $^1$H NMR (DMSO-$d_6$, 500 MHz) δ ppm 1.40-1.52 (4H, m), 1.72 (2H, br s), 1.82-1.91 (2H, m), 2.21 (3H, s), 2.84 (2H, s), 2.91 (2H, s), 3.78 (1H, br s), 3.88 (3H, s), 7.55-7.65 (2H, m), 7.82 (1H, s), 7.96 (1H, d, J=8.23 Hz), 8.13 (1H, s), 8.25 (1H, s), 13.49 (1H, br s); ESIMS found for $C_{21}H_{26}N_6O$ m/z 379.2 (M+1).

46

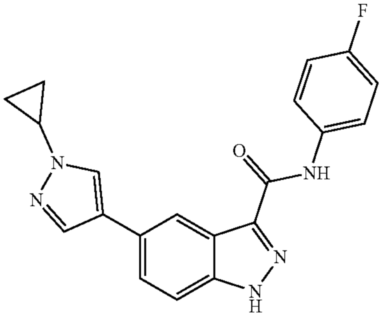

5-(1-Cyclopropyl-1H-pyrazol-4-yl)-N-(4-fluorophenyl)-1H-indazole-3-carboxamide 46

White solid (56 mg, 0.155 mmol, 76.7% yield). $^1$H NMR (DMSO-$d_6$, 500 MHz) δ ppm 0.96-1.03 (2H, m), 1.09-1.14 (2H, m), 3.76 (1H, tt, J=7.44, 3.81 Hz), 7.15-7.22 (2H, m), 7.62-7.66 (1H, m), 7.68-7.72 (1H, m), 7.87 (1H, s), 7.90-7.96 (2H, m), 8.28 (1H, s), 8.32-8.35 (1H, m), 10.40 (1H, s), 13.74 (1H, br s); ESIMS found for $C_{20}H_{16}FN_5O$ m/z 362.1 (M+1).

47

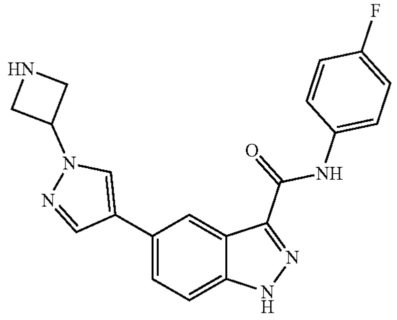

5-(1-(Azetidin-3-yl)-1H-pyrazol-4-yl)-N-(4-fluorophenyl)-1H-indazole-3-carboxamide 47

White solid (10 mg, 0.027 mmol, 12.41% yield). $^1$H NMR (DMSO-$d_6$, 500 MHz) δ ppm 3.76 (2H, brt, J=7.55 Hz), 3.97 (2H, brt, J=7.55 Hz), 5.21 (1H, quip, J=7.41 Hz), 7.19 (2H, t, J=8.78 Hz), 7.63-7.68 (1H, m), 7.69-7.74 (1H, m), 7.91-8.01 (3H, m), 8.36 (1H, s), 8.39 (1H, s), 10.40 (1H, s); ESIMS found for $C_{20}H_{17}FN_6O$ m/z 377.1 (M+1).

48

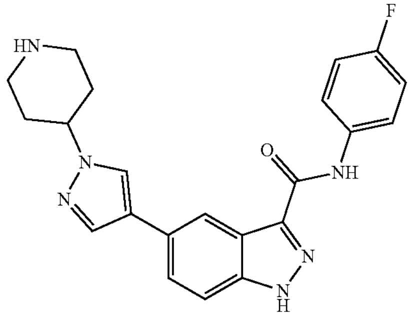

N-(4-Fluorophenyl)-5-(1-(piperidin-4-yl)-1H-pyrazol-4-yl)-1H-indazole-3-carboxamide 48

White solid (68 mg, 0.168 mmol, 77.4% yield). $^1$H NMR (DMSO-$d_6$, 500 MHz) δ ppm 1.83 (2H, qd, J=12.03, 3.98 Hz), 1.96-2.03 (2H, m), 2.60 (2H, td, J=12.35, 2.20 Hz), 3.05 (2H, br d, J=12.35 Hz), 4.21 (1H, tt, J=11.63, 4.15 Hz), 7.19 (2H, t, J=8.92 Hz), 7.62-7.66 (1H, m), 7.68-7.73 (1H, m), 7.88 (1H, s), 7.91-7.97 (2H, m), 8.26 (1H, s), 8.33 (1H, d, J=0.82 Hz), 10.40 (1H, s); ESIMS found for $C_{22}H_{21}FN_6O$ m/z 405.2 (M+1).

49

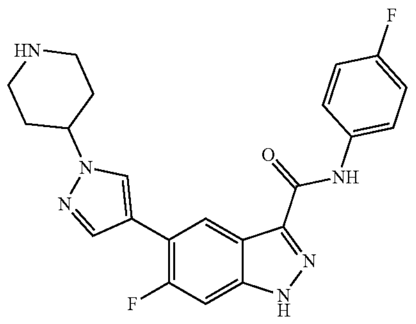

6-Fluoro-N-(4-fluorophenyl)-5-(1-(piperidin-4-yl)-1H-pyrazol-4-yl)-1H-indazole-3-carboxamide 49

White solid (38 mg, 0.090 mmol, 62.0% yield). $^1H$ NMR (DMSO-$d_6$, 500 MHz) δ ppm 1.85 (2H, qd, J=12.03, 4.25 Hz), 1.95-2.02 (2H, m), 2.56-2.65 (2H, m), 3.06 (2H, br d, J=12.35 Hz), 4.27 (1H, tt, J=11.49, 4.15 Hz), 7.19 (2H, t, J=8.78 Hz), 7.54 (1H, d, J=11.25 Hz), 7.87 (1H, d, J=1.65 Hz), 7.90-7.96 (2H, m), 8.20 (1H, d, J=1.65 Hz), 8.40 (1H, d, J=7.41 Hz), 10.44 (1H, s); ESIMS found for $C_{22}H_{20}F_2N_6O$ m/z 423.2 (M+1).

50

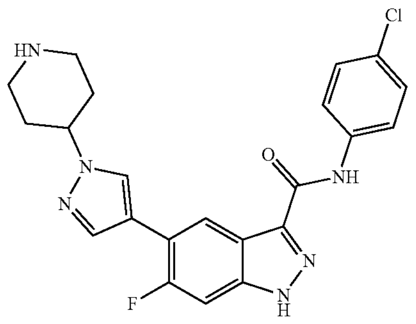

N-(4-Chlorophenyl)-6-fluoro-5-(1-(piperidin-4-yl)-1H-pyrazol-4-yl)-1H-indazole-3-carboxamide 50

White solid (50 mg, 0.114 mmol, 77.0% yield). $^1H$ NMR (DMSO-$d_6$, 500 MHz) δ ppm 1.85 (2H, qd, J=12.08, 3.84 Hz), 1.94-2.02 (2H, m), 2.60 (2H, td, J=12.28, 2.33 Hz), 3.05 (2H, br d, J=12.35 Hz), 4.27 (1H, tt, J=11.56, 4.08 Hz), 7.37-7.44 (2H, m), 7.55 (1H, d, J=10.98 Hz), 7.87 (1H, d, J=1.65 Hz), 7.93-7.98 (2H, m), 8.21 (1H, d, J=1.65 Hz), 8.40 (1H, d, J=7.41 Hz), 10.55 (1H, s); ESIMS found for $C_{22}H_{20}ClFN_6O$ m/z 439.1 (M+1).

51

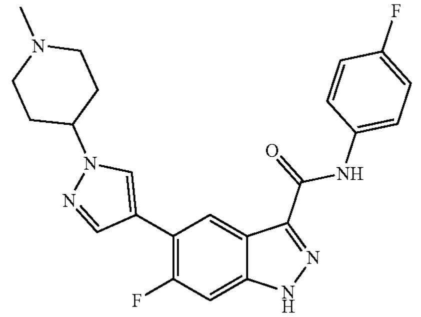

6-Fluoro-N-(4-fluorophenyl)-5-(1-(1-methylpiperidin-4-yl)-1H-pyrazol-4-yl)-1H-indazole-3-carboxamide 51

Beige solid (25 mg, 0.057 mmol, 21.3% yield). $^1H$ NMR ($CD_3OD$, 500 MHz) δ ppm 2.10-2.21 (4H, m), 2.23-2.32 (2H, m), 2.35 (3H, s), 3.03 (2H, br d, J=12.08 Hz), 4.26 (1H, tt, J=10.39, 5.25 Hz), 7.09-7.16 (2H, m), 7.38 (1H, d, J=10.98 Hz), 7.75-7.82 (2H, m), 7.94 (1H, d, J=1.65 Hz), 8.12 (1H, d, J=1.92 Hz), 8.49 (1H, d, J=7.41 Hz); ESIMS found for $C_{23}H_{22}F_2N_6O$ m/z 437.2 (M+1).

52

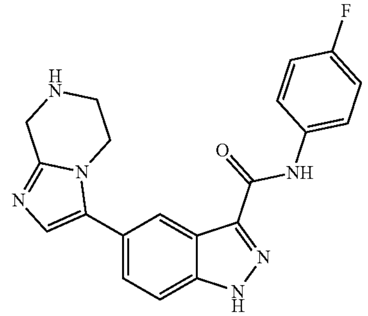

N-(4-Fluorophenyl)-5-(5,6,7,8-tetrahydroimidazo[1,2-a]pyrazin-3-yl)-1H-indazole-3-carboxamide 52

White solid (45 mg, 0.120 mmol, 81.1% yield). $^1H$ NMR (DMSO-$d_6$, 500 MHz) δ ppm 2.72 (1H, br s), 3.06 (2H, br t, J=5.21 Hz), 3.90-3.97 (4H, m), 7.04 (1H, s), 7.19 (2H, t, J=8.92 Hz), 7.57 (1H, dd, J=8.78, 1.65 Hz), 7.73 (1H, d, J=8.51 Hz), 7.89-7.95 (2H, m), 8.23 (1H, s), 10.45 (1H, s), 13.85 (1H, br s); ESIMS found for $C_{20}H_{17}FN_6O$ m/z 377.1 (M+1).

53

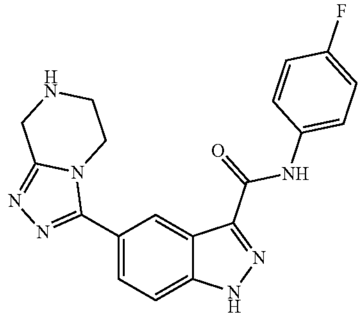

N-(4-Fluorophenyl)-5-(5,6,7,8-tetrahydro-[1,2,4]triazolo[4,3-a]pyrazin-3-yl)-1H-indazole-3-carboxamide 53

White solid (25 mg, 0.066 mmol, 53.1% yield). $^1$H NMR (DMSO-$d_6$, 500 MHz) δ ppm 2.73 (1H, br s), 3.08 (2H, br t, J=4.80 Hz), 4.02-4.09 (4H, m), 7.20 (2H, t, J=8.92 Hz), 7.79-7.84 (1H, m), 7.86-7.90 (1H, m), 7.90-7.96 (2H, m), 8.55 (1H, d, J=0.82 Hz), 10.52 (1H, s), 14.00 (1H, br s); ESIMS found for $C_{19}H_{16}FN_7O$ m/z 378.1 (M+1).

54

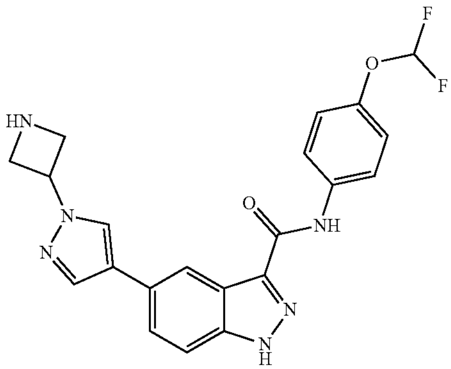

5-(1-(Azetidin-3-yl)-1H-pyrazol-4-yl)-N-(4-(difluoromethoxy)phenyl)-1H-indazole-3-carboxamide 54

White solid (19 mg, 0.045 mmol, 28.4% yield). $^1$H NMR (DMSO-$d_6$, 500 MHz) δ ppm 3.76 (2H, br t, J=7.96 Hz), 3.97 (2H, br t, J=7.68 Hz), 5.21 (1H, quip, J=7.41 Hz), 7.18 (1H, t, J=74.50 Hz), 7.16-7.20 (2H, m), 7.63-7.68 (1H, m), 7.69-7.75 (1H, m), 7.93-8.00 (3H, m), 8.36 (1H, s), 8.39 (1H, s), 10.43 (1H, s); ESIMS found for $C_{21}H_{18}F_2N_6O_2$ m/z 425.2 (M+1).

55

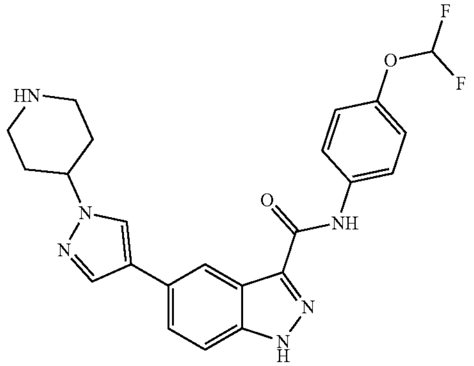

N-(4-(Difluoromethoxy)phenyl)-5-(1-(piperidin-4-yl)-1H-pyrazol-4-yl)-1H-indazole-3-carboxamide 55

White solid (68 mg, 0.150 mmol, 73.6% yield). $^1$H NMR (DMSO-$d_6$, 500 MHz) δ ppm 1.84 (2H, qd, J=12.03, 3.98 Hz), 1.96-2.02 (2H, m), 2.60 (2H, td, J=12.28, 2.06 Hz), 3.05 (2H, br d, J=12.62 Hz), 4.21 (1H, tt, J=11.60, 4.05 Hz), 7.18 (1H, t, J=74.50 Hz), 7.16-7.20 (2H, m), 7.62-7.67 (1H, m), 7.68-7.74 (1H, m), 7.88 (1H, s), 7.93-7.99 (2H, m), 8.26 (1H, s), 8.32-8.36 (1H, m), 10.42 (1H, s); ESIMS found for $C_{23}H_{22}F_2N_6O_2$ m/z 453.2 (M+1).

56

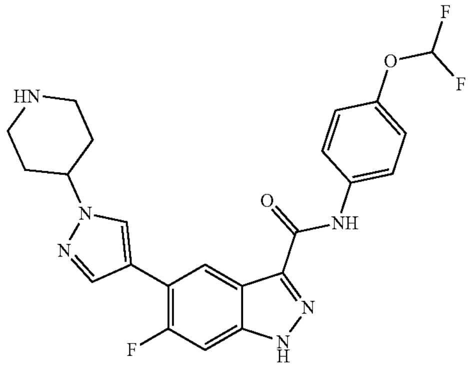

N-(4-(Difluoromethoxy)phenyl)-6-fluoro-5-(1-(piperidin-4-yl)-1H-pyrazol-4-yl)-1H-indazole-3-carboxamide 56

Off-white solid (28 mg, 0.060 mmol, 41.0% yield). $^1$H NMR (DMSO-$d_6$, 500 MHz) δ ppm 1.85 (2H, qd, J=12.03, 3.98 Hz), 1.95-2.02 (2H, m), 2.60 (2H, td, J=12.28, 2.06 Hz), 3.06 (2H, br d, J=12.62 Hz), 4.27 (1H, tt, J=11.66, 3.98 Hz), 7.18 (1H, t, J=74.50 Hz), 7.18 (2H, br d, J=9.06 Hz), 7.55 (1H, d, J=10.98 Hz), 7.87 (1H, d, J=1.65 Hz), 7.92-7.98 (2H, m), 8.20 (1H, d, J=1.65 Hz), 8.40 (1H, d, J=7.41 Hz), 10.47 (1H, s); ESIMS found for $C_{23}H_{21}F_3N_6O_2$ m/z 471.2 (M+1).

57

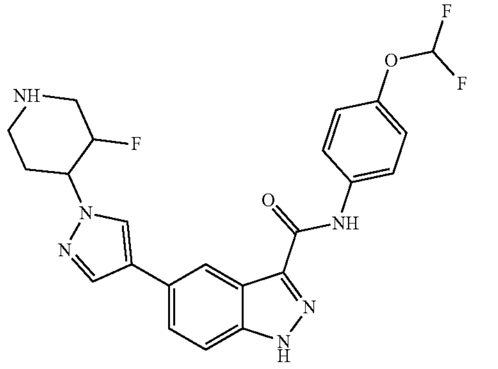

N-(4-(Difluoromethoxy)phenyl)-5-(1-(3-fluoropiperidin-4-yl)-1H-pyrazol-4-yl)-1H-indazole-3-carboxamide 57

White solid (26 mg, 0.055 mmol, 31.5% yield). $^1$H NMR (DMSO-d$_6$, 500 MHz) δ ppm 1.97-2.05 (2H, m), 2.53-2.61 (2H, m), 2.96 (1H, br d, J=10.43 Hz), 3.34 (1H, br s), 4.33-4.44 (1H, m), 4.73-4.91 (1H, m), 7.18 (1H, t, J=74.50 Hz), 7.16-7.20 (2H, m), 7.64-7.67 (1H, m), 7.68-7.73 (1H, m), 7.93-7.98 (3H, m), 8.34 (2H, d, J=9.06 Hz), 10.43 (1H, s), 13.75 (1H, s); ESIMS found for $C_{23}H_{21}F_3N_6O_2$ m/z 471.2 (M+1).

58

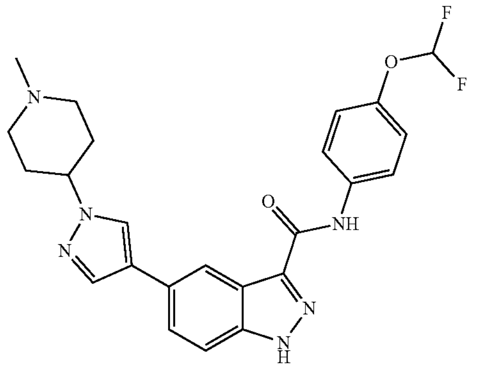

N-(4-(Difluoromethoxy)phenyl)-5-(1-(1-methylpiperidin-4-yl)-1H-pyrazol-4-yl)-1H-indazole-3-carboxamide 58

Off-white solid (0.6 g, 1.286 mmol, 54.5% yield). $^1$H NMR (DMSO-d$_6$, 500 MHz) δ ppm 1.98-2.10 (6H, m), 2.21 (3H, s), 2.84-2.90 (2H, m), 4.09-4.18 (1H, m), 7.18 (1H, t, J=74.50 Hz), 7.16-7.20 (2H, m), 7.62-7.66 (1H, m), 7.69-7.74 (1H, m), 7.89 (1H, s), 7.93-8.00 (2H, m), 8.29 (1H, s), 8.34 (1H, s), 10.44 (1H, s), 13.76 (1H, br s); ESIMS found for $C_{24}H_{24}F_2N_6O_2$ m/z 467.2 (M+1).

59

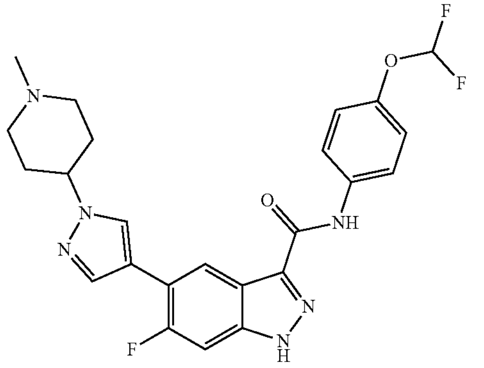

N-(4-(Difluoromethoxy)phenyl)-6-fluoro-5-(1-(1-methylpiperidin-4-yl)-1H-pyrazol-4-yl)-1H-indazole-3-carboxamide 59

Beige solid (25 mg, 0.052 mmol, 39.1% yield). $^1$H NMR (DMSO-d$_6$, 500 MHz) δ ppm 1.98-2.10 (6H, m), 2.21 (3H, s), 2.87 (2H, br d, J=6.31 Hz), 4.15-4.24 (1H, m), 7.18 (1H, t, J=74.50 Hz), 7.18 (2H, d, J=9.06 Hz), 7.56 (1H, d, J=10.98 Hz), 7.88 (1H, d, J=1.37 Hz), 7.92-7.98 (2H, m), 8.24 (1H, d, J=1.65 Hz), 8.40 (1H, d, J=7.41 Hz), 10.49 (1H, s), 13.84 (1H, br s); ESIMS found for $C_{24}H_{23}F_3N_6O_2$ m/z 485.2 (M+1).

60

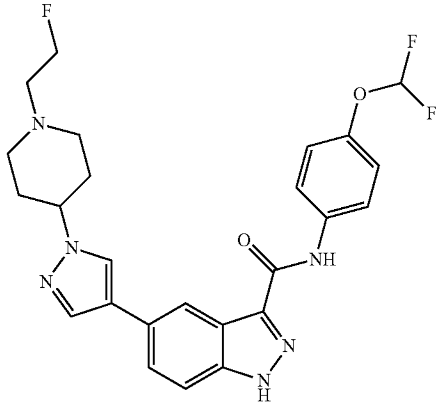

N-(4-(Difluoromethoxy)phenyl)-5-(1-(1-(2-fluoroethyl)piperidin-4-yl)-1H-pyrazol-4-yl)-1H-indazole-3-carboxamide 60

White solid (7 mg, 0.014 mmol, 23.37% yield). $^1$H NMR (DMSO-d$_6$, 500 MHz) δ ppm 1.96-2.09 (4H, m), 2.22 (2H, td, J=11.25, 3.02 Hz), 2.67 (2H, dt, J=28.30, 5.00 Hz), 3.01 (2H, br d, J=11.80 Hz), 4.12-4.22 (1H, m), 4.56 (2H, dt, J=46.80, 4.00 Hz), 7.18 (1H, t, J=74.50 Hz), 7.18 (2H, d, J=9.06 Hz), 7.62-7.67 (1H, m), 7.68-7.73 (1H, m), 7.89 (1H, s), 7.95 (2H, d, J=9.06 Hz), 8.31 (1H, s), 8.34 (1H, s), 10.43 (1H, s), 13.75 (1H, br s); ESIMS found for $C_{25}H_{25}F_3N_6O_2$ m/z 499.2 (M+1).

62

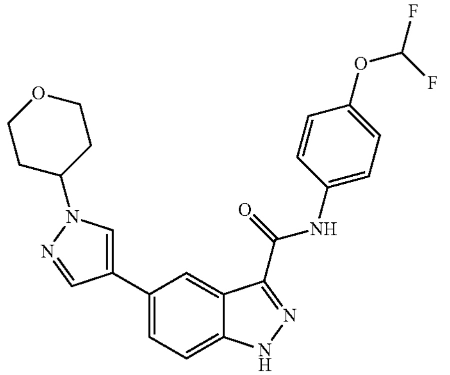

N-(4-(Difluoromethoxy)phenyl)-5-(1-(tetrahydro-2H-pyran-4-yl)-1H-pyrazol-4-yl)-1H-indazole-3-carboxamide 62

White solid (52 mg, 0.115 mmol, 64.9% yield). $^1$H NMR (DMSO-$d_6$, 500 MHz) δ ppm 1.95-2.08 (4H, m), 3.45-3.54 (2H, m), 3.96-4.03 (2H, m), 4.39-4.48 (1H, m), 7.18 (1H, t, J=74.80 Hz), 7.18 (2H, br d, J=9.06 Hz), 7.62-7.67 (1H, m), 7.69-7.74 (1H, m), 7.91 (1H, s), 7.96 (2H, d, J=9.06 Hz), 8.32 (1H, s), 8.35 (1H, s), 10.42 (1H, s), 13.75 (1H, br s); ESIMS found for $C_{23}H_{21}F_2N_5O_3$ m/z 454.2 (M+1).

63

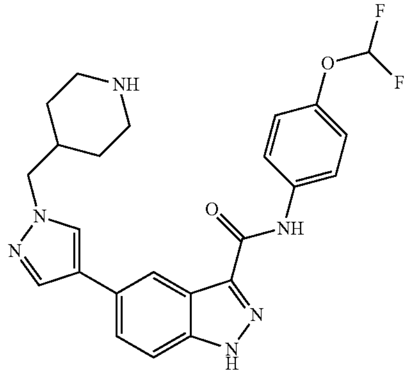

N-(4-(Difluoromethoxy)phenyl)-5-(1-(piperidin-4-ylmethyl)-1H-pyrazol-4-yl)-1H-indazole-3-carboxamide 63

White solid (44 mg, 0.094 mmol, 49.1% yield). $^1$H NMR (DMSO-$d_6$, 500 MHz) δ ppm 1.04-1.16 (2H, m), 1.44 (2H, br d, J=11.53 Hz), 1.87-1.99 (1H, m), 2.36-2.45 (2H, m), 2.91 (2H, br d, J=12.08 Hz), 3.99 (2H, br d, J=6.86 Hz), 7.18 (1H, t, J=74.50 Hz), 7.18 (2H, br d, J=8.78 Hz), 7.62-7.72 (2H, m), 7.89 (1H, s), 7.93-7.99 (2H, m), 8.22 (1H, s), 8.32 (1H, s), 10.44 (1H, s); ESIMS found for $C_{24}H_{24}F_2N_6O_2$ m/z 467.2 (M+1).

64

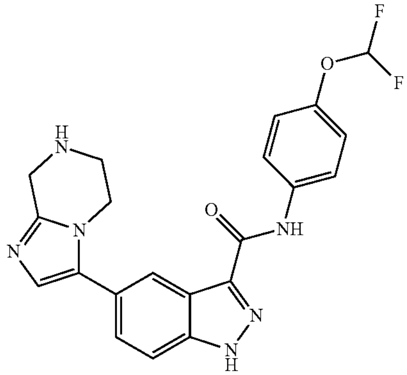

N-(4-(Difluoromethoxy)phenyl)-5-(5,6,7,8-tetrahydroimidazo[1,2-a]pyrazin-3-yl)-1H-indazole-3-carboxamide 64

White solid (38 mg, 0.090 mmol, 72.7% yield). $^1$H NMR (DMSO-$d_6$, 500 MHz) δ ppm 2.72 (1H, br s), 3.07 (2H, br t, J=5.21 Hz), 3.90-3.96 (4H, m), 7.17 (1H, t, J=74.80 Hz), 7.04 (1H, s), 7.18 (2H, br d, J=9.06 Hz), 7.57 (1H, dd, J=8.64, 1.51 Hz), 7.73 (1H, d, J=8.78 Hz), 7.91-7.97 (2H, m), 8.24 (1H, s), 10.47 (1H, s), 13.88 (1H, br s); ESIMS found for $C_{21}H_{18}F_2N_6O_2$ m/z 425.1 (M+1).

65

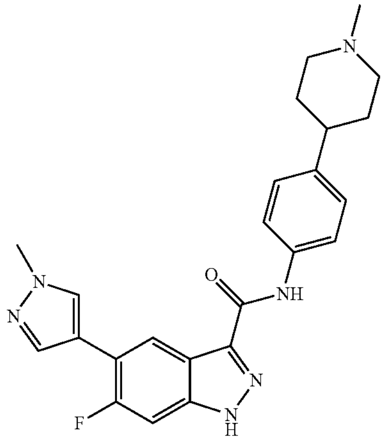

6-Fluoro-5-(1-methyl-1H-pyrazol-4-yl)-N-(4-(1-methylpiperidin-4-yl) phenyl)-1H-indazole-3-carboxamide 65

White solid (73 mg, 0.169 mmol, 69.8% yield). $^1$H NMR (DMSO-$d_6$, 500 MHz) δ ppm 1.58-1.70 (2H, m), 1.70-1.77 (2H, m), 1.95 (2H, td, J=11.60, 2.33 Hz), 2.19 (3H, s), 2.42 (1H, tt, J=11.84, 3.81 Hz), 2.86 (2H, br d, J=11.25 Hz), 3.91 (3H, s), 7.21 (2H, d, J=8.78 Hz), 7.55 (1H, d, J=11.25 Hz), 7.80 (2H, d, J=8.51 Hz), 7.85 (1H, d, J=1.10 Hz), 8.16 (1H, d, J=1.92 Hz), 8.39 (1H, d, J=7.41 Hz), 10.28 (1H, s), 13.77 (1H, br s); ESIMS found for $C_{24}H_{25}FN_6O$ m/z 433.2 (M+1).

66

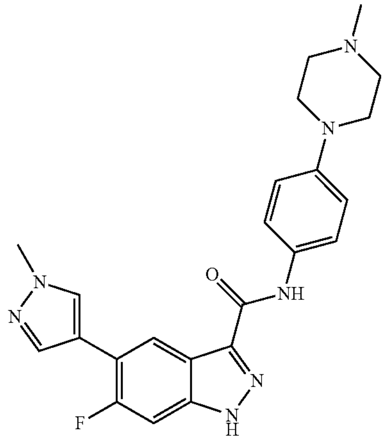

6-Fluoro-5-(1-methyl-1H-pyrazol-4-yl)-N-(4-(4-methylpiperazin-1-yl) phenyl)-1H-indazole-3-carboxamide 66

Beige solid (79 mg, 0.182 mmol, 72.6% yield). $^1$H NMR ($DMSO-d_6$, 500 MHz) δ ppm 2.27 (3H, s), 2.51-2.56 (4H, m), 3.12 (4H, br s), 3.91 (3H, s), 6.93 (2H, d, J=9.06 Hz), 7.54 (1H, d, J=10.98 Hz), 7.73 (2H, d, J=9.06 Hz), 7.85 (1H, d, J=0.82 Hz), 8.16 (1H, d, J=2.20 Hz), 8.39 (1H, d, J=7.41 Hz), 10.15 (1H, s), 13.76 (1H, br s); ESIMS found for $C_{23}H_{24}FN_7O$ m/z 434.2 (M+1).

67

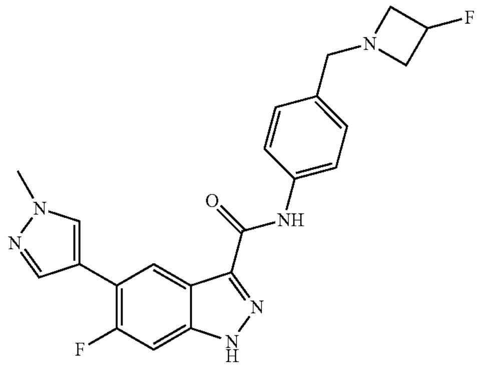

6-Fluoro-N-(4-((3-fluoroazetidin-1-yl)methyl)phenyl)-5-(1-methyl-1H-pyrazol-4-yl)-1H-indazole-3-carboxamide 67

Beige solid (12 mg, 0.028 mmol, 28.8% yield). $^1$H NMR ($DMSO-d_6$, 500 MHz) δ ppm 3.06-3.17 (2H, m), 3.48-3.57 (2H, m), 3.59 (2H, s), 3.91 (3H, s), 5.08-5.27 (1H, m), 7.24 (2H, d, J=8.51 Hz), 7.55 (1H, d, J=10.98 Hz), 7.83 (2H, d, J=8.51 Hz), 7.85 (1H, d, J=1.10 Hz), 8.16 (1H, d, J=2.20 Hz), 8.39 (1H, d, J=7.41 Hz), 10.31 (1H, s), 13.79 (1H, br s); ESIMS found for $C_{22}H_{20}F_2N_6O$ m/z 423.2 (M+1).

68

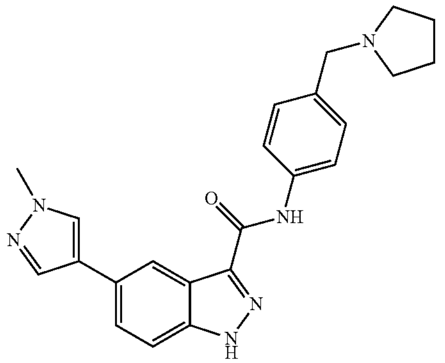

5-(1-Methyl-1H-pyrazol-4-yl)-N-(4-(pyrrolidin-1-ylmethyl)phenyl)-1H-indazole-3-carboxamide 68

White solid (0.49 g, 1.224 mmol, 54.9% yield). $^1$H NMR ($DMSO-d_6$, 500 MHz) δ ppm 1.69 (br s, 4H), 2.43 (br s, 4H), 3.54 (s, 2H), 3.89 (s, 3H), 7.27 (d, J=8.23 Hz, 2H), 7.63-7.70 (m, 2H), 7.83 (d, J=8.51 Hz, 2H), 7.87 (s, 1H), 8.19 (s, 1H), 8.32 (s, 1H), 10.24 (s, 1H), 13.72 (br s, 1H); ESIMS found for $C_{23}H_{24}N_6O$ m/z 401.3 (M+1).

69

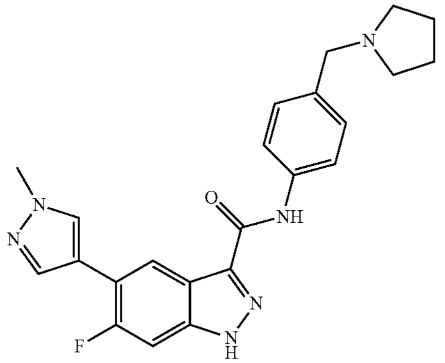

6-Fluoro-5-(1-methyl-1H-pyrazol-4-yl)-N-(4-(pyrrolidin-1-ylmethyl)phenyl)-1H-indazole-3-carboxamide 69

Off-white solid (700 mg, 1.673 mmol, 64.7% yield). $^1$H NMR ($DMSO-d_6$, 500 MHz) δ ppm 1.69 (4H, dt, J=6.66, 3.12 Hz), 2.42 (4H, br s), 3.54 (2H, s), 3.91 (3H, s), 7.27 (2H, d, J=8.51 Hz), 7.55 (1H, d, J=11.25 Hz), 7.83 (2H, d, J=8.51 Hz), 7.85 (1H, d, J=1.10 Hz), 8.16 (1H, d, J=2.20 Hz), 8.40 (1H, d, J=7.41 Hz), 10.30 (1H, s), 13.78 (1H, br s); ESIMS found for $C_{23}H_{23}FN_6O$ m/z 419.2 (M+1).

70

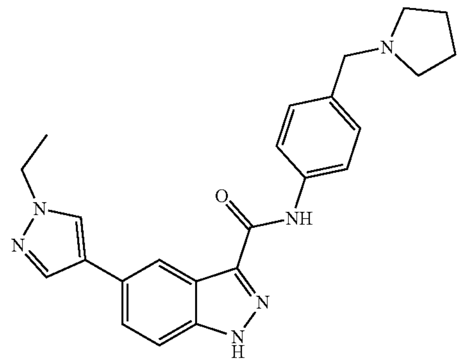

5-(1-Ethyl-1H-pyrazol-4-yl)-N-(4-(pyrrolidin-1-ylmethyl)phenyl)-1H-indazole-3-carboxamide 70

White solid (13.3 mg, 0.03 mmol, 13.8% yield). $^1$H NMR (DMSO-$d_6$, 500 MHz) δ ppm 1.43 (t, J=7.27 Hz, 3H), 1.69 (br s, 4H), 2.43 (br s, 4H), 3.54 (s, 2H), 4.17 (q, J=7.14 Hz, 2H), 7.27 (d, J=8.51 Hz, 2H), 7.62-7.66 (m, 1H), 7.67-7.71 (m, 1H), 7.84 (d, J=8.51 Hz, 2H), 7.88 (s, 1H), 8.24 (s, 1H), 8.34 (s, 1H), 10.24 (s, 1H), 13.72 (br s, 1H); ESIMS found for $C_{24}H_{26}N_6O$ m/z 415.2 (M+1).

71

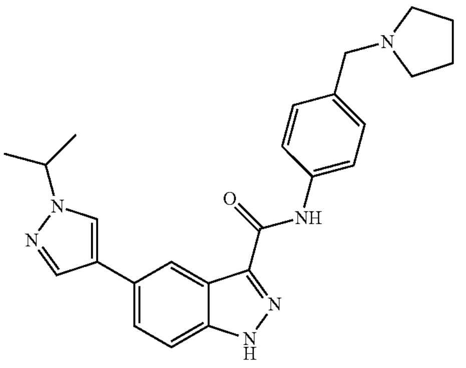

5-(1-Isopropyl-1H-pyrazol-4-yl)-N-(4-(pyrrolidin-1-ylmethyl)phenyl)-1H-indazole-3-carboxamide 71

Off-white solid (15 mg, 0.035 mmol, 39.9% yield). $^1$H NMR (DMSO-$d_6$, 500 MHz) δ ppm 1.47 (6H, d, J=6.59 Hz), 1.70 (4H, br s), 2.43 (4H, br s), 3.54 (2H, s), 4.53 (1H, quin, J=6.72 Hz), 7.27 (2H, d, J=8.51 Hz), 7.62-7.67 (1H, m), 7.69-7.73 (1H, m), 7.84 (2H, d, J=8.51 Hz), 7.88 (1H, s), 8.27 (1H, s), 8.34 (1H, s), 10.24 (1H, s), 13.69 (1H, br s); ESIMS found for $C_{25}H_{28}N_6O$ m/z 429.3 (M+1).

72

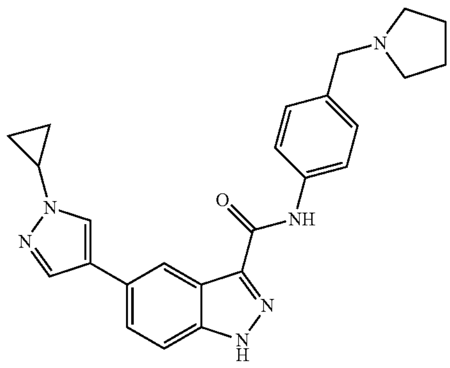

5-(1-Cyclopropyl-1H-pyrazol-4-yl)-N-(4-(pyrrolidin-1-ylmethyl)phenyl)-1H-indazole-3-carboxamide 72

Off-white solid (75 mg, 0.176 mmol, 49.9% yield). $^1$H NMR (DMSO-$d_6$, 500 MHz) δ ppm 0.96-1.02 (2H, m), 1.09-1.15 (2H, m), 1.69 (4H, dt, J=6.66, 3.12 Hz), 2.42 (4H, br s), 3.54 (2H, s), 3.76 (1H, tt, J=7.41, 3.70 Hz), 7.27 (2H, d, J=8.51 Hz), 7.62-7.66 (1H, m), 7.68-7.72 (1H, m), 7.83 (2H, d, J=8.51 Hz), 7.87 (1H, s), 8.28 (1H, s), 8.34 (1H, s), 10.24 (1H, s), 13.71 (1H, br s); ESIMS found for $C_{25}H_{26}N_6O$ m/z 427.3 (M+1).

73

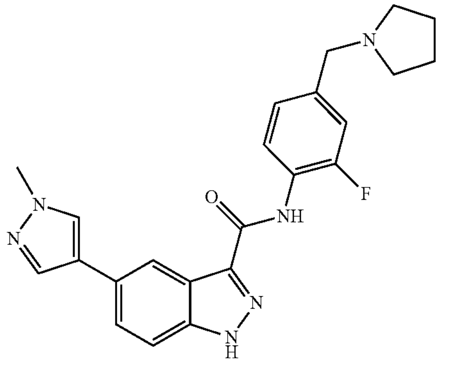

N-(2-Fluoro-4-(pyrrolidin-1-ylmethyl)phenyl)-5-(1-methyl-1H-pyrazol-4-yl)-1H-indazole-3-carboxamide 73

Yellow-white solid (24.4 mg, 0.058 mmol, 17.65% yield). $^1$H NMR (DMSO-$d_6$, 500 MHz) δ ppm 1.63-1.69 (m, 1H), 1.70-1.74 (m, 3H), 2.40 (br s, 1H), 2.46 (br s, 3H), 3.59 (s, 2H), 3.86-3.90 (m, 3H), 7.17 (br d, J=8.23 Hz, 1H), 7.21-7.26 (m, 1H), 7.65-7.69 (m, 2H), 7.84-7.92 (m, 2H), 8.18 (s, 1H), 8.28-8.30 (m, 1H), 9.76 (s, 1H), 13.77 (br s, 1H); ESIMS found for $C_{23}H_{23}FN_6O$ m/z 419.2 (M+1).

74

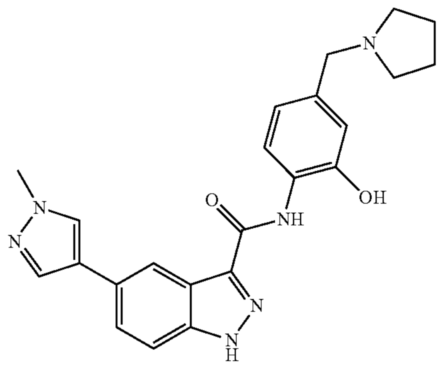

N-(2-Hydroxy-4-(pyrrolidin-1-ylmethyl)phenyl)-5-(1-methyl-1H-pyrazol-4-yl)-1H-indazole-3-carboxamide 74

Yellow-white solid (7.3 mg, 0.018 mmol, 17.62% yield). $^1$H NMR (DMSO-$d_6$, 500 MHz) δ ppm 1.93 (dt, J=6.11, 3.12 Hz, 4H), 3.14 (brt, J=6.17 Hz, 4H), 3.89 (s, 3H), 4.47 (d, J=5.76 Hz, 2H), 5.11 (t, J=5.76 Hz, 1H), 6.96 (d, J=6.86 Hz, 1H), 7.11 (s, 1H), 7.62-7.71 (m, 2H), 7.87 (s, 1H), 8.02 (d, J=7.96 Hz, 1H), 8.19 (s, 1H), 8.33 (s, 1H), 9.68 (s, 1H), 13.72 (br s, 1H); ESIMS found for $C_{23}H_{24}N_6O_2$ m/z 417.2 (M+1).

75

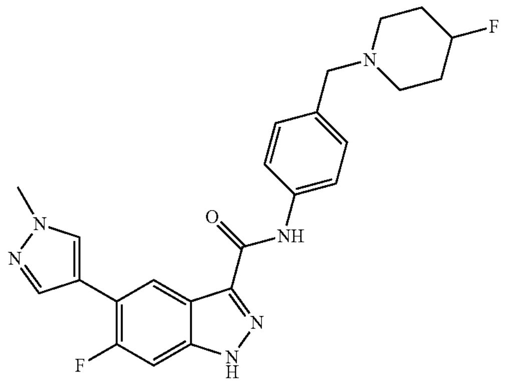

6-Fluoro-N-(4-((4-fluoropiperidin-1-yl)methyl)phenyl)-5-(1-methyl-1H-pyrazol-4-yl)-1H-indazole-3-carboxamide 75

White solid (40 mg, 0.089 mmol, 79.5% yield). $^1$H NMR (DMSO-$d_6$, 500 MHz) δ ppm 1.64-1.76 (2H, m), 1.79-1.92 (2H, m), 2.28 (2H, br s), 2.51-2.55 (2H, m), 3.44 (2H, s), 3.91 (3H, s), 4.60-4.77 (1H, m), 7.26 (2H, d, J=8.51 Hz), 7.55 (1H, d, J=10.98 Hz), 7.84 (2H, d, J=8.51 Hz), 7.85 (1H, br s), 8.17 (1H, d, J=1.92 Hz), 8.39 (1H, d, J=7.41 Hz), 10.33 (1H, s), 13.80 (1H, br s); ESIMS found for $C_{24}H_{24}F_2N_6O$ m/z 451.2 (M+1).

76

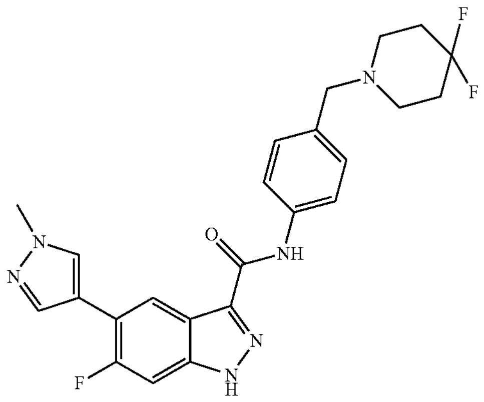

N-(4-((4,4-Difluoropiperidin-1-yl)methyl)phenyl)-6-fluoro-5-(1-methyl-1H-pyrazol-4-yl)-1H-indazole-3-carboxamide 76

White solid (50 mg, 0.107 mmol, 42.1% yield). $^1$H NMR (DMSO-$d_6$, 500 MHz) δ ppm 1.90-2.02 (4H, m), 2.45-2.49 (4H, m), 3.52 (2H, s), 3.91 (3H, s), 7.28 (2H, d, J=8.51 Hz), 7.55 (1H, d, J=10.98 Hz), 7.81-7.88 (3H, m), 8.16 (1H, d, J=2.20 Hz), 8.40 (1H, d, J=7.41 Hz), 10.33 (1H, s), 13.80 (1H, br s); ESIMS found for $C_{24}H_{23}F_3N_6O$ m/z 469.2 (M+1).

77

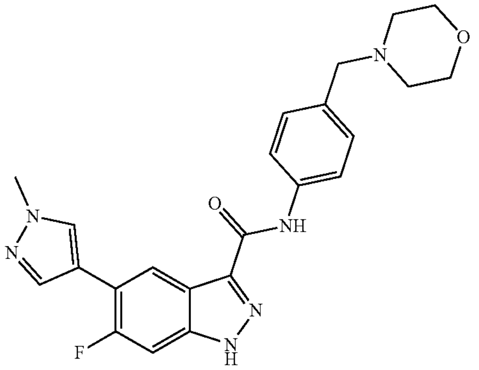

6-Fluoro-5-(1-methyl-1H-pyrazol-4-yl)-N-(4-(morpholinomethyl)phenyl)-1H-indazole-3-carboxamide 77

White solid (57.6 mg, 0.133 mmol, 55.0% yield). $^1$H NMR (DMSO-$d_6$, 500 MHz) δ ppm 2.35 (br s, 4H), 3.43 (s, 2H), 3.58 (t, J=4.53 Hz, 4H), 3.91 (s, 3H), 7.27 (d, J=8.51 Hz, 2H), 7.55 (d, J=11.25 Hz, 1H), 7.84 (d, J=8.51 Hz, 3H), 8.16 (d, J=1.92 Hz, 1H), 8.40 (d, J=7.41 Hz, 1H), 10.32 (s, 1H), 13.79 (br s, 1H); ESIMS found for $C_{23}H_{23}FN_6O_2$ m/z 435.2 (M+1).

78

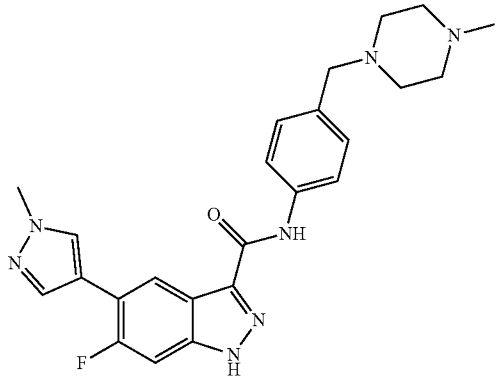

6-Fluoro-5-(1-methyl-1H-pyrazol-4-yl)-N-(4-((4-methylpiperazin-1-yl)methyl)phenyl)-1H-indazole-3-carboxamide 78

White solid (47 mg, 0.105 mmol, 62.7% yield). $^1$H NMR ($DMSO-d_6$, 500 MHz) δ ppm 2.15 (3H, s), 2.36 (8H, br s), 3.42 (2H, s), 3.91 (3H, s), 7.25 (2H, d, J=8.23 Hz), 7.55 (1H, d, J=11.25 Hz), 7.83 (2H, d, J=8.51 Hz), 7.85 (1H, d, J=1.10 Hz), 8.16 (1H, d, J=2.20 Hz), 8.40 (1H, d, J=7.41 Hz), 10.31 (1H, s), 13.79 (1H, br s); ESIMS found for $C_{24}H_{26}FN_7O$ m/z 448.2 (M+1).

79

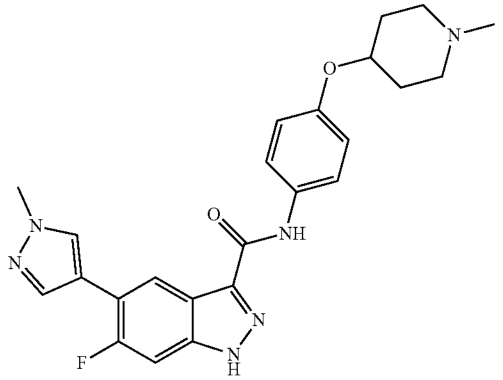

6-Fluoro-5-(1-methyl-1H-pyrazol-4-yl)-N-(4-((1-methylpiperidin-4-yl)oxy) phenyl)-1H-indazole-3-carboxamide 79

White solid (1.96 g, 4.37 mmol, 87.8% yield). $^1$H NMR ($DMSO-d_6$, 500 MHz) δ ppm 1.57-1.68 (2H, m), 1.87-1.96 (2H, m), 2.11-2.17 (2H, m), 2.17 (3H, s), 2.62 (2H, br dd, J=11.11, 4.53 Hz), 3.91 (3H, s), 4.28-4.36 (1H, m), 6.90-6.97 (2H, m), 7.54 (1H, d, J=10.98 Hz), 7.73-7.80 (2H, m), 7.85 (1H, d, J=1.10 Hz), 8.16 (1H, d, J=2.20 Hz), 8.39 (1H, d, J=7.41 Hz), 10.23 (1H, s), 13.76 (1H, br s); ESIMS found for $C_{24}H_{25}FN_6O_2$ m/z 449.2 (M+1).

80

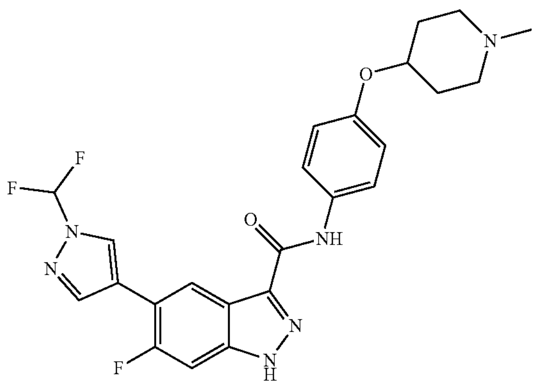

5-(1-(Difluoromethyl)-1H-pyrazol-4-yl)-6-fluoro-N-(4-((1-methylpiperidin-4-yl)oxy)phenyl)-1H-indazole-3-carboxamide 80

White solid (74 mg, 0.153 mmol, 69.5% yield). $^1$H NMR ($DMSO-d_6$, 500 MHz) δ ppm 1.57-1.68 (2H, m), 1.92 (2H, br d, J=11.25 Hz), 2.11-2.17 (2H, m), 2.17 (3H, s), 2.58-2.65 (2H, m), 4.31 (1H, dt, J=8.23, 4.12 Hz), 6.90-6.97 (2H, m), 7.62 (1H, d, J=10.98 Hz), 7.75-7.80 (2H, m), 7.91 (1H, t, J=59.10 Hz), 8.27 (1H, s), 8.49 (1H, d, J=7.41 Hz), 8.66 (1H, d, J=1.65 Hz), 10.27 (1H, s), 13.85 (1H, br s); ESIMS found for $C_{24}H_{23}F_3N_6O_2$ m/z 485.2 (M+1).

81

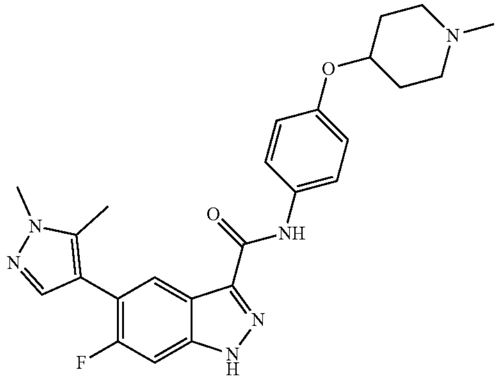

5-(1,5-Dimethyl-1H-pyrazol-4-yl)-6-fluoro-N-(4-((1-methylpiperidin-4-yl) oxy)phenyl)-1H-indazole-3-carboxamide 81

White solid (48 mg, 0.104 mmol, 40.5% yield). $^1$H NMR ($DMSO-d_6$, 500 MHz) δ ppm 1.57-1.67 (2H, m), 1.87-1.96 (2H, m), 2.11-2.16 (2H, m), 2.17 (3H, s), 2.28 (3H, s), 2.57-2.66 (2H, m), 3.82 (3H, s), 4.31 (1H, dt, J=8.30, 4.22 Hz), 6.90-6.95 (2H, m), 7.51 (1H, d, J=1.65 Hz), 7.55 (1H, d, J=10.15 Hz), 7.73-7.78 (2H, m), 8.11 (1H, d, J=7.41 Hz), 10.24 (1H, s), 13.80 (1H, br s); ESIMS found for $C_{25}H_{27}FN_6O_2$ m/z 463.2 (M+1).

82

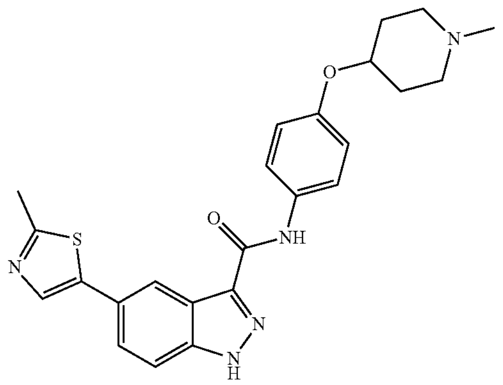

N-(4-((1-Methylpiperidin-4-yl)oxy)phenyl)-5-(2-methylthiazol-5-yl)-1H-indazole-3-carboxamide 82

Off-white solid (9.5 mg, 0.021 mmol, 9.65% yield). $^1$H NMR (DMSO-$d_6$, 500 MHz) δ ppm 1.57-1.68 (2H, m), 1.92 (2H, br d, J=9.61 Hz), 2.12-2.17 (2H, m), 2.17 (3H, s), 2.57-2.66 (2H, m), 2.69 (3H, s), 4.32 (1H, dt, J=8.30, 4.22 Hz), 6.91-6.97 (2H, m), 7.69-7.73 (1H, m), 7.75-7.80 (3H, m), 8.04 (1H, s), 8.33 (1H, d, J=0.82 Hz), 10.25 (1H, s), 13.86 (1H, br s); ESIMS found for $C_{24}H_{25}N_5O_2S$ m/z 448.0 (M+1).

83

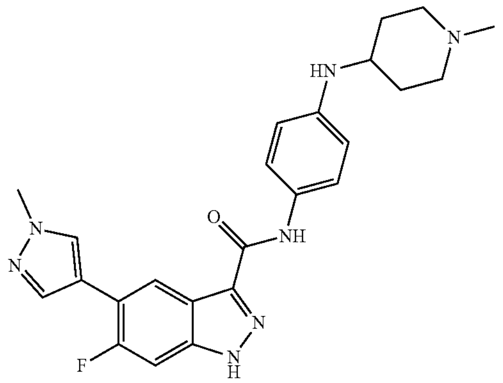

6-Fluoro-5-(1-methyl-1H-pyrazol-4-yl)-N-(4-((1-methylpiperidin-4-yl)amino) phenyl)-1H-indazole-3-carboxamide 83

Beige solid (88 mg, 0.197 mmol, 74.7% yield). $^1$H NMR ($CD_3OD$, 500 MHz) δ ppm 1.45-1.57 (2H, m), 2.04 (2H, br d, J=13.17 Hz), 2.22 (2H, br t, J=10.98 Hz), 2.31 (3H, s), 2.88 (2H, br d, J=11.80 Hz), 3.96 (3H, s), 6.68-6.75 (2H, m), 7.37 (1H, d, J=11.25 Hz), 7.44-7.52 (2H, m), 7.91 (1H, d, J=1.10 Hz), 8.02 (1H, d, J=2.20 Hz), 8.48 (1H, d, J=7.41 Hz); ESIMS found for $C_{24}H_{26}FN_7O$ m/z 448.2 (M+1).

84

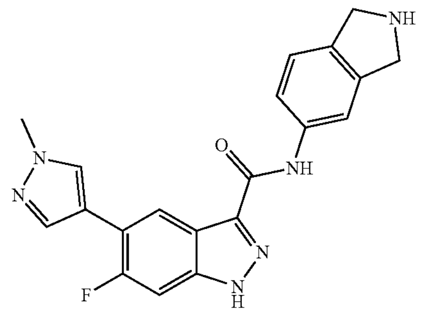

6-Fluoro-N-(isoindolin-5-yl)-5-(1-methyl-1H-pyrazol-4-yl)-1H-indazole-3-carboxamide 84

White solid (52 mg, 0.138 mmol, 47.6% yield). $^1$H NMR (DMSO-$d_6$, 500 MHz) δ ppm 3.91 (s, 3H), 4.05 (br s, 2H), 4.08 (br s, 2H), 7.22 (d, J=7.96 Hz, 1H), 7.54 (d, J=11.25 Hz, 1H), 7.62-7.68 (m, 1H), 7.85 (s, 2H), 8.16 (d, J=2.20 Hz, 1H), 8.40 (d, J=7.41 Hz, 1H), 10.27 (s, 1H); ESIMS found for $C_{20}H_{17}FN_6O$ m/z 377.1 (M+1).

85

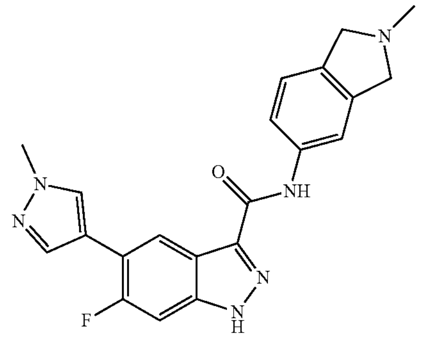

6-Fluoro-5-(1-methyl-1H-pyrazol-4-yl)-N-(2-methylisoindolin-5-yl)-1H-indazole-3-carboxamide 85

Tan solid (85.2 mg, 0.218 mmol, 75.2% yield). $^1$H NMR (DMSO-$d_6$, 500 MHz) δ ppm 2.49 (s, 3H), 3.78 (br s, 2H), 3.82 (br s, 2H), 3.91 (s, 3H), 7.18 (d, J=8.23 Hz, 1H), 7.55 (d, J=11.25 Hz, 1H), 7.64 (dd, J=7.96, 1.92 Hz, 1H), 7.81-7.87 (m, 2H), 8.16 (d, J=2.20 Hz, 1H), 8.40 (d, J=7.41 Hz, 1H), 10.28 (s, 1H), 13.78 (br s, 1H); ESIMS found for $C_{21}H_{19}FN_6O$ m/z 391.1 (M+1).

86

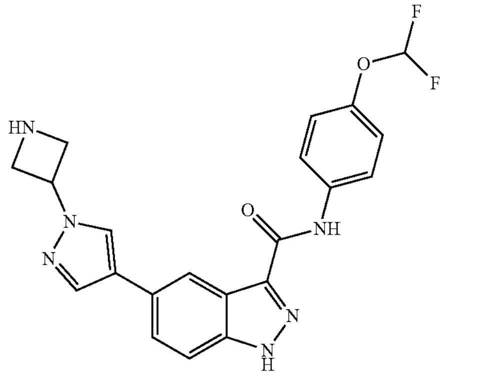

5-(1-(Azetidin-3-yl)-1H-pyrazol-4-yl)-N-(6-(difluoromethoxy)pyridin-3-yl)-1H-indazole-3-carboxamide 86

White solid (29 mg, 0.068 mmol, 59.4% yield). $^1$H NMR (DMSO-$d_6$, 500 MHz) δ ppm 3.76 (2H, t, J=8.10 Hz), 3.92-4.00 (2H, m), 5.21 (1H, quin, J=7.41 Hz), 7.13 (1H, d, J=9.06 Hz), 7.67 (1H, t, J=73.50 Hz), 7.66-7.68 (1H, m), 7.71-7.75 (1H, m), 7.97 (1H, s), 8.35 (1H, s), 8.38-8.44 (2H, m), 8.78 (1H, d, J=2.47 Hz), 10.66 (1H, s); ESIMS found for $C_{20}H_{17}F_2N_7O_2$ m/z 426.2 (M+1).

87

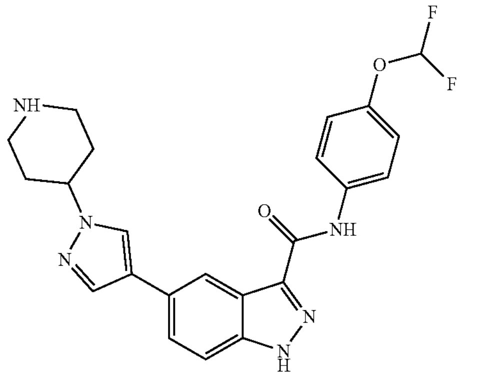

N-(6-(Difluoromethoxy)pyridin-3-yl)-5-(1-(piperidin-4-yl)-1H-pyrazol-4-yl)-1H-indazole-3-carboxamide 87

White solid (50 mg, 0.110 mmol, 74.0% yield). $^1$H NMR (DMSO-$d_6$, 500 MHz) δ ppm 1.79-1.90 (2H, m), 2.00 (2H, br d, J=8.51 Hz), 2.60 (2H, br t, J=11.53 Hz), 3.06 (2H, br d, J=12.35 Hz), 4.18-4.26 (1H, m), 7.13 (1H, d, J=8.78 Hz), 7.68 (1H, t, J=73.40 Hz), 7.64-7.67 (1H, m), 7.70-7.74 (1H, m), 7.89 (1H, s), 8.27 (1H, s), 8.33 (1H, s), 8.41 (1H, dd, J=8.78, 2.74 Hz), 8.78 (1H, d, J=2.47 Hz), 10.66 (1H, s); ESIMS found for $C_{22}H_{2}$, $F_2N_7O_2$ m/z 454.2 (M+1).

88

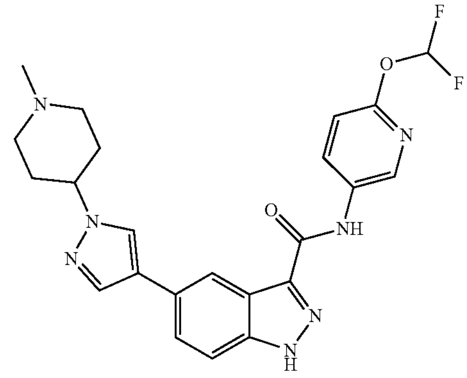

N-(6-(Difluoromethoxy)pyridin-3-yl)-5-(1-(1-methylpiperidin-4-yl)-1H-pyrazol-4-yl)-1H-indazole-3-carboxamide 88

White solid (71 mg, 0.152 mmol, 88.4% yield). $^1$H NMR (DMSO-$d_6$, 500 MHz) δ ppm 1.98-2.10 (6H, m), 2.21 (3H, s), 2.83-2.91 (2H, m), 4.09-4.18 (1H, m), 7.13 (1H, d, J=8.78 Hz), 7.68 (1H, t, J=73.10 Hz), 7.64-7.67 (1H, m), 7.70-7.74 (1H, m), 7.90 (1H, s), 8.30 (1H, s), 8.33 (1H, s), 8.41 (1H, dd, J=8.92, 2.61 Hz), 8.78 (1H, d, J=2.74 Hz), 10.67 (1H, s), 13.83 (1H, br s); ESIMS found for $C_{23}H_{23}F_2N_7O_2$ m/z 468.2 (M+1).

89

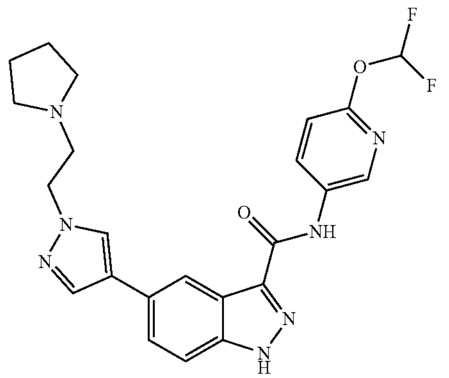

N-(6-(Difluoromethoxy)pyridin-3-yl)-5-(1-(2-(pyrrolidin-1-yl)ethyl)-1H-pyrazol-4-yl)-1H-indazole-3-carboxamide 89

White solid (27 mg, 0.058 mmol, 39.8% yield). $^1$H NMR (DMSO-$d_6$, 500 MHz) δ ppm 1.67 (4H, dt, J=6.72, 3.22 Hz), 2.45-2.49 (4H, m), 2.87 (2H, t, J=6.72 Hz), 4.24 (2H, t, J=6.72 Hz), 7.13 (1H, d, J=8.78 Hz), 7.68 (2H, t, J=73.50 Hz), 7.65-7.67 (1H, m), 7.68-7.72 (1H, m), 7.88 (1H, s), 8.26 (1H, s), 8.32 (1H, s), 8.41 (1H, dd, J=8.92, 2.61 Hz), 8.78 (1H, d, J=2.74 Hz), 10.66 (1H, s), 13.81 (1H, br s); ESIMS found for $C_{23}H_{23}F_2N_7O_2$ m/z 468.2 (M+1).

90

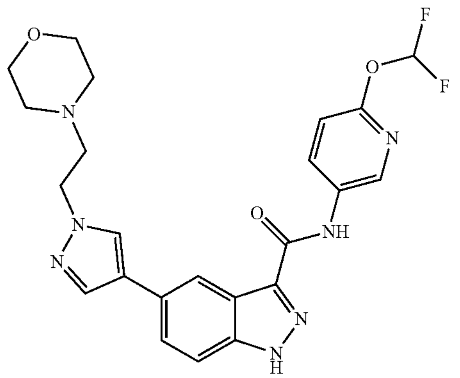

N-(6-(Difluoromethoxy)pyridin-3-yl)-5-(1-(2-morpholinoethyl)-1H-pyrazol-4-yl)-1H-indazole-3-carboxamide 90

White solid (60 mg, 0.124 mmol, 64.0% yield). $^1$H NMR (DMSO-$d_6$, 500 MHz) δ ppm 2.43 (4H, br s), 2.77 (2H, t, J=6.59 Hz), 3.52-3.59 (4H, m), 4.26 (2H, t, J=6.59 Hz), 7.13 (1H, d, J=8.78 Hz), 7.67 (1H, t, J=73.20 Hz), 7.65-7.68 (1H, m), 7.69-7.72 (1H, m), 7.89 (1H, s), 8.26 (1H, s), 8.32 (1H, s), 8.40 (1H, dd, J=8.78, 2.47 Hz), 8.78 (1H, d, J=2.74 Hz), 10.66 (1H, s), 13.82 (1H, br s); ESIMS found for $C_{23}H_{23}F_2N_7O_3$ m/z 484.2 (M+1).

91

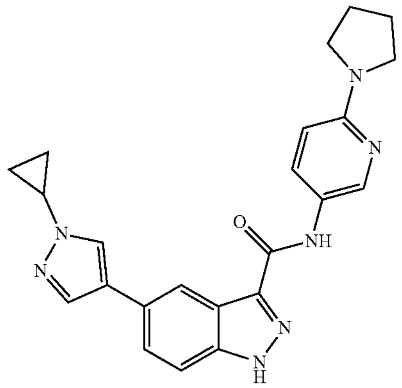

5-(1-Cyclopropyl-1H-pyrazol-4-yl)-N-(6-(pyrrolidin-1-yl)pyridin-3-yl)-1H-indazole-3-carboxamide 91

White solid (27 mg, 0.065 mmol, 72.2% yield). $^1$H NMR (DMSO-$d_6$, 500 MHz) δ ppm 0.95-1.02 (2H, m), 1.08-1.14 (2H, m), 1.95 (4H, dt, J=6.31, 3.43 Hz), 3.35-3.40 (4H, m), 3.76 (1H, tt, J=7.38, 3.88 Hz), 6.46 (1H, d, J=9.06 Hz), 7.59-7.65 (1H, m), 7.66-7.71 (1H, m), 7.86 (1H, s), 7.97 (1H, dd, J=9.06, 2.74 Hz), 8.28 (1H, s), 8.32 (1H, s), 8.49 (1H, d, J=2.47 Hz), 10.12 (1H, s), 13.68 (1H, br s); ESIMS found for $C_{23}H_{23}N_7O$ m/z 414.2 (M+1).

92

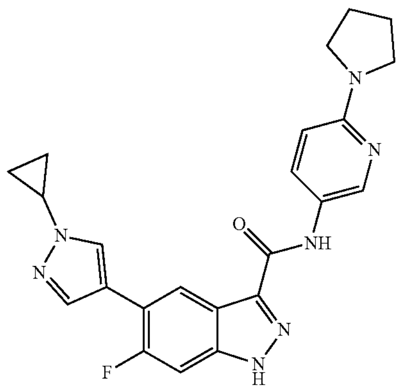

5-(1-Cyclopropyl-1H-pyrazol-4-yl)-6-fluoro-N-(6-(pyrrolidin-1-yl)pyridin-3-yl)-1H-indazole-3-carboxamide 92

Off-white solid (20.5 mg, 0.05 mmol). $^1$H NMR (DMSO-$d_6$, 500 MHz) δ ppm 0.96-1.03 (m, 2H), 1.10-1.16 (m, 2H), 1.92-1.97 (m, 4H), 3.37 (br t, J=6.59 Hz, 4H), 3.81 (tt, J=7.34, 3.77 Hz, 1H), 6.45 (d, J=9.06 Hz, 1H), 7.54 (d, J=11.25 Hz, 1H), 7.83 (d, J=1.37 Hz, 1H), 7.95 (dd, J=9.06, 2.47 Hz, 1H), 8.23 (d, J=1.65 Hz, 1H), 8.39 (d, J=7.41 Hz, 1H), 8.48 (d, J=2.47 Hz, 1H), 10.18 (s, 1H), 13.77 (s, 1H); ESIMS found for $C_{23}H_{22}FN_7O$ m/z 432.2 (M+1).

93

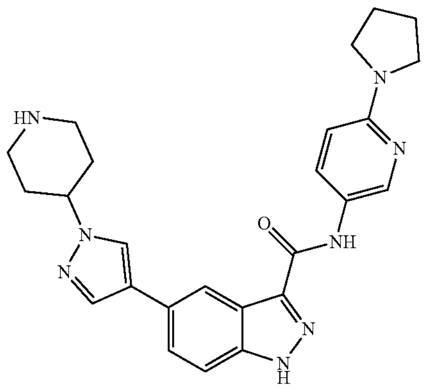

5-(1-(Piperidin-4-yl)-1H-pyrazol-4-yl)-N-(6-(pyrrolidin-1-yl)pyridin-3-yl)-1H-indazole-3-carboxamide 93

White solid (23 mg, 0.050 mmol, 36.7% yield). $^1$H NMR (DMSO-$d_6$, 500 MHz) δ ppm 1.83 (2H, qd, J=12.03, 4.25 Hz), 1.91-2.03 (6H, m), 2.56-2.64 (2H, m), 3.05 (2H, br d, J=12.62 Hz), 3.36-3.40 (4H, m), 4.21 (1H, tt, J=11.60, 3.91 Hz), 6.46 (1H, d, J=9.06 Hz), 7.60-7.64 (1H, m), 7.67-7.72 (1H, m), 7.88 (1H, s), 7.97 (1H, dd, J=9.06, 2.74 Hz), 8.26 (1H, s), 8.32 (1H, s), 8.49 (1H, d, J=2.74 Hz), 10.12 (1H, s), 13.67 (1H, br s); ESIMS found for $C_{25}H_{28}N_8O$ m/z 457.2 (M+1).

94

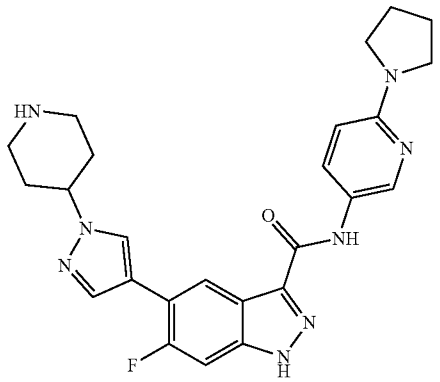

6-Fluoro-5-(1-(piperidin-4-yl)-1H-pyrazol-4-yl)-N-(6-(pyrrolidin-1-yl)pyridin-3-yl)-1H-indazole-3-carboxamide 94

White solid (52 mg, 0.110 mmol, 82.1% yield). $^1$H NMR (DMSO-$d_6$, 500 MHz) δ ppm 1.84 (2H, qd, J=12.03, 3.98 Hz), 1.91-2.01 (6H, m), 2.59 (2H, td, J=12.21, 2.20 Hz), 3.05 (2H, br d, J=12.62 Hz), 3.35-3.41 (4H, m), 4.27 (1H, tt, J=11.49, 4.01 Hz), 6.46 (1H, d, J=9.06 Hz), 7.53 (1H, d, J=11.25 Hz), 7.86 (1H, d, J=1.65 Hz), 7.96 (1H, dd, J=8.92, 2.61 Hz), 8.20 (1H, d, J=1.65 Hz), 8.39 (1H, d, J=7.41 Hz), 8.48 (1H, d, J=2.47 Hz), 10.18 (1H, s); ESIMS found for $C_{25}H_{27}FN_8O$ m/z 475.3 (M+1).

95

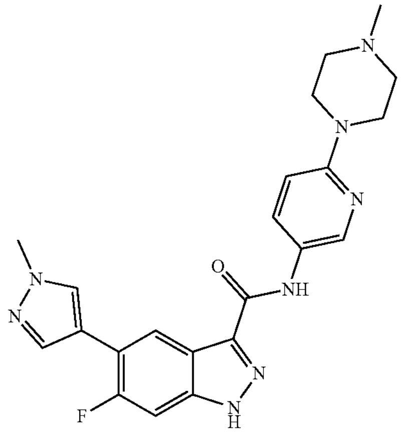

6-Fluoro-5-(1-methyl-1H-pyrazol-4-yl)-N-(6-(4-methylpiperazin-1-yl)pyridin-3-yl)-1H-indazole-3-carboxamide 95

White solid (20 mg, 0.046 mmol, 59.7% yield). $^1$H NMR (DMSO-$d_6$, 500 MHz) δ ppm 2.22 (3H, s), 2.37-2.43 (4H, m), 3.41-3.46 (4H, m), 3.91 (3H, s), 6.85 (1H, d, J=9.33 Hz), 7.54 (1H, d, J=10.98 Hz), 7.84 (1H, d, J=1.10 Hz), 8.02 (1H, dd, J=9.19, 2.61 Hz), 8.16 (1H, d, J=2.20 Hz), 8.38 (1H, d, J=7.41 Hz), 8.57 (1H, d, J=2.74 Hz), 10.28 (1H, s), 13.78 (1H, br s); ESIMS found for $C_{22}H_{23}FN_8O$ m/z 435.2 (M+1).

96

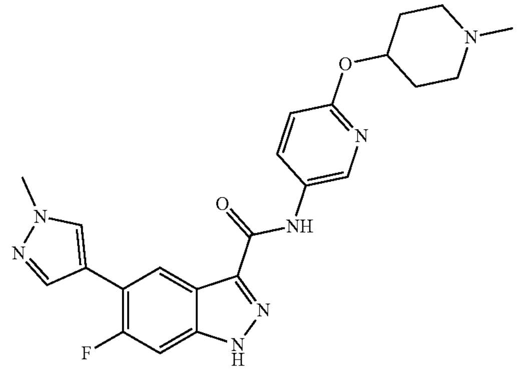

6-Fluoro-5-(1-methyl-1H-pyrazol-4-yl)-N-(6-((1-methylpiperidin-4-yl)oxy) pyridin-3-yl)-1H-indazole-3-carboxamide 96

White solid (60 mg, 0.133 mmol, 54.8% yield). $^1$H NMR (DMSO-$d_6$, 500 MHz) δ ppm 1.61-1.71 (2H, m), 1.96 (2H, br d, J=10.43 Hz), 2.11-2.17 (2H, m), 2.18 (3H, s), 2.64 (2H, br s), 3.91 (3H, s), 4.94 (1H, dt, J=8.71, 4.56 Hz), 6.80 (1H, d, J=9.06 Hz), 7.56 (1H, d, J=10.98 Hz), 7.85 (1H, s), 8.13-8.17 (2H, m), 8.38 (1H, d, J=7.41 Hz), 8.59 (1H, d, J=2.47 Hz), 10.46 (1H, s), 13.82 (1H, br s); ESIMS found for $C_{23}H_{24}FN_7O_2$ m/z 450.2 (M+1).

97

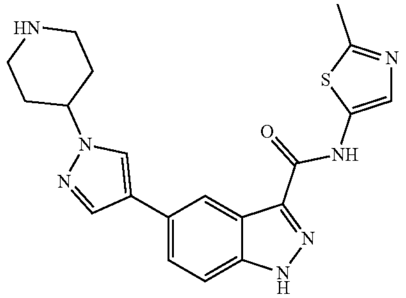

N-(2-Methylthiazol-5-yl)-5-(1-(piperidin-4-yl)-1H-pyrazol-4-yl)-1H-indazole-3-carboxamide 97

White solid (88 mg, 0.216 mmol, 85.4% yield). $^1$H NMR (DMSO-$d_6$, 500 MHz) δ ppm 1.79-1.90 (2H, m), 1.96-2.04 (2H, m), 2.57 (3H, s), 2.58-2.65 (2H, m), 3.06 (2H, br d, J=12.35 Hz), 4.21 (1H, tt, J=11.60, 3.91 Hz), 7.62 (1H, s), 7.64-7.68 (1H, m), 7.70-7.75 (1H, m), 7.91 (1H, d, J=0.82 Hz), 8.30 (1H, s), 8.32 (1H, d, J=0.82 Hz); ESIMS found for $C_{20}H_{21}N_7OS$ m/z 408.1 (M+1).

98

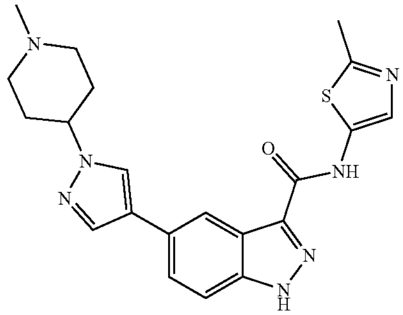

5-(1-(1-Methylpiperidin-4-yl)-1H-pyrazol-4-yl)-N-(2-methylthiazol-5-yl)-1H-indazole-3-carboxamide 98

White solid (55 mg, 0.130 mmol, 84.4% yield). $^1$H NMR (DMSO-$d_6$, 500 MHz) δ ppm 1.98-2.10 (6H, m), 2.21 (3H, s), 2.57 (3H, s), 2.84-2.90 (2H, m), 4.09-4.18 (1H, m), 7.62 (1H, s), 7.64-7.68 (1H, m), 7.70-7.74 (1H, m), 7.91 (1H, s), 8.32 (2H, d, J=3.57 Hz), 11.79 (1H, br s), 13.86 (1H, br s); ESIMS found for $C_{11}H_{23}N_7OS$ m/z 422.2 (M+1).

99

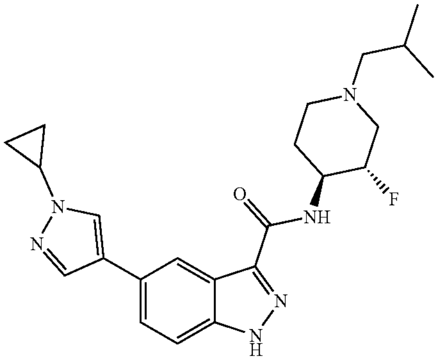

5-(1-Cyclopropyl-1H-pyrazol-4-yl)-N-((3S,4S)-3-fluoro-1-isobutylpiperidin-4-yl)-1H-indazole-3-carboxamide 99

White solid (15.7 mg, 0.038 mmol, 41.8% yield). $^1$H NMR (499 MHz, DMSO-$d_6$) δ ppm 0.86 (6H, d, J=6.59 Hz), 0.95-1.01 (2H, m), 1.07-1.14 (2H, m), 1.63-1.74 (1H, m), 1.74-1.80 (1H, m), 1.80-1.87 (1H, m), 1.93-2.04 (2H, m), 2.08-2.17 (2H, m), 2.79 (1H, br d, J=9.61 Hz), 3.13-3.21 (1H, m), 3.75 (1H, tt, J=7.44, 3.81 Hz), 3.95-4.08 (1H, m), 4.62-4.79 (1H, m), 7.56-7.62 (1H, m), 7.63-7.68 (1H, m), 7.83 (1H, s), 8.24 (1H, s), 8.27 (1H, s), 8.51 (1H, d, J=8.78 Hz), 13.56 (1H, br s); ESIMS found for $C_{23}H_{29}FN_6O$ m/z 425.2 (M+1).

100

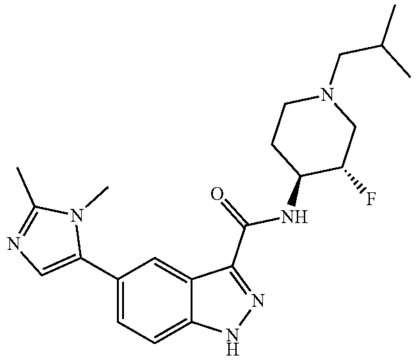

5-(1,2-Dimethyl-1H-imidazol-5-yl)-N-((3S,4S)-3-fluoro-1-isobutylpiperidin-4-yl)-1H-indazole-3-carboxamide 100

Beige solid (8.2 mg, 0.083 mmol, 9.9% yield). $^1$H NMR (499 MHz, DMSO-$d_6$) δ ppm 0.86 (6H, d, J=6.31 Hz), 1.63-1.73 (1H, m), 1.73-1.86 (2H, m), 1.93-2.04 (2H, m), 2.07-2.18 (2H, m), 2.36 (3H, s), 2.74-2.81 (1H, m), 3.12-3.20 (1H, m), 3.52 (3H, s), 3.96-4.09 (1H, m), 4.61-4.79 (1H, m), 6.86 (1H, s), 7.47 (1H, dd, J=8.64, 1.51 Hz), 7.69 (1H, d, J=8.78 Hz), 8.15 (1H, s), 8.57 (1H, d, J=9.06 Hz), 13.71 (1H, br s); ESIMS found for $C_{22}H_{29}FN_6O$ m/z 413.2 (M+1).

101

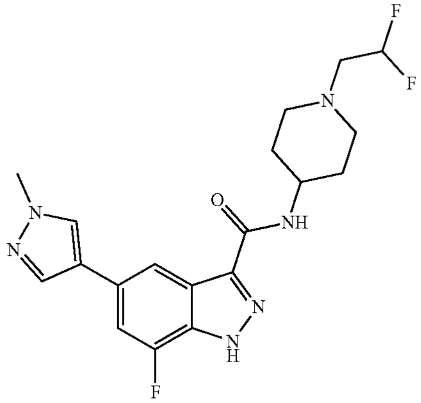

N-(1-(2,2-Difluoroethyl)piperidin-4-yl)-7-fluoro-5-(1-methyl-1H-pyrazol-4-yl)-1H-indazole-3-carboxamide 101

White solid (48 mg, 0.118 mmol, 59.1% yield). $^1$H NMR (DMSO-$d_6$, 500 MHz) δ ppm 1.64-1.73 (2H, m), 1.73-1.80 (2H, m), 2.21-2.30 (2H, m), 2.73 (2H, td, J=15.64, 4.39 Hz), 2.92 (2H, br d, J=11.80 Hz), 3.78-3.86 (1H, m), 3.87 (3H, s), 6.14 (1H, tt, J=56.10, 4.40 Hz), 7.53 (1H, dd, J=12.62, 1.10 Hz), 7.87 (1H, s), 8.08 (1H, d, J=0.82 Hz), 8.19 (1H, s), 8.28 (1H, d, J=8.23 Hz), 14.07 (1H, br s); ESIMS found for $C_{19}H_{21}F_3N_6O$ m/z 407.2 (M+1).

106

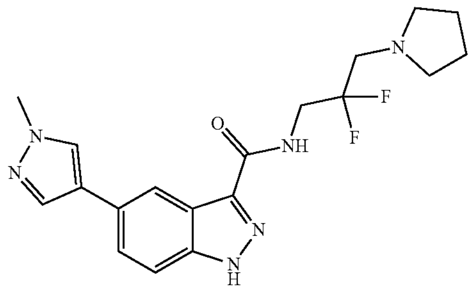

N-(2,2-Difluoro-3-(pyrrolidin-1-yl)propyl)-5-(1-methyl-1H-pyrazol-4-yl)-1H-indazole-3-carboxamide 106

Off-white solid (0.038 g, 0.098 mmol, 51.4% yield). $^1$H NMR (DMSO-$d_6$, 500 MHz) δ ppm 1.72 (dt, J=6.59, 3.29 Hz, 4H), 2.58-2.65 (m, 4H), 2.97 (t, J=14.55 Hz, 2H), 3.82-3.92 (m, 5H), 7.59-7.67 (m, 2H), 7.85 (s, 1H), 8.16 (s, 1H), 8.26 (s, 1H), 8.53 (t, J=6.31 Hz, 1H), 13.61 (br s, 1H); ESIMS found for $C_{19}H_{22}F_2N_6O$ m/z 389 (M+1).

119

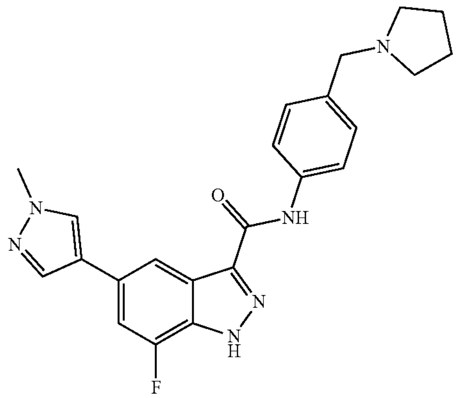

7-Fluoro-5-(1-methyl-1H-pyrazol-4-yl)-N-(4-(pyrrolidin-1-ylmethyl)phenyl)-1H-indazole-3-carboxamide 119

Off-white solid (34 mg, 0.081 mmol, 40.6% yield). $^1$H NMR (DMSO-$d_6$, 500 MHz) δ ppm 1.69 (4H, dt, J=6.52, 3.19 Hz), 2.43 (4H, br s), 3.54 (2H, s), 3.88 (3H, s), 7.27 (2H, d, J=8.51 Hz), 7.58 (1H, dd, J=12.35, 1.10 Hz), 7.83 (2H, d, J=8.51 Hz), 7.92 (1H, d, J=0.82 Hz), 8.14 (1H, d, J=1.10 Hz), 8.25 (1H, s), 10.35 (1H, s), 14.24 (1H, br s); ESIMS found for $C_{23}H_{23}FN_6O$ m/z 419.2 (M+1).

122

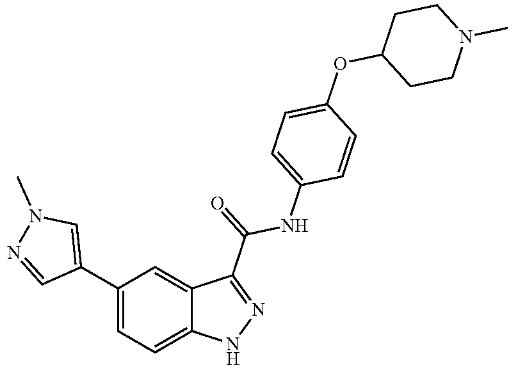

5-(1-Methyl-1H-pyrazol-4-yl)-N-(4-((1-methylpiperidin-4-yl)oxy)phenyl)-1H-indazole-3-carboxamide 122

White solid (82 mg, 0.190 mmol, 75.1% yield). $^1$H NMR (DMSO-$d_6$, 500 MHz) δ ppm 1.58-1.67 (m, 2H), 1.88-1.96 (m, 2H), 2.12-2.17 (m, 2H), 2.17 (s, 3H), 2.58-2.66 (m, 2H), 3.88 (s, 3H), 4.31 (dt, J=8.16, 4.29 Hz, 1H), 6.93 (d, J=8.78 Hz, 2H), 7.62-7.70 (m, 2H), 7.78 (d, J=9.06 Hz, 2H), 7.86 (s, 1H), 8.18 (s, 1H), 8.31 (s, 1H), 10.17 (s, 1H), 13.68 (br s, 1H); ESIMS found for $C_{24}H_{26}N_6O_2$ m/z 431.2 (M+1).

124

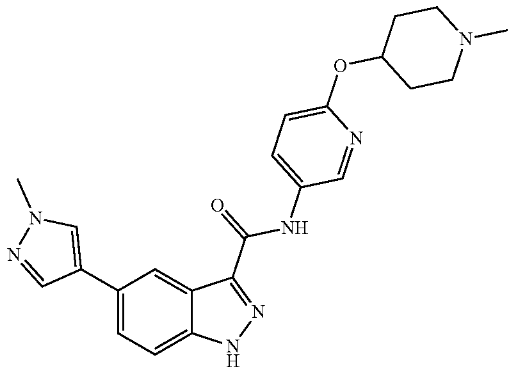

5-(1-Methyl-1H-pyrazol-4-yl)-N-(6-((1-methylpiperidin-4-yl)oxy)pyridin-3-yl)-1H-indazole-3-carboxamide 124

White solid (70 mg, 0.162 mmol, 62.0% yield). $^1$H NMR (DMSO-$d_6$, 500 MHz) δ ppm 1.60-1.71 (m, 2H), 1.97 (br dd, J=8.92, 3.70 Hz, 2H), 2.10-2.17 (m, 2H), 2.18 (s, 3H), 2.60-2.68 (m, 2H), 3.88 (s, 3H), 4.94 (tt, J=8.54, 4.08 Hz, 1H), 6.79 (d, J=8.78 Hz, 1H), 7.63-7.70 (m, 2H), 7.86 (d, J=0.82 Hz, 1H), 8.16 (dd, J=8.78, 2.74 Hz, 1H), 8.19 (s, 1H), 8.31 (s, 1H), 8.60 (d, J=2.74 Hz, 1H), 10.40 (s, 1H), 13.75 (br s, 1H); ESIMS found for $C_{23}H_{25}N_7O_2$ m/z 432.2 (M+1).

125

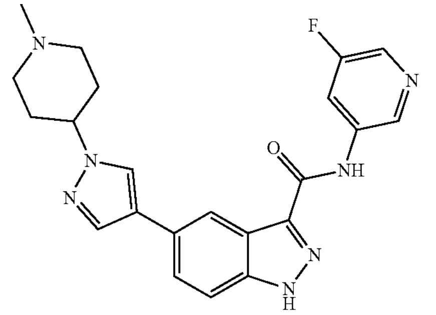

N-(5-Fluoropyridin-3-yl)-5-(1-(1-methylpiperidin-4-yl)-1H-pyrazol-4-yl)-1H-indazole-3-carboxamide 125

White solid (87 mg, 0.207 mmol, 80.2% yield). $^1$H NMR (DMSO-$d_6$, 500 MHz) δ ppm 1.98-2.10 (m, 6H), 2.21 (s, 3H), 2.84-2.91 (m, 2H), 4.09-4.19 (m, 1H), 7.65-7.69 (m, 1H), 7.71-7.76 (m, 1H), 7.91 (s, 1H), 8.30-8.36 (m, 4H), 8.97-9.01 (m, 1H), 10.88 (s, 1H), 13.89 (br s, 1H); ESIMS found for $C_{22}H_{22}FN_7O$ m/z 420.2 (M+1).

126

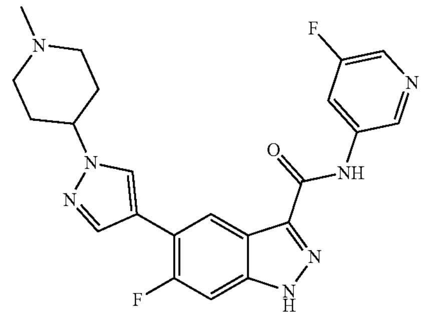

6-Fluoro-N-(5-fluoropyridin-3-yl)-5-(1-(1-methylpiperidin-4-yl)-1H-pyrazol-4-yl)-1H-indazole-3-carboxamide 126

White solid (22.6 mg, 0.052 mmol, 48.1% yield). $^1$H NMR (DMSO-$d_6$, 500 MHz) δ ppm 1.98-2.11 (m, 6H), 2.22 (s, 3H), 2.88 (br d, J=7.41 Hz, 2H), 4.15-4.26 (m, 1H), 7.59 (d, J=10.98 Hz, 1H), 7.89 (d, J=1.65 Hz, 1H), 8.26 (d, J=1.37 Hz, 1H), 8.29-8.35 (m, 2H), 8.41 (d, J=7.41 Hz, 1H), 8.96-9.01 (m, 1H), 10.93 (s, 1H), 13.97 (br s, 1H); ESIMS found for $C_{22}H_{21}F_2N_7O$ m/z 438.1 (M+1).

127

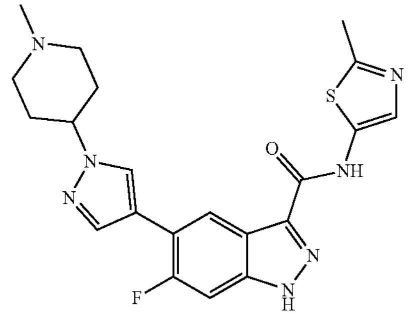

6-Fluoro-5-(1-(1-methylpiperidin-4-yl)-1H-pyrazol-4-yl)-N-(2-methylthiazol-5-yl)-1H-indazole-3-carboxamide 127

White solid (27.9 mg, 0.06 mmol, 59.4%). $^1$H NMR (DMSO-$d_6$, 500 MHz) δ ppm 1.99-2.10 (m, 6H), 2.21 (s, 3H), 2.57 (s, 3H), 2.87 (br d, J=4.94 Hz, 2H), 4.20 (br s, 1H), 7.58 (d, J=10.98 Hz, 1H), 7.63 (s, 1H), 7.89 (d, J=1.65 Hz, 1H), 8.27 (d, J=1.37 Hz, 1H), 8.39 (d, J=7.14 Hz, 1H), 11.85 (br s, 1H), 13.95 (br s, 1H); ESIMS found for $C_{21}H_{22}FN_7OS$ m/z 440.1 (M+1).

128

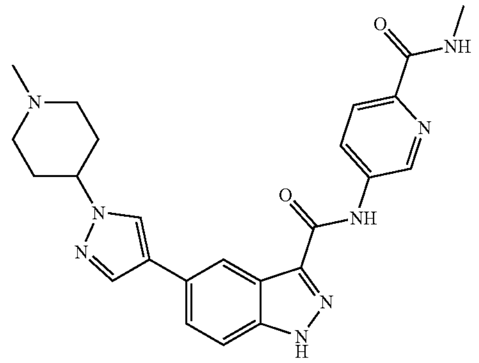

N-(6-(Methylcarbamoyl)pyridin-3-yl)-5-(1-(1-methylpiperidin-4-yl)-1H-pyrazol-4-yl)-1H-indazole-3-carboxamide 128

Cream colored solid (76 mg, 0.166 mmol, 75.0% yield). $^1$H NMR (DMSO-$d_6$, 500 MHz) δ ppm 1.98-2.12 (m, 6H), 2.21 (s, 3H), 2.82 (d, J=4.94 Hz, 3H), 2.85-2.90 (m, 2H), 4.09-4.19 (m, 1H), 7.65-7.69 (m, 1H), 7.71-7.76 (m, 1H), 7.91 (s, 1H), 8.03 (d, J=8.51 Hz, 1H), 8.32 (s, 1H), 8.35 (s, 1H), 8.52 (dd, J=8.51, 2.47 Hz, 1H), 8.68 (q, J=4.85 Hz, 1H), 9.16 (d, J=2.47 Hz, 1H), 10.87 (s, 1H), 13.88 (br s, 1H); ESIMS found for $C_{24}H_{26}N_8O_2$ m/z 458.7 (M+1).

129

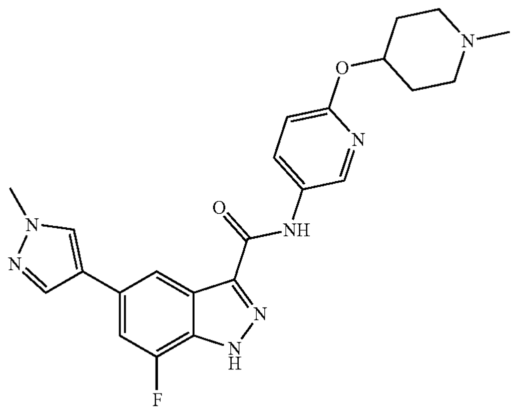

7-Fluoro-5-(1-methyl-1H-pyrazol-4-yl)-N-(6-((1-methylpiperidin-4-yl)oxy) pyridin-3-yl)-1H-indazole-3-carboxamide 129

White solid (95 mg, 0.211 mmol, 80.5% yield). $^1$H NMR ($DMSO-d_6$, 500 MHz) δ ppm 1.61-1.72 (m, 2H), 1.93-2.01 (m, 2H), 2.12-2.21 (m, 2H), 2.19 (s, 3H), 2.61-2.70 (m, 2H), 3.88 (s, 3H), 4.95 (tt, J=8.61, 4.29 Hz, 1H), 6.80 (d, J=8.78 Hz, 1H), 7.58 (d, J=12.62 Hz, 1H), 7.91 (s, 1H), 8.13 (d, J=1.10 Hz, 1H), 8.15 (dd, J=8.92, 2.61 Hz, 1H), 8.24 (s, 1H), 8.59 (d, J=2.47 Hz, 1H), 10.49 (s, 1H), 14.28 (br s, 1H); ESIMS found for $C_{23}H_{24}FN_7O_2$ m/z 449.8 (M+1).

131

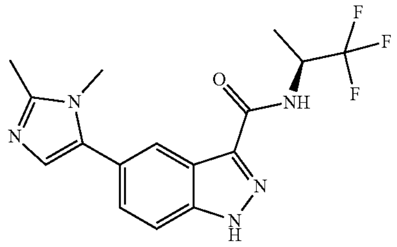

(S)-5-(1,2-Dimethyl-1H-imidazol-5-yl)-N-(1,1,1-trifluoropropan-2-yl)-1H-indazole-3-carboxamide 131

White solid (31.0 mg, 0.088 mmol, 42.7% yield). $^1$H NMR (499 MHz, $DMSO-d_6$) δ ppm 1.41 (3H, d, J=7.14 Hz), 2.36 (3H, s), 3.53 (3H, s), 4.90 (1H, dq, J=15.64, 7.87 Hz), 6.88 (1H, s), 7.49 (1H, dd, J=8.64, 1.51 Hz), 7.72 (1H, d, J=8.78 Hz), 8.13 (1H, d, J=0.82 Hz), 8.93 (1H, d, J=9.06 Hz), 13.84 (1H, s); ESIMS found for $C_{16}H_{16}F_3N_5O$ m/z 352.2 (M+1).

132

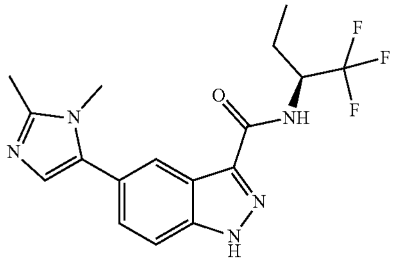

(S)-5-(1,2-Dimethyl-1H-imidazol-5-yl)-N-(1,1,1-trifluorobutan-2-yl)-1H-indazole-3-carboxamide 132

White solid (33.0 mg, 0.090 mmol, 50.2% yield). NMR (499 MHz, $DMSO-d_6$) δ ppm 0.94 (3H, t, J=7.41 Hz), 1.72-1.84 (1H, m), 1.84-1.96 (1H, m), 2.36 (3H, s), 3.53 (3H, s), 4.62-4.75 (1H, m), 6.88 (1H, s), 7.49 (1H, dd, J=8.64, 1.51 Hz), 7.73 (1H, d, J=8.78 Hz), 8.13 (1H, s), 8.85 (1H, d, J=9.33 Hz), 13.85 (1H, br s); ESIMS found for $C_{17}H_{18}F_3N_5O$ m/z 366.1 (M+1).

133

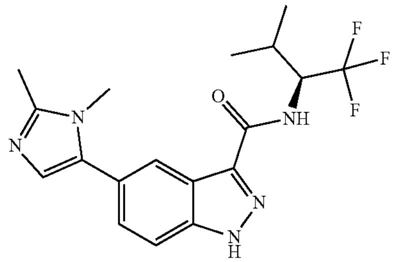

(S)-5-(1,2-Dimethyl-1H-imidazol-5-yl)-N-(1,1,1-trifluoro-3-methylbutan-2-yl)-1H-indazole-3-carboxamide 133

Off-white solid (37.0 mg, 0.098 mmol, 54.5% yield). $^1$H NMR (499 MHz, $DMSO-d_6$) δ ppm 0.99 (3H, d, J=6.86 Hz), 1.04 (3H, d, J=6.86 Hz), 2.30 (1H, dq, J=14.10, 6.83 Hz), 2.36 (3H, s), 3.53 (3H, s), 4.58 (1H, sxt, J=8.78 Hz), 6.88 (1H, s), 7.50 (1H, dd, J=8.51, 1.65 Hz), 7.73 (1H, d, J=8.78 Hz), 8.12 (1H, s), 8.68 (1H, d, J=9.88 Hz), 13.85 (1H, br s); ESIMS found for $C_{18}H_{20}F_3N_5O$ m/z 380.15 (M+1).

134

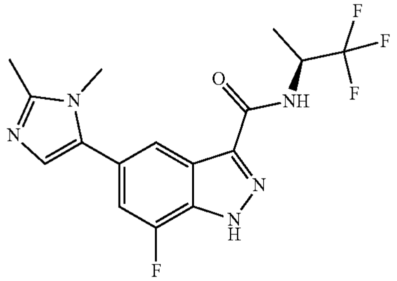

(S)-5-(1,2-Dimethyl-1H-imidazol-5-yl)-7-fluoro-N-(1,1,1-trifluoropropan-2-yl)-1H-indazole-3-carboxamide 134

White solid (33.0 mg, 0.089 mmol, 28.9% yield). $^1H$ NMR (499 MHz, DMSO-$d_6$) δ ppm 1.41 (3H, d, J=7.14 Hz), 2.36 (3H, s), 3.55 (3H, s), 4.90 (1H, dq, J=15.75, 7.74 Hz), 6.94 (1H, s), 7.41 (1H, dd, J=11.94, 0.96 Hz), 7.95 (1H, d, J=0.82 Hz), 9.06 (1H, d, J=9.06 Hz), 14.42 (1H, br s); ESIMS found for $C_{16}H_{15}F_4N_5O$ m/z 370.1 (M+1).

135

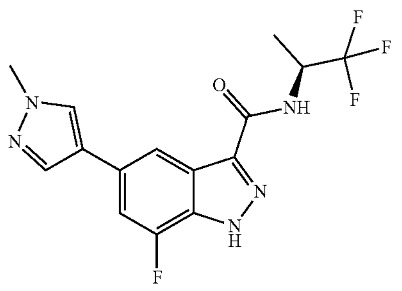

(S)-7-Fluoro-5-(1-methyl-1H-pyrazol-4-yl)-N-(1,1,1-trifluoropropan-2-yl)-1H-indazole-3-carboxamide 135

White solid (13.0 mg, 0.037 mmol, 25.1% yield). $^1H$ NMR (499 MHz, DMSO-$d_6$) δ ppm 1.41 (3H, d, J=7.14 Hz), 3.87 (3H, s), 4.90 (1H, dq, J=15.75, 7.83 Hz), 7.57 (1H, dd, J=12.49, 0.96 Hz), 7.90 (1H, s), 8.07 (1H, d, J=0.82 Hz), 8.23 (1H, s), 8.99 (1H, d, J=9.06 Hz), 14.25 (1H, br s); ESIMS found for $C_{15}H_{13}F_4N_5O$ m/z 356.1 (M+1).

137

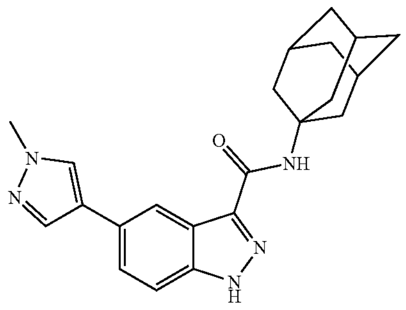

N-((3s,5s,7s)-Adamantan-1-yl)-5-(1-methyl-1H-pyrazol-4-yl)-1H-indazole-3-carboxamide 137

White solid (35 mg, 0.089 mmol, 40.7% yield). $^1H$ NMR (DMSO-$d_6$, 500 MHz) δ ppm 1.68 (br s, 6H), 2.08 (br s, 3H), 2.12 (s, 6H), 3.87 (s, 3H), 7.22 (s, 1H), 7.55-7.60 (m, 1H), 7.60-7.64 (m, 1H), 7.84 (s, 1H), 8.17 (s, 1H), 8.26 (s, 1H), 13.45 (br s, 1H); ESIMS found for $C_{22}H_{25}N_5O$ m/z 376.2 (M+1).

138

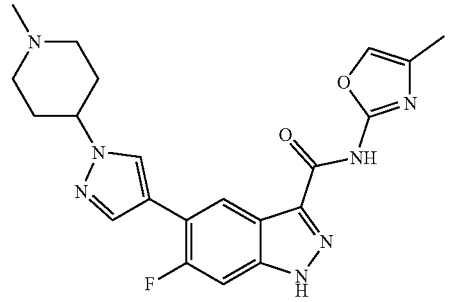

6-Fluoro-N-(4-methyloxazol-2-yl)-5-(1-(1-methylpiperidin-4-yl)-1H-pyrazol-4-yl)-1H-indazole-3-carboxamide 138

Off-white solid (11.6 g, 27.4 mmol, 20.48% yield). $^1H$ NMR (DMSO-$d_6$, 500 MHz) δ ppm $^1H$ NMR (499 MHz, DMSO-$d_6$) δ ppm 1.98-2.11 (m, 6H), 2.22 (s, 3H), 2.88 (br d, J=7.41 Hz, 2H), 3.83 (s, 3H), 4.16-4.24 (m, 1H), 7.53 (d, J=10.98 Hz, 1H), 7.69 (s, 1H), 7.87 (d, J=1.37 Hz, 1H), 8.22 (d, J=1.65 Hz, 1H), 8.40 (d, J=7.41 Hz, 1H), 10.60 (s, 1H), 13.76 (br s, 1H); ESIMS found for $C_{21}H_{22}FN_7O_2$ m/z 424.2 (M+1).

139

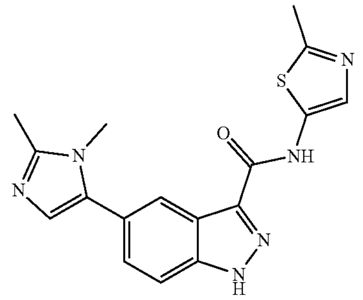

5-(1,2-Dimethyl-1H-imidazol-5-yl)-N-(2-methylthiazol-5-yl)-1H-indazole-3-carboxamide 139

White solid (28.0 mg, 0.079 mmol, 49.5% yield). $^1H$ NMR (499 MHz, DMSO-$d_6$) δ ppm 2.37 (3H, s), 2.57 (3H, s), 3.55 (3H, s), 6.91 (1H, s), 7.52 (1H, dd, J=8.78, 1.65 Hz), 7.63 (1H, s), 7.76 (1H, d, J=8.78 Hz), 8.17 (1H, s), 11.85 (1H, br s), 14.03 (1H, br s); ESIMS found for $C_{17}H_{16}N_6OS$ m/z 353.1 (M+1).

140

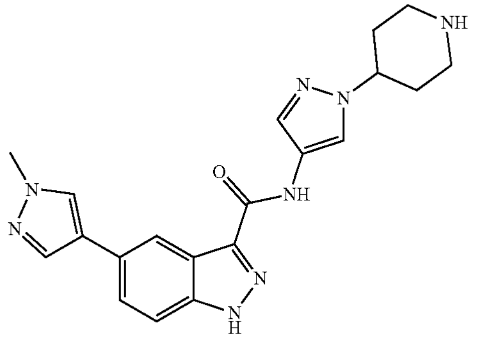

5-(1-Methyl-1H-pyrazol-4-yl)-N-(1-(piperidin-4-yl)-1H-pyrazol-4-yl)-1H-indazole-3-carboxamide 140

Off-white solid (33.0 mg, 0.085 mmol, 47.9% yield). $^1$H NMR (499 MHz, DMSO-$d_6$) δ ppm 2.12-2.23 (4H, m), 3.01-3.11 (2H, m), 3.38 (2H, br d, J=12.90 Hz), 3.89 (3H, s), 4.45-4.55 (1H, m), 7.61-7.69 (2H, m), 7.77 (1H, s), 7.86 (1H, s), 8.12 (1H, s), 8.19 (1H, s), 8.32 (1H, s), 10.61 (1H, s), 13.79 (1H, br s); ESIMS found for $C_{20}H_{22}N_8O$ m/z 391.2 (M+1).

141

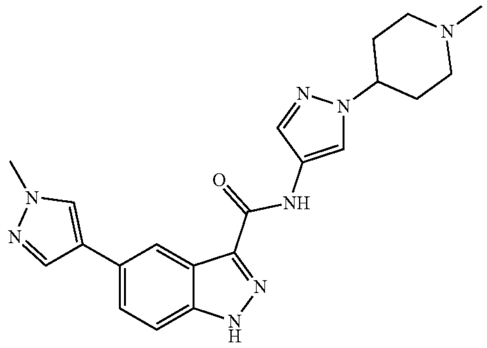

5-(1-Methyl-1H-pyrazol-4-yl)-N-(1-(1-methylpiperidin-4-yl)-1H-pyrazol-4-yl)-1H-indazole-3-carboxamide 141

Off-white solid (43.6 mg, 0.108 mmol, 52.7% yield). $^1$H NMR (499 MHz, DMSO-$d_6$) δ ppm 1.88-2.01 (4H, m), 2.07 (2H, br t, J=11.11 Hz), 2.22 (3H, s), 2.86 (2H, br d, J=11.25 Hz), 3.89 (3H, s), 4.06-4.14 (1H, m), 7.60-7.69 (2H, m), 7.73 (1H, s), 7.86 (1H, s), 8.09 (1H, s), 8.19 (1H, s), 8.33 (1H, s), 10.53 (1H, s), 13.67 (1H, s); ESIMS found for $C_{21}H_{24}N_8O$ m/z 405.2 (M+1).

142

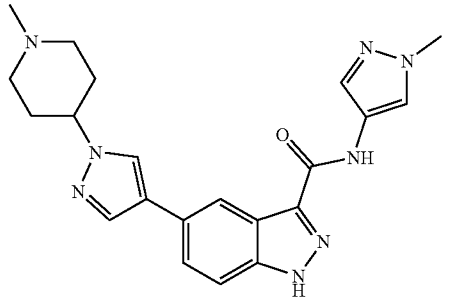

N-(1-Methyl-1H-pyrazol-4-yl)-5-(1-(1-methylpiperidin-4-yl)-1H-pyrazol-4-yl)-1H-indazole-3-carboxamide 142

Off-white solid (19.4 mg, 0.048 mmol, 32.3% yield). $^1$H NMR (499 MHz, DMSO-$d_6$) δ ppm 1.98-2.09 (6H, m), 2.21 (3H, s), 2.85-2.90 (2H, m), 3.83 (3H, s), 4.09-4.18 (1H, m), 7.61-7.65 (1H, m), 7.67-7.72 (2H, m), 7.88 (1H, s), 8.05 (1H, s), 8.28 (1H, s), 8.34 (1H, s), 10.54 (1H, s), 13.67 (1H, br s); ESIMS found for $C_{21}H_{24}N_8O$ m/z 405.2 (M+1).

143

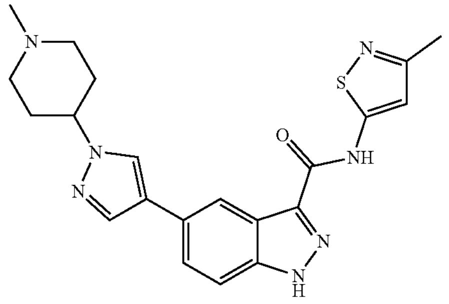

N-(3-Methylisothiazol-5-yl)-5-(1-(1-methylpiperidin-4-yl)-1H-pyrazol-4-yl)-1H-indazole-3-carboxamide 143

Off-white solid (26.2 mg, 0.062 mmol, 38.1% yield). $^1$H NMR (499 MHz, DMSO-$d_6$) δ ppm 1.98-2.11 (6H, m), 2.22 (3H, s), 2.34 (3H, s), 2.84-2.91 (2H, m), 4.09-4.18 (1H, m), 7.02 (1H, s), 7.66-7.71 (1H, m), 7.72-7.78 (1H, m), 7.94 (1H, s), 8.33 (1H, s), 8.36 (1H, s), 12.47 (1H, br s), 14.01 (1H, br s); ESIMS found for $C_{21}H_{23}N_7OS$ m/z 422.2 (M+1).

144

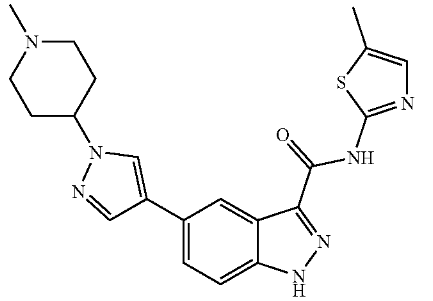

5-(1-(1-Methylpiperidin-4-yl)-1H-pyrazol-4-yl)-N-(5-methylthiazol-2-yl)-1H-indazole-3-carboxamide 144

Off-white solid (17.9 mg, 0.043 mmol, 33.7% yield). $^1$H NMR (499 MHz, DMSO-$d_6$) δ ppm 1.98-2.10 (6H, m), 2.22 (3H, s), 2.40 (3H, s), 2.84-2.92 (2H, m), 4.10-4.18 (1H, m), 7.21 (1H, s), 7.64-7.69 (1H, m), 7.71-7.75 (1H, m), 7.93 (1H, s), 8.31 (1H, s), 8.34 (1H, s), 11.92 (1H, br s), 13.92 (1H, br s); ESIMS found for $C_{21}H_{23}N_7OS$ m/z 422.15 (M+1).

145

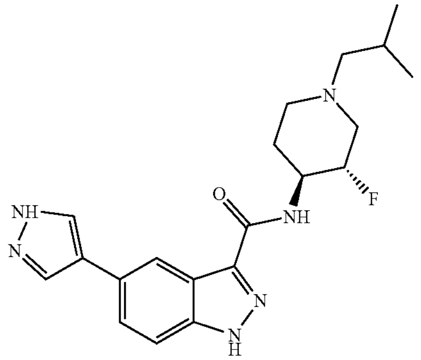

N-((3S,4S)-3-Fluoro-1-isobutylpiperidin-4-yl)-5-(1H-pyrazol-4-yl)-1H-indazole-3-carboxamide 145

Beige solid (111.0 mg, 0.289 mmol, 25.7% yield). $^1$H NMR (499 MHz, DMSO-$d_6$) δ ppm 0.86 (6H, d, J=6.31 Hz), 1.64-1.75 (1H, m), 1.75-1.80 (1H, m), 1.80-1.88 (1H, m), 1.94-2.04 (2H, m), 2.08-2.18 (2H, m), 2.79 (1H, br d, J=10.43 Hz), 3.12-3.22 (1H, m), 3.96-4.08 (1H, m), 4.62-4.80 (1H, m), 7.60 (1H, d, J=8.78 Hz), 7.68 (1H, dd, J=8.78, 1.65 Hz), 7.90 (1H, br s), 8.18 (1H, br s), 8.30 (1H, s), 8.51 (1H, d, J=8.78 Hz), 12.94 (1H, br s), 13.55 (1H, s); ESIMS found for $C_{20}H_{25}FN_6O$ m/z 385.2 (M+1).

146

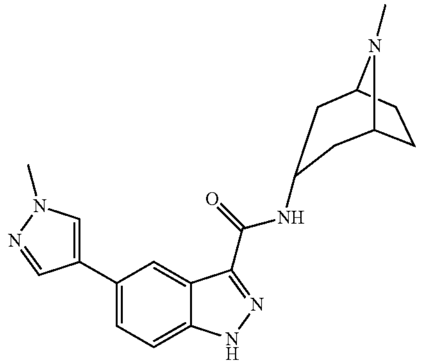

5-(1-Methyl-1H-pyrazol-4-yl)-N-((1R,5S)-8-methyl-8-azabicyclo[3.2.1]octan-3-yl)-1H-indazole-3-carboxamide 146

White solid (10.1 mg, 0.028 mmol, 13.8% yield). $^1$H NMR (499 MHz, DMSO-$d_6$) δ ppm 1.75 (2H, br d, J=14.00

Hz), 1.83-1.89 (2H, m), 2.01-2.06 (2H, m), 2.09 (2H, ddd, J=14.34, 6.52, 4.12 Hz), 2.17 (3H, s), 3.07 (2H, br s), 3.88 (3H, s), 4.07 (1H, q, J=6.59 Hz), 7.57-7.66 (2H, m), 7.75 (1H, d, J=6.86 Hz), 7.83 (1H, s), 8.14 (1H, s), 8.24 (1H, s), 13.51 (1H, br s); ESIMS found for $C_{20}H_{24}N_6O$ m/z 365.2 (M+1).

147

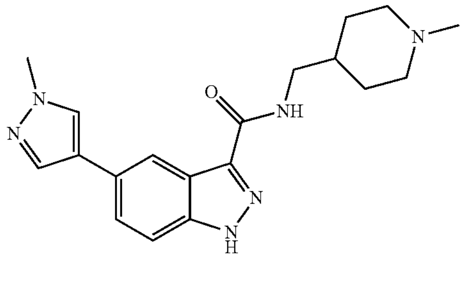

5-(1-Methyl-1H-pyrazol-4-yl)-N-((1-methylpiperidin-4-yl)methyl)-1H-indazole-3-carboxamide 147

Beige solid (14.7 mg, 0.042 mmol, 14.7% yield). $^1$H NMR (499 MHz, DMSO-$d_6$) δ ppm 1.19 (2H, qd, J=11.94, 4.25 Hz), 1.49-1.59 (1H, m), 1.60-1.66 (2H, m), 1.74-1.84 (2H, m), 2.12 (3H, s), 2.73 (2H, br d, J=11.25 Hz), 3.19 (2H, t, J=6.59 Hz), 3.88 (2H, s), 7.56-7.60 (1H, m), 7.61-7.66 (1H, m), 7.83 (1H, s), 8.15 (1H, s), 8.26 (1H, s), 8.35 (1H, t, J=6.17 Hz), 13.50 (1H, br s); ESIMS found for $C_{19}H_{24}N_6O$ m/z 353.2 (M+1).

148

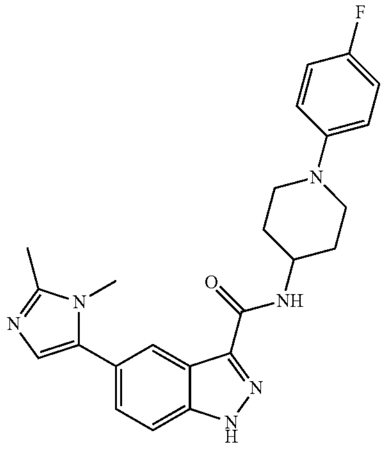

5-(1,2-Dimethyl-1H-imidazol-5-yl)-N-(1-(4-fluorophenyl)piperidin-4-yl)-1H-indazole-3-carboxamide 148

Off-white solid (61.0 mg, 0.141 mmol, 56.0% yield). $^1$H NMR (499 MHz, DMSO-$d_6$) δ ppm 1.74-1.85 (2H, m), 1.86-1.93 (2H, m), 2.37 (3H, s), 2.74 (2H, td, J=12.14, 2.33 Hz), 3.52 (3H, s), 3.63 (2H, br d, J=12.35 Hz), 3.95-4.06 (1H, m), 6.87 (1H, s), 6.95-7.00 (2H, m), 7.01-7.08 (2H, m), 7.46 (1H, dd, J=8.51, 1.65 Hz), 7.69 (1H, d, J=8.78 Hz), 8.13-8.18 (1H, m), 8.33 (1H, d, J=8.23 Hz), 13.67 (1H, br s); ESIMS found for $C_{24}H_{25}FN_6O$ m/z 433.2 (M+1).

149

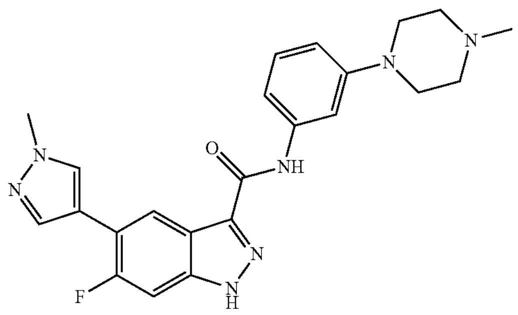

6-Fluoro-5-(1-methyl-1H-pyrazol-4-yl)-N-(3-(4-methylpiperazin-1-yl)phenyl)-1H-indazole-3-carboxamide 149

White solid (63.0 mg, 0.134 mmol, 49.8% yield). $^1$H NMR (499 MHz, DMSO-$d_6$) δ ppm 2.23 (3H, s), 2.44-2.48 (4H, m), 3.09-3.18 (4H, m), 3.91 (3H, s), 6.68 (1H, dd, J=8.10, 2.06 Hz), 7.16 (1H, t, J=8.10 Hz), 7.35 (1H, dd, J=7.96, 1.10 Hz), 7.55 (1H, d, J=10.98 Hz), 7.58 (1H, t, J=1.92 Hz), 7.86 (1H, d, J=1.10 Hz), 8.17 (1H, d, J=1.92 Hz), 8.39 (1H, d, J=7.41 Hz), 10.11 (1H, s), 13.80 (1H, br s); ESIMS found for $C_{23}H_{24}FN_7O$ m/z 434.2 (M+1).

150

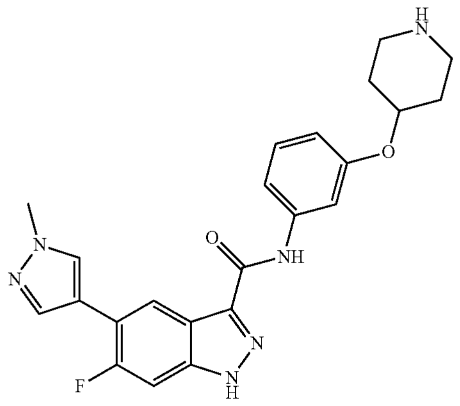

6-Fluoro-5-(1-methyl-1H-pyrazol-4-yl)-N-(3-(piperidin-4-yloxy)phenyl)-1H-indazole-3-carboxamide 150

White solid (70.0 mg, 0.148 mmol, 55.6% yield). $^1$H NMR (499 MHz, DMSO-$d_6$) δ ppm 1.39-1.52 (2H, m), 1.90-2.00 (2H, m), 2.54-2.63 (2H, m), 2.97 (2H, dt, J=12.56, 4.15 Hz), 3.91 (3H, s), 4.30-4.41 (1H, m), 6.67 (1H, dd, J=8.23, 1.92 Hz), 7.21 (1H, t, J=8.10 Hz), 7.50 (1H, dd, J=8.23, 1.10 Hz), 7.55 (1H, d, J=10.98 Hz), 7.57 (1H, t, J=2.20 Hz), 7.86 (1H, d, J=1.10 Hz), 8.17 (1H, d, J=2.20 Hz), 8.39 (1H, d, J=7.41 Hz), 10.27 (1H, s); ESIMS found for $C_{23}H_{23}FN_6O_2$ m/z 435.2 (M+1).

151

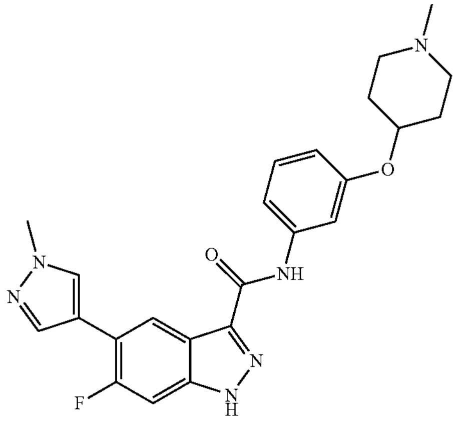

6-Fluoro-5-(1-methyl-1H-pyrazol-4-yl)-N-(3-((1-methylpiperidin-4-yl)oxy)phenyl)-1H-indazole-3-carboxamide 151

White solid (113.0 mg, 0.232 mmol, 63.3% yield). $^1$H NMR (499 MHz, DMSO-$d_6$) δ ppm 1.60-1.72 (2H, m), 1.92-1.98 (2H, m), 2.14-2.22 (2H, m), 2.19 (3H, s), 2.58-2.68 (2H, m), 3.91 (3H, s), 4.32 (1H, tt, J=7.86, 3.81 Hz), 6.68 (1H, dd, J=8.10, 2.33 Hz), 7.22 (1H, t, J=8.23 Hz), 7.51 (1H, d, J=7.96 Hz), 7.56 (1H, d, J=10.98 Hz), 7.58 (1H, t, J=2.06 Hz), 7.86 (1H, d, J=1.10 Hz), 8.17 (1H, d, J=2.20 Hz), 8.40 (1H, d, J=7.41 Hz), 10.29 (1H, s), 13.82 (1H, br s); ESIMS found for $C_{24}H_{25}FN_6O_2$ m/z 449.2 (M+1).

152

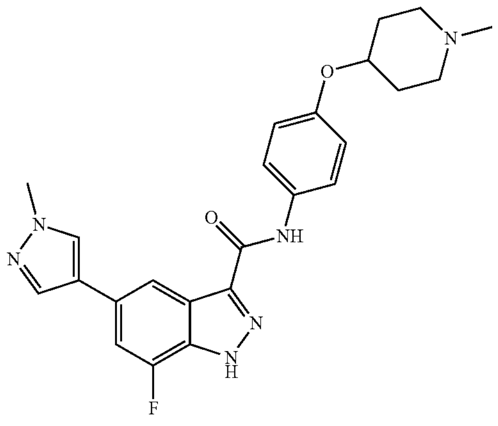

7-Fluoro-5-(1-methyl-1H-pyrazol-4-yl)-N-(4-((1-methylpiperidin-4-yl)oxy)phenyl)-1H-indazole-3-carboxamide 152

White solid (92.0 mg, 0.205 mmol, 75.4% yield). $^1$H NMR (499 MHz, DMSO-$d_6$) δ ppm 1.58-1.68 (2H, m), 1.88-1.97 (2H, m), 2.11-2.22 (2H, m), 2.18 (3H, s), 2.57-2.67 (2H, m), 3.88 (3H, s), 4.32 (1H, tt, J=8.23, 3.84 Hz), 6.90-6.97 (2H, m), 7.58 (1H, dd, J=12.49, 0.96 Hz), 7.77 (2H, d, J=9.06 Hz), 7.91 (1H, s), 8.14 (1H, d, J=0.82 Hz), 8.24 (1H, s), 10.27 (1H, s), 14.22 (1H, br s); ESIMS found for $C_{24}H_{25}FN_6O_2$ m/z 449.2 (M+1).

153

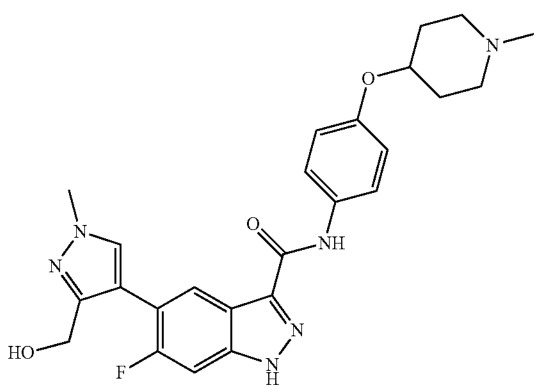

6-Fluoro-5-(3-(hydroxymethyl)-1-methyl-1H-pyrazol-4-yl)-N-(4-((1-methylpiperidin-4-yl)oxy)phenyl)-1H-indazole-3-carboxamide 153

White solid (23.0 mg, 0.048 mmol, 38.7% yield). $^1$H NMR (499 MHz, DMSO-$d_6$) δ ppm 1.56-1.68 (2H, m), 1.87-1.97 (2H, m), 2.09-2.22 (2H, m), 2.17 (3H, s), 2.57-2.67 (2H, m), 3.87 (3H, s), 4.26-4.34 (1H, m), 4.46 (2H, d, J=5.21 Hz), 4.95 (1H, t, J=5.21 Hz), 6.92 (2H, d, J=9.06 Hz), 7.51 (1H, d, J=10.43 Hz), 7.75 (2H, d, J=9.06 Hz), 7.88 (1H, d, J=2.47 Hz), 8.44 (1H, d, J=7.68 Hz), 10.20 (1H, s), 13.75 (1H, br s); ESIMS found for $C_{25}H_{27}FN_6O_3$ m/z 479.2 (M+1).

154

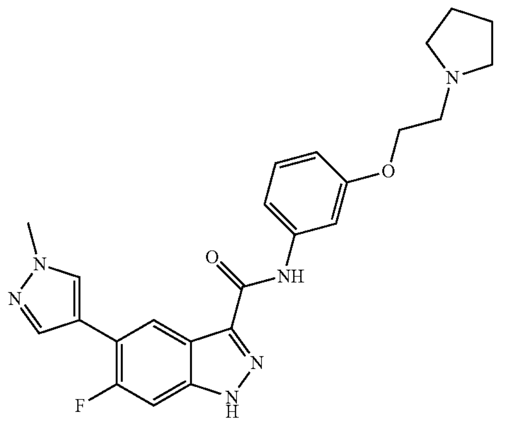

6-Fluoro-5-(1-methyl-1H-pyrazol-4-yl)-N-(3-(2-(pyrrolidin-1-yl)ethoxy)phenyl)-1H-indazole-3-carboxamide 154

Off-white solid (66.0 mg, 0.135 mmol, 58.6% yield). $^1$H NMR (499 MHz, DMSO-$d_6$) δ ppm 1.64-1.74 (4H, m), 2.52-2.56 (4H, m), 2.80 (2H, t, J=5.90 Hz), 3.91 (3H, s), 4.06 (2H, t, J=5.90 Hz), 6.68 (1H, dd, J=8.23, 2.20 Hz), 7.23 (1H, t, J=8.23 Hz), 7.48 (1H, dd, J=8.10, 1.23 Hz), 7.56 (1H, d, J=10.98 Hz), 7.62 (1H, t, J=2.06 Hz), 7.86 (1H, d, J=1.10 Hz), 8.17 (1H, d, J=1.92 Hz), 8.40 (1H, d, J=7.41 Hz), 10.29 (1H, s), 13.81 (1H, br s); ESIMS found for $C_{24}H_{25}FN_6O_2$ m/z 449.2 (M+1).

155

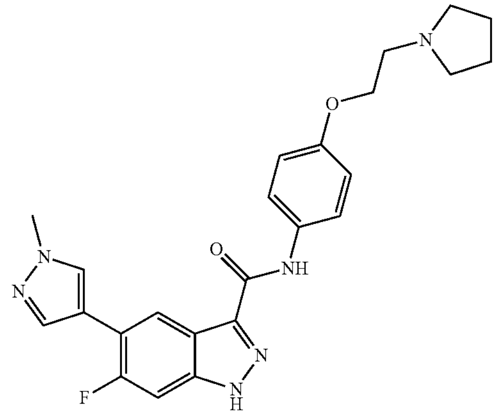

6-Fluoro-5-(1-methyl-1H-pyrazol-4-yl)-N-(4-(2-(pyrrolidin-1-yl)ethoxy)phenyl)-1H-indazole-3-carboxamide 155

White solid (36.0 mg, 0.074 mmol, 49.2% yield). $^1$H NMR (499 MHz, DMSO-$d_6$) δ ppm 1.69 (4H, dt, J=6.72, 3.22 Hz), 2.51-2.55 (4H, m), 2.78 (2H, t, J=5.90 Hz), 3.91 (3H, s), 4.05 (2H, t, J=5.90 Hz), 6.89-6.96 (2H, m), 7.54 (1H, d, J=11.25 Hz), 7.78 (2H, d, J=9.06 Hz), 7.85 (1H, d, J=1.10 Hz), 8.16 (1H, d, J=2.20 Hz), 8.39 (1H, d, J=7.41 Hz), 10.24 (1H, s), 13.76 (1H, br s); ESIMS found for $C_{24}H_{25}FN_6O_2$ m/z 449.2 (M+1).

156

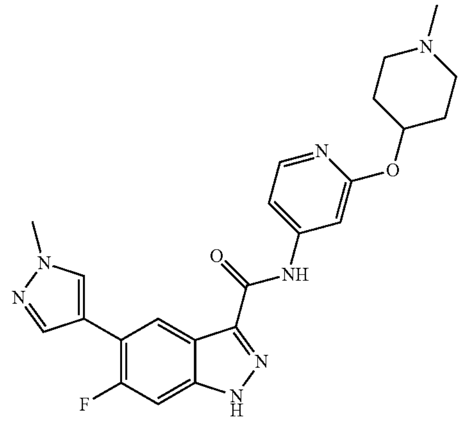

6-Fluoro-5-(1-methyl-1H-pyrazol-4-yl)-N-(2-((1-methylpiperidin-4-yl)oxy)pyridin-4-yl)-1H-indazole-3-carboxamide 156

Beige solid (81.0 mg, 0.166 mmol, 65.5% yield). $^1$H NMR (499 MHz, DMSO-$d_6$) δ ppm 1.58-1.74 (2H, m), 1.95 (2H, br dd, J=9.19, 3.70 Hz), 2.11-2.22 (2H, m), 2.18 (3H, s), 2.58-2.68 (2H, m), 3.91 (3H, s), 4.97 (1H, tt, J=8.44, 4.19 Hz), 7.40 (1H, d, J=1.37 Hz), 7.47 (1H, dd, J=5.76, 1.65 Hz), 7.58 (1H, d, J=10.98 Hz), 7.87 (1H, d, J=0.82 Hz), 8.04 (1H, d, J=5.76 Hz), 8.18 (1H, d, J=2.20 Hz), 8.39 (1H, d, J=7.41 Hz), 10.71 (1H, s), 13.92 (1H, br s); ESIMS found for $C_{23}H_{24}FN_7O_2$ m/z 450.2 (M+1).

157

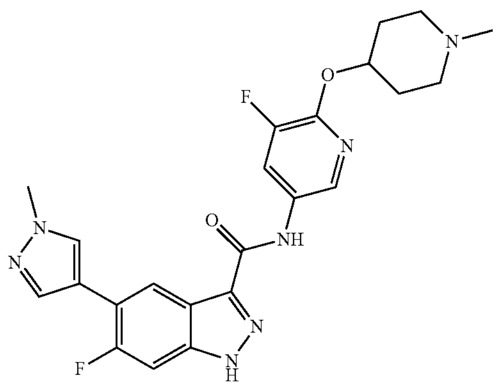

6-Fluoro-N-(5-fluoro-6-((1-methylpiperidin-4-yl)oxy)pyridin-3-yl)-5-(1-methyl-1H-pyrazol-4-yl)-1H-indazole-3-carboxamide 157

White solid (120.0 mg, 0.257 mmol, 67.4% yield). $^1$H NMR (499 MHz, DMSO-$d_6$) δ ppm 1.65-1.75 (2H, m), 1.94-2.02 (2H, m), 2.14-2.22 (2H, br s), 2.18 (3H, s), 2.59-2.68 (2H, m), 3.91 (3H, s), 5.00-5.09 (1H, m), 7.57 (1H, d, J=10.98 Hz), 7.85 (1H, d, J=1.10 Hz), 8.17 (1H, d, J=2.20 Hz), 8.23 (1H, dd, J=12.35, 2.20 Hz), 8.38 (1H, d, J=7.41 Hz), 8.47 (1H, d, J=2.20 Hz), 10.66 (1H, s), 13.89 (1H, br s); ESIMS found for $C_{23}H_{23}F_2N_7O_2$ m/z 468.2 (M+1).

158

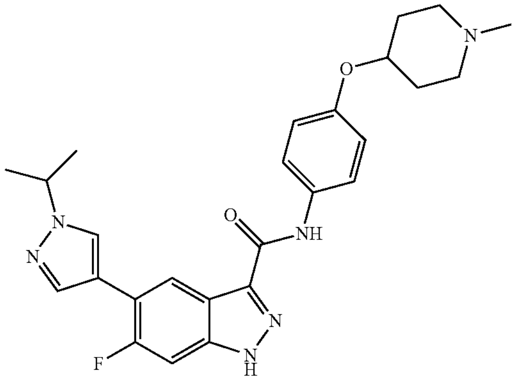

6-Fluoro-5-(1-isopropyl-1H-pyrazol-4-yl)-N-(4-((1-methylpiperidin-4-yl)oxy)phenyl)-1H-indazole-3-carboxamide 158

White solid (86.0 mg, 0.180 mmol, 74.9% yield). $^1$H NMR (500 MHz, DMSO-$d_6$) δ ppm 1.47 (6H, d, J=6.59 Hz), 1.57-1.68 (2H, m), 1.92 (2H, br dd, J=13.31, 2.88 Hz), 2.11-2.22 (2H, m), 2.18 (3H, s), 2.56-2.66 (2H, m), 4.27-4.36 (1H, m), 4.58 (1H, dquin, J=13.22, 6.78, 6.78, 6.78, 6.78 Hz), 6.93 (2H, d, J=8.78 Hz), 7.54 (1H, d, J=11.25 Hz), 7.77 (2H, d, J=8.78 Hz), 7.85 (1H, d, J=1.92 Hz), 8.21 (1H, d, J=1.65 Hz), 8.40 (1H, d, J=7.41 Hz), 10.22 (1H, s), 13.75 (1H, br s); ESIMS found for $C_{26}H_{29}FN_6O_2$ m/z 477.2 (M+1).

159

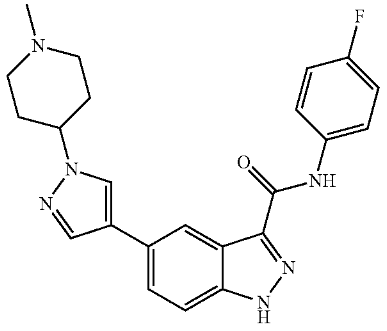

N-(4-Fluorophenyl)-5-(1-(1-methylpiperidin-4-yl)-1H-pyrazol-4-yl)-1H-indazole-3-carboxamide 159

White solid (85.0 mg, 0.203 mmol, 78.4% yield). $^1$H NMR (499 MHz, DMSO-$d_6$) δ ppm 2.00-2.11 (6H, m), 2.21 (3H, s), 2.83-2.91 (2H, m), 4.09-4.18 (1H, m), 7.19 (2H, t, J=8.92 Hz), 7.61-7.67 (1H, m), 7.69-7.74 (1H, m), 7.89 (1H, s), 7.91-7.96 (2H, m), 8.29 (1H, s), 8.33 (1H, s), 10.41 (1H, s), 13.74 (1H, br s); ESIMS found for $C_{23}H_{23}FN_6O$ m/z 419.2 (M+1).

160

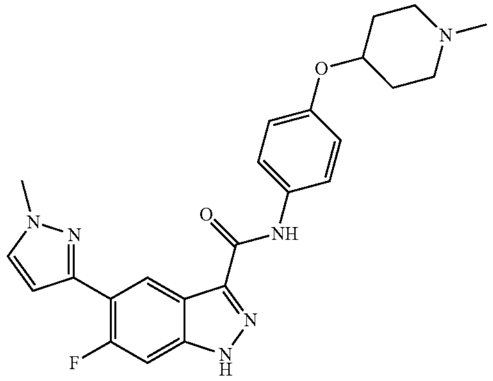

6-Fluoro-5-(1-methyl-1H-pyrazol-3-yl)-N-(4-((1-methylpiperidin-4-yl)oxy)phenyl)-1H-indazole-3-carboxamide 160

Off-white solid (5.2 mg, 0.012 mmol, 15.8% yield). $^1$H NMR (499 MHz, DMSO-$d_6$) δ ppm 1.58-1.68 (2H, m), 1.88-1.97 (2H, m), 2.11-2.24 (2H, m), 2.18 (3H, s), 2.56-2.67 (2H, m), 3.95 (3H, s), 4.32 (1H, tt, J=7.99, 3.81 Hz), 6.61 (1H, dd, J=4.53, 2.06 Hz), 6.94 (2H, d, J=9.06 Hz), 7.53 (1H, d, J=11.25 Hz), 7.77 (2H, d, J=9.06 Hz), 7.80 (1H, d, J=2.20 Hz), 8.76 (1H, d, J=7.68 Hz), 10.25 (1H, s), 13.79 (1H, br s); ESIMS found for $C_{24}H_{25}FN_6O_2$ m/z 449.25 (M+1).

161

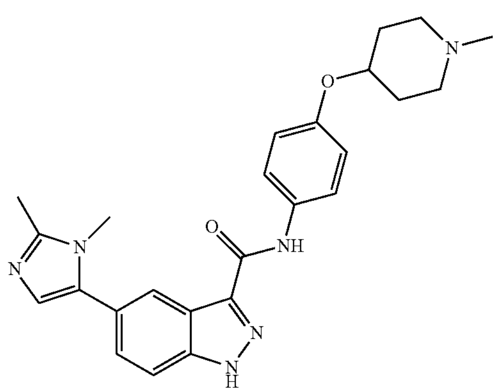

5-(1,2-Dimethyl-1H-imidazol-5-yl)-N-(4-((1-methylpiperidin-4-yl)oxy)phenyl)-1H-indazole-3-carboxamide 161

Off-white solid (30.0 mg, 0.068 mmol, 70.3% yield). $^{1}$H NMR (499 MHz, DMSO-$d_6$) δ ppm 1.57-1.68 (2H, m), 1.88-1.97 (2H, m), 2.12-2.21 (2H, m), 2.18 (3H, s), 2.37 (3H, s), 2.57-2.66 (2H, m), 3.54 (3H, s), 4.27-4.36 (1H, m), 6.89 (1H, s), 6.93 (2H, d, J=9.06 Hz), 7.50 (1H, dd, J=8.51, 1.37 Hz), 7.73 (1H, d, J=8.78 Hz), 7.76 (2H, d, J=8.78 Hz), 8.19 (1H, s), 10.24 (1H, s), 13.83 (1H, br s); ESIMS found for $C_{25}H_{28}N_6O_2$ m/z 445.2 (M+1).

162

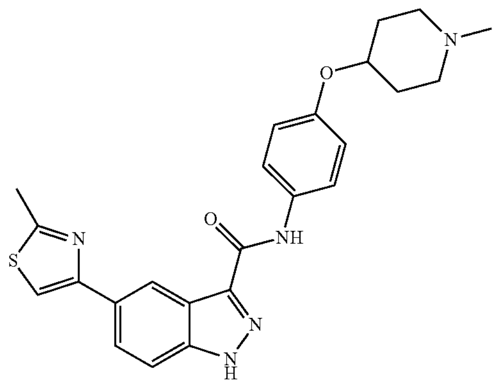

N-(4-((1-Methylpiperidin-4-yl)oxy)phenyl)-5-(2-methylthiazol-4-yl)-1H-indazole-3-carboxamide 162

Off-white solid (16.0 mg, 0.036 mmol, 31.7% yield). $^{1}$H NMR (499 MHz, DMSO-$d_6$) δ ppm 1.68 (2H, br d, J=7.96 Hz), 1.95 (2H, br s), 2.29 (3H, br s), 2.35 (2H, br s), 2.70-2.82 (2H, m), 2.75 (3H, s), 4.37 (1H, br s), 6.95 (2H, br d, J=8.78 Hz), 7.69 (1H, br d, J=8.78 Hz), 7.80 (2H, br d, J=8.51 Hz), 7.93 (1H, s), 8.03 (1H, br d, J=8.78 Hz), 8.82 (1H, s), 10.23 (1H, s), 13.80 (1H, br s); ESIMS found for $C_{24}H_{25}N_5O_2S$ m/z 448.2 (M+1).

163

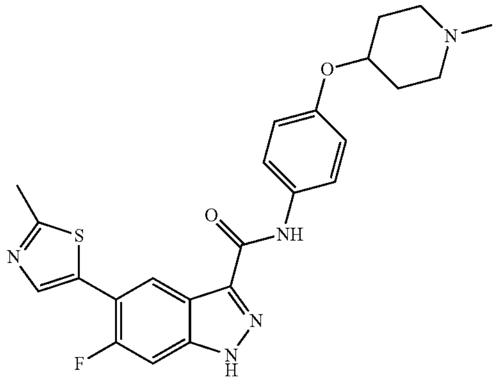

6-Fluoro-N-(4-((1-methylpiperidin-4-yl)oxy)phenyl)-5-(2-methylthiazol-5-yl)-1H-indazole-3-carboxamide 163

Off-white solid (13.7 mg, 0.029 mmol, 87.9% yield). $^{1}$H NMR (499 MHz, DMSO-$d_6$) δ ppm 1.74-1.88 (2H, m), 1.97-2.10 (2H, m), 2.58 (3H, br s), 2.72 (3H, s), 2.75-2.93 (2H, m), 3.00-3.14 (2H, m), 4.49 (1H, br s), 6.99 (2H, d, J=9.06 Hz), 7.67 (1H, d, J=11.25 Hz), 7.79 (2H, d, J=9.06 Hz), 7.99 (1H, d, J=1.37 Hz), 8.42 (1H, d, J=7.41 Hz), 10.34 (1H, s), 13.98 (1H, br s); ESIMS found for $C_{24}H_{24}FN_5O_2S$ m/z 466.15 (M+1).

164

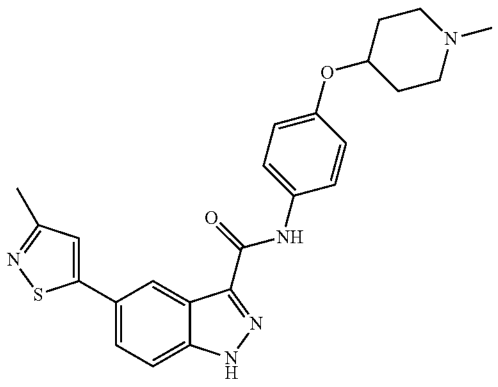

5-(3-Methylisothiazol-5-yl)-N-(4-((1-methylpiperidin-4-yl) oxy)phenyl)-1H-indazole-3-carboxamide 164

Tan solid (15.6 mg, 0.035 mmol, 31.4% yield). $^{1}$H NMR (499 MHz, DMSO-$d_6$) δ ppm 1.60-1.72 (2H, m), 1.90-1.99 (2H, m), 2.18-2.33 (2H, m), 2.24 (3H, br s), 2.47 (3H, s), 2.62-2.76 (2H, m), 4.35 (1H, br s), 6.95 (2H, d, J=9.06 Hz), 7.63 (1H, s), 7.76-7.83 (4H, m), 8.49 (1H, s), 10.31 (1H, s), 13.96 (1H, br s); ESIMS found for $C_{24}H_{25}N_5O_2S$ m/z 448.2 (M+1).

Example 3

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with a DMEM medium containing 1% fetal bovine serum, and 1% Penicillin-Streptomycin and incubated for 36 to 48 hours at 37° C. and 5% $CO_2$. Following incubation, 15 μl of BriteLite Plus luminescence reagent (Perkin Elmer) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for $EC_{50}$ calculations using the dose-response log (inhibitor) vs. response variable slope (four parameters) nonlinear regression feature available in GraphPad Prism 5.0 (or Dotmatics). For $EC_{50}$ of >10 μM, the percent inhibition at 10 μM is provided.

Table 2 shows the measured activity for representative compounds of Formula I as described herein.

TABLE 2

| Compound | $EC_{50}$ (μM) |
|---|---|
| 1 | 0.358 |
| 2 | 0.819 |
| 3 | >10 |
| 4 | 3.835 |
| 5 | 0.655 |
| 6 | 0.325 |
| 7 | 2.600 |
| 8 | 0.565 |
| 9 | 1.980 |
| 10 | 3.405 |
| 11 | >10 |
| 12 | 5.470 |
| 13 | >10 |
| 14 | 0.903 |
| 15 | >10 |
| 16 | >10 |
| 17 | >10 |
| 18 | 0.801 |
| 19 | 1.046 |
| 20 | >10 |
| 21 | >10 |
| 22 | 2.014 |
| 23 | 0.768 |
| 24 | 1.336 |
| 25 | >10 |
| 26 | 1.184 |
| 27 | 0.677 |
| 28 | 0.688 |
| 29 | >10 |
| 30 | >10 |
| 31 | 0.610 |

TABLE 2-continued

| Compound | $EC_{50}$ (μM) |
|---|---|
| 32 | 1.830 |
| 33 | 0.267 |
| 34 | >10 |
| 35 | 0.345 |
| 36 | 0.474 |
| 37 | 0.747 |
| 38 | >10 |
| 39 | 3.881 |
| 40 | 1.717 |
| 41 | 0.828 |
| 42 | 0.507 |
| 43 | >10 |
| 44 | 0.279 |
| 45 | 1.649 |
| 46 | 1.462 |
| 47 | 4.580 |
| 48 | 0.239 |
| 49 | 0.256 |
| 50 | 1.191 |
| 51 | 0.560 |
| 52 | >10 |
| 53 | 1.842 |
| 54 | 4.381 |
| 55 | 0.428 |
| 56 | 0.376 |
| 57 | 1.086 |
| 58 | 1.503 |
| 59 | 0.555 |
| 60 | 3.848 |
| 61 | >10 |
| 62 | 2.280 |
| 63 | 9.435 |
| 64 | 0.937 |
| 65 | 0.805 |
| 66 | 0.953 |
| 67 | 0.549 |
| 68 | 0.264 |
| 69 | 0.308 |
| 70 | 0.512 |
| 71 | 1.493 |
| 72 | 0.545 |
| 73 | 1.549 |
| 74 | 2.167 |
| 75 | 0.542 |
| 76 | 1.287 |
| 77 | 0.411 |
| 78 | 0.249 |
| 79 | 0.266 |
| 80 | 8.515 |
| 81 | 0.115 |
| 82 | 1.465 |
| 83 | 0.275 |
| 84 | 1.343 |
| 85 | 0.566 |
| 86 | 1.838 |
| 87 | 0.216 |
| 88 | 0.435 |
| 89 | 4.338 |
| 90 | 2.127 |
| 91 | 1.130 |
| 92 | 2.309 |
| 93 | 1.586 |
| 94 | 0.798 |
| 95 | 0.175 |
| 96 | 0.165 |
| 97 | 0.269 |
| 98 | 0.100 |
| 99 | 0.840 |
| 100 | 1.025 |
| 101 | >10 |
| 106 | 0.685 |
| 119 | 3.055 |
| 122 | 0.205 |
| 124 | 0.140 |
| 125 | 0.355 |
| 126 | 0.335 |
| 127 | 0.100 |

TABLE 2-continued

| Compound | $EC_{50}$ (μM) |
|---|---|
| 128 | 0.180 |
| 129 | 6.115 |
| 131 | >10 |
| 132 | >10 |
| 133 | >10 |
| 134 | >10 |
| 135 | >10 |
| 137 | 4.235 |
| 138 | 0.125 |
| 139 | 0.335 |
| 140 | 0.713 |
| 141 | 0.079 |
| 142 | 0.130 |
| 143 | 0.090 |
| 144 | >10 |
| 145 | 0.345 |
| 146 | 1.585 |
| 147 | 3.869 |
| 148 | 4.489 |
| 149 | 0.217 |
| 150 | 0.248 |
| 151 | 0.113 |
| 152 | 1.460 |
| 153 | >10 |
| 154 | 0.306 |
| 155 | 0.315 |
| 156 | 0.109 |
| 157 | 1.149 |
| 158 | 1.161 |
| 159 | 0.680 |
| 160 | 3.560 |
| 161 | 0.642 |
| 162 | >10 |
| 163 | 1.530 |
| 164 | 1.385 |

Example 4

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 μM to 0.00016 μM) and compound transfer was performed using the ECHO 550 (Labcyte, Sunnyvale, Calif.) into 1536-well black-walled round bottom plates (Corning).

The DYRK1A kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.19 μg/mL, 30 μM, and 4 μM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio×(F100%−F0%)))]. Dose-response curves were generated and inhibitory concentration ($IC_{50}$) values were calculated using non-linear regression curve fit in the Dotmatics' Studies Software (Bishops Stortford, UK).

Table 3 shows the measured activity for representative compounds of Formula I as described herein.

TABLE 3

| Compound | $EC_{50}$ (μM) |
|---|---|
| 1 | 0.030 |
| 2 | 0.025 |
| 3 | 0.134 |
| 4 | 0.026 |
| 5 | 0.025 |
| 6 | 0.207 |
| 7 | 0.055 |
| 8 | 0.031 |
| 9 | 0.018 |
| 10 | 0.016 |
| 11 | 0.198 |
| 12 | 0.171 |
| 13 | 0.046 |
| 14 | 0.018 |
| 15 | 0.036 |
| 16 | 0.378 |
| 17 | >10 |
| 18 | 0.121 |
| 19 | 0.117 |
| 20 | 0.013 |
| 21 | 1.820 |
| 22 | 0.025 |
| 23 | 0.001 |
| 24 | 0.002 |
| 25 | 0.618 |
| 26 | 0.005 |
| 27 | 0.004 |
| 28 | 0.002 |
| 29 | >10 |
| 30 | 0.012 |
| 31 | 0.026 |
| 32 | 0.005 |
| 33 | 0.024 |
| 34 | 0.016 |
| 35 | 0.261 |
| 36 | 0.007 |
| 37 | 0.005 |
| 38 | >10 |
| 39 | 0.022 |
| 40 | 0.045 |
| 41 | 0.250 |
| 42 | 0.028 |
| 43 | 0.067 |
| 44 | 0.007 |
| 45 | 0.006 |
| 46 | 4.450 |
| 47 | 0.190 |
| 48 | 0.023 |
| 49 | 0.015 |
| 50 | 0.034 |
| 51 | 0.016 |
| 52 | 0.011 |
| 53 | 0.027 |
| 54 | 0.244 |
| 55 | 0.037 |
| 56 | 0.027 |
| 57 | 1.050 |
| 58 | 0.053 |
| 59 | 0.028 |

TABLE 3-continued

| Compound | $EC_{50}$ (μM) |
|---|---|
| 60 | 1.500 |
| 61 | 9.940 |
| 62 | 3.920 |
| 63 | 0.767 |
| 64 | 0.016 |
| 65 | 0.004 |
| 66 | 0.002 |
| 67 | 0.009 |
| 68 | 0.001 |
| 69 | 0.002 |
| 70 | 0.005 |
| 71 | 0.025 |
| 72 | 0.006 |
| 73 | 0.003 |
| 74 | 0.305 |
| 75 | 0.003 |
| 76 | 0.107 |
| 77 | 0.004 |
| 78 | 0.001 |
| 79 | 0.002 |
| 80 | 0.019 |
| 81 | 0.001 |
| 82 | 0.007 |
| 83 | 0.002 |
| 84 | 0.002 |
| 85 | 0.002 |
| 86 | 0.098 |
| 87 | 0.008 |
| 88 | 0.016 |
| 89 | 0.304 |
| 90 | 0.329 |
| 91 | 0.050 |
| 92 | 0.039 |
| 93 | 0.006 |
| 94 | 0.004 |
| 95 | 0.001 |
| 96 | 0.001 |
| 97 | 0.002 |
| 98 | 0.002 |
| 99 | 0.813 |
| 100 | 0.046 |
| 101 | 0.408 |
| 106 | 0.040 |
| 119 | 0.021 |
| 122 | 0.002 |
| 124 | 0.001 |
| 125 | 0.008 |
| 126 | 0.009 |
| 127 | 0.004 |
| 128 | 0.005 |
| 129 | 0.030 |
| 131 | 0.220 |
| 132 | 0.453 |
| 133 | 0.930 |
| 134 | 0.482 |
| 135 | 0.439 |
| 137 | 8.291 |
| 138 | 0.006 |
| 139 | 0.004 |
| 140 | 0.002 |
| 141 | 0.001 |
| 142 | 0.008 |
| 143 | 0.005 |
| 144 | 0.008 |
| 145 | 0.037 |
| 146 | 0.010 |
| 147 | 0.026 |
| 148 | 0.049 |
| 149 | 0.001 |
| 150 | 0.004 |
| 151 | 0.005 |
| 152 | 0.038 |
| 153 | 1.213 |
| 154 | 0.005 |
| 155 | 0.001 |
| 156 | 0.002 |
| 157 | 0.001 |
| 158 | 0.023 |
| 159 | 0.023 |
| 160 | 0.061 |
| 161 | 0.005 |
| 162 | 0.141 |
| 163 | 0.004 |
| 164 | 0.003 |

Example 5

Representative compounds were screened using the assay procedure for GSK3β kinase activity as described below.

Each compound is dissolved in DMSO as a 10 mM stock and used to prepare compound source plates. Serial dilution (1:3, 11-point dose-response curves from 10 μM to 0.0003 μM) and compound transfer was performed using the ECHO 550 (Labcyte, Sunnyvale, Calif.) into 1536-well black-walled round bottom plates (Corning).

The GSK3β kinase assay is run using the Ser/Thr 09 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as ratio of coumarin emission/fluorescein emission.

Briefly, recombinant GSK3β kinase, ATP and Ser/Thr peptide 09 are prepared in 1× Kinase buffer to final concentrations of 0.04 μg/mL, 46 μM, and 4 μM respectively. The mixture is allowed to incubate with the representative compounds for one hour at room temperature. All reactions were performed in duplicate. Unphosphorylated ("0% Control") and phosphorylated ("100% control") forms of Ser/Thr 18 serve as control reactions.

After incubation, diluted Development Buffer is added to the reaction and allowed to further incubate for one hour at room temperature. The plate is read at Ex 400 Em 455 to detect the coumarin signal and Ex 400 Em 520 to measure the signal (EnVision Multilabel Plate Reader, PerkinElmer).

The Emission ratio (Em) is calculated as a ratio of the coumarin (C) emission signal (at 445 nm)/Fluorescein (F) emission signal (at 520 nm). The percent phosphorylation is then calculated using the following formula: [1−((Em ratio×F100%)−C100%)/((C0%−C100%)+(Em ratio×(F100%−F0%)))].

Dose-response curves are generated and inhibitory concentration ($IC_{50}$) values are calculated using non-linear regression curve fit in the Dotmatics' Studies Software (Bishops Stortford, UK).

Table 4 shows the activity of representative compounds of Formula I as provided herein.

TABLE 4

| Compound | $EC_{50}$ (μM) |
|---|---|
| 1 | 0.028 |
| 2 | 0.011 |
| 3 | 0.106 |
| 4 | 0.024 |
| 5 | 0.008 |
| 6 | 0.015 |
| 7 | 0.255 |
| 8 | 0.022 |

TABLE 4-continued

| Compound | $EC_{50}$ (μM) |
|---|---|
| 9 | 0.006 |
| 10 | 0.009 |
| 11 | 0.020 |
| 12 | 0.038 |
| 13 | 0.024 |
| 14 | 0.023 |
| 15 | 0.058 |
| 16 | 0.041 |
| 17 | >10 |
| 18 | 0.060 |
| 19 | 0.064 |
| 20 | 0.021 |
| 21 | 0.903 |
| 22 | 0.061 |
| 23 | 0.005 |
| 24 | 0.022 |
| 25 | 0.788 |
| 26 | 0.034 |
| 27 | 0.012 |
| 28 | 0.011 |
| 29 | >10 |
| 30 | 0.061 |
| 31 | 0.055 |
| 32 | 0.031 |
| 33 | 0.036 |
| 34 | 0.050 |
| 35 | 0.157 |
| 36 | 0.023 |
| 37 | 0.014 |
| 38 | >10 |
| 39 | 0.033 |
| 40 | 0.687 |
| 41 | 0.076 |
| 42 | 0.029 |
| 43 | 1.056 |
| 44 | 0.007 |
| 45 | 0.031 |
| 46 | 0.704 |
| 47 | 0.674 |
| 48 | 0.260 |
| 49 | 0.187 |
| 50 | 0.476 |
| 51 | 0.558 |
| 52 | 0.011 |
| 53 | 0.001 |
| 54 | 2.080 |
| 55 | 1.230 |
| 56 | 0.330 |
| 57 | 5.380 |
| 58 | 3.020 |
| 59 | 1.290 |
| 60 | >10 |
| 61 | 9.370 |
| 62 | >10 |
| 63 | 2.320 |
| 64 | 0.021 |
| 65 | 0.044 |
| 66 | 0.065 |
| 67 | 0.035 |
| 68 | 0.006 |
| 69 | 0.020 |
| 70 | 0.025 |
| 71 | 0.169 |
| 72 | 0.040 |
| 73 | 0.068 |
| 74 | 0.878 |
| 75 | 0.039 |
| 76 | 0.302 |
| 77 | 0.026 |
| 78 | 0.018 |
| 79 | 0.060 |
| 80 | 0.783 |
| 81 | 0.035 |
| 82 | 0.041 |
| 83 | 0.074 |
| 84 | 0.021 |
| 85 | 0.035 |

TABLE 4-continued

| Compound | $EC_{50}$ (μM) |
|---|---|
| 86 | 0.354 |
| 87 | 0.182 |
| 88 | 0.774 |
| 89 | 0.656 |
| 90 | 0.403 |
| 91 | 0.332 |
| 92 | 0.699 |
| 93 | 0.430 |
| 94 | 0.272 |
| 95 | 0.046 |
| 96 | 0.030 |
| 97 | 0.098 |
| 98 | 0.208 |
| 99 | 0.068 |
| 100 | 0.043 |
| 101 | 0.086 |
| 106 | 0.014 |
| 119 | 0.041 |
| 122 | 0.038 |
| 124 | 0.023 |
| 125 | 0.278 |
| 126 | 0.237 |
| 127 | 0.245 |
| 128 | 0.633 |
| 129 | 0.087 |
| 131 | 0.027 |
| 132 | 0.106 |
| 133 | 1.354 |
| 134 | 0.046 |
| 135 | 0.043 |
| 137 | 1.338 |
| 138 | 0.193 |
| 139 | 0.020 |
| 140 | 0.005 |
| 141 | 0.004 |
| 142 | 0.208 |
| 143 | 0.052 |
| 144 | 6.443 |
| 145 | 0.041 |
| 146 | 0.008 |
| 147 | 0.015 |
| 148 | 0.057 |
| 149 | 0.049 |
| 150 | 0.052 |
| 151 | 0.080 |
| 152 | 0.065 |
| 153 | >10 |
| 154 | 0.020 |
| 155 | 0.038 |
| 156 | 0.053 |
| 157 | 0.020 |
| 158 | 0.349 |
| 159 | 0.548 |
| 160 | 3.256 |
| 161 | 0.120 |
| 162 | 5.056 |
| 163 | 0.094 |
| 164 | 0.088 |

Example 6

Representative compounds were screened using the assay procedure to assess the effect on cell viability as described below.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 8-point dose-response curves from 10 μM to 0.0045 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%.

For the Cell Viability Assays, the cells were plated at 2,000 cells/well in 384-well plates with a DMEM medium containing 1% fetal bovine serum, and 1% Penicillin-Streptomycin and incubated for four days hours at 37° C. and 5% $CO_2$. Eight replicates of DMSO-treated cells served as controls and cells treated with compound were performed in duplicate.

After incubation, 10 μL of CellTiter-Glo (Promega) was added to each well allowed to incubate for approximately 12 minutes. This reagent "results in cell lysis and generation of a luminescent signal proportional to the amount of ATP present. The amount of ATP is directly proportional to the number of cells present in culture, in agreement with previous reports. The CellTiter-Glo® Assay generates a "glow-type" luminescent signal, produced by the luciferase reaction (Promega.com)".

After incubation, the plates were read at Ex 560 nm Em 590 nm (Cytation 3, BioTek). Dose-response curves were generated and $EC_{50}$ concentration values were calculated using non-linear regression curve fit in the GraphPad Prism (San Diego, Calif.) or Dotmatics' Studies Software (Bishops Stortford, UK). For $EC_{50}$ of >10 μM, the percent inhibition at 10 μM is provided.

Table 5 shows the activity of representative compounds of Formula I as provided herein.

TABLE 5

| Compound | $EC_{50}$ (μM) |
|---|---|
| 1 | 2.575 |
| 2 | 5.984 |
| 3 | 8.951 |
| 4 | 2.550 |
| 5 | 2.525 |
| 6 | 0.737 |
| 7 | 5.600 |
| 8 | 0.511 |
| 9 | 1.328 |
| 10 | 1.075 |
| 11 | 1.939 |
| 12 | 2.257 |
| 13 | >10 |
| 14 | >10 |
| 15 | 2.598 |
| 16 | 7.892 |
| 17 | >10 |
| 18 | 7.463 |
| 19 | 3.073 |
| 20 | >10 |
| 21 | >10 |
| 22 | >10 |
| 23 | 0.409 |
| 24 | 0.829 |
| 25 | 6.019 |
| 26 | 0.849 |
| 27 | 6.452 |
| 28 | 0.442 |
| 29 | 9.242 |
| 30 | >10 |
| 31 | >10 |
| 32 | 1.323 |
| 33 | >10 |
| 34 | 1.842 |
| 35 | 8.280 |
| 36 | 0.691 |
| 37 | 0.849 |

TABLE 5-continued

| Compound | $EC_{50}$ (μM) |
|---|---|
| 38 | >10 |
| 39 | 1.310 |
| 40 | 1.083 |
| 41 | 3.001 |
| 42 | >10 |
| 43 | >10 |
| 44 | 1.519 |
| 45 | 4.768 |
| 46 | 4.500 |
| 47 | >10 |
| 48 | 0.354 |
| 49 | 0.208 |
| 50 | 0.648 |
| 51 | 0.305 |
| 52 | >10 |
| 53 | >10 |
| 54 | >10 |
| 55 | 1.343 |
| 56 | 0.201 |
| 57 | 0.570 |
| 58 | 0.328 |
| 59 | 0.327 |
| 60 | 3.727 |
| 61 | >10 |
| 62 | >10 |
| 63 | 0.768 |
| 64 | 1.700 |
| 65 | 1.100 |
| 66 | 0.759 |
| 67 | 1.000 |
| 68 | 0.360 |
| 69 | 0.191 |
| 70 | 0.518 |
| 71 | 1.100 |
| 72 | 0.228 |
| 73 | 6.968 |
| 74 | >10 |
| 75 | 1.100 |
| 76 | 6.200 |
| 77 | 2.831 |
| 78 | 0.454 |
| 79 | 0.140 |
| 80 | 5.000 |
| 81 | 0.139 |
| 82 | 1.250 |
| 83 | 0.220 |
| 84 | 0.300 |
| 85 | 0.203 |
| 86 | >10 |
| 87 | 0.554 |
| 88 | 0.338 |
| 89 | 4.600 |
| 90 | 7.394 |
| 91 | 2.100 |
| 92 | >10 |
| 93 | 0.823 |
| 94 | 0.732 |
| 95 | 0.286 |
| 96 | 0.118 |
| 97 | 0.354 |
| 98 | 0.116 |
| 99 | 5.184 |
| 100 | 8.017 |
| 101 | >10 |
| 106 | >10 |
| 119 | 1.874 |
| 122 | 0.380 |
| 124 | 0.170 |
| 125 | 0.664 |
| 126 | 1.534 |
| 127 | 0.093 |
| 128 | 0.493 |
| 129 | 3.015 |
| 131 | 3.037 |
| 132 | >10 |
| 133 | >10 |
| 134 | >10 |

TABLE 5-continued

| Compound | $EC_{50}$ (μM) |
|---|---|
| 135 | >10 |
| 137 | 5.222 |
| 138 | 0.105 |
| 139 | 0.473 |
| 140 | 2.600 |
| 141 | 0.064 |
| 142 | 0.116 |
| 143 | 0.060 |
| 144 | 1.300 |
| 145 | 0.372 |
| 146 | >10 |
| 147 | 6.703 |
| 148 | 8.021 |
| 149 | 0.331 |
| 150 | 0.214 |
| 151 | 0.258 |
| 152 | 0.783 |
| 153 | >10 |
| 154 | 0.414 |
| 155 | 0.414 |
| 156 | 0.064 |
| 157 | 1.300 |
| 158 | 0.784 |
| 159 | 0.810 |
| 160 | 2.600 |
| 161 | 0.833 |
| 162 | 4.600 |
| 163 | 0.331 |
| 164 | 0.268 |

Example 7

Representative compounds were screened using primary human fibroblasts (derived from IPF patients) treated with TGF-β1 to determine their ability to inhibit the fibrotic process.

Human Fibroblast Cell Culture: Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and 1% Penicillin/Streptomycin.

Compound Screening: Each compound was dissolved in DMSO as a 10 mM stock and used to prepare compound source plates. Serial dilution (1:2, 11-point dose-response curves from 10 μM to 0.94 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 70 μL/well F12 medium supplemented with 1% Fetal Bovine Serum. TGF-β1 (Peprotech; 20 ng/mL) was added to the plates to induce fibrosis (ref 1 and 2 above). Wells treated with TGF-β1 and containing DMSO were used as positive control, and cells with only DMSO were negative control. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 μM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI in 3% Bovine Serum Albumin (BSA; Sigma) and 0.3% Triton X-100 (Sigma) in PBS at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. For $EC_{50}$ of >10 μM, the percent inhibition at 10 μM is provided.

Table 6 shows the activity of representative compounds of Formula I as provided herein.

TABLE 6

| Compound | $EC_{50}$ (μM) |
|---|---|
| 1 | 0.160 |
| 2 | 0.075 |
| 3 | 2.581 |
| 4 | 0.171 |
| 5 | 0.151 |
| 6 | 0.148 |
| 7 | >10 |
| 8 | 0.146 |
| 9 | 0.324 |
| 10 | 0.331 |
| 11 | >10 |
| 12 | 0.621 |
| 13 | 1.391 |
| 14 | 0.114 |
| 15 | 3.316 |
| 16 | 1.013 |
| 17 | 1.195 |
| 18 | 0.950 |
| 19 | 1.178 |
| 20 | 3.407 |
| 21 | 0.294 |
| 22 | 2.199 |
| 23 | 0.149 |
| 24 | 0.125 |
| 25 | 1.892 |
| 26 | >10 |
| 27 | 0.346 |
| 28 | 0.409 |
| 29 | >10 |
| 30 | >10 |
| 31 | 2.456 |
| 32 | 0.372 |
| 33 | 0.043 |
| 34 | 0.439 |
| 35 | 0.288 |
| 36 | 0.147 |
| 37 | 0.118 |
| 38 | >10 |
| 39 | 0.272 |

TABLE 6-continued

| Compound | $EC_{50}$ (μM) |
|---|---|
| 40 | 0.068 |
| 41 | 0.342 |
| 42 | 1.363 |
| 43 | 2.171 |
| 44 | 0.199 |
| 45 | 0.355 |
| 46 | 0.543 |
| 47 | 5.211 |
| 48 | 0.449 |
| 49 | 1.006 |
| 50 | 1.113 |
| 51 | 0.816 |
| 52 | 0.540 |
| 53 | >10 |
| 54 | 2.917 |
| 55 | 0.236 |
| 56 | 1.533 |
| 57 | 0.597 |
| 58 | 5.139 |
| 59 | 2.543 |
| 60 | 1.283 |
| 61 | 0.009 |
| 62 | 3.105 |
| 63 | 2.028 |
| 64 | 1.527 |
| 65 | 0.620 |
| 66 | 0.650 |
| 67 | 0.150 |
| 68 | 0.074 |
| 69 | 0.328 |
| 70 | 0.126 |
| 71 | 0.322 |
| 72 | 0.242 |
| 73 | 0.799 |
| 74 | 0.035 |
| 75 | 0.159 |
| 76 | 0.174 |
| 77 | 0.291 |
| 78 | 0.545 |
| 79 | 0.061 |
| 80 | 1.302 |
| 81 | 0.341 |
| 82 | 0.288 |
| 83 | 0.250 |
| 84 | 1.687 |
| 85 | 0.904 |
| 86 | 1.192 |
| 87 | 0.672 |
| 88 | 0.624 |
| 89 | 1.196 |
| 90 | >10 |
| 91 | 1.487 |
| 92 | 0.313 |
| 93 | 1.204 |
| 94 | 1.385 |
| 95 | 0.195 |
| 96 | 0.367 |
| 97 | 0.291 |
| 98 | 0.119 |
| 99 | 0.855 |
| 100 | 2.357 |
| 101 | >10 |
| 106 | 0.795 |
| 119 | 0.315 |
| 122 | 2.635 |
| 124 | 0.101 |
| 125 | 0.599 |
| 126 | 2.448 |
| 127 | 0.048 |
| 128 | 0.439 |
| 129 | 1.842 |
| 131 | 4.491 |
| 132 | >10 (48.8%) |
| 133 | >10 (35.8%) |
| 134 | 1.074 |
| 135 | >10 |
| 137 | 2.086 |

TABLE 6-continued

| Compound | $EC_{50}$ (μM) |
|---|---|
| 138 | 0.435 |
| 139 | 1.239 |
| 140 | 0.301 |
| 141 | 0.103 |
| 142 | 0.115 |
| 143 | 0.207 |
| 144 | 2.186 |
| 145 | 0.100 |
| 146 | >10 |
| 147 | 0.723 |
| 148 | 4.625 |
| 149 | >10 |
| 150 | 0.317 |
| 151 | >10 |
| 152 | 1.120 |
| 153 | >10 |
| 154 | 1.127 |
| 155 | 0.167 |
| 156 | 1.378 |
| 157 | 2.578 |
| 158 | 1.146 |
| 159 | 1.366 |
| 160 | 3.240 |
| 161 | 3.716 |
| 162 | 2.636 |
| 163 | 1.005 |
| 164 | 0.305 |

Example 8

Representative compounds were screened using the following assay procedure to determine their ability to inhibit IL-6 and therefore demonstrate their anti-inflammatory properties.

Human Peripheral Blood Mononuclear Cells: Fresh Normal PB MNC (Catalog #PB001, AllCells, Alameda, Calif.) were shipped overnight at 4° C. and resuspended in Roswell Park Memorial Institute (RPMI) 1640 Medium, with GlutaMAX Supplement (Catalog #61870127, ThermoFisher Scientific, Waltham, Mass.) supplemented with 1% Penicillin-Streptomycin (Catalog #15140163, ThermoFisher Scientific, Waltham, Mass.) and 1% fetal bovine serum (FBS) (Catalog #16140089, ThermoFisher Scientific, Waltham, Mass.) assay media.

Compound Screening: Fresh normal human peripheral blood mononuclear cells (huPBMCs) were resuspended in 1% FBS-RPMI assay media with 1% Penicillin-Streptomycin 1% to a cell concentration of 1×10e6 cells/mL. Each compound was dissolved in DMSO (Catalog #D8418-100 ml, Sigma-Aldrich, St. Louis, Mo.) as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white Proxiplate-Plus assay plates (Catalog #6008289, PerkinElmer, Shelton, Conn.) with appropriate DMSO backfill for a final DMSO concentration of 0.25%. huPBMCs were plated at 5000 cells/well in the 384-well Proxiplate-Plus assay plates and incubated at 37° C.-5% $CO_2$ for 2 hours. 50 ng/mL of Lipopolysaccharides from *Escherichia coli* 0111:B4 (Catalog #L5293-2ML, Sigma-Aldrich, St. Louis, Mo.) was added after 2 hours and cells were incubated for another 22 hours at 37° C.-5% $CO_2$. After 22 hour incubation, a mixture of anti-IL6 XL665 and anti-IL-6 Cryptate diluted in reconstitution buffer (Catalog #62IL6PEC, Cisbio Inc., Bedford, Mass.) was added to each well. Following incubation for 3 hours at room temperature, Homogeneous Time-Resolved Fluorescence (HTRF) was measured using the Envision (Perkin Elmer, Shelton, Conn.) at 665 nm and 620 nM. The ratio of fluorescence at 665 nm to 620 nm was used as a readout for IL-6 quantification. All samples were processed in duplicate. Readings were normalized to DMSO treated cells and normalized activities were utilized for $EC_{50}$ calculations. $EC_{50}$ was determined using software generated by Dotmatics Limited (Windhill Bishops Stortford Herts, UK) using the Levenberg-Marquardt 4 parameter fitting procedure with finite different gradients. For $EC_{50}$ of >10 µM, the percent inhibition at 10 µM is provided.

Table 7 shows the activity of representative compounds of Formula I as provided herein.

TABLE 7

| Compound | $EC_{50}$ (µM) |
|---|---|
| 1 | 1.166 |
| 2 | 3.009 |
| 3 | 9.069 |
| 4 | 2.893 |
| 5 | 2.935 |
| 6 | >10 (37.8%) |
| 7 | 2.009 |
| 8 | 3.357 |
| 9 | 1.091 |
| 10 | 0.903 |
| 11 | 3.321 |
| 12 | 1.161 |
| 13 | >10 |
| 14 | 3.542 |
| 15 | 3.549 |
| 16 | >10 (37.5%) |
| 18 | 3.824 |
| 19 | 3.682 |
| 20 | >10 (36.4%) |
| 21 | >10 (15.5%) |
| 22 | >10 (10.2%) |
| 23 | 0.345 |
| 24 | 0.419 |
| 26 | 1.041 |
| 27 | 3.821 |
| 28 | 0.401 |
| 30 | >10 |
| 31 | 4.258 |
| 32 | 1.269 |
| 33 | 3.149 |
| 34 | 3.106 |
| 35 | >10 (9.2%) |
| 36 | 0.348 |
| 37 | 0.546 |
| 38 | >10 (8.8%) |
| 39 | 1.261 |
| 40 | 1.929 |
| 41 | 2.861 |
| 42 | >10 (10.4%) |
| 43 | 9.150 |
| 44 | 1.027 |
| 45 | 1.266 |
| 46 | >10 (48.3%) |
| 48 | 5.415 |
| 49 | 3.729 |
| 50 | 6.046 |
| 51 | 2.557 |
| 54 | >10 (9.7%) |
| 55 | 3.854 |
| 56 | 2.148 |
| 59 | 2.588 |
| 60 | 8.977 |
| 63 | >10 (6.2%) |
| 65 | 3.176 |
| 66 | 1.279 |
| 68 | >10 |
| 69 | 1.324 |
| 70 | 1.375 |

TABLE 7-continued

| Compound | $EC_{50}$ (µM) |
|---|---|
| 71 | 4.800 |
| 72 | 1.201 |
| 73 | 1.160 |
| 74 | >10 (22.1%) |
| 75 | 1.156 |
| 78 | 1.137 |
| 79 | 1.755 |
| 80 | 3.444 |
| 81 | 1.064 |
| 82 | 3.934 |
| 83 | 1.239 |
| 84 | >10 (2.1%) |
| 85 | 2.992 |
| 86 | >10 (14.8%) |
| 87 | 3.848 |
| 88 | 8.781 |
| 89 | 6.587 |
| 90 | >10 (37.0%) |
| 91 | >10 (53.6%) |
| 92 | >10 (0%) |
| 93 | >10 (5.5%) |
| 94 | >10 (5.0%) |
| 95 | 1.000 |
| 96 | 1.211 |
| 97 | 2.275 |
| 98 | 1.125 |
| 99 | 3.277 |
| 100 | >10 (5.5%) |
| 101 | >10 (14.1%) |
| 106 | 6.854 |
| 119 | 1.931 |
| 122 | 0.948 |
| 124 | 0.989 |
| 125 | 3.518 |
| 126 | 5.776 |
| 127 | 0.786 |
| 128 | 3.278 |
| 129 | 6.766 |
| 131 | >10 (15.1%) |
| 132 | >10 (12.7%) |
| 133 | >10 (20.2%) |
| 134 | >10 (8.1%) |
| 135 | >10 (50.6%) |
| 137 | >10 |
| 138 | 2.733 |
| 139 | 3.108 |
| 140 | 1.249 |
| 141 | 0.382 |
| 142 | 1.096 |
| 143 | 1.414 |
| 144 | >10 (49.0%) |
| 145 | 1.144 |
| 146 | >10 (4.7%) |
| 147 | 1.066 |
| 148 | >10 (24.2%) |
| 149 | >10 (44.7%) |
| 150 | 3.574 |
| 151 | 7.366 |
| 152 | 6.847 |
| 153 | >10 (3.7%) |
| 154 | 1.864 |
| 155 | 2.051 |
| 156 | 4.291 |
| 157 | 1.313 |
| 158 | 5.990 |
| 159 | 2.822 |
| 160 | >10 (27.9%) |
| 161 | 3.398 |
| 162 | 7.686 |
| 163 | 8.832 |
| 164 | 1.332 |

Example 9

Representative compounds were screened using primary human mesenchymal stem cells (hMSCs) to determine their ability to induce tenocyte differentiation (process by which tendon is developed).

Human Mesenchymal Stem Cell Culture: Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening: Each compound was dissolved in DMSO as a 10 mM stock and used to prepare compound source plates. For the tenocyte differentiation assay, serial dilution (1:2, 10-point dose-response curves from 10 μM to 19.5 nM) and compound transfer was performed using the ECHO 550 (Labcyte, Sunnyvale, Calif.) into 384-well black clear bottom assay plates (Greiner Bio-One) with appropriate DMSO backfill for a final DMSO concentration of 0.17%. hMSCs were plated at 3,000 cells/well in 70 μL/well Dulbecco's modified Eagle's medium (DMEM, Life Technologies, Carlsbad, Calif.) with 1% Fetal Bovine Serum (FBS, Life Technologies). Bone Morphogenic Factor (BMP) and Fetal Growth Factor (FGF) (10 ng/ml each, Peprotech, Inc., Rocky Hill, N.J.) were used as a positive-controls for differentiation while negative control wells were treated with 120 nL DMSO for normalization and calculating $EC_{50}$ values. Cells were incubated at 37° C. and 5% $CO_2$ for 4 days. Cells were fixed using 4% formaldehyde (Electron Microscopy Sciences), and stained with anti-Sclerasis (anti-SCXA) antibodies (Abgent, San Diego, Calif.) [Webb S., et. al., Retinoic acid receptor signaling preserves tendon stem cell characteristics and prevents spontaneous differentiation in vitro, *Stem Cell Research & Therapy* 2016, 7:45] overnight at 4° C. The cells were washed with Phosphate Buffered Saline (PBS, Life Technologies) and incubated with anti-rabbit Alexa-flor 647 secondary antibodies (Life Technologies) and DAPI (Life Technologies) for 1 hour at room temperature. Cells were washed using PBS, and imaged using the CellInsight CX5 (Life Technologies, 594/633 nm filter). Number of cells positive for SCXA in each well was quantified using the CellInsight CX5. Data was normalized to the average of 12 DMSO treated wells on the same plate using Dotmatics Studies module. The normalized averages (fold change over DMSO) of 3 replicate wells for each compound concentration were calculated. Due to solubility limitations of some of the compounds, values for higher doses were manually corrected and curve fitting and $EC_{50}$ determinations were performed using Dotmatics Studies.

Table 8 shows the activity of representative compounds of Formula I as provided herein.

TABLE 8

| Compound | $EC_{50}$ (μM) |
|---|---|
| 16 | 1.379 |
| 30 | 1.472 |
| 34 | 1.323 |
| 35 | 2.066 |
| 82 | >100 (2.9%) |
| 88 | 2.547 |
| 99 | 2.827 |
| 100 | 1.879 |
| 101 | >100 (33.0%) |
| 106 | 1.296 |
| 119 | 13.986 |

TABLE 8-continued

| Compound | $EC_{50}$ (μM) |
|---|---|
| 122 | >100 (37.4%) |
| 124 | 0.315 |
| 125 | >100 (12.3%) |
| 126 | 2.587 |
| 127 | 2.494 |
| 128 | 5.719 |
| 129 | >100 (13.0%) |
| 131 | 2.772 |
| 132 | >100 (26.5%) |
| 133 | >100 (15.8%) |
| 134 | >100 (38.8%) |
| 135 | >100 (16.1%) |
| 137 | 2.481 |
| 138 | 4.925 |
| 139 | >100 (21.2%) |
| 140 | >100 (12.6%) |
| 141 | 0.930 |
| 142 | >100 (38.2%) |
| 143 | >100 (23.0%) |
| 144 | >100 (27.4%) |
| 145 | 0.863 |
| 146 | >100 (35.9%) |
| 147 | 2.638 |
| 148 | 3.094 |
| 149 | >100 (36.0%) |
| 150 | >100 (17.4%) |
| 151 | >100 (3.5%) |
| 152 | >100 (34.7%) |
| 153 | >100 (20.7%) |
| 154 | >100 (21.0%) |
| 156 | 2.641 |
| 157 | >100 (35.3%) |
| 158 | >100 (17.4%) |
| 159 | >100 (15.5%) |
| 160 | >100 (18.6%) |
| 161 | >100 (31.8%) |
| 162 | >100 (12.7%) |
| 163 | >100 (40.7%) |
| 164 | >100 (33.1%) |

What is claimed is:

1. A compound, or a pharmaceutically acceptable salt thereof, of Formula I:

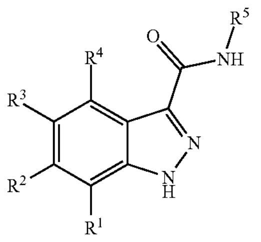

I wherein:

$R^1$, $R^2$, and $R^4$ are independently selected from the group consisting of H and halide;

$R^3$ is a 5-membered heteroaryl ring optionally substituted with from 1-4 $R^{42}$;

$R^5$ is aryl optionally substituted with 1-5 $R^{29}$;

each $R^{29}$ is independently selected from the group consisting of halide, —$OR^{38}$, unsubstituted —($C_1$-9 alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{39}$, —NHheterocyclyl optionally substituted with 1-10 $R^{40}$, and —O($C_{1-4}$ alkylene)$_p$heterocyclyl optionally substituted with 1-10 $R^{40}$; wherein each —($C_{1-4}$ alkylene) is, independently, optionally substituted with 1-5 halo or 1-5 unsubstituted —($C_{1-3}$ alkyl);

each $R^{38}$ is independently selected from the group consisting of H, unsubstituted —($C_{1-4}$ alkyl), unsubstituted —($C_{2-4}$ alkenyl), unsubstituted —($C_{2-4}$ alkynyl), and unsubstituted —($C_{1-4}$ haloalkyl);

each $R^{39}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{40}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{42}$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OH, —($C_{1-4}$ alkylene)$_p$heterocyclyl optionally substituted with 1-10 $R^{43}$, and -carbocyclyl optionally substituted with 1-12 $R^{44}$; wherein each —($C_{1-4}$ alkylene) is, independently, optionally substituted with 1-5 halo or 1-5 unsubstituted —($C_{1-3}$ alkyl);

alternatively, two adjacent $R^{42}$ groups are taken together to form a ring which is selected from the group consisting of -heterocyclyl optionally substituted with 1-10 $R^{45}$ and -carbocyclyl optionally substituted with 1-12 $R^{46}$;

each $R^{43}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{44}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{45}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{46}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN; and each p is independently 0 or 1.

2. A compound, or a pharmaceutically acceptable salt thereof, of Formula I:

I

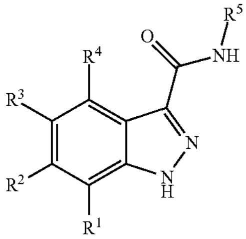

wherein:

$R^1$, $R^2$, and $R^4$ are independently selected from the group consisting of H and halide;

$R^3$ is selected from the group consisting of:

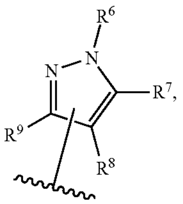

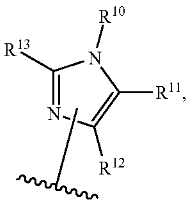

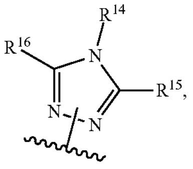

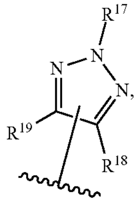

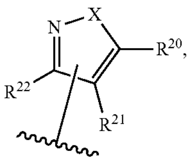

and

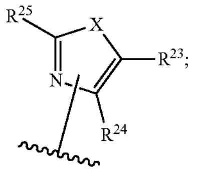

wherein each of $R^6$-$R^{25}$ is, independently, a substituent as defined below or a single bond connecting $R^3$ to the indazole ring; wherein only one of $R^6$-$R^9$ (when present) is a bond, only one of $R^{10}$-$R^{13}$ (when present) is a bond, only one of $R^{14}$-$R^{16}$ (when present) is a bond, only one of $R^{17}$-$R^{19}$ (when present) is a bond, only one of $R^{20}$-$R^{22}$ is a bond, and only one of $R^{23}$-$R^{25}$ (when present) is a bond; for purposes of clarification, any one of the nitrogen atoms attached to $R^6$, $R^{10}$, $R^{14}$, or $R^{17}$ can serve as the point of attachment of $R^3$ to the indazole ring; likewise, any one of the carbon atoms attached to $R^7$, $R^8$, $R^9$, $R^{11}$, $R^{12}$, $R^{13}$, $R^{15}$, $R^{16}$, $R^{18}$, $R^{19}$, $R^{20}$, $R^{21}$, $R^{22}$, $R^{23}$, $R^{24}$, $R^{25}$ can serve as the point of attachment of $R^3$ to the indazole ring; accordingly:

when the nitrogen atom to which $R^6$ is attached serves as the point of attachment of $R^3$ to the indazole ring, then $R^6$ is a single bond connecting $R^3$ to the indazole ring;

when the carbon atom to which $R^7$ is attached serves as the point of attachment of $R^3$ to the indazole ring, then $R^7$ is a single bond connecting $R^3$ to the indazole ring;

when the carbon atom to which $R^8$ is attached serves as the point of attachment of $R^3$ to the indazole ring, then $R^8$ is a single bond connecting $R^3$ to the indazole ring;

when the carbon atom to which $R^9$ is attached serves as the point of attachment of $R^3$ to the indazole ring, then $R^9$ is a single bond connecting $R^3$ to the indazole ring;

when the nitrogen atom to which $R^{10}$ is attached serves as the point of attachment of $R^3$ to the indazole ring, then $R^{10}$ is a single bond connecting $R^3$ to the indazole ring;

when the carbon atom to which $R^{11}$ is attached serves as the point of attachment of $R^3$ to the indazole ring, then $R^{11}$ is a single bond connecting $R^3$ to the indazole ring;

when the carbon atom to which $R^{12}$ is attached serves as the point of attachment of $R^3$ to the indazole ring, then $R^{12}$ is a single bond connecting $R^3$ to the indazole ring;

when the carbon atom to which $R^{13}$ is attached serves as the point of attachment of $R^3$ to the indazole ring, then $R^{13}$ is a single bond connecting $R^3$ to the indazole ring;

when the nitrogen atom to which $R^{14}$ is attached serves as the point of attachment of $R^3$ to the indazole ring, then $R^{14}$ is a single bond connecting $R^3$ to the indazole ring;

when the carbon atom to which $R^{15}$ is attached serves as the point of attachment of $R^3$ to the indazole ring, then $R^{15}$ is a single bond connecting $R^3$ to the indazole ring;

when the carbon atom to which $R^{16}$ is attached serves as the point of attachment of $R^3$ to the indazole ring, then $R^{16}$ is a single bond connecting $R^3$ to the indazole ring;

when the nitrogen to which $R^{17}$ is attached serves as the point of attachment of $R^3$ to the indazole ring, then $R^{17}$ is a single bond connecting $R^3$ to the indazole ring;

when the carbon atom to which $R^{18}$ is attached serves as the point of attachment of $R^3$ to the indazole ring, then $R^{18}$ is a single bond connecting $R^3$ to the indazole ring;

when the carbon atom to which $R^{19}$ is attached is instead attached to the indazole ring then $R^{19}$ is a single bond connecting $R^3$ to the indazole ring;

when the carbon atom to which $R^{20}$ is attached serves as the point of attachment of $R^3$ to the indazole ring, then $R^{20}$ is a single bond connecting $R^3$ to the indazole ring;

when the carbon atom to which $R^{21}$ is attached serves as the point of attachment of $R^3$ to the indazole ring, then $R^{21}$ is a single bond connecting $R^3$ to the indazole ring;

when the carbon atom to which $R^{22}$ is attached serves as the point of attachment of $R^3$ to the indazole ring, then $R^{22}$ is a single bond connecting $R^3$ to the indazole ring;

when the carbon atom to which $R^{23}$ is attached serves as the point of attachment of $R^3$ to the indazole ring, then $R^{23}$ is a single bond connecting $R^3$ to the indazole ring;

when the carbon atom to which $R^{24}$ is attached serves as the point of attachment of $R^3$ to the indazole ring, then $R^{24}$ is a single bond connecting $R^3$ to the indazole ring;

when the carbon to which $R^{25}$ is attached serves as the point of attachment of $R^3$ to the indazole ring, then $R^{25}$ is a single bond connecting $R^3$ to the indazole ring;

$R^5$ is aryl optionally substituted with 1-5 $R^{29}$;

$R^6$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with 1-5 halo or 1-5 unsubstituted —($C_{1-3}$ alkyl);

$R^7$, $R^8$, and $R^9$ are independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OH, and —($C_{1-4}$ alkylene)$_p$heterocyclyl optionally substituted with 1-10 $R^{27}$; wherein each —($C_{1-4}$ alkylene) is, independently, optionally substituted with 1-5 halo or 1-5 unsubstituted —($C_{1-3}$ alkyl);

alternatively, one of $R^6$ and $R^7$, $R^7$ and $R^8$, or $R^8$ and $R^9$ are taken together to form a ring which is selected from the group consisting of -heterocyclyl optionally substituted with 1-10 $R^{32}$ and -carbocyclyl optionally substituted with 1-12 $R^{33}$;

$R^{10}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with a substituent as defined anywhere herein 1-5 halo or 1-5 unsubstituted —($C_{1-3}$ alkyl);

$R^{11}$, $R^{12}$, and $R^{13}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{10}$ and $R^{11}$, $R^{11}$ and $R^{12}$, or $R^{13}$ and $R^{10}$ are taken together to form a ring which is selected from the group consisting of -heterocyclyl optionally substituted with 1-10 $R^{32}$ and -carbocyclyl optionally substituted with 1-12 $R^{33}$;

$R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with 1-5 halo or 1-5 unsubstituted —($C_{1-3}$ alkyl);

$R^{15}$ and $R^{16}$ are independently selected from the group consisting of H, halide, unsubstituted 9 alkyl), unsubstituted —($C_{2-9}$ alkenyl), unsubstituted —($C_{2-9}$ alkynyl), and unsubstituted —($C_{1-9}$ haloalkyl);

alternatively, one of $R^{14}$ and $R^{15}$ or $R^{16}$ and $R^{14}$ are taken together to form a heterocyclyl optionally substituted with 1-10 $R^{32}$;

$R^{17}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted haloalkyl), —($C_{1-4}$ alkylene)$_p$heterocyclyl optionally substituted with 1-10 $R^{30}$, and -carbocyclyl optionally substituted with 1-12 $R^{31}$; wherein —($C_{1-4}$ alkylene) is, optionally substituted with 1-5 halo or 1-5 unsubstituted —($C_{1-3}$ alkyl);

$R^{18}$ and $R^{19}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{18}$ and $R^{19}$ are taken together to form a ring which is selected from the group consisting of -heterocyclyl optionally substituted with 1-10 $R^{32}$ and -carbocyclyl optionally substituted with 1-12 $R^{33}$;

$R^{20}$, $R^{21}$, and $R^{22}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, one of $R^{20}$ and $R^{21}$ or $R^{21}$ and $R^{22}$ are taken together to form a ring which is selected from the group consisting of -heterocyclyl optionally substituted with 1-10 $R^{32}$ and -carbocyclyl optionally substituted with 1-12 $R^{33}$;

$R^{23}$, $R^{24}$, and $R^{25}$ are independently selected from the group consisting of H, halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, $R^{23}$ and $R^{24}$ are taken together to form a ring which is selected from the group consisting of -heterocyclyl optionally substituted with 1-10 $R^{32}$ and -carbocyclyl optionally substituted with 1-12 $R^{33}$;

each $R^{29}$ is independently selected from the group consisting of halide, —$OR^{38}$, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{39}$, —NHheterocyclyl optionally substituted with 1-10 $R^{40}$, and —O($C_{1-4}$ alkylene)$_p$heterocyclyl optionally substituted with 1-10 $R^{40}$; wherein —($C_{1-4}$ alkylene) is, optionally substituted with 1-5 halo or 1-5 unsubstituted —($C_{1-3}$ alkyl);

each $R^{30}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{31}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{32}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{33}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{38}$ is independently selected from the group consisting of H, unsubstituted —($C_{1-4}$ alkyl), unsubstituted —($C_{2-4}$ alkenyl), unsubstituted —($C_{2-4}$ alkynyl), and unsubstituted —($C_{1-4}$ haloalkyl);

each $R^{39}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{40}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each $R^{46}$ is independently selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), halide, and —CN;

each X is O or S; and each p is independently 0 or 1.

3. The compound of claim 1, wherein $R^1$, $R^2$ and $R^4$ are H.

4. The compound of claim 2, wherein $R^1$, $R^2$ and $R^4$ are H.

5. The compound of claim 4, wherein $R^3$ is

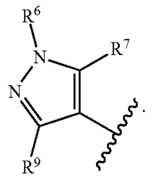

6. The compound of claim 5, wherein $R^6$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{31}$.

7. The compound of claim 5, wherein $R^7$ is selected from the group consisting of H, halide, unsubstituted —($C_{1-2}$ alkyl), and unsubstituted —($C_{1-2}$ haloalkyl).

8. The compound of claim 5, wherein $R^9$ is selected from the group consisting of H and halide.

9. The compound of claim 4, wherein $R^3$ is

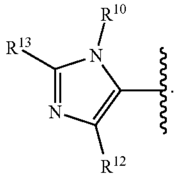

10. The compound of claim 9, wherein $R^{10}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{31}$.

11. The compound of claim 9, wherein $R^{12}$ is selected from the group consisting of H and halide.

12. The compound of claim 9, wherein $R^{13}$ is selected from the group consisting of H, halide, unsubstituted —($C_{1-2}$ alkyl), and unsubstituted —($C_{1-2}$ haloalkyl).

13. The compound of claim 4, wherein $R^3$ is

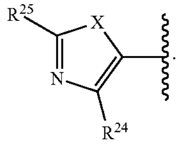

14. The compound of claim 13, wherein $R^{24}$ is selected from the group consisting of H and halide.

15. The compound of claim 13, wherein $R^{25}$ is selected from the group consisting of H, halide, unsubstituted —($C_{1-2}$ alkyl), and unsubstituted —($C_{1-2}$ haloalkyl).

16. The compound of claim 4, wherein $R^3$ is

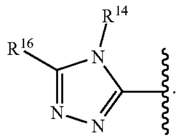

17. The compound of claim 16, wherein $R^{14}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{31}$.

18. The compound of claim 16, wherein $R^{16}$ is selected from the group consisting of H, halide, unsubstituted —($C_{1-2}$ alkyl), and unsubstituted —($C_{1-2}$ haloalkyl).

19. The compound of claim 4, wherein $R^5$ is aryl optionally substituted with 1-2 $R^{29}$.

20. The compound of claim 19, wherein $R^5$ is -phenyl substituted with 1-2 $R^{29}$.

21. The compound of claim 20, wherein $R^{29}$ is independently selected from the group consisting of F, —OH, —$OCHF_2$, —$OCF_3$, methyl, —$CF_3$,

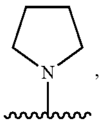, 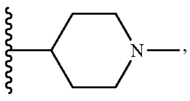, 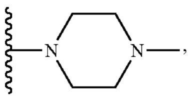,

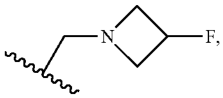, 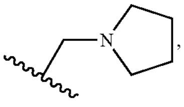,

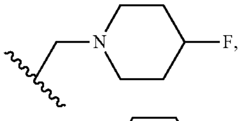, 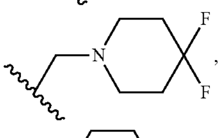,

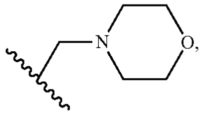, 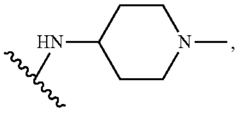,

-continued
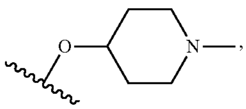
, and
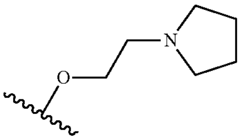
.
22. The compound of claim 1, wherein the compound of Formula I is selected from the group consisting of:
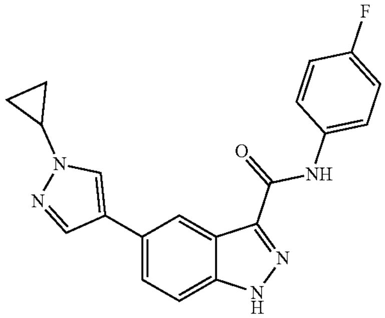
,
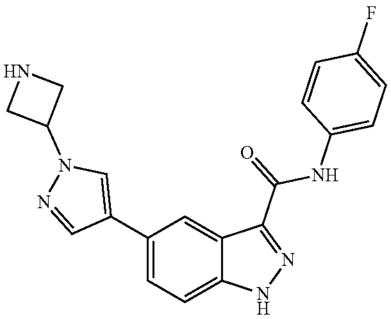
,
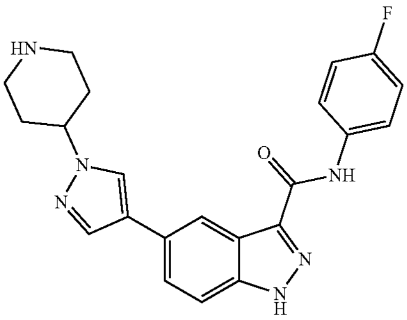
,
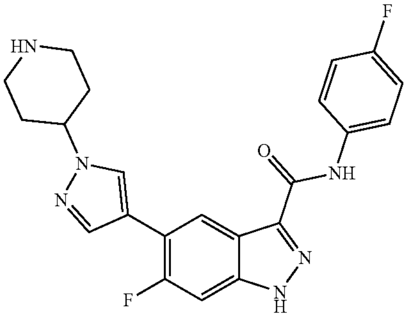
,
-continued
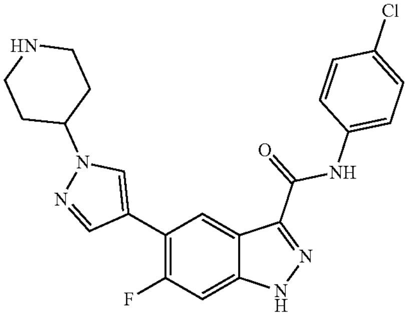
,
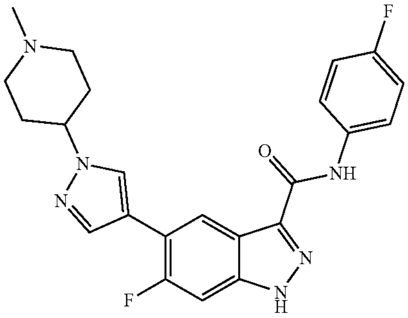
,
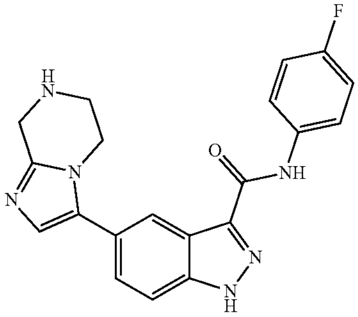
,
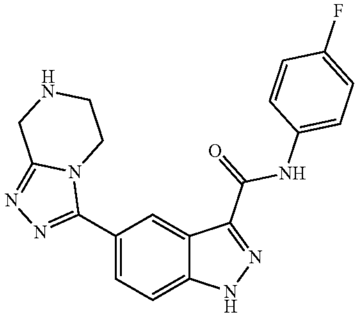
,
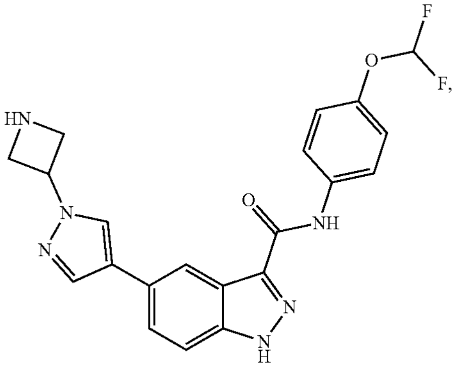

-continued
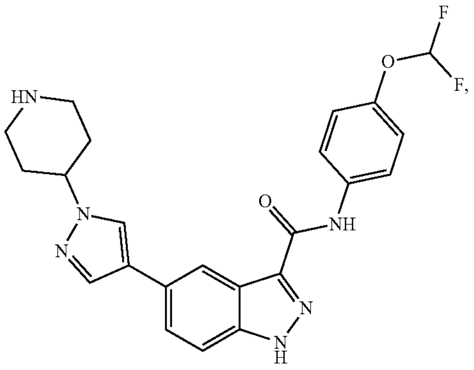
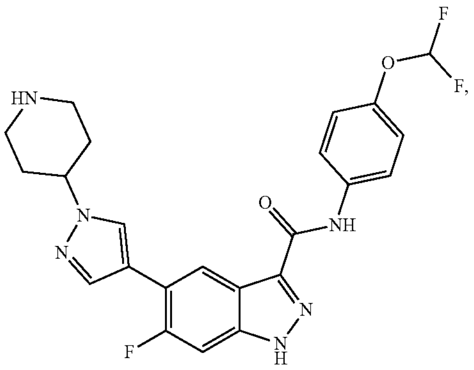
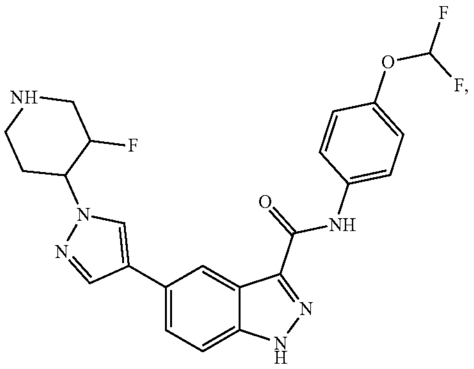
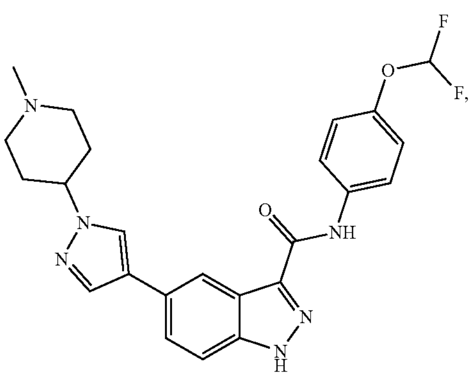
-continued
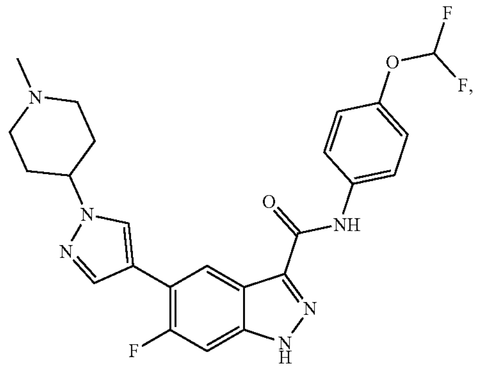
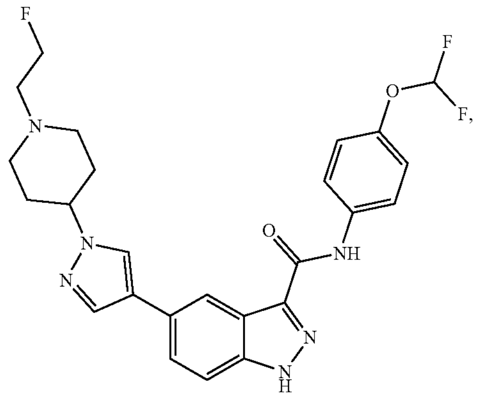
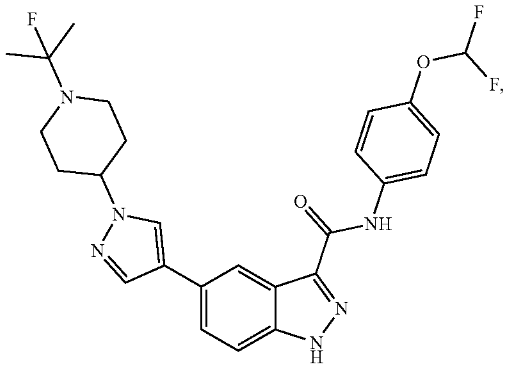
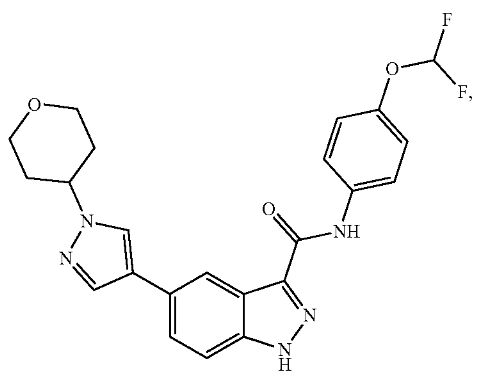

-continued
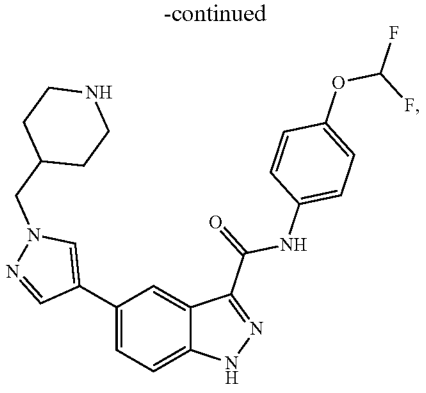
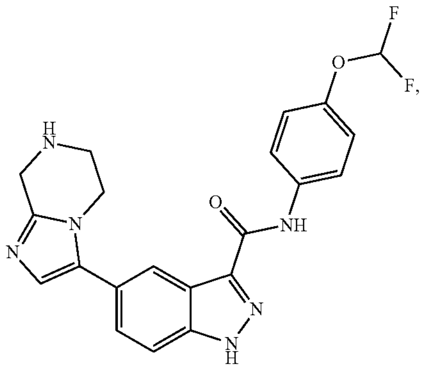
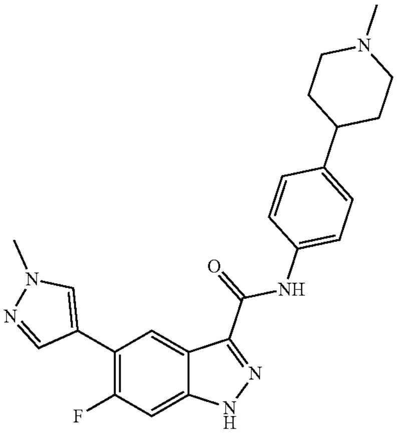
,
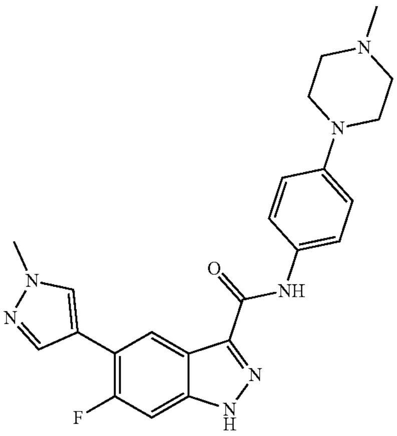
,
-continued
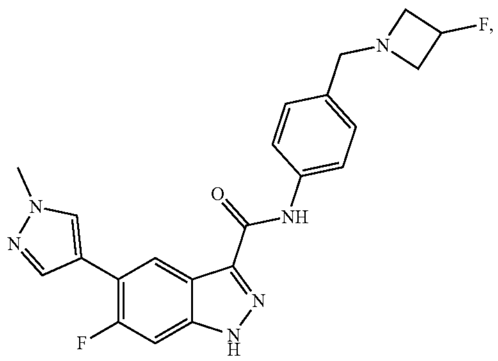
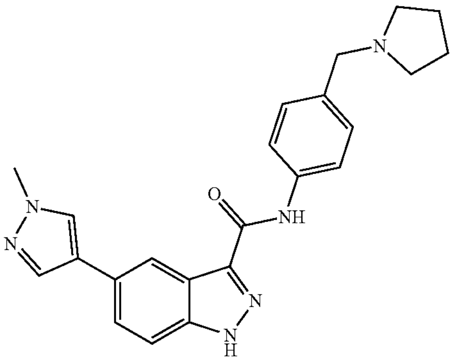
,
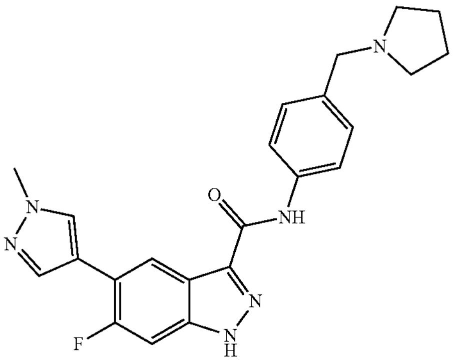
,
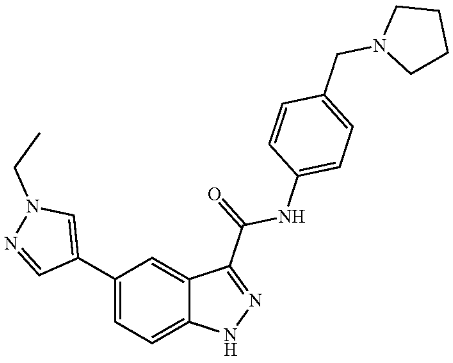
, -continued
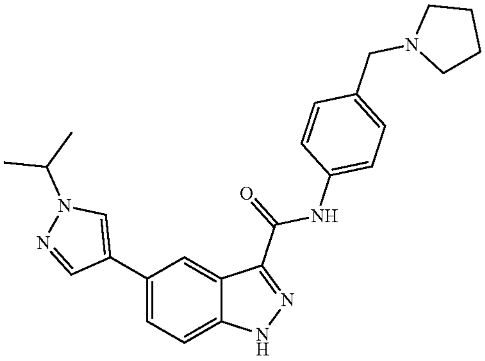
,
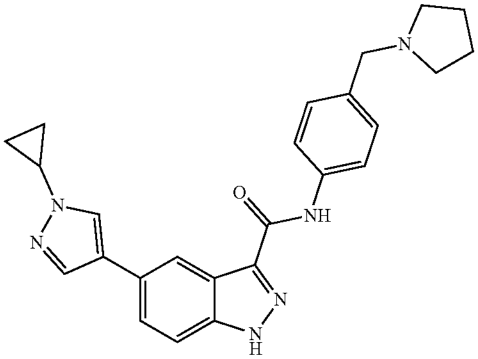
,
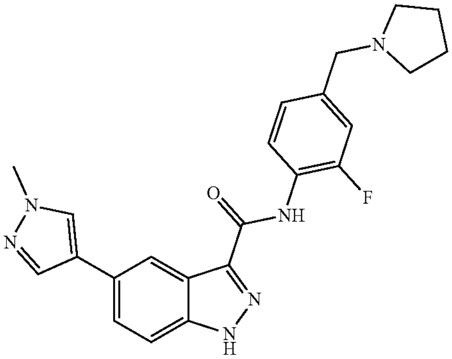
,
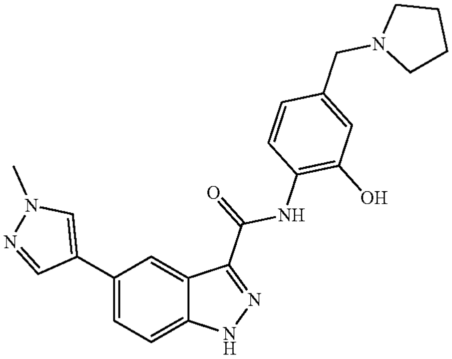
,
-continued
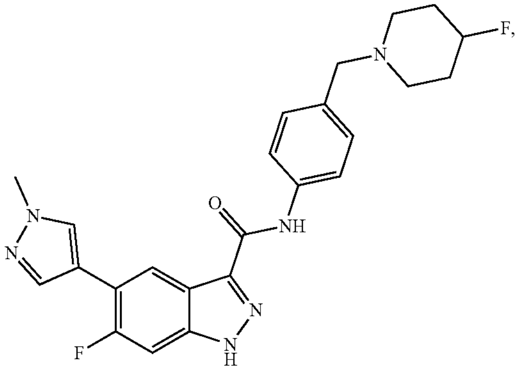
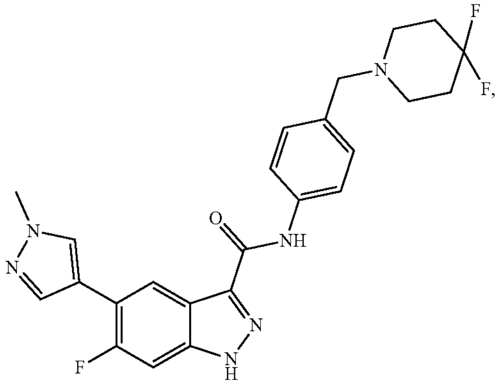
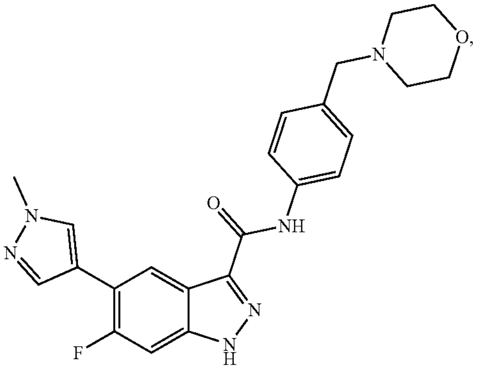
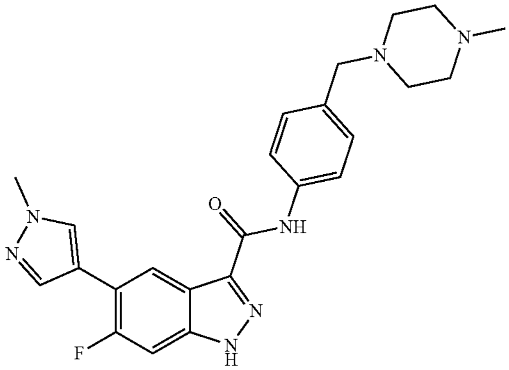
, -continued
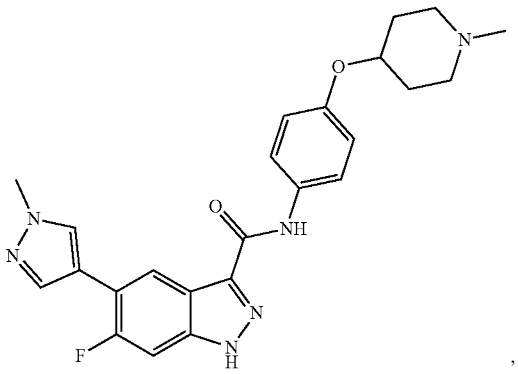
,
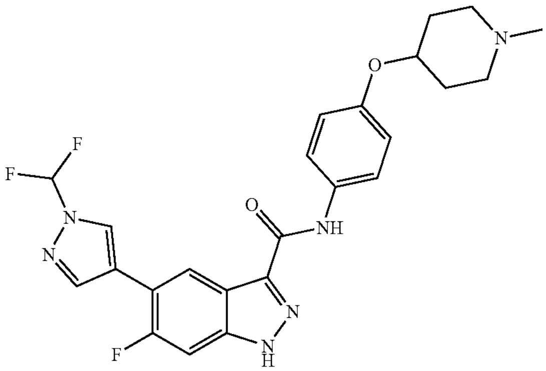
,
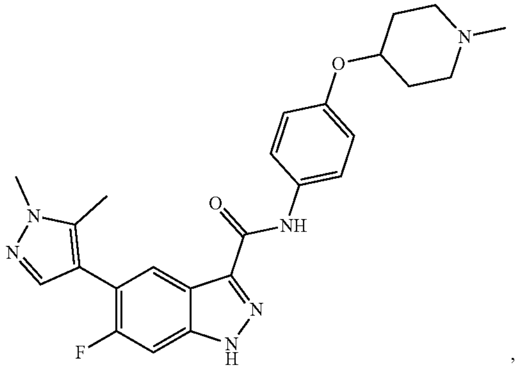
,
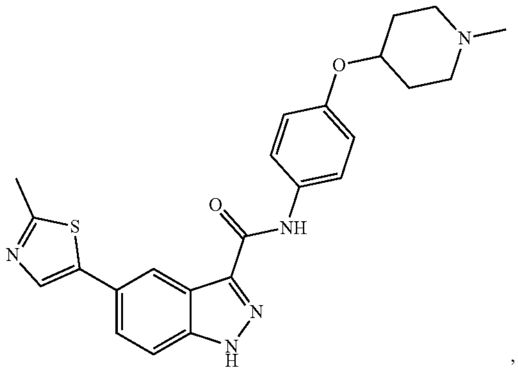
,
-continued
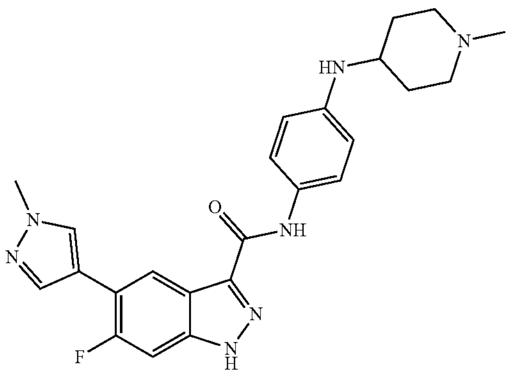
,
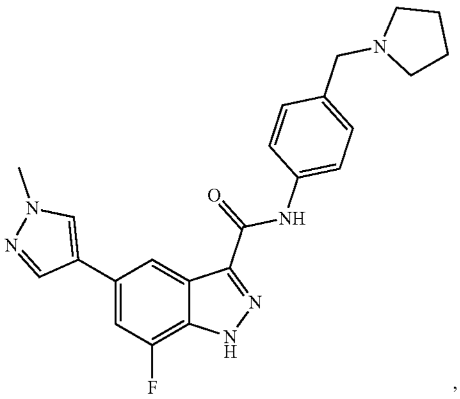
,
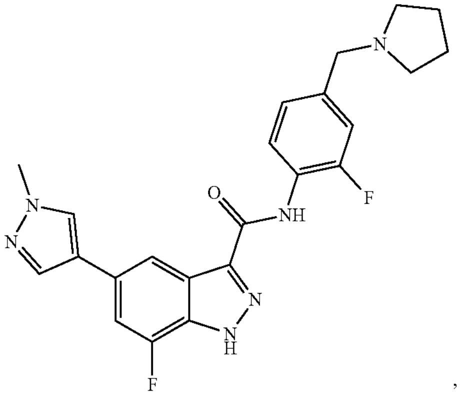
,
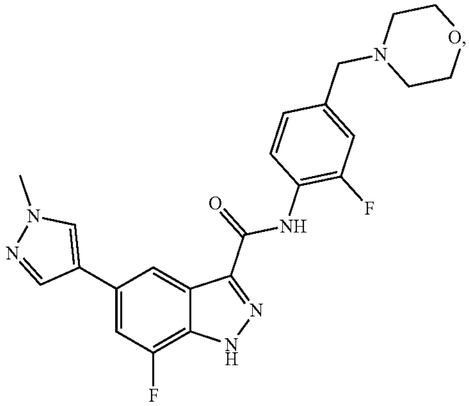

-continued
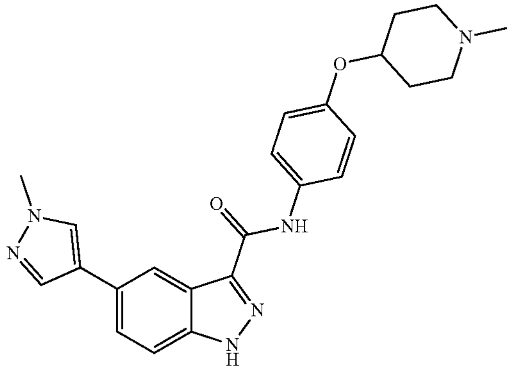
,
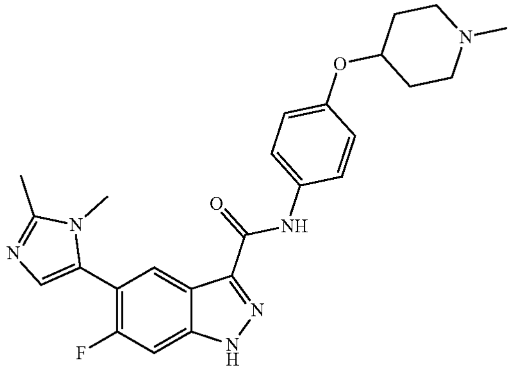
,
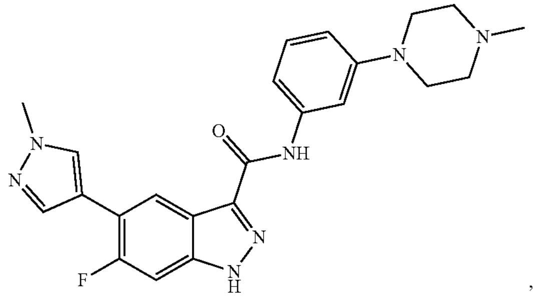
,
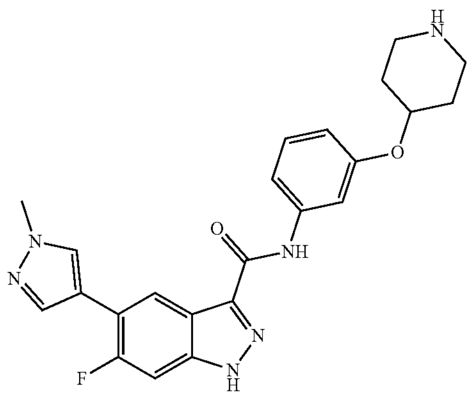
,
-continued
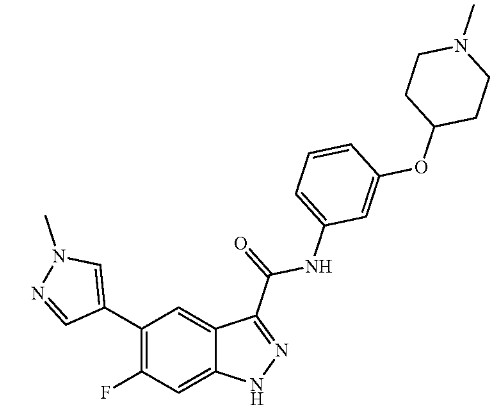
,
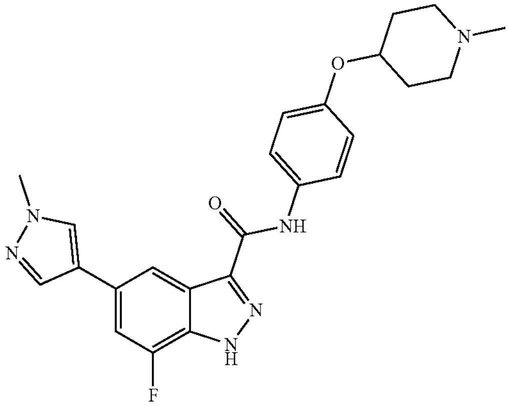
,
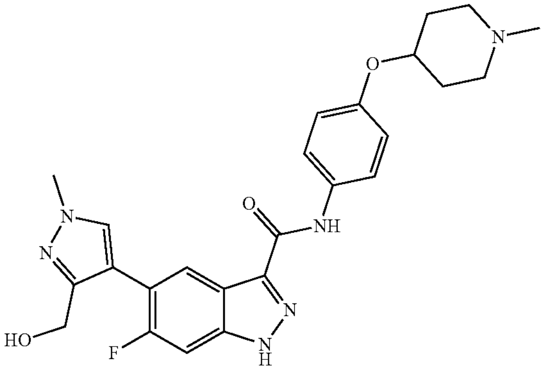
,
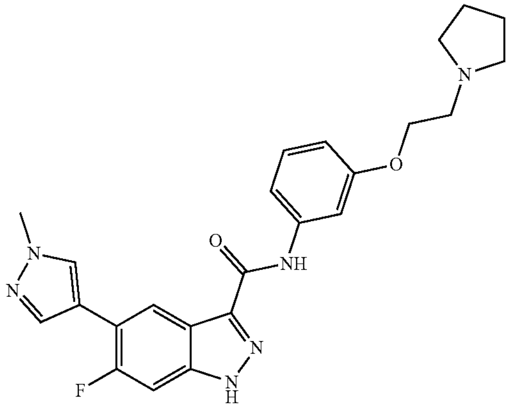
, -continued
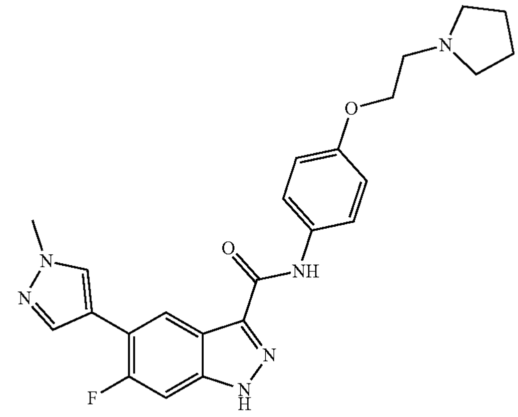
,
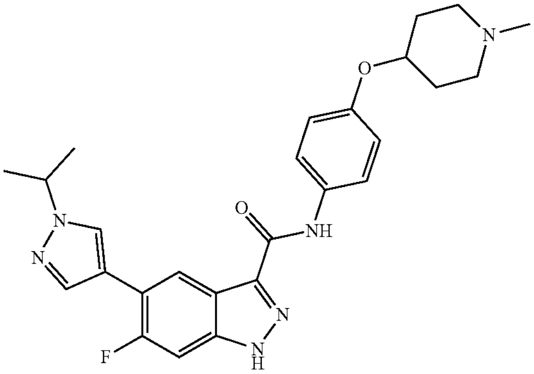
,
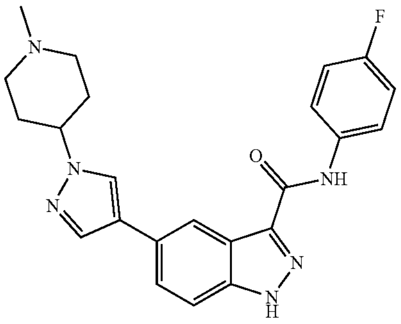
,
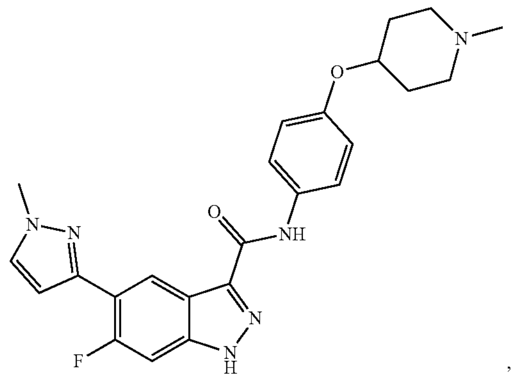
,
-continued
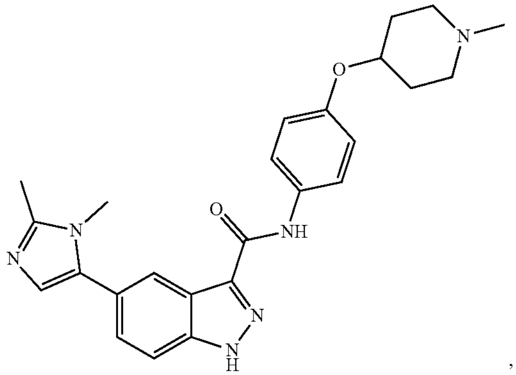
,
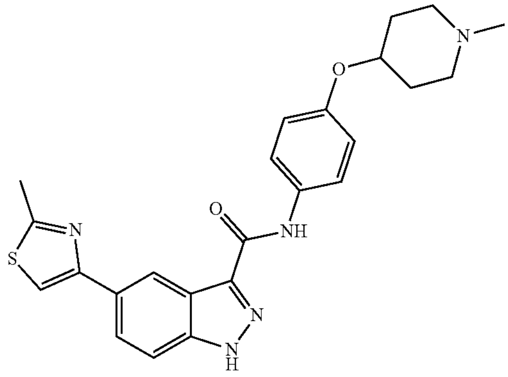
,
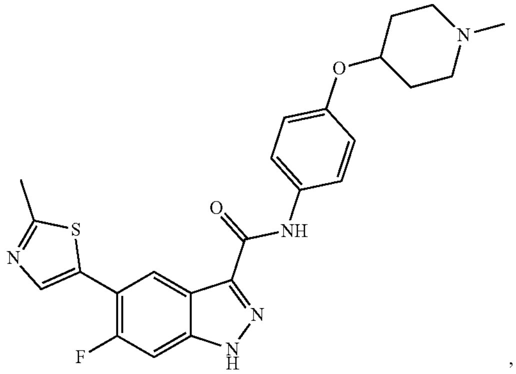 [SMILES: Cc1ncc(-c2cc3c(C(=O)Nc4ccc(OC5CCN(C)CC5)cc4)n[nH]c3cc2F)n1C]
, and
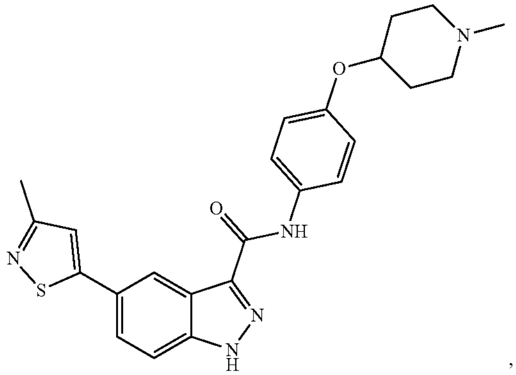
,
or a pharmaceutically acceptable salt thereof.
23. A pharmaceutical composition comprising a therapeutically effective amount of a compound of claim 1, or a pharmaceutically acceptable salt thereof, and a pharmaceutically acceptable excipient.

24. A pharmaceutical composition comprising a therapeutically effective amount of a compound of claim 2, or a pharmaceutically acceptable salt thereof, and a pharmaceutically acceptable excipient.

* * * * *

UNITED STATES PATENT AND TRADEMARK OFFICE

CERTIFICATE OF CORRECTION

PATENT NO. : 11,713,320 B2
APPLICATION NO. : 17/138098
DATED : August 1, 2023
INVENTOR(S) : Sunil Kumar KC et al.

It is certified that error appears in the above-identified patent and that said Letters Patent is hereby corrected as shown below:

In the Claims

Column 233, Line 34, in Claim 2, before "to" insert -- atom --.

Column 233, Line 41, in Claim 2, delete "haloalkyl)," and insert -- —($C_{1-9}$ haloalkyl), --.

Column 233, Line 62, in Claim 2, delete "haloalkyl)," and insert -- —($C_{1-9}$ haloalkyl), --.

Column 233, Lines 65-66, in Claim 2, after "with" delete "a substituent as defined anywhere herein".

Column 234, Line 13, in Claim 2, delete "haloalkyl)," and insert -- —($C_{1-9}$ haloalkyl), --.

Column 234, Line 19, in Claim 2, delete "9" and insert -- —($C_{1-9}$ --.

Column 234, Line 28, in Claim 2, delete "haloalkyl)," and insert -- —($C_{1-9}$ haloalkyl), --.

Signed and Sealed this
Twenty-sixth Day of September, 2023

Katherine Kelly Vidal

Katherine Kelly Vidal
*Director of the United States Patent and Trademark Office*